US012702721B2

(12) United States Patent
Hageman et al.

(10) Patent No.: US 12,702,721 B2
(45) Date of Patent: Aug. 11, 2026

(54) GENE THERAPY FOR MACULAR DEGENERATION

(71) Applicant: University of Utah Research Foundation, Salt Lake City, UT (US)

(72) Inventors: Gregory Scott Hageman, Salt Lake City, UT (US); Burt Timothy Richards, Midway, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 977 days.

(21) Appl. No.: 17/261,559

(22) PCT Filed: Jul. 22, 2019

(86) PCT No.: PCT/US2019/042891
§ 371 (c)(1),
(2) Date: Jan. 19, 2021

(87) PCT Pub. No.: WO2020/019002
PCT Pub. Date: Jan. 23, 2020

(65) Prior Publication Data

US 2021/0338838 A1 Nov. 4, 2021

Related U.S. Application Data

(60) Provisional application No. 62/859,628, filed on Jun. 10, 2019, provisional application No. 62/701,464, filed on Jul. 20, 2018.

(51) Int. Cl.
*A61K 48/00* (2006.01)
*C12N 15/86* (2006.01)

(52) U.S. Cl.
CPC ...... *A61K 48/0058* (2013.01); *A61K 48/0075* (2013.01); *C12N 15/86* (2013.01); *C12N 2750/14143* (2013.01); *C12N 2830/50* (2013.01)

(58) Field of Classification Search
CPC ............ A61K 48/0058; A61K 48/0075; A61K 48/005; A61K 31/7088; C12N 15/86; C12N 2750/14143; C12N 2830/50
See application file for complete search history.

(56) References Cited

U.S. PATENT DOCUMENTS

2012/0232133 A1* 9/2012 Balazs .............. C07K 16/1045 536/23.53
2013/0259924 A1* 10/2013 Bancel ................ C07K 14/705 530/358

(Continued)

FOREIGN PATENT DOCUMENTS

CA 2638916 A1 8/2007
WO 2006062716 A2 6/2006

(Continued)

OTHER PUBLICATIONS

Robert J. Klein et al. ,Complement Factor H Polymorphism in Age-Related Macular Degeneration. Science308,385-389(2005). (Year: 2005).*

(Continued)

*Primary Examiner* — Catherine Konopka
*Assistant Examiner* — Shabana S Meyering
(74) *Attorney, Agent, or Firm* — Kilpatrick Townsend & Stockton LLP

(57) ABSTRACT

The invention provides compositions and methods for treatment of age-related macular degeneration, including gene therapy employing vectors and transgenes expressing protective CFH polypeptide and CFHT polypeptide sequences.

16 Claims, 31 Drawing Sheets

Specification includes a Sequence Listing.

(56) References Cited

U.S. PATENT DOCUMENTS

| | | | |
|---|---|---|---|
| 2014/0005151 A1 | 1/2014 | Lockwood | |
| 2015/0259395 A1 | 9/2015 | Chalberg et al. | |
| 2019/0381194 A1* | 12/2019 | Tretiakova | A61K 35/761 |
| 2020/0069817 A1 | 3/2020 | Liu et al. | |
| 2021/0338838 A1 | 11/2021 | Hageman et al. | |
| 2021/0395776 A1 | 12/2021 | Patzke et al. | |
| 2022/0073576 A1 | 3/2022 | Joel | |

FOREIGN PATENT DOCUMENTS

| | | | | |
|---|---|---|---|---|
| WO | WO-2006088950 A2 * | 8/2006 | A61K 38/1703 |
| WO | WO 2011077102 A1 * | 6/2011 | A61P 9/10 |
| WO | 2013151666 A2 | 10/2013 | |
| WO | 2016164609 A2 | 10/2016 | |
| WO | 2016170176 A1 | 10/2016 | |
| WO | 2017191274 A2 | 11/2017 | |
| WO | WO-2019079718 A1 * | 4/2019 | A61K 48/005 |
| WO | 2020069461 A1 | 4/2020 | |
| WO | 2020128516 A2 | 6/2020 | |

OTHER PUBLICATIONS

NIH research matters (Year: 2013).*

Millen et al., JAMA Ophthalmol. 2015;133(10):1171-1179 (Year: 2015).*

Alberts B, Johnson A, Lewis J, et al., New York: Garland Science (Year: 2002).*

Hemmrich (Mol. Biol. Evol. 29 (11), 3267-3280, 2012). (Year: 2012).*

Fang et al (Nature Biotechnology, 2005, 23(5), 584-590) (Year: 2005).*

Kelly et al., "Rapid and Sensitive Method for Detection of Y402, H402, I62, and V62 Variants of Complement Factor H in Human Plasma Samples Using Mass Spectrometry", Investigative Ophthalmology & Visual Science, vol. 50, No. 4, Apr. 2009, pp. 1540-1545.

Magnusson et al., "CFH Y402H Confers Similar Risk of Soft Drusen and Both Forms of Advanced AMD", Plos Medicine, vol. 3, Issue 1, Nov. 29, 2005, pp. 1-6.

International Patent Application No. PCT/US2019/042891, International Search Report and Written Opinion, Mailed on Dec. 12, 2019, 11 pages.

International Patent Application No. PCT/US2019/042891, "Invitation to Pay Additional Fees and, Where Applicable, Protest Fee", Oct. 9, 2019, 2 pages.

Powell et al., "Viral Expression Cassette Elements to Enhance Transgene Target Specificity and Expression in Gene Therapy", Discovery Medicine, vol. 19, No. 102, Jan. 2015, pp. 49-57.

Application No. EP19837407.6 , Extended European Search Report, Mailed on Mar. 17, 2022, 8 pages.

Hageman et al., "A Common Haplotype in the Complement Regulatory Gene Factor H (HF1/CFH) Predisposes Individuals to Age-Related Macular Degeneration", Proceedings of the National Academy of Sciences, vol. 102, No. 20, May 17, 2005, pp. 7227-7232.

Haines et al., "Complement Factor H Variant Increases the Risk of Age-Related Macular Degeneration", Science, vol. 308, No. 5720, 2005, pp. 419-421.

Klein et al., "Complement Factor H Polymorphism in Age-Related Macular Degeneration", Science, vol. 308, No. 5720, 2005, pp. 385-389.

* cited by examiner

Human RPE65 Promoter Region
ATG
TSS +1
-750
R9 Series
Position +22
R20 Series
Position -42
R26 Series
Position -92
R12 Series
Position -147
R8 Series
Position -203
R30 Series
Position -259
R25 Series
Position -322
R11 Series
Position -421

FIG. 9A
pTR-BEST1-EP-454-EGFP
EGFP
SV40 poly(A)
CMV enhancer
TR
TR
f1 (+) origin
Amp R
ColE1 ori

FIG. 9B
pTR-RPE65-EP-415-EGFP
EGFP
SV40 poly(A)
CMV enhancer
TR
TR
f1 (+) origin
Amp R
ColE1 ori

Nucleotide sequence coordinates that correlate to SEQ ID:5 = 1294 - 1667

Nucleotide sequence coordinates that correlate to SEQ ID:5 = 1294 - 1577

Nucleotide sequence coordinates that correlate to SEQ ID:5 = 1294 - 1583

Nucleotide sequence coordinates that correlate to SEQ ID:5 =

1294 - 1583

Lane: 1. RPE-1, EGFP
2. RPE-1, CFHT (I62_Y402)
3. RPE-1, CFH/CFHT v4.0
4. RPE-1, CFH/CFHT v4.1
5. RPE-1, CFH/CFHT v4.2
6. RPE-1, CFH/CFHT v4.3
7. RPE-1, CFH (I62_Y402)

Diagram of dissection strategy and tissue collection for OD eye.

Diagram of dissection strategy and tissue collection for OS eye (Histology).

*In Vivo* Expression of Protective Human CFH Protein in AGM #B190
OS Retina-RPE-Choroid (RRC) Tissue (RX19.03 Study)

*In Vivo* Expression of Protective Human CFH Protein in AGM #B193
OS Retina-RPE-Choroid (RRC) Tissue (RX19.03 Study)

SEQUENCE LISTING

<160> NUMBER OF SEQ ID NOS: 127

<210> SEQ ID NO 1
<211> LENGTH: 3696
<212> TYPE: DNA
<213> ORGANISM: Homo sapiens

<400> SEQUENCE: 1

```
atgagactgc tggccaagat catctgcctg atgctgtggg ccatctgcgt ggccgaggac      60

tgcaacgagc tgccccccag aagaaacacc gagatcctga ccggctcttg gagcgaccag     120

acctaccctg agggcaccca ggccatctac aagtgcagac ccggctaccg gtccctgggc     180

aacatcatca tggtgtgcag aaagggcgag tgggtggccc tgaacccccct gagaaagtgc    240

cagaagaggc cctgcggaca ccccggcgat accccttttg gcaccttcac actgaccggc     300

ggcaacgtgt tcgagtacgg cgtgaaggcc gtgtacacct gtaacgaggg ctaccagctg     360

ctgggcgaga tcaactacag agagtgcgac accgacggct ggaccaacga tatccccatc     420

tgcgaggtcg tgaagtgcct gcctgtgacc gccccagaga acggcaagat cgtgtccagc     480

gccatggaac ccgacagaga gtaccacttc ggccaggccg tcagattcgt gtgcaacagc     540

ggctacaaga tcgagggcga cgaggaaatg cactgcagcg acgacggctt ctggtccaaa     600

gaaaagccta agtgcgtgga aatcagctgc aagagccccg acgtgatcaa cggcagcccc     660

atcagccaga agatcatcta caaagagaac gagcggttcc agtacaagtg taacatgggc     720

tacgagtaca gcgagcgggg cgacgccgtg tgtacagaat ctggatggcg gcctctgccc     780

agctgcgagg aaaagagctg cgacaacccc tacatcccca acggcgacta cagccccctg     840

cggatcaagc acagaaccgg cgacgagatc acctaccagt gccggaacgg cttctacccc     900

gccaccagag gcaataccgc caagtgtacc agcaccggct ggatccctgc ccccagatgt     960

accctgaagc cctgcgacta ccctgacatc aagcacggcg gcctgtacca cgagaacatg    1020

cggaggccct acttccctgt ggccgtgggc aagtactaca gctactactg cgacgagcac    1080

ttcgagacac ccagcggcag ctactgggac cacatccact gtacccagga cggctggtcc    1140

cctgccgtgc cctgcctgag gaagtgctac ttcccctacc tggaaaacgg ctacaaccag    1200

aactacggcc ggaagttcgt gcagggcaag agcatcgatg tggcctgcca ccctggatac    1260

gccctgccta aggcccagac caccgtgacc tgcatggaaa atggatggtc cccccacccc    1320

cggtgcatca gagtgaaaac ctgcagcaag agcagcatcg acatcgagaa tggcttcatc    1380

agcgagagcc agtacaccta cgccctgaaa gagaaggcca agtaccagtg caagctgggc    1440

tacgtgaccg ccgacggcga gacaagcggc agcatcacct gtggcaagga tgggtggagc    1500

gcccagccca cctgtatcaa gtcctgcgac atccctgtgt tcatgaatgc ccggaccaag    1560

aacgacttca cctggttcaa gctgaacgac acactggact acgagtgcca cgacggctac    1620

gagagcaaca ccggcagcac cacaggcagc atcgtgtgtg gctacaacgg gtggagtgac    1680

ctgcccatct gttacgagcg cgagtgcgag ctgcctaaga tcgacgtgca cctggtgccc    1740

gaccggaaga aagaccagta caaagtgggc gaggtgctga agttctcctg caagcccggc    1800

ttcaccatcg tgggccccaa tagcgtgcag tgctaccact ttggcctgtc cccccgatctg   1860

cctatctgca aagaacaggt gcagagctgc ggccctccac ccgagctgct gaacggcaat    1920
```

-continued

```
gtgaaagaaa agaccaaaga ggaatacggc cactccgagg tggtggaata ttactgcaac   1980

ccccggttcc tgatgaaggg ccccaacaag attcagtgtg tggacggcga gtggaccacc   2040

ctgcccgtgt gtatcgtgga agagtctacc tgcggagaca tccccgagct ggaacacgga   2100

tgggcccagc tgagcagccc cccttactac tacggcgaca gcgtggaatt caactgctcc   2160

gagagcttta ccatgatcgg ccaccggtcc atcacatgca tccacggcgt gtggacacag   2220

ctgccacagt gcgtggccat cgacaagctg aagaagtgca agtccagcaa cctgatcatc   2280

ctggaagaac acctgaagaa caagaaagag ttcgaccaca acagcaacat ccggtacaga   2340

tgccggggca aagagggatg gatccacacc gtgtgcatca atggcagatg ggaccccgaa   2400

gtgaactgca gcatggccca gatccagctg tgcccccac ctccccagat ccccaacagc    2460

cacaacatga ccaccaccct gaactaccgg gatggcgaga aggtgtccgt gctgtgccag   2520

gaaaactacc tgatccagga aggcgaagag attacctgca aggacggccg gtggcagagc   2580

atccccctgt gtgtggaaaa gatcccctgc agccagcccc cccagatcga gcacggcacc   2640

atcaacagca gcagaagcag ccaggaatcc tacgcccacg gcacaaagct gagctacaca   2700

tgcgagggcg gcttccggat ctccgaggaa aacgagacaa cctgctacat gggcaagtgg   2760

tcctccccac ctcagtgcga gggactgcct tgcaagtccc cacccgagat ctctcatggc   2820

gtggtggccc acatgagcga cagctaccag tacggcgagg aagtgaccta caagtgtttc   2880

gagggcttcg gcatcgacgg ccctgccatt gccaagtgcc tgggagagaa gtggtcccac   2940

cctcccagct gcatcaagac cgactgcctg agcctgccta gcttcgagaa cgccatcccc   3000

atgggcgaga aaaaggacgt gtacaaggcc ggcgaacaag tgacatacac ctgtgccacc   3060

tactacaaga tggacggcgc cagcaacgtg acctgtatta acagccggtg gaccggcagg   3120

cctacctgca gagatacctc ctgcgtgaac cccccccaccg tgcagaacgc ctacatcgtg  3180

tctcggcaga tgagcaagta ccccagcggc gaacgcgtgc gctaccagtg tagaagcccc   3240

tacgagatgt tcggcgacga agaagtgatg tgcctgaatg gcaactggac cgagcccccct  3300

cagtgcaagg atagcaccgg caagtgtggc ccccctcccc ccatcgataa cggcgacatc   3360

accagcttcc ccctgtccgt gtatgcccct gccagctccg tggaatatca gtgccagaac   3420

ctgtaccagc tggaaggcaa caagcggatc acctgtcgga acggccagtg gagcgagcct   3480

cccaagtgtc tgcacccctg cgtgatctcc agagaaatca tggaaaacta taatatcgcc   3540

ctgcgctgga ccgccaagca gaagctgtac tctaggaccg gcgagtctgt ggaatttgtg   3600

tgcaagcggg gatacagact gagcagcaga tcccacaccc tgagaaccac ctgttgggac   3660

ggcaagctgg aataccctac ctgcgccaag agatga                             3696
```

<210> SEQ ID NO 2
<211> LENGTH: 1231
<212> TYPE: PRT
<213> ORGANISM: Homo sapiens

<400> SEQUENCE: 2

```
Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Ile Ile Met
    50                  55                  60
```

-continued

```
Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285

Glu Ile Thr Tyr Gln Cys Arg Asn Gly Phe Tyr Pro Ala Thr Arg Gly
    290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
            340                 345                 350

Tyr Ser Tyr Tyr Cys Asp Glu His Phe Glu Thr Pro Ser Gly Ser Tyr
        355                 360                 365

Trp Asp His Ile His Cys Thr Gln Asp Gly Trp Ser Pro Ala Val Pro
    370                 375                 380

Cys Leu Arg Lys Cys Tyr Phe Pro Tyr Leu Glu Asn Gly Tyr Asn Gln
385                 390                 395                 400

Asn Tyr Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
            420                 425                 430

Glu Asn Gly Trp Ser Pro Thr Pro Arg Cys Ile Arg Val Lys Thr Cys
        435                 440                 445

Ser Lys Ser Ser Ile Asp Ile Glu Asn Gly Phe Ile Ser Glu Ser Gln
    450                 455                 460

Tyr Thr Tyr Ala Leu Lys Glu Lys Ala Lys Tyr Gln Cys Lys Leu Gly
465                 470                 475                 480
```

-continued

```
Tyr Val Thr Ala Asp Gly Glu Thr Ser Gly Ser Ile Thr Cys Gly Lys
                485                 490                 495

Asp Gly Trp Ser Ala Gln Pro Thr Cys Ile Lys Ser Cys Asp Ile Pro
            500                 505                 510

Val Phe Met Asn Ala Arg Thr Lys Asn Asp Phe Thr Trp Phe Lys Leu
        515                 520                 525

Asn Asp Thr Leu Asp Tyr Glu Cys His Asp Gly Tyr Glu Ser Asn Thr
    530                 535                 540

Gly Ser Thr Thr Gly Ser Ile Val Cys Gly Tyr Asn Gly Trp Ser Asp
545                 550                 555                 560

Leu Pro Ile Cys Tyr Glu Arg Glu Cys Glu Leu Pro Lys Ile Asp Val
                565                 570                 575

His Leu Val Pro Asp Arg Lys Lys Asp Gln Tyr Lys Val Gly Glu Val
            580                 585                 590

Leu Lys Phe Ser Cys Lys Pro Gly Phe Thr Ile Val Gly Pro Asn Ser
        595                 600                 605

Val Gln Cys Tyr His Phe Gly Leu Ser Pro Asp Leu Pro Ile Cys Lys
    610                 615                 620

Glu Gln Val Gln Ser Cys Gly Pro Pro Pro Glu Leu Leu Asn Gly Asn
625                 630                 635                 640

Val Lys Glu Lys Thr Lys Glu Glu Tyr Gly His Ser Glu Val Val Glu
                645                 650                 655

Tyr Tyr Cys Asn Pro Arg Phe Leu Met Lys Gly Pro Asn Lys Ile Gln
            660                 665                 670

Cys Val Asp Gly Glu Trp Thr Thr Leu Pro Val Cys Ile Val Glu Glu
        675                 680                 685

Ser Thr Cys Gly Asp Ile Pro Glu Leu Glu His Gly Trp Ala Gln Leu
    690                 695                 700

Ser Ser Pro Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
            740                 745                 750

Cys Lys Ser Ser Asn Leu Ile Ile Leu Glu Glu His Leu Lys Asn Lys
        755                 760                 765

Lys Glu Phe Asp His Asn Ser Asn Ile Arg Tyr Arg Cys Arg Gly Lys
    770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Pro Gln
                805                 810                 815

Ile Pro Asn Ser His Asn Met Thr Thr Thr Leu Asn Tyr Arg Asp Gly
            820                 825                 830

Glu Lys Val Ser Val Leu Cys Gln Glu Asn Tyr Leu Ile Gln Glu Gly
        835                 840                 845

Glu Glu Ile Thr Cys Lys Asp Gly Arg Trp Gln Ser Ile Pro Leu Cys
    850                 855                 860

Val Glu Lys Ile Pro Cys Ser Gln Pro Pro Gln Ile Glu His Gly Thr
865                 870                 875                 880

Ile Asn Ser Ser Arg Ser Ser Gln Glu Ser Tyr Ala His Gly Thr Lys
                885                 890                 895

Leu Ser Tyr Thr Cys Glu Gly Gly Phe Arg Ile Ser Glu Glu Asn Glu
```

```
            900                 905                 910

Thr Thr Cys Tyr Met Gly Lys Trp Ser Ser Pro Pro Gln Cys Glu Gly
        915                 920                 925

Leu Pro Cys Lys Ser Pro Pro Glu Ile Ser His Gly Val Val Ala His
    930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
            980                 985                 990

Pro Ser Phe Glu Asn Ala Ile Pro  Met Gly Glu Lys Lys  Asp Val Tyr
        995                 1000                1005

Lys Ala  Gly Glu Gln Val Thr  Tyr Thr Cys Ala Thr  Tyr Tyr Lys
    1010                 1015                 1020

Met Asp  Gly Ala Ser Asn Val  Thr Cys Ile Asn Ser  Arg Trp Thr
    1025                 1030                 1035

Gly Arg  Pro Thr Cys Arg Asp  Thr Ser Cys Val Asn  Pro Pro Thr
    1040                 1045                 1050

Val Gln  Asn Ala Tyr Ile Val  Ser Arg Gln Met Ser  Lys Tyr Pro
    1055                 1060                 1065

Ser Gly  Glu Arg Val Arg Tyr  Gln Cys Arg Ser Pro  Tyr Glu Met
    1070                 1075                 1080

Phe Gly  Asp Glu Glu Val Met  Cys Leu Asn Gly Asn  Trp Thr Glu
    1085                 1090                 1095

Pro Pro  Gln Cys Lys Asp Ser  Thr Gly Lys Cys Gly  Pro Pro Pro
    1100                 1105                 1110

Pro Ile  Asp Asn Gly Asp Ile  Thr Ser Phe Pro Leu  Ser Val Tyr
    1115                 1120                 1125

Ala Pro  Ala Ser Ser Val Glu  Tyr Gln Cys Gln Asn  Leu Tyr Gln
    1130                 1135                 1140

Leu Glu  Gly Asn Lys Arg Ile  Thr Cys Arg Asn Gly  Gln Trp Ser
    1145                 1150                 1155

Glu Pro  Pro Lys Cys Leu His  Pro Cys Val Ile Ser  Arg Glu Ile
    1160                 1165                 1170

Met Glu  Asn Tyr Asn Ile Ala  Leu Arg Trp Thr Ala  Lys Gln Lys
    1175                 1180                 1185

Leu Tyr  Ser Arg Thr Gly Glu  Ser Val Glu Phe Val  Cys Lys Arg
    1190                 1195                 1200

Gly Tyr  Arg Leu Ser Ser Arg  Ser His Thr Leu Arg  Thr Thr Cys
    1205                 1210                 1215

Trp Asp  Gly Lys Leu Glu Tyr  Pro Thr Cys Ala Lys  Arg
    1220                 1225                 1230


<210> SEQ ID NO 3
<211> LENGTH: 1350
<212> TYPE: DNA
<213> ORGANISM: Homo sapiens

<400> SEQUENCE: 3

atgagactgc tggccaagat catctgcctg atgctgtggg ccatctgcgt ggccgaggac      60

tgcaacgagc tgccccccag aagaaacacc gagatcctga ccggctcttg gagcgaccag     120

acctaccctg agggcaccca ggccatctac aagtgcagac ccggctaccg gtccctgggc     180
```

-continued

```
aacatcatca tggtgtgcag aaagggcgag tgggtggccc tgaaccccct gagaaagtgc    240

cagaagaggc cctgcggaca ccccggcgat accccttttg gcaccttcac actgaccggc    300

ggcaacgtgt tcgagtacgg cgtgaaggcc gtgtacacct gtaacgaggg ctaccagctg    360

ctgggcgaga tcaactacag agagtgcgac accgacggct ggaccaacga tatccccatc    420

tgcgaggtcg tgaagtgcct gcctgtgacc gccccagaga acggcaagat cgtgtccagc    480

gccatggaac ccgacagaga gtaccacttc ggccaggccg tcagattcgt gtgcaacagc    540

ggctacaaga tcgagggcga cgaggaaatg cactgcagcg acgacggctt ctggtccaaa    600

gaaaagccta agtgcgtgga aatcagctgc aagagccccg acgtgatcaa cggcagcccc    660

atcagccaga agatcatcta caaagagaac gagcggttcc agtacaagtg taacatgggc    720

tacgagtaca gcgagcgggg cgacgccgtg tgtacagaat ctggatggcg gcctctgccc    780

agctgcgagg aaaagagctg cgacaacccc tacatcccca acggcgacta cagccccctg    840

cggatcaagc acagaaccgg cgacgagatc acctaccagt gccggaacgg cttctacccc    900

gccaccagag gcaataccgc caagtgtacc agcaccggct ggatccctgc ccccagatgt    960

accctgaagc cctgcgacta ccctgacatc aagcacggcg gcctgtacca cgagaacatg   1020

cggaggccct acttccctgt ggccgtgggc aagtactaca gctactactg cgacgagcac   1080

ttcgagacac ccagcggcag ctactgggac cacatccact gtacccagga cggctggtcc   1140

cctgccgtgc cctgcctgag gaagtgctac ttcccctacc tggaaaacgg ctacaaccag   1200

aactacggcc ggaagttcgt gcagggcaag agcatcgatg tggcctgcca ccctggatac   1260

gccctgccta aggcccagac caccgtgacc tgcatggaaa atggatggtc ccccaccccc   1320

cggtgcatca gagtgtcctt caccctgtga                                    1350
```

<210> SEQ ID NO 4
<211> LENGTH: 449
<212> TYPE: PRT
<213> ORGANISM: Homo sapiens

<400> SEQUENCE: 4

```
Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Ile Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
```

```
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285

Glu Ile Thr Tyr Gln Cys Arg Asn Gly Phe Tyr Pro Ala Thr Arg Gly
    290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
            340                 345                 350

Tyr Ser Tyr Tyr Cys Asp Glu His Phe Glu Thr Pro Ser Gly Ser Tyr
        355                 360                 365

Trp Asp His Ile His Cys Thr Gln Asp Gly Trp Ser Pro Ala Val Pro
    370                 375                 380

Cys Leu Arg Lys Cys Tyr Phe Pro Tyr Leu Glu Asn Gly Tyr Asn Gln
385                 390                 395                 400

Asn Tyr Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
            420                 425                 430

Glu Asn Gly Trp Ser Pro Thr Pro Arg Cys Ile Arg Val Ser Phe Thr
        435                 440                 445

Leu
```

<210> SEQ ID NO 5
<211> LENGTH: 3860
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 5

```
atgagactgc tggccaagat catctgcctg atgctgtggg ccatctgcgt ggccgaggac     60

tgcaacgagc tgccccccag aagaaacacc gagatcctga ccggctcttg gagcgaccag    120

acctaccctg agggcaccca ggccatctac aagtgcagac ccggctaccg gtccctgggc    180

aacatcatca tggtgtgcag aaagggcgag tgggtggccc tgaacccccct gagaaagtgc    240

cagaagaggc cctgcggaca ccccggcgat accccttttg gcaccttcac actgaccggc    300

ggcaacgtgt tcgagtacgg cgtgaaggcc gtgtacacct gtaacgaggg ctaccagctg    360

ctgggcgaga tcaactacag agagtgcgac accgacggct ggaccaacga tatccccatc    420
```

-continued

```
tgcgaggtcg tgaagtgcct gcctgtgacc gccccagaga acggcaagat cgtgtccagc    480
gccatggaac ccgacagaga gtaccacttc ggccaggccg tcagattcgt gtgcaacagc    540
ggctacaaga tcgagggcga cgaggaaatg cactgcagcg acgacggctt ctggtccaaa    600
gaaaagccta agtgcgtgga aatcagctgc aagagccccg acgtgatcaa cggcagcccc    660
atcagccaga agatcatcta caaagagaac gagcggttcc agtacaagtg taacatgggc    720
tacgagtaca gcgagcgggg cgacgccgtg tgtacagaat ctggatggcg gcctctgccc    780
agctgcgagg aaaagagctg cgacaacccc tacatcccca acggcgacta cagccccctg    840
cggatcaagc acagaaccgg cgacgagatc acctaccagt gccggaacgg cttctacccc    900
gccaccagag gcaataccgc caagtgtacc agcaccggct ggatccctgc ccccagatgt    960
accctgaagc cctgcgacta ccctgacatc aagcacggcg gcctgtacca cgagaacatg   1020
cggaggccct acttccctgt ggccgtgggc aagtactaca gctactactg cgacgagcac   1080
ttcgagacac ccagcggcag ctactgggac cacatccact gtacccagga cggctggtcc   1140
cctgccgtgc cctgcctgag gaagtgctac ttcccctacc tggaaaacgg ctacaaccag   1200
aactacggcc ggaagttcgt gcagggcaag agcatcgatg tggcctgcca ccctggatac   1260
gccctgccta aggcccagac caccgtgacc tgcatggaaa atggatggtc ccccaccccc   1320
cggtgcatca gagtcagtaa gtccttcact ctgtgaaact tgtttattgc agcttataat   1380
ggttacaaat aaagcaatag catcacaaat ttcacaaata aagcattttt ttcactgcat   1440
tctagttgtg gtttgtccaa actcatcaat gtatcttatt ctaattctct tccctttttag   1500
aaacctgcag caagagcagc atcgacatcg agaatggctt catcagcgag agccagtaca   1560
cctacgccct gaaagagaag gccaagtacc agtgcaagct gggctacgtg accgccgacg   1620
gcgagacaag cggcagcatc acctgtggca aggatgggtg gagcgcccag cccacctgta   1680
tcaagtcctg cgacatccct gtgttcatga atgcccggac caagaacgac ttcacctggt   1740
tcaagctgaa cgacacactg gactacgagt gccacgacgg ctacgagagc aacaccggca   1800
gcaccacagg cagcatcgtg tgtggctaca acgggtggag tgacctgccc atctgttacg   1860
agcgcgagtg cgagctgcct aagatcgacg tgcacctggt gcccgaccgg aagaaagacc   1920
agtacaaagt gggcgaggtg ctgaagttct cctgcaagcc cggcttcacc atcgtgggcc   1980
ccaatagcgt gcagtgctac cactttggcc tgtcccccga tctgcctatc tgcaaagaac   2040
aggtgcagag ctgcggccct ccacccgagc tgctgaacgg caatgtgaaa gaaaagacca   2100
aagaggaata cggccactcc gaggtggtgg aatattactg caaccccccgg ttcctgatga   2160
agggccccaa caagattcag tgtgtggacg gcgagtggac caccctgccc gtgtgtatcg   2220
tggaagagtc tacctgcgga gacatccccg agctggaaca cggatgggcc cagctgagca   2280
gcccccctta ctactacggc gacagcgtgg aattcaactg ctccgagagc tttaccatga   2340
tcggccaccg gtccatcaca tgcatccacg gcgtgtggac acagctgcca cagtgcgtgg   2400
ccatcgacaa gctgaagaag tgcaagtcca gcaacctgat catcctggaa gaacacctga   2460
agaacaagaa agagttcgac cacaacagca acatccggta cagatgccgg ggcaaagagg   2520
gatggatcca caccgtgtgc atcaatggca gatgggaccc cgaagtgaac tgcagcatgg   2580
cccagatcca gctgtgcccc ccacctcccc agatccccaa cagccacaac atgaccacca   2640
ccctgaacta ccgggatggc gagaaggtgt ccgtgctgtg ccaggaaaac tacctgatcc   2700
aggaaggcga agagattacc tgcaaggacg gccggtggca gagcatcccc ctgtgtgtgg   2760
```

-continued

```
aaaagatccc ctgcagccag cccccccaga tcgagcacgg caccatcaac agcagcagaa   2820

gcagccagga atcctacgcc cacggcacaa agctgagcta cacatgcgag ggcggcttcc   2880

ggatctccga ggaaaacgag acaacctgct acatgggcaa gtggtcctcc ccacctcagt   2940

gcgagggact gccttgcaag tccccacccg agatctctca tggcgtggtg gcccacatga   3000

gcgacagcta ccagtacggc gaggaagtga cctacaagtg tttcgagggc ttcggcatcg   3060

acggccctgc cattgccaag tgcctgggag agaagtggtc ccaccctccc agctgcatca   3120

agaccgactg cctgagcctg cctagcttcg agaacgccat ccccatgggc gagaaaaagg   3180

acgtgtacaa ggccggcgaa caagtgacat acacctgtgc cacctactac aagatggacg   3240

gcgccagcaa cgtgacctgt attaacagcc ggtggaccgg caggcctacc tgcagagata   3300

cctcctgcgt gaaccccccc accgtgcaga acgcctacat cgtgtctcgg cagatgagca   3360

agtaccccag cggcgaacgc gtgcgctacc agtgtagaag cccctacgag atgttcggcg   3420

acgaagaagt gatgtgcctg aatggcaact ggaccgagcc ccctcagtgc aaggatagca   3480

ccggcaagtg tggccccccct cccccatcg ataacggcga catcaccagc ttccccctgt   3540

ccgtgtatgc ccctgccagc tccgtggaat atcagtgcca gaacctgtac cagctggaag   3600

gcaacaagcg gatcacctgt cggaacggcc agtggagcga gcctcccaag tgtctgcacc   3660

cctgcgtgat ctccagagaa atcatggaaa actataatat cgccctgcgc tggaccgcca   3720

agcagaagct gtactctagg accggcgagt ctgtggaatt tgtgtgcaag cggggataca   3780

gactgagcag cagatcccac accctgagaa ccacctgttg ggacggcaag ctggaatacc   3840

ctacctgcgc caagagatga                                               3860
```

<210> SEQ ID NO 6
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Ile Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
    130                 135                 140

Lys Cys Leu Pro Val Thr Ala Pro Glu Asn Gly Lys Ile Val Ser Ser
145                 150                 155                 160
```

```
Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
    210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285

Glu Ile Thr Tyr Gln Cys Arg Asn Gly Phe Tyr Pro Ala Thr Arg Gly
    290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
            340                 345                 350

Tyr Ser Tyr Tyr Cys Asp Glu His Phe Glu Thr Pro Ser Gly Ser Tyr
        355                 360                 365

Trp Asp His Ile His Cys Thr Gln Asp Gly Trp Ser Pro Ala Val Pro
    370                 375                 380

Cys Leu Arg Lys Cys Tyr Phe Pro Tyr Leu Glu Asn Gly Tyr Asn Gln
385                 390                 395                 400

Asn Tyr Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
            420                 425                 430

Glu Asn Gly Trp Ser Pro Thr Pro Arg Cys Ile Arg Val Ser Lys Ser
        435                 440                 445

Phe Thr Leu
    450


<210> SEQ ID NO 7
<211> LENGTH: 304
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

cgttacataa cttacggtaa atggcccgcc tggctgaccg cccaacgacc cccgcccatt     60

gacgtcaata atgacgtatg ttcccatagt aacgccaata gggactttcc attgacgtca    120

atgggtggag tatttacggt aaactgccca cttggcagta catcaagtgt atcatatgcc    180

aagtacgccc cctattgacg tcaatgacgg taaatggccc gcctggcatt atgcccagta    240

catgacctta tgggactttc ctacttggca gtacatctac gtattagtca tcgctattac    300

catg                                                                 304
```

<210> SEQ ID NO 8
<211> LENGTH: 454
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 8
cgttacataa cttacggtaa atggcccgcc tggctgaccg cccaacgacc cccgcccatt 60
gacgtcaata atgacgtatg ttcccatagt aacgccaata gggactttcc attgacgtca 120
atgggtggag tatttacggt aaactgccca cttggcagta catcaagtgt atcatatgcc 180
aagtacgccc cctattgacg tcaatgacgg taaatggccc gcctggcatt atgcccagta 240
catgacctta tgggactttc ctacttggca gtacatctac gtattagtca tcgctattac 300
catgctcgag ctagggtgat gaaattccca agcaacacca tccttttcaa gtgacggcgg 360
ctcagcactc acgtgggcag tgccagcctc taagagtggg caggggcact ggccacagag 420
tcccagggag tcccaccagc ctagtcgcca gacc 454

<210> SEQ ID NO 9
<211> LENGTH: 415
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 9
cgttacataa cttacggtaa atggcccgcc tggctgaccg cccaacgacc cccgcccatt 60
gacgtcaata atgacgtatg ttcccatagt aacgccaata gggactttcc attgacgtca 120
atgggtggag tatttacggt aaactgccca cttggcagta catcaagtgt atcatatgcc 180
aagtacgccc cctattgacg tcaatgacgg taaatggccc gcctggcatt atgcccagta 240
catgacctta tgggactttc ctacttggca gtacatctac gtattagtca tcgctattac 300
catgctcgag caaataaagc caagcatcag ggggatctga gagctgaaag caacttctgt 360
tccccctccc tcagctgaag ggtggggaa gggctcccaa agccataact ccttt 415

<210> SEQ ID NO 10
<211> LENGTH: 419
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 10
cgttacataa cttacggtaa atggcccgcc tggctgaccg cccaacgacc cccgcccatt 60
gacgtcaata atgacgtatg ttcccatagt aacgccaata gggactttcc attgacgtca 120
atgggtggac tatttacggt aaactgccca cttggcagta catcaagtgt atcatatgcc 180
aagtacgccc cctattgacg tcaatgacgg taaatggccc gcctggcatt atgcccagta 240
catgacctta tgggactttc ctacttggca gtacatctac gtattagtca tcgctattac 300
catgctcgag gaaggattga ggtctctgga aaacagccaa acaactgtta tgggaacagc 360
aagcccaaat aaagccaagc atcaggggga tctgagagct gaaagcaact tctgttccc 419

<210> SEQ ID NO 11
<211> LENGTH: 723
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
ctctgaagca acttactgat gggccctgcc agccaatcac agccagaata acgtatgatg     60

tcaccagcag ccaatcagag ctcctcgtca gcatatgcag aattctgtca ttttactagg    120

gtgatgaaat tcccaagcaa caccatcctt ttcagataag ggcactgagg ctgagagagg    180

agctgaaacc tacccggggt caccacacac aggtggcaag gctgggacca gaaaccagga    240

ctgttgactg cagcccggta ttcattcttt ccatagccca cagggctgtc aaagacccca    300

gggcctagtc agaggctcct ccttcctgga gagttcctgg cacagaagtt gaagctcagc    360

acagccccct aacccccaac tctctctgca aggcctcagg ggtcagaaca ctggtggagc    420

agatccttta gcctctggat tttagggcca tggtagaggg ggtgttgccc taaattccag    480

ccctggtctc agcccaacac cctccaagaa gaaattagag gggccatggc caggctgtgc    540

tagccgttgc ttctgagcag attacaagaa gggactaaga caaggactcc tttgtggagg    600

tcctggctta gggagtcaag tgacggcggc tcagcactca cgtgggcagt gccagcctct    660

aagagtgggc aggggcactg gccacagagt cccagggagt cccaccagcc tagtcgccag    720

acc                                                                  723
```

<210> SEQ ID NO 12
<211> LENGTH: 939
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
ctagttatta atagtaatca attacggggt cattagttca tagcccatat atggagttcc     60

gcgttacata acttacggta aatggcccgc ctggctgacc gcccaacgac ccccgcccat    120

tgacgtcaat aatgacgtat gttcccatag taacgccaat agggactttc cattgacgtc    180

aatgggtgga ctatttacgg taaactgccc acttggcagt acatcaagtg tatcatatgc    240

caagtacgcc ccctattgac gtcaatgacg gtaaatggcc cgcctggcat tatgcccagt    300

acatgacctt atgggacttt cctacttggc agtacatcta cgtattagtc atcgctatta    360

ccatggtcga ggtgagcccc acgttctgct tcactctccc catctccccc ccctccccac    420

ccccaatttt gtatttattt atttttttaat tattttgtgc agcgatgggg gcgggggggg    480

gggggggcg cgcgccaggc ggggcggggc ggggcgaggg gcggggcggg gcgaggcgga    540

gaggtgcggc ggcagccaat cagagcggcg cgctccgaaa gtttcctttt atggcgaggc    600

ggcggcggcg gcggccctat aaaaagcgaa gcgcgcggcg ggcgggagtc gctgcgacgc    660

tgccttcgcc ccgtgccccg ctccgccgcc gcctcgcgcc gcccgccccg gctctgactg    720

accgcgttac tcccacaggt gagcgggcgg gacggccctt ctcctccggg ctgtaattag    780

cgcttggttt aatgacggct tgtttctttt ctgtggctgc gtgaaagcct tgaggggctc    840

cgggagctag agcctctgct aaccatgttc atgccttctt ctttttccta cagctcctgg    900

gcaacgtgct ggttattgtg ctgtctcatc attttggca                           939
```

<210> SEQ ID NO 13
<211> LENGTH: 1657
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 13
ccgcgttaca taacttacgg taaatggccc gcctggctga ccgcccaacg acccccgccc 60
attgacgtca ataatgacgt atgttcccat agtaacgcca atagggactt tccattgacg 120
tcaatgggtg gagtatttac ggtaaactgc ccacttggca gtacatcaag tgtatcatat 180
gccaagtacg ccccctattg acgtcaatga cggtaaatgg cccgcctggc attatgccca 240
gtacatgacc ttatgggact ttcctacttg gcagtacatc tacgtattag tcatcgctat 300
taccatggtc gaggtgagcc ccacgttctg cttcactctc cccatctccc ccccctcccc 360
acccccaatt ttgtatttat ttatttttta attattttgt gcagcgatgg gggcgggggg 420
gggggggggg cgcgcgccag gcggggcggg gcggggcgag gggcggggcg gggcgaggcg 480
gagaggtgcg gcggcagcca atcagagcgg cgcgctccga aagtttcctt ttatggcgag 540
gcggcggcgg cggcggccct ataaaaagcg aagcgcgcgg cgggcgggag tcgctgcgcg 600
ctgccttcgc cccgtgcccc gctccgccgc cgcctcgcgc cgcccgcccc ggctctgact 660
gaccgcgtta ctcccacagg tgagcgggcg ggacggccct tctcctccgg gctgtaatta 720
gcgcttggtt taatgacggc ttgtttcttt tctgtggctg cgtgaaagcc ttgaggggct 780
ccgggagggc cctttgtgcg gggggagcgg ctcggggggt gcgtgcgtgt gtgtgtgcgt 840
ggggagcgcc gcgtgcggct ccgcgctgcc cggcggctgt gagcgctgcg ggcgcggcgc 900
ggggctttgt gcgctccgca gtgtgcgcga ggggagcgcg gccgggggcg gtgccccgcg 960
gtgcgggggg ggctgcgagg ggaacaaagg ctgcgtgcgg ggtgtgtgcg tgggggggtg 1020
agcagggggt gtgggcgcgt cggtcgggct gcaacccccc ctgcaccccc ctccccgagt 1080
tgctgagcac ggcccggctt cgggtgcggg gctccgtacg gggcgtggcg cggggctcgc 1140
cgtgccgggc ggggggtggc ggcaggtggg ggtgccgggc ggggcggggc cgcctcgggc 1200
cggggagggc tcgggggagg ggcgcggcgg cccccggagc gccggcggct gtcgaggcgc 1260
ggcgagccgc agccattgcc ttttatggta atcgtgcgag agggcgcagg gacttccttt 1320
gtcccaaatc tgtgcggagc cgaaatctgg gaggcgccgc cgcaccccct ctagcgggcg 1380
cggggcgaag cggtgcggcg ccggcaggaa ggaaatgggc ggggagggcc ttcgtgcgtc 1440
gccgcgccgc cgtccccttc tccctctcca gcctcggggc tgtccgcggg gggacggctg 1500
ccttcggggg ggacggggca gggcggggtt cggcttctgg cgtgtgaccg gcggctctag 1560
agcctctgct aaccatgttc atgccttctt ctttttccta cagctcctgg gcaacgtgct 1620
ggttattgtg ctgtctcatc attttggcaa agaattc 1657

<210> SEQ ID NO 14
<211> LENGTH: 719
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 14
cgttacataa cttacggtaa atggcccgcc tggctgaccg cccaacgacc cccgcccatt 60

```
gacgtcaata atgacgtatg ttcccatagt aacgccaata gggactttcc attgacgtca    120

atgggtggag tatttacggt aaactgccca cttggcagta catcaagtgt atcatatgcc    180

aagtacgccc cctattgacg tcaatgacgg taaatggccc gcctggcatt atgcccagta    240

catgacctta tgggactttc ctacttggca gtacatctac gtattagtca tcgctattac    300

catggtcgag gtgagcccca cgttctgctt cactctcccc atctcccccc cctccccacc    360

cccaattttg tatttattta tttttaatt attttgtgca gcgatggggg cggggggggg     420

gggggggcgc gcgccaggcg gggcggggcg gggcgagggg cggggcgggg cgaggcggag    480

aggtgcggcg gcagccaatc agagcggcgc gctccgaaag tttcctttta tggcgaggcg    540

gcggcggcgg cggccctata aaaagcgaag cgcgcggcgg gcgggagtcg ctgcgcgctg    600

ccttcgcccc gtgccccgct ccgccgccgc ctcgcgccgc ccgccccggc tctgactgac    660

cgcgttactc ccacaggtga gcgggcggga cggcccttct cctccgggct gtaattagc     719
```

<210> SEQ ID NO 15
<211> LENGTH: 189
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 15

```
catttctggg cttgtggctt gtggttgatt ttttatttac tttgcaaaag tttctgatag     60

gcggagcatc tagtttcaac ttccttttgc agcaagttct ttcctgcact aatcacaatt    120

cttggaagag gagaactgga cgttgtgaac agagttagct ggtaattgtc ctcttaaaag    180

atccaaaaa                                                            189
```

<210> SEQ ID NO 16
<211> LENGTH: 144
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 16

```
ctagggtgat gaaattccca agcaacacca tccttttcaa gtgacggcgg ctcagcactc     60

acgtgggcag tgccagcctc taagagtggg caggggcact ggccacagag tcccagggag    120

tcccaccagc ctagtcgcca gacc                                           144
```

<210> SEQ ID NO 17
<211> LENGTH: 750
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 17

```
atactctcag agtgccaaac atataccaat ggacaagaag gtgaggcaga gagcagacag     60

gcattagtga caagcaaaga tatgcagaat ttcattctca gcaaatcaaa agtcctcaac    120

ctggttggaa gaatattggc actgaatggt atcaataagg ttgctagaga gggttagagg    180

tgcacaatgt gcttccataa cattttatac ttctccaatc ttagcactaa tcaaacatgg    240

ttgaatactt tgtttactat aactcttaca gagttataag atctgtgaag acagggacag    300
```

```
ggacaatacc catctctgtc tggttcatag gtggtatgta atagatattt ttaaaaataa    360

gtgagttaat gaatgagggt gagaatgaag gcacagaggt attaggggga ggtgggcccc    420

agagaatggt gccaaggtcc agtggggtga ctgggatcag ctcaggcctg acgctggcca    480

ctcccaccta gctcctttct ttctaatctg ttctcattct ccttgggaag gattgaggtc    540

tctggaaaac agccaaacaa ctgttatggg aacagcaagc ccaaataaag ccaagcatca    600

gggggatctg agagctgaaa gcaacttctg ttccccctcc ctcagctgaa ggggtgggga    660

agggctccca aagccataac tccttttaag ggatttagaa ggcataaaaa ggcccctggc    720

tgagaacttc cttcttcatt ctgcagttgg                                      750

<210> SEQ ID NO 18
<211> LENGTH: 142
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

ggccactccc tctctgcgcg ctcgctcgct cactgaggcc gggcgaccaa aggtcgcccg     60

acgcccgggc tttgcccggg cggcctcagt gagcgagcga gcgcgcagag agggagtggc    120

caactccatc actaggggtt cc                                              142

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

cgttacataa cttacggtaa atgg                                             24

<210> SEQ ID NO 20
<211> LENGTH: 1213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Asp Cys Asn Glu Leu Pro Pro Arg Arg Asn Thr Glu Ile Leu Thr
1               5                   10                  15

Gly Ser Trp Ser Asp Gln Thr Tyr Pro Glu Gly Thr Gln Ala Ile Tyr
            20                  25                  30

Lys Cys Arg Pro Gly Tyr Arg Ser Leu Gly Asn Ile Ile Met Val Cys
        35                  40                  45

Arg Lys Gly Glu Trp Val Ala Leu Asn Pro Leu Arg Lys Cys Gln Lys
    50                  55                  60

Arg Pro Cys Gly His Pro Gly Asp Thr Pro Phe Gly Thr Phe Thr Leu
65                  70                  75                  80

Thr Gly Gly Asn Val Phe Glu Tyr Gly Val Lys Ala Val Tyr Thr Cys
                85                  90                  95

Asn Glu Gly Tyr Gln Leu Leu Gly Glu Ile Asn Tyr Arg Glu Cys Asp
            100                 105                 110
```

-continued

```
Thr Asp Gly Trp Thr Asn Asp Ile Pro Ile Cys Glu Val Val Lys Cys
        115                 120                 125

Leu Pro Val Thr Ala Pro Glu Asn Gly Lys Ile Val Ser Ser Ala Met
    130                 135                 140

Glu Pro Asp Arg Glu Tyr His Phe Gly Gln Ala Val Arg Phe Val Cys
145                 150                 155                 160

Asn Ser Gly Tyr Lys Ile Glu Gly Asp Glu Glu Met His Cys Ser Asp
                165                 170                 175

Asp Gly Phe Trp Ser Lys Glu Lys Pro Lys Cys Val Glu Ile Ser Cys
            180                 185                 190

Lys Ser Pro Asp Val Ile Asn Gly Ser Pro Ile Ser Gln Lys Ile Ile
        195                 200                 205

Tyr Lys Glu Asn Glu Arg Phe Gln Tyr Lys Cys Asn Met Gly Tyr Glu
    210                 215                 220

Tyr Ser Glu Arg Gly Asp Ala Val Cys Thr Glu Ser Gly Trp Arg Pro
225                 230                 235                 240

Leu Pro Ser Cys Glu Glu Lys Ser Cys Asp Asn Pro Tyr Ile Pro Asn
                245                 250                 255

Gly Asp Tyr Ser Pro Leu Arg Ile Lys His Arg Thr Gly Asp Glu Ile
            260                 265                 270

Thr Tyr Gln Cys Arg Asn Gly Phe Tyr Pro Ala Thr Arg Gly Asn Thr
        275                 280                 285

Ala Lys Cys Thr Ser Thr Gly Trp Ile Pro Ala Pro Arg Cys Thr Leu
    290                 295                 300

Lys Pro Cys Asp Tyr Pro Asp Ile Lys His Gly Gly Leu Tyr His Glu
305                 310                 315                 320

Asn Met Arg Arg Pro Tyr Phe Pro Val Ala Val Gly Lys Tyr Tyr Ser
                325                 330                 335

Tyr Tyr Cys Asp Glu His Phe Glu Thr Pro Ser Gly Ser Tyr Trp Asp
            340                 345                 350

His Ile His Cys Thr Gln Asp Gly Trp Ser Pro Ala Val Pro Cys Leu
        355                 360                 365

Arg Lys Cys Tyr Phe Pro Tyr Leu Glu Asn Gly Tyr Asn Gln Asn Tyr
    370                 375                 380

Gly Arg Lys Phe Val Gln Gly Lys Ser Ile Asp Val Ala Cys His Pro
385                 390                 395                 400

Gly Tyr Ala Leu Pro Lys Ala Gln Thr Thr Val Thr Cys Met Glu Asn
                405                 410                 415

Gly Trp Ser Pro Thr Pro Arg Cys Ile Arg Val Lys Thr Cys Ser Lys
            420                 425                 430

Ser Ser Ile Asp Ile Glu Asn Gly Phe Ile Ser Glu Ser Gln Tyr Thr
        435                 440                 445

Tyr Ala Leu Lys Glu Lys Ala Lys Tyr Gln Cys Lys Leu Gly Tyr Val
    450                 455                 460

Thr Ala Asp Gly Glu Thr Ser Gly Ser Ile Thr Cys Gly Lys Asp Gly
465                 470                 475                 480

Trp Ser Ala Gln Pro Thr Cys Ile Lys Ser Cys Asp Ile Pro Val Phe
                485                 490                 495

Met Asn Ala Arg Thr Lys Asn Asp Phe Thr Trp Phe Lys Leu Asn Asp
            500                 505                 510

Thr Leu Asp Tyr Glu Cys His Asp Gly Tyr Glu Ser Asn Thr Gly Ser
        515                 520                 525

Thr Thr Gly Ser Ile Val Cys Gly Tyr Asn Gly Trp Ser Asp Leu Pro
```

-continued

```
    530                 535                 540

Ile Cys Tyr Glu Arg Glu Cys Glu Leu Pro Lys Ile Asp Val His Leu
545                 550                 555                 560

Val Pro Asp Arg Lys Lys Asp Gln Tyr Lys Val Gly Glu Val Leu Lys
                565                 570                 575

Phe Ser Cys Lys Pro Gly Phe Thr Ile Val Gly Pro Asn Ser Val Gln
            580                 585                 590

Cys Tyr His Phe Gly Leu Ser Pro Asp Leu Pro Ile Cys Lys Glu Gln
        595                 600                 605

Val Gln Ser Cys Gly Pro Pro Pro Glu Leu Leu Asn Gly Asn Val Lys
    610                 615                 620

Glu Lys Thr Lys Glu Glu Tyr Gly His Ser Glu Val Val Glu Tyr Tyr
625                 630                 635                 640

Cys Asn Pro Arg Phe Leu Met Lys Gly Pro Asn Lys Ile Gln Cys Val
                645                 650                 655

Asp Gly Glu Trp Thr Thr Leu Pro Val Cys Ile Val Glu Glu Ser Thr
            660                 665                 670

Cys Gly Asp Ile Pro Glu Leu Glu His Gly Trp Ala Gln Leu Ser Ser
        675                 680                 685

Pro Pro Tyr Tyr Tyr Gly Asp Ser Val Glu Phe Asn Cys Ser Glu Ser
    690                 695                 700

Phe Thr Met Ile Gly His Arg Ser Ile Thr Cys Ile His Gly Val Trp
705                 710                 715                 720

Thr Gln Leu Pro Gln Cys Val Ala Ile Asp Lys Leu Lys Lys Cys Lys
                725                 730                 735

Ser Ser Asn Leu Ile Ile Leu Glu Glu His Leu Lys Asn Lys Lys Glu
            740                 745                 750

Phe Asp His Asn Ser Asn Ile Arg Tyr Arg Cys Arg Gly Lys Glu Gly
        755                 760                 765

Trp Ile His Thr Val Cys Ile Asn Gly Arg Trp Asp Pro Glu Val Asn
    770                 775                 780

Cys Ser Met Ala Gln Ile Gln Leu Cys Pro Pro Pro Pro Gln Ile Pro
785                 790                 795                 800

Asn Ser His Asn Met Thr Thr Thr Leu Asn Tyr Arg Asp Gly Glu Lys
                805                 810                 815

Val Ser Val Leu Cys Gln Glu Asn Tyr Leu Ile Gln Glu Gly Glu Glu
            820                 825                 830

Ile Thr Cys Lys Asp Gly Arg Trp Gln Ser Ile Pro Leu Cys Val Glu
        835                 840                 845

Lys Ile Pro Cys Ser Gln Pro Pro Gln Ile Glu His Gly Thr Ile Asn
    850                 855                 860

Ser Ser Arg Ser Ser Gln Glu Ser Tyr Ala His Gly Thr Lys Leu Ser
865                 870                 875                 880

Tyr Thr Cys Glu Gly Gly Phe Arg Ile Ser Glu Glu Asn Glu Thr Thr
                885                 890                 895

Cys Tyr Met Gly Lys Trp Ser Ser Pro Pro Gln Cys Glu Gly Leu Pro
            900                 905                 910

Cys Lys Ser Pro Pro Glu Ile Ser His Gly Val Val Ala His Met Ser
        915                 920                 925

Asp Ser Tyr Gln Tyr Gly Glu Glu Val Thr Tyr Lys Cys Phe Glu Gly
    930                 935                 940

Phe Gly Ile Asp Gly Pro Ala Ile Ala Lys Cys Leu Gly Glu Lys Trp
945                 950                 955                 960
```

```
Ser His Pro Pro Ser Cys Ile Lys Thr Asp Cys Leu Ser Leu Pro Ser
                965                 970                 975

Phe Glu Asn Ala Ile Pro Met Gly Glu Lys Lys Asp Val Tyr Lys Ala
            980                 985                 990

Gly Glu Gln Val Thr Tyr Thr Cys  Ala Thr Tyr Tyr Lys  Met Asp Gly
        995                 1000                 1005

Ala Ser  Asn Val Thr Cys Ile  Asn Ser Arg Trp Thr  Gly Arg Pro
    1010                 1015                 1020

Thr Cys  Arg Asp Thr Ser Cys  Val Asn Pro Pro Thr  Val Gln Asn
    1025                 1030                 1035

Ala Tyr  Ile Val Ser Arg Gln  Met Ser Lys Tyr Pro  Ser Gly Glu
    1040                 1045                 1050

Arg Val  Arg Tyr Gln Cys Arg  Ser Pro Tyr Glu Met  Phe Gly Asp
    1055                 1060                 1065

Glu Glu  Val Met Cys Leu Asn  Gly Asn Trp Thr Glu  Pro Pro Gln
    1070                 1075                 1080

Cys Lys  Asp Ser Thr Gly Lys  Cys Gly Pro Pro Pro  Pro Ile Asp
    1085                 1090                 1095

Asn Gly  Asp Ile Thr Ser Phe  Pro Leu Ser Val Tyr  Ala Pro Ala
    1100                 1105                 1110

Ser Ser  Val Glu Tyr Gln Cys  Gln Asn Leu Tyr Gln  Leu Glu Gly
    1115                 1120                 1125

Asn Lys  Arg Ile Thr Cys Arg  Asn Gly Gln Trp Ser  Glu Pro Pro
    1130                 1135                 1140

Lys Cys  Leu His Pro Cys Val  Ile Ser Arg Glu Ile  Met Glu Asn
    1145                 1150                 1155

Tyr Asn  Ile Ala Leu Arg Trp  Thr Ala Lys Gln Lys  Leu Tyr Ser
    1160                 1165                 1170

Arg Thr  Gly Glu Ser Val Glu  Phe Val Cys Lys Arg  Gly Tyr Arg
    1175                 1180                 1185

Leu Ser  Ser Arg Ser His Thr  Leu Arg Thr Thr Cys  Trp Asp Gly
    1190                 1195                 1200

Lys Leu  Glu Tyr Pro Thr Cys  Ala Lys Arg
    1205                 1210


<210> SEQ ID NO 21
<211> LENGTH: 431
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Asp Cys Asn Glu Leu Pro Pro Arg Arg Asn Thr Glu Ile Leu Thr
1               5                   10                  15

Gly Ser Trp Ser Asp Gln Thr Tyr Pro Glu Gly Thr Gln Ala Ile Tyr
            20                  25                  30

Lys Cys Arg Pro Gly Tyr Arg Ser Leu Gly Asn Ile Ile Met Val Cys
        35                  40                  45

Arg Lys Gly Glu Trp Val Ala Leu Asn Pro Leu Arg Lys Cys Gln Lys
    50                  55                  60

Arg Pro Cys Gly His Pro Gly Asp Thr Pro Phe Gly Thr Phe Thr Leu
65                  70                  75                  80

Thr Gly Gly Asn Val Phe Glu Tyr Gly Val Lys Ala Val Tyr Thr Cys
```

-continued

```
                85                  90                  95

Asn Glu Gly Tyr Gln Leu Leu Gly Glu Ile Asn Tyr Arg Glu Cys Asp
            100                 105                 110

Thr Asp Gly Trp Thr Asn Asp Ile Pro Ile Cys Glu Val Val Lys Cys
        115                 120                 125

Leu Pro Val Thr Ala Pro Glu Asn Gly Lys Ile Val Ser Ser Ala Met
    130                 135                 140

Glu Pro Asp Arg Glu Tyr His Phe Gly Gln Ala Val Arg Phe Val Cys
145                 150                 155                 160

Asn Ser Gly Tyr Lys Ile Glu Gly Asp Glu Glu Met His Cys Ser Asp
                165                 170                 175

Asp Gly Phe Trp Ser Lys Glu Lys Pro Lys Cys Val Glu Ile Ser Cys
            180                 185                 190

Lys Ser Pro Asp Val Ile Asn Gly Ser Pro Ile Ser Gln Lys Ile Ile
        195                 200                 205

Tyr Lys Glu Asn Glu Arg Phe Gln Tyr Lys Cys Asn Met Gly Tyr Glu
    210                 215                 220

Tyr Ser Glu Arg Gly Asp Ala Val Cys Thr Glu Ser Gly Trp Arg Pro
225                 230                 235                 240

Leu Pro Ser Cys Glu Glu Lys Ser Cys Asp Asn Pro Tyr Ile Pro Asn
                245                 250                 255

Gly Asp Tyr Ser Pro Leu Arg Ile Lys His Arg Thr Gly Asp Glu Ile
            260                 265                 270

Thr Tyr Gln Cys Arg Asn Gly Phe Tyr Pro Ala Thr Arg Gly Asn Thr
        275                 280                 285

Ala Lys Cys Thr Ser Thr Gly Trp Ile Pro Ala Pro Arg Cys Thr Leu
    290                 295                 300

Lys Pro Cys Asp Tyr Pro Asp Ile Lys His Gly Gly Leu Tyr His Glu
305                 310                 315                 320

Asn Met Arg Arg Pro Tyr Phe Pro Val Ala Val Gly Lys Tyr Tyr Ser
                325                 330                 335

Tyr Tyr Cys Asp Glu His Phe Glu Thr Pro Ser Gly Ser Tyr Trp Asp
            340                 345                 350

His Ile His Cys Thr Gln Asp Gly Trp Ser Pro Ala Val Pro Cys Leu
        355                 360                 365

Arg Lys Cys Tyr Phe Pro Tyr Leu Glu Asn Gly Tyr Asn Gln Asn Tyr
    370                 375                 380

Gly Arg Lys Phe Val Gln Gly Lys Ser Ile Asp Val Ala Cys His Pro
385                 390                 395                 400

Gly Tyr Ala Leu Pro Lys Ala Gln Thr Thr Val Thr Cys Met Glu Asn
                405                 410                 415

Gly Trp Ser Pro Thr Pro Arg Cys Ile Arg Val Ser Phe Thr Leu
            420                 425                 430


<210> SEQ ID NO 22
<211> LENGTH: 433
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Asp Cys Asn Glu Leu Pro Pro Arg Arg Asn Thr Glu Ile Leu Thr
1               5                   10                  15
```

-continued

```
Gly Ser Trp Ser Asp Gln Thr Tyr Pro Glu Gly Thr Gln Ala Ile Tyr
            20                  25                  30

Lys Cys Arg Pro Gly Tyr Arg Ser Leu Gly Asn Ile Ile Met Val Cys
        35                  40                  45

Arg Lys Gly Glu Trp Val Ala Leu Asn Pro Leu Arg Lys Cys Gln Lys
    50                  55                  60

Arg Pro Cys Gly His Pro Gly Asp Thr Pro Phe Gly Thr Phe Thr Leu
65                  70                  75                  80

Thr Gly Gly Asn Val Phe Glu Tyr Gly Val Lys Ala Val Tyr Thr Cys
                85                  90                  95

Asn Glu Gly Tyr Gln Leu Leu Gly Glu Ile Asn Tyr Arg Glu Cys Asp
            100                 105                 110

Thr Asp Gly Trp Thr Asn Asp Ile Pro Ile Cys Glu Val Val Lys Cys
        115                 120                 125

Leu Pro Val Thr Ala Pro Glu Asn Gly Lys Ile Val Ser Ser Ala Met
    130                 135                 140

Glu Pro Asp Arg Glu Tyr His Phe Gly Gln Ala Val Arg Phe Val Cys
145                 150                 155                 160

Asn Ser Gly Tyr Lys Ile Glu Gly Asp Glu Glu Met His Cys Ser Asp
                165                 170                 175

Asp Gly Phe Trp Ser Lys Glu Lys Pro Lys Cys Val Glu Ile Ser Cys
            180                 185                 190

Lys Ser Pro Asp Val Ile Asn Gly Ser Pro Ile Ser Gln Lys Ile Ile
        195                 200                 205

Tyr Lys Glu Asn Glu Arg Phe Gln Tyr Lys Cys Asn Met Gly Tyr Glu
    210                 215                 220

Tyr Ser Glu Arg Gly Asp Ala Val Cys Thr Glu Ser Gly Trp Arg Pro
225                 230                 235                 240

Leu Pro Ser Cys Glu Glu Lys Ser Cys Asp Asn Pro Tyr Ile Pro Asn
                245                 250                 255

Gly Asp Tyr Ser Pro Leu Arg Ile Lys His Arg Thr Gly Asp Glu Ile
            260                 265                 270

Thr Tyr Gln Cys Arg Asn Gly Phe Tyr Pro Ala Thr Arg Gly Asn Thr
        275                 280                 285

Ala Lys Cys Thr Ser Thr Gly Trp Ile Pro Ala Pro Arg Cys Thr Leu
    290                 295                 300

Lys Pro Cys Asp Tyr Pro Asp Ile Lys His Gly Gly Leu Tyr His Glu
305                 310                 315                 320

Asn Met Arg Arg Pro Tyr Phe Pro Val Ala Val Gly Lys Tyr Tyr Ser
                325                 330                 335

Tyr Tyr Cys Asp Glu His Phe Glu Thr Pro Ser Gly Ser Tyr Trp Asp
            340                 345                 350

His Ile His Cys Thr Gln Asp Gly Trp Ser Pro Ala Val Pro Cys Leu
        355                 360                 365

Arg Lys Cys Tyr Phe Pro Tyr Leu Glu Asn Gly Tyr Asn Gln Asn Tyr
    370                 375                 380

Gly Arg Lys Phe Val Gln Gly Lys Ser Ile Asp Val Ala Cys His Pro
385                 390                 395                 400

Gly Tyr Ala Leu Pro Lys Ala Gln Thr Thr Val Thr Cys Met Glu Asn
                405                 410                 415

Gly Trp Ser Pro Thr Pro Arg Cys Ile Arg Val Ser Lys Ser Phe Thr
            420                 425                 430

Leu
```

<210> SEQ ID NO 23
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 23

Met Arg Leu Leu Ala Lys Ile Ile Cys Leu Met Leu Trp Ala Ile Cys
1 5 10 15

Val Ala

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 24

Cys Ile Arg Val Ser Phe Thr Leu
1 5

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 25

Cys Ile Arg Val Ser Lys Ser Phe Thr Leu
1 5 10

<210> SEQ ID NO 26
<211> LENGTH: 122
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 26
aacttgttta ttgcagctta taatggttac aaataaagca atagcatcac aaatttcaca 60
aataaagcat ttttttcact gcattctagt tgtggtttgt ccaaactcat caatgtatct 120
ta 122

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 27
caaataaagc caagcatcag gg 22

<210> SEQ ID NO 28
<211> LENGTH: 49
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 28
cggcaataaa aagacagaat aaaacgcacg ggtgttgggt cgtttgttc 49

<210> SEQ ID NO 29
<211> LENGTH: 208
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
ctgtgccttc tagttgccag ccatctgttg tttgcccctc ccccgtgcct tccttgaccc 60
tggaaggtgc cactcccact gtcctttcct aataaaatga ggaaattgca tcgcattgtc 120
tgagtaggtg tcattctatt ctggggggtg gggtggggca ggacagcaag ggggaggatt 180
gggaagacaa tagcaggcat gctgggga 208

<210> SEQ ID NO 30
<211> LENGTH: 374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
atggaaaatg gatggtcccc caccccccgg tgcatcagag tcagtaagta cactactctg 60
aaatcctagg gccgcagcgg ccgtaatcat ctgctcttca atctttccca gaagctttac 120
cctctgaaac ttgtttattg cagcttataa tggttacaaa taaagcaata gcatcacaaa 180
tttcacaaat aaagcatttt tttcactgca ttctagttgt ggtttgtcca aactcatcaa 240
tgtatcttag gcccgcatgg cctctttttc ttattctctt ccctttttaga aaaacctgca 300 gcaagagcag catcgacatc gagaatggct tcatcagcga gagccagtac acctacgccc 360
tgaaagagaa ggcc 374

<210> SEQ ID NO 31
<211> LENGTH: 284
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
atggaaaatg gatggtcccc caccccccgg tgcatcagag tcagttttac cctctgaaac 60
ttgtttattg cagcttataa tggttacaaa taaagcaata gcatcacaaa tttcacaaat 120
aaagcatttt tttcactgca ttctagttgt ggtttgtcca aactcatcaa tgtatcttat 180
tctaattctc ttccctttta gaaacctgca gcaagagcag catcgacatc gagaatggct 240
tcatcagcga gagccagtac acctacgccc tgaaagagaa ggcc 284

<210> SEQ ID NO 32
<211> LENGTH: 290
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32
atggaaaatg gatggtcccc caccccccgg tgcatcagag tcagtaagtc cttcactctg 60
tgaaacttgt ttattgcagc ttataatggt tacaaataaa gcaatagcat cacaaatttc 120
acaaataaag catttttttc actgcattct agttgtggtt tgtccaaact catcaatgta 180
tcttattcta attctcttcc cttttagaaa cctgcagcaa gagcagcatc gacatcgaga 240
atggcttcat cagcgagagc cagtacacct acgccctgaa agagaaggcc 290

<210> SEQ ID NO 33
<211> LENGTH: 290
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33
atggaaaatg gatggtcccc caccccccgg tgcatcagag tcagtgagtc cttcactctg 60
tgaaacttgt ttattgcagc ttataatggt tacaaataaa gcaatagcat cacaaatttc 120
acaaataaag catttttttc actgcattct agttgtggtt tgtccaaact catcaatgta 180
tcttattcta attctcttcc cttttagaaa cctgcagcaa gagcagcatc gacatcgaga 240
atggcttcat cagcgagagc cagtacacct acgccctgaa agagaaggcc 290

<210> SEQ ID NO 34
<211> LENGTH: 3944
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34
atgagactgc tggccaagat catctgcctg atgctgtggg ccatctgcgt ggccgaggac 60
tgcaacgagc tgccccccag aagaaacacc gagatcctga ccggctcttg gagcgaccag 120
acctaccctg agggcaccca ggccatctac aagtgcagac ccggctaccg gtccctgggc 180
aacatcatca tggtgtgcag aaagggcgag tgggtggccc tgaacccccct gagaaagtgc 240 cagaagaggc cctgcggaca ccccggcgat accccttttg gcaccttcac actgaccggc 300
ggcaacgtgt tcgagtacgg cgtgaaggcc gtgtacacct gtaacgaggg ctaccagctg 360
ctgggcgaga tcaactacag agagtgcgac accgacggct ggaccaacga tatccccatc 420
tgcgaggtcg tgaagtgcct gcctgtgacc gccccagaga acggcaagat cgtgtccagc 480
gccatggaac ccgacagaga gtaccacttc ggccaggccg tcagattcgt gtgcaacagc 540
ggctacaaga tcgagggcga cgaggaaatg cactgcagcg acgacggctt ctggtccaaa 600
gaaaagccta agtgcgtgga aatcagctgc aagagccccg acgtgatcaa cggcagcccc 660
atcagccaga agatcatcta caaagagaac gagcggttcc agtacaagtg taacatgggc 720
tacgagtaca gcgagcgggg cgacgccgtg tgtacagaat ctggatggcg gcctctgccc 780
agctgcgagg aaaagagctg cgacaacccc tacatcccca acggcgacta cagccccctg 840
cggatcaagc acagaaccgg cgacgagatc acctaccagt gccggaacgg cttctacccc 900
gccaccagag gcaataccgc caagtgtacc agcaccggct ggatccctgc ccccagatgt 960

```
accctgaagc cctgcgacta ccctgacatc aagcacggcg gcctgtacca cgagaacatg   1020
cggaggccct acttccctgt ggccgtgggc aagtactaca gctactactg cgacgagcac   1080
ttcgagacac ccagcggcag ctactgggac cacatccact gtacccagga cggctggtcc   1140
cctgccgtgc cctgcctgag gaagtgctac ttcccctacc tggaaaacgg ctacaaccag   1200
aactacggcc ggaagttcgt gcagggcaag agcatcgatg tggcctgcca ccctggatac   1260
gccctgccta aggcccagac caccgtgacc tgcatggaaa atggatggtc ccccaccccc   1320
cggtgcatca gagtcagtaa gtacactact ctgaaatcct agggccgcag cggccgtaat   1380
catctgctct tcaatctttc ccagaagctt taccctctga aacttgttta ttgcagctta   1440
taatggttac aaataaagca atagcatcac aaatttcaca aataaagcat ttttttcact   1500
gcattctagt tgtggtttgt ccaaactcat caatgtatct taggcccgca tggcctcttt   1560
ttcttattct cttccctttt agaaaaacct gcagcaagag cagcatcgac atcgagaatg   1620
gcttcatcag cgagagccag tacacctacg ccctgaaaga gaaggccaag taccagtgca   1680
agctgggcta cgtgaccgcc gacggcgaga caagcggcag catcacctgt ggcaaggatg   1740
ggtggagcgc ccagcccacc tgtatcaagt cctgcgacat ccctgtgttc atgaatgccc   1800
ggaccaagaa cgacttcacc tggttcaagc tgaacgacac actggactac gagtgccacg   1860
acggctacga gagcaacacc ggcagcacca caggcagcat cgtgtgtggc tacaacgggt   1920
ggagtgacct gcccatctgt tacgagcgcg agtgcgagct gcctaagatc gacgtgcacc   1980
tggtgcccga ccggaagaaa gaccagtaca aagtgggcga ggtgctgaag ttctcctgca   2040
agcccggctt caccatcgtg ggccccaata gcgtgcagtg ctaccacttt ggcctgtccc   2100
ccgatctgcc tatctgcaaa gaacaggtgc agagctgcgg ccctccaccc gagctgctga   2160
acggcaatgt gaaagaaaag accaaagagg aatacggcca ctccgaggtg gtggaatatt   2220
actgcaaccc ccggttcctg atgaagggcc ccaacaagat tcagtgtgtg gacggcgagt   2280
ggaccaccct gcccgtgtgt atcgtggaag agtctacctg cggagacatc cccgagctgg   2340
aacacggatg ggcccagctg agcagccccc cttactacta cggcgacagc gtggaattca   2400
actgctccga gagctttacc atgatcggcc accggtccat cacatgcatc cacggcgtgt   2460
ggacacagct gccacagtgc gtggccatcg acaagctgaa gaagtgcaag tccagcaacc   2520
tgatcatcct ggaagaacac ctgaagaaca agaaagagtt cgaccacaac agcaacatcc   2580
ggtacagatg ccggggcaaa gagggatgga tccacaccgt gtgcatcaat ggcagatggg   2640
accccgaagt gaactgcagc atggcccaga tccagctgtg ccccccacct ccccagatcc   2700
ccaacagcca caacatgacc accaccctga actaccggga tggcgagaag gtgtccgtgc   2760
tgtgccagga aaactacctg atccaggaag gcgaagagat tacctgcaag gacggccggt   2820
ggcagagcat ccccctgtgt gtggaaaaga tcccctgcag ccagcccccc cagatcgagc   2880
acggcaccat caacagcagc agaagcagcc aggaatccta cgcccacggc acaaagctga   2940
gctacacatg cgagggcggc ttccggatct ccgaggaaaa cgagacaacc tgctacatgg   3000
gcaagtggtc ctccccacct cagtgcgagg gactgccttg caagtcccca cccgagatct   3060
ctcatggcgt ggtggcccac atgagcgaca gctaccagta cggcgaggaa gtgacctaca   3120
agtgtttcga gggcttcggc atcgacggcc ctgccattgc caagtgcctg ggagagaagt   3180
ggtcccaccc tcccagctgc atcaagaccg actgcctgag cctgcctagc ttcgagaacg   3240
ccatccccat gggcgagaaa aaggacgtgt acaaggccgg cgaacaagtg acatacacct   3300
```

gtgccaccta ctacaagatg gacggcgcca gcaacgtgac ctgtattaac agccggtgga 3360
ccggcaggcc tacctgcaga gatacctcct gcgtgaaccc ccccaccgtg cagaacgcct 3420
acatcgtgtc tcggcagatg agcaagtacc ccagcggcga acgcgtgcgc taccagtgta 3480 gaagcccccta cgagatgttc ggcgacgaag aagtgatgtg cctgaatggc aactggaccg 3540
agccccctca gtgcaaggat agcaccggca agtgtggccc ccctcccccc atcgataacg 3600
gcgacatcac cagcttcccc ctgtccgtgt atgcccctgc cagctccgtg gaatatcagt 3660
gccagaacct gtaccagctg gaaggcaaca agcggatcac ctgtcggaac ggccagtgga 3720
gcgagcctcc caagtgtctg cacccctgcg tgatctccag agaaatcatg gaaaactata 3780
atatcgccct gcgctggacc gccaagcaga agctgtactc taggaccggc gagtctgtgg 3840
aatttgtgtg caagcgggga tacagactga gcagcagatc ccacaccctg agaaccacct 3900
gttgggacgg caagctggaa taccctacct gcgccaagag atga 3944

<210> SEQ ID NO 35
<211> LENGTH: 3854
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 35
atgagactgc tggccaagat catctgcctg atgctgtggg ccatctgcgt ggccgaggac 60
tgcaacgagc tgcccccccag aagaaacacc gagatcctga ccggctcttg gagcgaccag 120
acctaccctg agggcaccca ggccatctac aagtgcagac ccggctaccg gtccctgggc 180
aacatcatca tggtgtgcag aaagggcgag tgggtggccc tgaacccccct gagaaagtgc 240 cagaagaggc cctgcggaca ccccggcgat accccttttg gcaccttcac actgaccggc 300
ggcaacgtgt tcgagtacgg cgtgaaggcc gtgtacacct gtaacgaggg ctaccagctg 360
ctgggcgaga tcaactacag agagtgcgac accgacggct ggaccaacga tatccccatc 420
tgcgaggtcg tgaagtgcct gcctgtgacc gccccagaga acggcaagat cgtgtccagc 480
gccatggaac ccgacagaga gtaccacttc ggccaggccg tcagattcgt gtgcaacagc 540
ggctacaaga tcgagggcga cgaggaaatg cactgcagcg acgacggctt ctggtccaaa 600
gaaaagccta agtgcgtgga aatcagctgc aagagccccg acgtgatcaa cggcagcccc 660
atcagccaga agatcatcta caaagagaac gagcggttcc agtacaagtg taacatgggc 720
tacgagtaca gcgagcgggg cgacgccgtg tgtacagaat ctggatggcg gcctctgccc 780
agctgcgagg aaaagagctg cgacaacccc tacatcccca acggcgacta cagccccctg 840
cggatcaagc acagaaccgg cgacgagatc acctaccagt gccggaacgg cttctacccc 900
gccaccagag gcaataccgc caagtgtacc agcaccggct ggatccctgc ccccagatgt 960
accctgaagc cctgcgacta ccctgacatc aagcacggcg gcctgtacca cgagaacatg 1020
cggaggccct acttccctgt ggccgtgggc aagtactaca gctactactg cgacgagcac 1080
ttcgagacac ccagcggcag ctactgggac cacatccact gtacccagga cggctggtcc 1140
cctgccgtgc cctgcctgag gaagtgctac ttcccctacc tggaaaacgg ctacaaccag 1200
aactacggcc ggaagttcgt gcagggcaag agcatcgatg tggcctgcca ccctggatac 1260
gccctgccta aggcccagac caccgtgacc tgcatggaaa atggatggtc ccccaccccc 1320
cggtgcatca gagtcagttt taccctctga aacttgttta ttgcagctta taatggttac 1380

-continued

```
aaataaagca atagcatcac aaatttcaca aataaagcat ttttttcact gcattctagt   1440
tgtggtttgt ccaaactcat caatgtatct tattctaatt ctcttccctt ttagaaacct   1500
gcagcaagag cagcatcgac atcgagaatg gcttcatcag cgagagccag tacacctacg   1560
ccctgaaaga gaaggccaag taccagtgca agctgggcta cgtgaccgcc gacggcgaga   1620
caagcggcag catcacctgt ggcaaggatg ggtggagcgc ccagcccacc tgtatcaagt   1680
cctgcgacat ccctgtgttc atgaatgccc ggaccaagaa cgacttcacc tggttcaagc   1740
tgaacgacac actggactac gagtgccacg acggctacga gagcaacacc ggcagcacca   1800
caggcagcat cgtgtgtggc tacaacgggt ggagtgacct gcccatctgt tacgagcgcg   1860
agtgcgagct gcctaagatc gacgtgcacc tggtgcccga ccggaagaaa gaccagtaca   1920
aagtgggcga ggtgctgaag ttctcctgca agcccggctt caccatcgtg ggccccaata   1980
gcgtgcagtg ctaccacttt ggcctgtccc ccgatctgcc tatctgcaaa gaacaggtgc   2040
agagctgcgg ccctccaccc gagctgctga acggcaatgt gaaagaaaag accaaagagg   2100
aatacggcca ctccgaggtg gtggaatatt actgcaaccc ccggttcctg atgaagggcc   2160
ccaacaagat tcagtgtgtg gacggcgagt ggaccaccct gcccgtgtgt atcgtggaag   2220
agtctacctg cggagacatc cccgagctgg aacacggatg ggcccagctg agcagccccc   2280
cttactacta cggcgacagc gtggaattca actgctccga gagctttacc atgatcggcc   2340
accggtccat cacatgcatc cacggcgtgt ggacacagct gccacagtgc gtggccatcg   2400
acaagctgaa gaagtgcaag tccagcaacc tgatcatcct ggaagaacac ctgaagaaca   2460
agaaagagtt cgaccacaac agcaacatcc ggtacagatg ccggggcaaa gagggatgga   2520
tccacaccgt gtgcatcaat ggcagatggg accccgaagt gaactgcagc atggcccaga   2580
tccagctgtg ccccccacct ccccagatcc ccaacagcca caacatgacc accaccctga   2640
actaccggga tggcgagaag gtgtccgtgc tgtgccagga aaactacctg atccaggaag   2700
gcgaagagat tacctgcaag gacggccggt ggcagagcat ccccctgtgt gtggaaaaga   2760
tcccctgcag ccagcccccc cagatcgagc acggcaccat caacagcagc agaagcagcc   2820
aggaatccta cgcccacggc acaaagctga gctacacatg cgagggcggc ttccggatct   2880
ccgaggaaaa cgagacaacc tgctacatgg gcaagtggtc ctccccacct cagtgcgagg   2940
gactgccttg caagtcccca cccgagatct ctcatggcgt ggtggcccac atgagcgaca   3000
gctaccagta cggcgaggaa gtgacctaca agtgtttcga gggcttcggc atcgacggcc   3060
ctgccattgc caagtgcctg ggagagaagt ggtcccaccc tcccagctgc atcaagaccg   3120
actgcctgag cctgcctagc ttcgagaacg ccatccccat gggcgagaaa aaggacgtgt   3180
acaaggccgg cgaacaagtg acatacacct gtgccaccta ctacaagatg gacggcgcca   3240
gcaacgtgac ctgtattaac agccggtgga ccggcaggcc tacctgcaga gatacctcct   3300
gcgtgaaccc ccccaccgtg cagaacgcct acatcgtgtc tcggcagatg agcaagtacc   3360
ccagcggcga acgcgtgcgc taccagtgta gaagccccta cgagatgttc ggcgacgaag   3420
aagtgatgtg cctgaatggc aactggaccg agccccctca gtgcaaggat agcaccggca   3480
agtgtggccc ccctcccccc atcgataacg gcgacatcac cagcttcccc ctgtccgtgt   3540
atgcccctgc cagctccgtg gaatatcagt gccagaacct gtaccagctg gaaggcaaca   3600
agcggatcac ctgtcggaac ggccagtgga gcgagcctcc caagtgtctg cacccctgcg   3660
tgatctccag agaaatcatg gaaaactata atatcgccct gcgctggacc gccaagcaga   3720
agctgtactc taggaccggc gagtctgtgg aatttgtgtg caagcgggga tacagactga   3780
```

gcagcagatc ccacaccctg agaaccacct gttgggacgg caagctggaa taccctacct 3840
gcgccaagag atga 3854

<210> SEQ ID NO 36
<211> LENGTH: 3860
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 36
atgagactgc tggccaagat catctgcctg atgctgtggg ccatctgcgt ggccgaggac 60
tgcaacgagc tgccccccag aagaaacacc gagatcctga ccggctcttg gagcgaccag 120
acctaccctg agggcaccca ggccatctac aagtgcagac ccggctaccg gtccctgggc 180
aacatcatca tggtgtgcag aaagggcgag tgggtggccc tgaacccccct gagaaagtgc 240 cagaagaggc cctgcggaca ccccggcgat accccttttg gcaccttcac actgaccggc 300
ggcaacgtgt tcgagtacgg cgtgaaggcc gtgtacacct gtaacgaggg ctaccagctg 360
ctgggcgaga tcaactacag agagtgcgac accgacggct ggaccaacga tatccccatc 420
tgcgaggtcg tgaagtgcct gcctgtgacc gccccagaga acggcaagat cgtgtccagc 480
gccatggaac ccgacagaga gtaccacttc ggccaggccg tcagattcgt gtgcaacagc 540
ggctacaaga tcgagggcga cgaggaaatg cactgcagcg acgacggctt ctggtccaaa 600
gaaaagccta agtgcgtgga aatcagctgc aagagccccg acgtgatcaa cggcagcccc 660
atcagccaga agatcatcta caaagagaac gagcggttcc agtacaagtg taacatgggc 720
tacgagtaca gcgagcgggg cgacgccgtg tgtacagaat ctggatggcg gcctctgccc 780
agctgcgagg aaaagagctg cgacaacccc tacatcccca acggcgacta cagccccctg 840
cggatcaagc acagaaccgg cgacgagatc acctaccagt gccggaacgg cttctacccc 900
gccaccagag gcaataccgc caagtgtacc agcaccggct ggatccctgc ccccagatgt 960
accctgaagc cctgcgacta ccctgacatc aagcacggcg gcctgtacca cgagaacatg 1020
cggaggccct acttccctgt ggccgtgggc aagtactaca gctactactg cgacgagcac 1080
ttcgagacac ccagcggcag ctactgggac cacatccact gtacccagga cggctggtcc 1140
cctgccgtgc cctgcctgag gaagtgctac ttcccctacc tggaaaacgg ctacaaccag 1200
aactacggcc ggaagttcgt gcagggcaag agcatcgatg tggcctgcca ccctggatac 1260
gccctgccta aggcccagac caccgtgacc tgcatggaaa atggatggtc ccccaccccc 1320
cggtgcatca gagtcagtaa gtccttcact ctgtgaaact tgtttattgc agcttataat 1380
ggttacaaat aaagcaatag catcacaaat ttcacaaata aagcattttt ttcactgcat 1440
tctagttgtg gtttgtccaa actcatcaat gtatcttatt ctaattctct tccttttag 1500 aaacctgcag caagagcagc atcgacatcg agaatggctt catcagcgag agccagtaca 1560
cctacgccct gaaagagaag gccaagtacc agtgcaagct gggctacgtg accgccgacg 1620
gcgagacaag cggcagcatc acctgtggca aggatgggtg gagcgcccag cccacctgta 1680
tcaagtcctg cgacatccct gtgttcatga atgcccggac caagaacgac ttcacctggt 1740
tcaagctgaa cgacacactg gactacgagt gccacgacgg ctacgagagc aacaccggca 1800
gcaccacagg cagcatcgtg tgtggctaca acgggtggag tgacctgccc atctgttacg 1860
agcgcgagtg cgagctgcct aagatcgacg tgcacctggt gcccgaccgg aagaaagacc 1920
agtacaaagt gggcgaggtg ctgaagttct cctgcaagcc cggcttcacc atcgtgggcc 1980
ccaatagcgt gcagtgctac cactttggcc tgtcccccga tctgcctatc tgcaaagaac 2040
aggtgcagag ctgcggccct ccacccgagc tgctgaacgg caatgtgaaa gaaaagacca 2100
aagaggaata cggccactcc gaggtggtgg aatattactg caacccccgg ttcctgatga 2160
agggccccaa caagattcag tgtgtggacg gcgagtggac caccctgccc gtgtgtatcg 2220
tggaagagtc tacctgcgga gacatccccg agctggaaca cggatgggcc cagctgagca 2280
gcccccctta ctactacggc gacagcgtgg aattcaactg ctccgagagc tttaccatga 2340
tcggccaccg gtccatcaca tgcatccacg gcgtgtggac acagctgcca cagtgcgtgg 2400
ccatcgacaa gctgaagaag tgcaagtcca gcaacctgat catcctggaa gaacacctga 2460
agaacaagaa agagttcgac cacaacagca acatccggta cagatgccgg ggcaaagagg 2520
gatggatcca caccgtgtgc atcaatggca gatgggaccc cgaagtgaac tgcagcatgg 2580
cccagatcca gctgtgcccc ccacctcccc agatccccaa cagccacaac atgaccacca 2640
ccctgaacta ccgggatggc gagaaggtgt ccgtgctgtg ccaggaaaac tacctgatcc 2700
aggaaggcga agagattacc tgcaaggacg gccggtggca gagcatcccc ctgtgtgtgg 2760
aaaagatccc ctgcagccag ccccccaga tcgagcacgg caccatcaac agcagcagaa 2820
gcagccagga atcctacgcc cacggcacaa agctgagcta cacatgcgag ggcggcttcc 2880
ggatctccga ggaaaacgag acaacctgct acatgggcaa gtggtcctcc ccacctcagt 2940
gcgagggact gccttgcaag tccccacccg agatctctca tggcgtggtg gcccacatga 3000
gcgacagcta ccagtacggc gaggaagtga cctacaagtg tttcgagggc ttcggcatcg 3060
acggccctgc cattgccaag tgcctgggag agaagtggtc ccaccctccc agctgcatca 3120
agaccgactg cctgagcctg cctagcttcg agaacgccat ccccatgggc gagaaaaagg 3180
acgtgtacaa ggccggcgaa caagtgacat acacctgtgc cacctactac aagatggacg 3240
gcgccagcaa cgtgacctgt attaacagcc ggtggaccgg caggcctacc tgcagagata 3300
cctcctgcgt gaaccccccc accgtgcaga acgcctacat cgtgtctcgg cagatgagca 3360
agtaccccag cggcgaacgc gtgcgctacc agtgtagaag cccctacgag atgttcggcg 3420
acgaagaagt gatgtgcctg aatggcaact ggaccgagcc ccctcagtgc aaggatagca 3480
ccggcaagtg tggcccccct ccccccatcg ataacggcga catcaccagc ttcccccctgt 3540 ccgtgtatgc ccctgccagc tccgtggaat atcagtgcca gaacctgtac cagctggaag 3600
gcaacaagcg gatcacctgt cggaacggcc agtggagcga gcctcccaag tgtctgcacc 3660
cctgcgtgat ctccagagaa atcatggaaa actataatat cgccctgcgc tggaccgcca 3720
agcagaagct gtactctagg accggcgagt ctgtggaatt tgtgtgcaag cggggataca 3780
gactgagcag cagatcccac accctgagaa ccacctgttg ggacggcaag ctggaatacc 3840
ctacctgcgc caagagatga 3860

<210> SEQ ID NO 37
<211> LENGTH: 3860
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37
atgagactgc tggccaagat catctgcctg atgctgtggg ccatctgcgt ggccgaggac 60

-continued

```
tgcaacgagc tgccccccag aagaaacacc gagatcctga ccggctcttg gagcgaccag    120
acctaccctg agggcaccca ggccatctac aagtgcagac ccggctaccg gtccctgggc    180
aacatcatca tggtgtgcag aaagggcgag tgggtggccc tgaacccccct gagaaagtgc    240
cagaagaggc cctgcggaca ccccggcgat accccttttg gcaccttcac actgaccggc    300
ggcaacgtgt tcgagtacgg cgtgaaggcc gtgtacacct gtaacgaggg ctaccagctg    360
ctgggcgaga tcaactacag agagtgcgac accgacggct ggaccaacga tatccccatc    420
tgcgaggtcg tgaagtgcct gcctgtgacc gccccagaga acggcaagat cgtgtccagc    480
gccatggaac ccgacagaga gtaccacttc ggccaggccg tcagattcgt gtgcaacagc    540
ggctacaaga tcgagggcga cgaggaaatg cactgcagcg acgacggctt ctggtccaaa    600
gaaaagccta agtgcgtgga aatcagctgc aagagccccg acgtgatcaa cggcagcccc    660
atcagccaga agatcatcta caaagagaac gagcggttcc agtacaagtg taacatgggc    720
tacgagtaca gcgagcgggg cgacgccgtg tgtacagaat ctggatggcg gcctctgccc    780
agctgcgagg aaaagagctg cgacaacccc tacatcccca acggcgacta cagcccccctg    840
cggatcaagc acagaaccgg cgacgagatc acctaccagt gccggaacgg cttctacccc    900
gccaccagag gcaataccgc caagtgtacc agcaccggct ggatccctgc ccccagatgt    960
accctgaagc cctgcgacta ccctgacatc aagcacggcg gcctgtacca cgagaacatg   1020
cggaggccct acttccctgt ggccgtgggc aagtactaca gctactactg cgacgagcac   1080
ttcgagacac ccagcggcag ctactgggac cacatccact gtacccagga cggctggtcc   1140
cctgccgtgc cctgcctgag gaagtgctac ttcccctacc tggaaaacgg ctacaaccag   1200
aactacggcc ggaagttcgt gcagggcaag agcatcgatg tggcctgcca ccctggatac   1260
gccctgccta aggcccagac caccgtgacc tgcatggaaa atggatggtc ccccaccccc   1320
cggtgcatca gagtcagtga gtccttcact ctgtgaaact tgtttattgc agcttataat   1380
ggttacaaat aaagcaatag catcacaaat ttcacaaata aagcattttt ttcactgcat   1440
tctagttgtg gtttgtccaa actcatcaat gtatcttatt ctaattctct tccctttttag   1500
aaacctgcag caagagcagc atcgacatcg agaatggctt catcagcgag agccagtaca   1560
cctacgccct gaaagagaag gccaagtacc agtgcaagct gggctacgtg accgccgacg   1620
gcgagacaag cggcagcatc acctgtggca aggatgggtg gagcgcccag cccacctgta   1680
tcaagtcctg cgacatccct gtgttcatga atgcccggac caagaacgac ttcacctggt   1740
tcaagctgaa cgacacactg gactacgagt gccacgacgg ctacgagagc aacaccggca   1800
gcaccacagg cagcatcgtg tgtggctaca acgggtggag tgacctgccc atctgttacg   1860
agcgcgagtg cgagctgcct aagatcgacg tgcacctggt gcccgaccgg aagaaagacc   1920
agtacaaagt gggcgaggtg ctgaagttct cctgcaagcc cggcttcacc atcgtgggcc   1980
ccaatagcgt gcagtgctac cactttggcc tgtcccccga tctgcctatc tgcaaagaac   2040
aggtgcagag ctgcggccct ccacccgagc tgctgaacgg caatgtgaaa gaaaagacca   2100
aagaggaata cggccactcc gaggtggtgg aatattactg caaccccgg ttcctgatga   2160
agggccccaa caagattcag tgtgtggacg gcgagtggac caccctgccc gtgtgtatcg   2220
tggaagagtc tacctgcgga gacatccccg agctggaaca cggatgggcc cagctgagca   2280
gcccccctta ctactacggc gacagcgtgg aattcaactg ctccgagagc tttaccatga   2340
tcggccaccg gtccatcaca tgcatccacg gcgtgtggac acagctgcca cagtgcgtgg   2400
```

-continued

```
ccatcgacaa gctgaagaag tgcaagtcca gcaacctgat catcctggaa gaacacctga   2460

agaacaagaa agagttcgac cacaacagca acatccggta cagatgccgg ggcaaagagg   2520

gatggatcca caccgtgtgc atcaatggca gatgggaccc cgaagtgaac tgcagcatgg   2580

cccagatcca gctgtgcccc ccacctcccc agatccccaa cagccacaac atgaccacca   2640

ccctgaacta ccgggatggc gagaaggtgt ccgtgctgtg ccaggaaaac tacctgatcc   2700

aggaaggcga agagattacc tgcaaggacg gccggtggca gagcatcccc ctgtgtgtgg   2760

aaaagatccc ctgcagccag cccccccaga tcgagcacgg caccatcaac agcagcagaa   2820

gcagccagga atcctacgcc cacggcacaa agctgagcta cacatgcgag ggcggcttcc   2880

ggatctccga ggaaaacgag acaacctgct acatgggcaa gtggtcctcc ccacctcagt   2940

gcgagggact gccttgcaag tccccacccg agatctctca tggcgtggtg gcccacatga   3000

gcgacagcta ccagtacggc gaggaagtga cctacaagtg tttcgagggc ttcggcatcg   3060

acggccctgc cattgccaag tgcctgggag agaagtggtc ccaccctccc agctgcatca   3120

agaccgactg cctgagcctg cctagcttcg agaacgccat ccccatgggc gagaaaaagg   3180

acgtgtacaa ggccggcgaa caagtgacat acacctgtgc cacctactac aagatggacg   3240

gcgccagcaa cgtgacctgt attaacagcc ggtggaccgg caggcctacc tgcagagata   3300

cctcctgcgt gaaccccccc accgtgcaga acgcctacat cgtgtctcgg cagatgagca   3360

agtaccccag cggcgaacgc gtgcgctacc agtgtagaag cccctacgag atgttcggcg   3420

acgaagaagt gatgtgcctg aatggcaact ggaccgagcc ccctcagtgc aaggatagca   3480

ccggcaagtg tggcccccct ccccccatcg ataacggcga catcaccagc ttcccccctgt   3540

ccgtgtatgc ccctgccagc tccgtggaat atcagtgcca gaacctgtac cagctggaag   3600

gcaacaagcg gatcacctgt cggaacggcc agtggagcga gcctcccaag tgtctgcacc   3660

cctgcgtgat ctccagagaa atcatggaaa actataatat cgccctgcgc tggaccgcca   3720

agcagaagct gtactctagg accggcgagt ctgtggaatt tgtgtgcaag cggggataca   3780

gactgagcag cagatcccac accctgagaa ccacctgttg ggacggcaag ctggaatacc   3840

ctacctgcgc caagagatga                                                3860
```

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 38

```
tctcagagtg ccaaacatat acc                                            23
```

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 39

```
caggcattag tgacaagcaa ag                                             22
```

<210> SEQ ID NO 40
<211> LENGTH: 22

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

gaaggattga ggtctctgga aa                                              22


<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41

gagaatgaag gcacagaggt att                                             23


<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42

gagggttaga ggtgcacaat                                                 20


<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

cccacctagc tcctttcttt c                                               21


<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44

aacctggttg gaagaatatt gg                                              22


<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45

agagaatggt gccaaggt                                                   18


<210> SEQ ID NO 46
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 46

cttctccaat cttagcacta atcaa                                          25


<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47

ctggttcata ggtggtatgt aataga                                         26


<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48

cagagttata agatctgtga agaca                                          25


<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49

ccaaggagaa tgagaacaga ttaga                                          25


<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50

actgcagaat gaagaaggaa                                                20


<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51

tattgtccct gtccctgtct                                                20


<210> SEQ ID NO 52
<211> LENGTH: 20
<212> TYPE: DNA
<213> ORGANISM: Artificial Sequence
```

<220> FEATURE:
<223> OTHER INFORMATION: Description of Artificial Sequence: Synthetic
primer

<400> SEQUENCE: 52
ggcttgctgt tcccataaca 20

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 53
aaaggagtta tggctttggg a 21

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 54
ccctaatacc tctgtgcctt 20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 55
gggaacagaa gttgctttca 20

<210> SEQ ID NO 56
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 56
caggcctgag ctgatcc 17

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 57
ccagaaacca ggactgttga 20

<210> SEQ ID NO 58
<211> LENGTH: 22
<212> TYPE: DNA
<213> ORGANISM: Artificial Sequence
<220> FEATURE:

<223> OTHER INFORMATION: Description of Artificial Sequence: Synthetic
primer

<400> SEQUENCE: 58
tgagagagga gctgaaacct ac 22

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 59
gaaattcccc agcaacacca tc 22

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 60
caatcagagc tcctcgtcag 20

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 61
ccaacaccct ccaagaagaa a 21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 62
ccgttgtctc tgagcagatt a 21

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 63
ttagggagtc aagtgacggc 20

<210> SEQ ID NO 64
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
cctgccagcc aatcaca 17

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 65
agtgccagcc tctaagagt 19

<210> SEQ ID NO 66
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 66
gaacactggt ggagcagat 19

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 67
ccaacagggc tgtcaaagac 20

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 68
gagagttcct ggcacaga 18

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 69
tttcttcttg gagggtgttg g 21

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 70
actccctggg actctgtg 18

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
aaatccagag gctaaaggat ctg 23

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
ctgtgctgag cttcaacttc tg 22

<210> SEQ ID NO 73
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
cccacgtgag tgctgag 17

<210> SEQ ID NO 74
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
ggtctggcga ctaggct 17

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 75
aggagtcctt gtcttagtcc 20

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 76
cgttacataa cttacggtaa atgg 24

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 77
catggtaata gcgatgacta atac 24

<210> SEQ ID NO 78
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 78
gcctaaggcc cagaccaccg tgacc 25

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 79
ctggtacttg gccttctctt t 21

<210> SEQ ID NO 80
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 80

```
Met Glu Asn Gly Trp Ser Pro Thr Pro Arg Cys Ile Arg Val Ser Lys
1               5                   10                  15

Tyr Thr Thr Leu Lys Ser
            20
```

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 81

```
Ser Phe Thr Leu
1
```

<210> SEQ ID NO 82
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Cys Ser Lys Ser Ser Ile Asp Ile Glu Asn Gly Phe Ile Ser Glu
1               5                   10                  15

Ser Gln Tyr Thr Tyr Ala Leu Lys Glu Lys Ala
            20                  25

<210> SEQ ID NO 83
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Met Glu Asn Gly Trp Ser Pro Thr Pro Arg Cys Ile Arg Val Ser Phe
1               5                   10                  15

Thr Leu

<210> SEQ ID NO 84
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Met Glu Asn Gly Trp Ser Pro Thr Pro Arg Cys Ile Arg Val Ser Lys
1               5                   10                  15

Ser Phe Thr Leu
            20

<210> SEQ ID NO 85
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Met Glu Asn Gly Trp Ser Pro Thr Pro Arg Cys Ile Arg Val Ser Glu
1               5                   10                  15

Ser Phe Thr Leu
            20

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
caaataaagc caagcatcag gg                                              22

<210> SEQ ID NO 87
<211> LENGTH: 23
<212> TYPE: DNA

-continued

<213> ORGANISM: Artificial Sequence
<220> FEATURE:
<223> OTHER INFORMATION: Description of Artificial Sequence: Synthetic primer

<400> SEQUENCE: 87
tctcagagtg ccaaacatat acc 23

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 88
caggcattag tgacaagcaa ag 22

<210> SEQ ID NO 89
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 89
gaaggattga ggtctctgga aa 22

<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 90
gagaatgaag gcacagaggt att 23

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 91
gagggttaga ggtgcacaat 20

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 92
cccacctagc tcctttcttt c 21

<210> SEQ ID NO 93
<211> LENGTH: 22
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 93

aacctggttg gaagaatatt gg                                              22


<210> SEQ ID NO 94
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94

agagaatggt gccaaggt                                                   18


<210> SEQ ID NO 95
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95

cttctccaat cttagcacta atcaa                                           25


<210> SEQ ID NO 96
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96

ctggttcata ggtggtatgt aataga                                          26


<210> SEQ ID NO 97
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97

cagagttata agatctgtga agaca                                           25


<210> SEQ ID NO 98
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98

ccaaggagaa tgagaacaga ttaga                                           25


<210> SEQ ID NO 99
<211> LENGTH: 20
<212> TYPE: DNA
<213> ORGANISM: Artificial Sequence
<220> FEATURE:
```

<223> OTHER INFORMATION: Description of Artificial Sequence: Synthetic
primer

<400> SEQUENCE: 99
actgcagaat gaagaaggaa 20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 100
tattgtccct gtccctgtct 20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 101
ggcttgctgt tcccataaca 20

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 102
aaaggagtta tggctttggg a 21

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 103
ccctaatacc tctgtgcctt 20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 104
gggaacagaa gttgctttca 20

<210> SEQ ID NO 105
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 105
caggcctgag ctgatcc 17

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 106
ccagaaacca ggactgttga 20

<210> SEQ ID NO 107
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
tgagagagga gctgaaacct ac 22

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 108
gaaattcccc agcaacacca tc 22

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 109
caatcagagc tcctcgtcag 20

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 110
ccaacaccct ccaagaagaa a 21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 111
ccgttgtctc tgagcagatt a 21

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 112
ttagggagtc aagtgacggc 20

<210> SEQ ID NO 113
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 113
cctgccagcc aatcaca 17

<210> SEQ ID NO 114
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 114
agtgccagcc tctaagagt 19

<210> SEQ ID NO 115
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 115
gaacactggt ggagcagat 19

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 116
ccaacagggc tgtcaaagac 20

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 117
gagagttcct ggcacaga 18

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 118
tttcttcttg gagggtgttg g 21

<210> SEQ ID NO 119
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 119
actccctggg actctgtg 18

<210> SEQ ID NO 120
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 120
aaatccagag gctaaaggat ctg 23

<210> SEQ ID NO 121
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 121
ctgtgctgag cttcaacttc tg 22

<210> SEQ ID NO 122
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 122
cccacgtgag tgctgag 17

<210> SEQ ID NO 123
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 123

```
ggtctggcga ctaggct                                                   17


<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124

aggagtcctt gtcttagtcc                                                20


<210> SEQ ID NO 125
<211> LENGTH: 128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125

gcgcgctcgc tcgctcactg aggccgcccg ggcaaagccc gggcgtcggg cgacctttgg     60

tcgcccggcc tcagtgagcg agcgagcgcg cagagaggga gtggccaact ccatcactag    120

gggttcct                                                             128


<210> SEQ ID NO 126
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126

catggtaata gcgatgacta atac                                           24


<210> SEQ ID NO 127
<211> LENGTH: 1657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127

ccgcgttaca taacttacgg taaatggccc gcctggctga ccgcccaacg acccccgccc     60

attgacgtca ataatgacgt atgttcccat agtaacgcca atagggactt tccattgacg    120

tcaatgggtg gagtatttac ggtaaactgc ccacttggca gtacatcaag tgtatcatat    180

gccaagtacg ccccctattg acgtcaatga cggtaaatgg cccgcctggc attatgccca    240

gtacatgacc ttatgggact ttcctacttg gcagtacatc tacgtattag tcatcgctat    300

taccatggtc gaggtgagcc ccacgttctg cttcactctc cccatctccc ccccctcccc    360

acccccaatt ttgtatttat ttatttttta attattttgt gcagcgatgg gggcgggggg    420

gggggggggg cgcgcgccag gcggggcggg gcggggcgag gggcggggcg gggcgaggcg    480

gagaggtgcg gcggcagcca atcagagcgg cgcgctccga aagtttcctt ttatggcgag    540

gcggcggcgg cggcggccct ataaaaagcg aagcgcgcgg cgggcgggag tcgctgcgcg    600

ctgccttcgc cccgtgcccc gctccgccgc cgcctcgcgc cgcccgcccc ggctctgact    660
```

-continued

```
gaccgcgtta ctcccacagg tgagcgggcg ggacggccct tctcctccgg gctgtaatta    720

gcgcttggtt taatgacggc ttgtttcttt tctgtggctg cgtgaaagcc ttgaggggct    780

ccgggagggc cctttgtgcg gggggagcgg ctcggggggt gcgtgcgtgt gtgtgtgcgt    840

ggggagcgcc gcgtgcggct ccgcgctgcc cggcggctgt gagcgctgcg ggcgcggcgc    900

ggggctttgt gcgctccgca gtgtgcgcga ggggagcgcg gccgggggcg gtgccccgcg    960

gtgcgggggg ggctgcgagg ggaacaaagg ctgcgtgcgg ggtgtgtgcg tgggggggtg   1020

agcagggggt gtgggcgcgt cggtcgggct gcaacccccc ctgcaccccc ctccccgagt   1080

tgctgagcac ggcccggctt cgggtgcggg gctccgtacg gggcgtggcg cggggctcgc   1140

cgtgccgggc ggggggtggc ggcaggtggg ggtgccgggc ggggcggggc cgcctcgggc   1200

cggggagggc tcgggggagg ggcgcggcgg cccccggagc gccggcggct gtcgaggcgc   1260

ggcgagccgc agccattgcc ttttatggta atcgtgcgag agggcgcagg gacttccttt   1320

gtcccaaatc tgtgcggagc cgaaatctgg gaggcgccgc cgcacccccct ctagcgggcg   1380

cggggcgaag cggtgcggcg ccggcaggaa ggaaatgggc ggggagggcc ttcgtgcgtc   1440

gccgcgccgc cgtccccttc tccctctcca gcctcggggc tgtccgcggg gggacggctg   1500

ccttcggggg ggacggggca gggcggggtt cggcttctgg cgtgtgaccg gcggctctag   1560

agcctctgct aaccatgttc atgccttctt ctttttccta cagctcctgg gcaacgtgct   1620

ggttattgtg ctgtctcatc attttggcaa agaattc                             1657
```

GENE THERAPY FOR MACULAR DEGENERATION

CROSS-REFERENCE TO RELATED APPLICATIONS

This application is a national phase application of PCT Application No. PCT/US2019/042891, filed Jul. 22, 2019, which claims the benefit of priority to U.S. Provisional Application 62/701,464, filed Jul. 20, 2018 and U.S. Provisional Application 62/859,628, filed Jun. 10, 2019, the disclosures of which are hereby incorporated by reference.

FIELD OF THE INVENTION

The invention finds application in the field of medicine.

SEQUENCE LISTING

The instant application contains a Sequence Listing which has been submitted electronically in ASCII format and is hereby incorporated by reference in its entirety. Said ASCII copy, created on Jul. 22, 2019, is named 098846-000610PC-1143012_SL.txt and is 109,157 bytes in size.

BACKGROUND OF THE INVENTION

Age-related macular degeneration (AMD) is the leading cause of irreversible vision loss in the developed world (for reviews see Zarbin, *Eur Ophthalmol* 8:199-206, 1998; Zarbin, *Arch Ophthalmol* 122(4):598-614, 2004; Klein et al., *Am J Ophthalmol* 137(3):504-510, 2004; Ambati et al., *Surv Ophthalmol* 48(3):257-293, 2003; de Jong, *Ophthalmologio* 218 Suppl 1:5-16, 2004; Van Leeuwen et al., *Eur Epidemiol* 18(9):845-854, 2003) affecting approximately 15% of individuals over the age of 60. An estimated 600 million individuals are in this age demographic. The prevalence of AMD increases with age; mild, or early forms occur in nearly 30%, and advanced forms in about 7%, of the population that is 75 years and older; Vingerling et al., *Epidemiol Rev.* 17(2):347-360, 1995; Vingerling et al., *Ophthalmol* 102(2):205-210, 1995). A need exists for improved AMD therapies.

BRIEF SUMMARY OF THE INVENTION

Compositions and methods for prevention and treatment of age-related macular degeneration, including gene therapy employing vectors and transgenes expressing protective CFH polypeptide and/or CFHT polypeptide sequences.

In one aspect described herein is a recombinant polynucleotide construct comprising: (i) a polynucleotide sequence that encodes a protective Factor H polypeptide(s) selected from (a) a truncated CFH polypeptide (CFHT); (b) a truncated CFH polypeptide comprising an amino-terminal sequence CIRVSKSFTL (eCFHT); (c) both a full length CFH polypeptide and a truncated CFH polypeptide (CFH/T); and (d) both a full length CFH polypeptide and a truncated CFH polypeptide comprising an carboxy-terminal sequence CIRVSKSFTL (eCFH/T). In one embodiment the Factor H polypeptide(s) comprise isoleucine (I) at position 62 and tyrosine (Y) at position 402. In one embodiment the recombinant polynucleotide construct comprises a promoter operably linked to the polynucleotide sequence. In various embodiments the introduction of the polynucleotide construct into a mammalian cell results in expression of the protective Factor H polypeptide(s). Exemplary mammalian cells include HEK293 (ATCC # CRL-1573), A549 (ATCC # CRL-185), RPE1 (ATCC # CRL-4000), COS-7 (ATCC # CRL-1651), RPE7 (Sigma 09061602) and human undifferentiated fetal RPE cells. In one approach the polynucleotide construct encodes a full-length CFH protein, wherein the amino acid at 936 is glutamic acid (E). In some embodiments the full-length CFH polypeptide comprises (a) residues 1-1231 of SEQ ID NO:2; (b) residues 19-1231 of SEQ ID NO:2 [SEQ ID NO:20]; or (c) a sequence with at least 90% identical to residues 19-1231 of SEQ ID NO:2. In some embodiments the truncated CFH polypeptide comprises (a) residues 1-449 of SEQ ID NO:4; (b) residues 19-449 of SEQ ID NO:4 [SEQ ID NO:21]; or (c) a sequence at least 90% identity to residues 19-449 of SEQ ID NO:4. In some embodiments the truncated CFH polypeptide comprises (a) residues 1-4451 of SEQ ID NO:6; (b) residues 19-452 of SEQ ID NO:6 [SEQ ID NO:22]; (c) or a sequence with at least 90% identity to residues 19-451 of SEQ ID NO:6, with the proviso that the carboxy-terminal sequence is CIRVSKSFTL. In some embodiments, the promoter is not the human Complement Factor H gene promoter. The promoter may be selected from CBA, BEST1-EP-454, RPE65-EP-415, VMD2, and smCBA. In some embodiments the polyadenylation site or signal is a Herpes Simplex Virus thymidine kinase (TK) polyadenylation sequence, a Bovine Growth Factor (bGH) polyadenylation sequence, or an SV40 polyadenylation sequence. In some embodiments the polynucleotide construct has a combination of elements selected from (a) CBA—CFHT—bGH; (b) BEST1-EP-454—CFH—TK; (c) RPE65-EP-415—CFH—TK; (d) BEST1-EP-454—eCFH/T—TK; or (e) RPE65-EP-415—eCFH/T—TK (wherein (a)-(e) are presented in the format: [promoter/enhancer]—[FH protein(s)]—[polyadenylation sequence].

In some embodiments the polynucleotide construct comprises an artificial DNA sequence that encodes both full-length and truncated CFH proteins, wherein full-length and truncated CFH proteins are produced by a process involving alternative splicing of RNA transcribed from the DNA sequence. In one embodiment the truncated CFH protein is longer than 450 amino acids. In one embodiment the C-terminal sequence of the truncated CFH protein is not CIRVSFTL In one embodiment the truncated CFH protein has the C-terminal sequence CIRVSKSFTL.

In an aspect the disclosure provides a viral vector comprising the polynucleotide construct described above. In some embodiments. The viral vector may be an adeno-associated virus (AAV), and preferably is AAV2. Preferably Complement Factor H polypeptides are when (a) non-human retinal or choroidal cells from a non-human primate or (b) isolated human retinal cells or choroidal cells are transduced with the AAV.

Also disclosed are a pharmaceutical composition comprising a therapeutic amount of the polynucleotide construct or virus particle and a pharmaceutically acceptable carrier or excipient. A pre-filled syringe comprising a unit dose of the pharmaceutical composition may be used.

In an aspect a method of treating a human patient in need of treatment for AMD or at risk of developing AMD is disclosed, comprising introducing into the eye of the patient a therapeutically effective amount of a vector comprising a polynucleotide construct described herein above, under conditions in which the factor H polypeptide(s) encoded by the polynucleotide construct are expressed in tissues of the eye, preferably retinal cells(e.g., retinal pigment epithelial cells) and/or choroidal cells.

In an aspect the expression of the polypeptides in the retinal cells and/or choroidal cells stabilizes, reverses or ameliorates a symptom or sign of AMD in the patient, or prevents development of symptoms or signs of AMD in the patient.

In some embodiments at the time of initial treatment the treated patient does not have symptoms of AMD; or does not manifest small drusen, soft drusen, retinal pigmentations or pigment epithelial detachment; or does not exhibit pigmented epithelium detachment (PED); or does not have geographic atrophy (GA).

In some embodiments the patient is homozygous for a Chromosome 1 risk allele. In some embodiments the patient is heterozygous for a Chromosome 1 risk allele. In some embodiments the patient does not have any chromosome 10 risk alleles. In some embodiments the patient's genetic profile is selected from the group consisting of G4, G2, G13, G14, G1, G12, G11, G23, G24, G21, or G22.

In one aspect a method of treating a human patient in need of treatment for AMD or at risk of developing AMD is disclosed, comprising introducing into the eye of the patient a therapeutically effective amount of a vector comprising a polynucleotide construct, viral vector, virus particle, or pharmaceutical composition described hereinabove under conditions in which the factor H polypeptide(s) encoded by the polynucleotide construct are expressed in tissues of the eye, wherein the injection site is not the patient's macula. In one approach the method comprises introducing into the eye of the patient a therapeutically effective amount of a vector encoding exogenous protective Factor H protein, wherein said introducing comprises subretinal injection of the vector, wherein said introducing results in transduction of cells in the retinal pigment epithelium and expression in at least one cell of exogenous protective CFHT protein. In an embodiment the exogenous protective Factor H protein is a CFHT protein and said introducing results in transduction of cells in the retinal pigment epithelium and expression in at least one cell of exogenous protective CFHT protein, with the proviso that introducing does not result in expression of protective full-length Complement Factor H (CFH) protein in the cells. In an embodiment the exogenous protective Factor H protein is co-expressed CFH and CFHT proteins. In an embodiment the vector encoding exogenous protective Factor H protein is a viral vector and 106 to 1012 viral particles are administered per injection in a volume of 25 to 250 microliters. In an embodiment the vector encoding exogenous protective Factor H protein is an adeno-associated viral vector, preferably an adeno-associated virus 2 (AAV2) vector, comprising a promoter sequence and a polyadenylation signal sequence. In an embodiment the expression of exogenous protective CFHT protein in transduced retinal pigment epithelium is greater than the expression of endogenous CFHT protein in the cells. In an embodiment the expression of exogenous protective CFHT protein is greater than the expression of endogenous CFHT protein in the transduced cells, as measured in African Green Monkey (AGM) retina-RPE-choroid (RRC) tissue isolated from AGM at the site of subretinal injection of 108 viral particles in 100 μL saline. In an embodiment the expression of exogenous protective CFHT protein by COS-7 cells (ATCC # CRL-1651) transduced with the vector is more than 1.5-fold the expression of exogenous protective CFHT protein by COS-7 cells transduced with pCTM259.

In some embodiments the promotor is a large CMV enhancer and chicken beta actin promoter (CBA) promoter or is a BEST1-EP-454 promoter enhancer. In some embodiments the CFHT protein comprises SEQ ID NO:21.

Also disclosed is a method described herein in which the subretinal injection is not an injection into the macular subretinal space. In an embodiment a bleb formed by the subretinal injection has a bleb boundary outside the macula or outside the fovea, e.g., the bleb margin is at least 5 mm outside or is 5 to 20 mm outside the macula or fovea. In some approaches the center-to-center distance from the center of a bleb to the center of the macula (or fovea) is at least 10 mm is 10 mm to 30 mm.

In some embodiments the treating comprises one or more injections per day on one to twelve different days. The treating may results in an improvement in the patient's visual acuity; in drusen regression in the patient; in stabilization, reversal or amelioration of a sign of AMD in the patient or delays development of a sign of AMD in the patient.

In one aspect disclosed is a recombinant polynucleotide transgene comprising: (i) a polynucleotide sequence that encodes (a1) a transcript encoding a truncated complement factor H (CFH) polypeptide (CFHT) but not a transcript encoding a full-length CFH polypeptide; or (a2) a transcript encoding a full length CFH polypeptide and a truncated CFH polypeptide comprising an carboxy-terminal sequence CIRVSKSFTL (eCFH/T); with the proviso that the polypeptide(s) comprise(s) isoleucine (I) at position 62 and tyrosine (Y) at position 402; (ii) a promoter operably linked to the polynucleotide sequence; (iii) a polyadenylation signal; and (iv) left and right inverted terminal repeat sequences, wherein introduction of the polynucleotide transgene into a mammalian cell results in expression of the polypeptide(s). In one embodiment the truncated CFH polypeptide comprises (a) residues 1-449 of SEQ ID NO:4; (b) residues 19-452 of SEQ ID NO:6; or (c) a variant CFHT with at least 90% identity to (a) or (b). In one embodiment the full-length CFH polypeptide that comprises (a) residues 19-1231 of SEQ ID NO:2; or (b) a sequence with at least 90% identity to (a). In some embodiment the promoter is selected from the group consisting of CBA, BEST1-EP-454, RPE65-EP-415, VMD2, and smCBA. In some embodiments the polyadenylation signal is selected from a Herpes Simplex Virus thymidine kinase (TK) polyadenylation sequence, a Bovine Growth Factor (bGH) polyadenylation sequence, and an SV40 polyadenylation signal.

In an aspect disclosed is a viral vector comprising a polynucleotide transgene as described above, such as an adeno-associated virus (AAV), preferably is AAV2. Also disclosed is a pharmaceutical composition comprising a therapeutic amount of the polynucleotide transgene or viral vector and a pharmaceutically acceptable carrier or excipient.

In an aspect disclosed is a method of treating a human patient in need of treatment for AMD or at risk of developing AMD, comprising introducing the pharmaceutical composition by one or more subretinal injections, thereby producing one or more blebs. In an embodiment $10^6$ to $10^{12}$ viral particles are administered per injection in a volume of 25 to 250 microliters. In an embodiment retinal pigment epithelial cells (RPE) cells under the bleb(s) express the polypeptide(s). In an embodiment RPE cells outside the bleb do not express the polypeptide(s).

In one aspect of the method the subretinal injection is not an injection into the fovea. In an embodiment a bleb formed by the subretinal injection has a bleb boundary outside the fovea. In one aspect of the method the subretinal injection is not an injection into the macula. In an embodiment The bleb boundary is at least about 1 mm, optionally at least about 5 mm, outside the fovea or at least about 1 mm, optionally at least about 5 mm, outside the macula. In an embodiment the bleb margin is 5 to 20 mm outside the fovea or at least 5 to 20 mm outside the macula. In an embodiment the center-to-center distance from the center of a bleb to the center of the fovea or to the center of the fovea is at least 5 mm or at least 10 mm.

In an aspect of the method the treating comprises one or more injections per day on one to twelve different days.

In an aspect of the method the patient is homozygous or heterozygous for a Chromosome 1 risk allele. The patient's genetic profile may be selected from the group consisting of G4, G2, G13, G14, G1, G12, G11, G23, G24, G21, and G22. In some embodiments the patient does not have chromosome 10 risk alleles.

In some embodiments the patient does not have signs of AMD; the patient does not manifest small drusen, soft drusen, retinal pigmentations or pigment epithelial detachment; at the time of treatment introduction the patient does not exhibit pigmented epithelium detachment (PED).

In some embodiments the treating results in an improvement in the patient's visual acuity; results in drusen regression in the patient; results in stabilization, reversal or amelioration of a sign of AMD in the patient; or delays development of a sign of AMD in the patient.

BRIEF DESCRIPTION OF THE DRAWINGS

FIG. 3A: CFH family variant protein activity in CFI-dependent cofactor assay –20 min at 37° C. with 526 nM C3b, 23 nM CFI & indicated concentrations of CFH and CFHT protein variants; FIG. 3B: CFH family variant protein activity in rabbit RBC lysis assay –30 min at 37° C. with indicated variants, 15% FH-depleted NHS, 5 μl MgEGTA (0.1M) & 1.25+E7 rabbit RBCs; results normalized to 15% NHS treated RBCs; FIG. 3C: AP assay—LPS coated plates treated with indicated CFH family protein variants and 12.5% NHS for 1.5 hours at 37° C. PBS & 5 mM EDTA included as positive and negative controls.

FIG. 9A shows a construct with the BEST1-EP-454 enhancer promoter directly upstream of the EGFP reporter coding sequence. FIG. 9B shows a construct with RPE65-EP-415 enhancer promoter directly upstream of the EGFP reporter coding sequence. FIG. 9C shows a construct with the RPE65-EP-419 enhancer promoter directly upstream of the EGFP reporter coding sequence.

that removes the CFHT C-terminal tail and SV40 poly(A) signal) and terminates with an HSV TK poly(A) signal (not shown in this figure). A consensus branch site has been included in this construct to increase efficiency of splicing.

Figure 15:
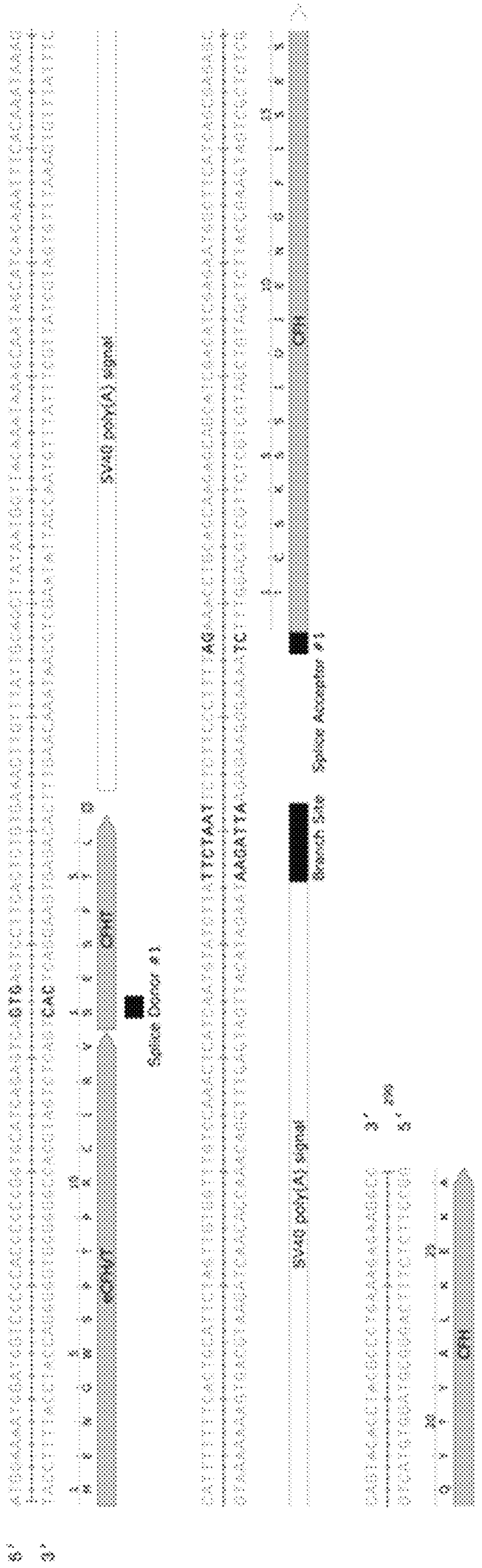

FIG. 15 shows key features of v4.3 eCFH/T construct at CFHT and CFH splicing junction. In v4.3 the SFTL C-terminus of CFHT is encoded without the need for a splicing event and the small transcript terminates with an SV40 poly(A) signal. A modified splice donor site (GTG) has been added that requires two additional amino acid residues (SE) prior to SFTL C-terminus of CFHT. The larger CFH transcript is generated using the highlighted splice donor #1 (GTG) and downstream highlighted splice acceptor #1 (AG) that removes the CFHT C-terminal tail and SV40 poly(A) signal) and terminates with an HSV TK poly(A) signal (not shown in this figure). A consensus branch site has been included in this construct to increase efficiency of splicing.

Figure 16:
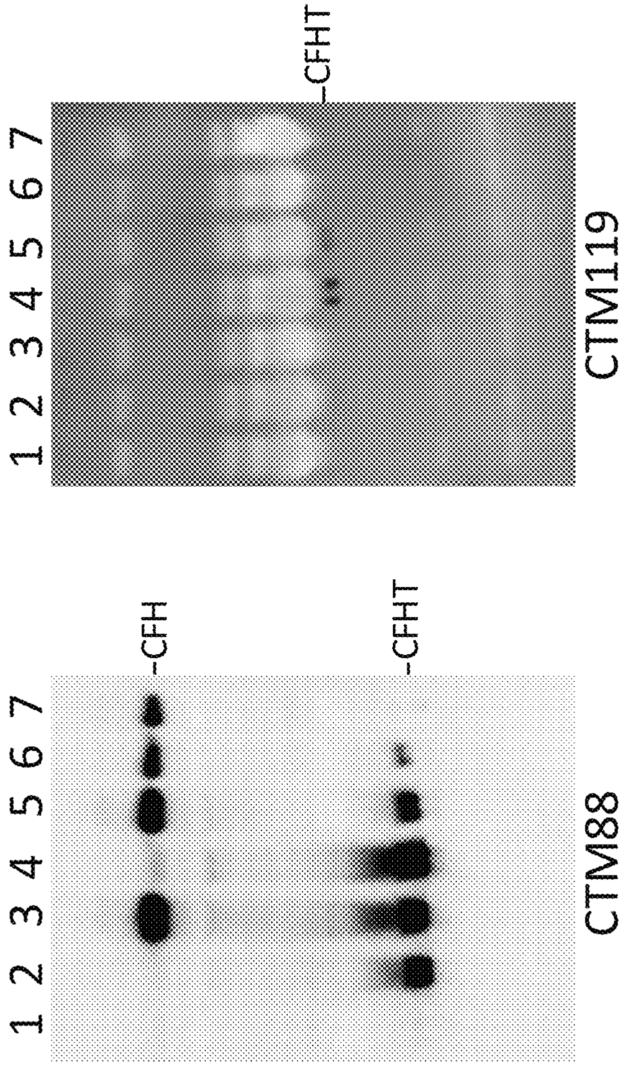

FIG. 16 shows protein expression of CFH, CFHT and eCFHT protein in RPE1 cells transfected with mammalian pcDNA3.1-based transgene expression plasmids (lane 2 and 7) and eCFH/T co-expression plasmids (lane 3-6) as determined by Western blot. The aCTM88 antibody detects an epitope in SCR2 (exon 3-4) in both CFH and CFHT proteins. The aCTM119 antibody was designed to specifically detect the C-terminal SFTL residues of CFHT protein.

Figure 17:
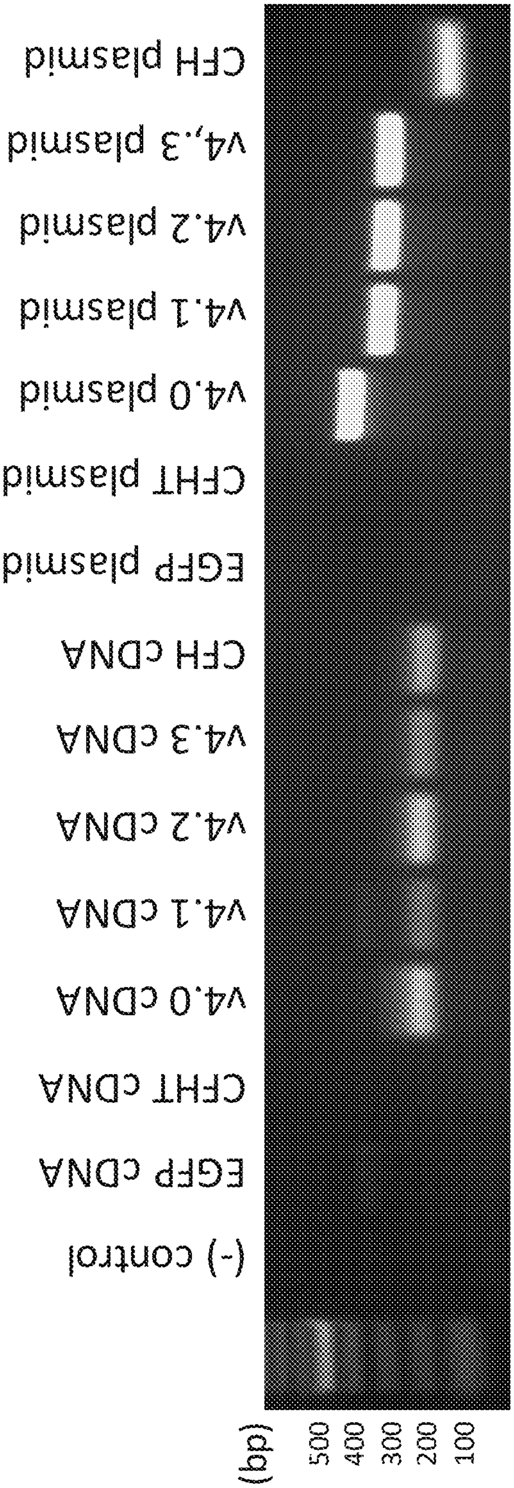

FIG. 17 shows RT-PCR products of CFH transgene expression in RPE1 cells transfected with eCFH/T plasmids and plasmid DNA constructs for confirmation of transgene splicing.

Figure 18:
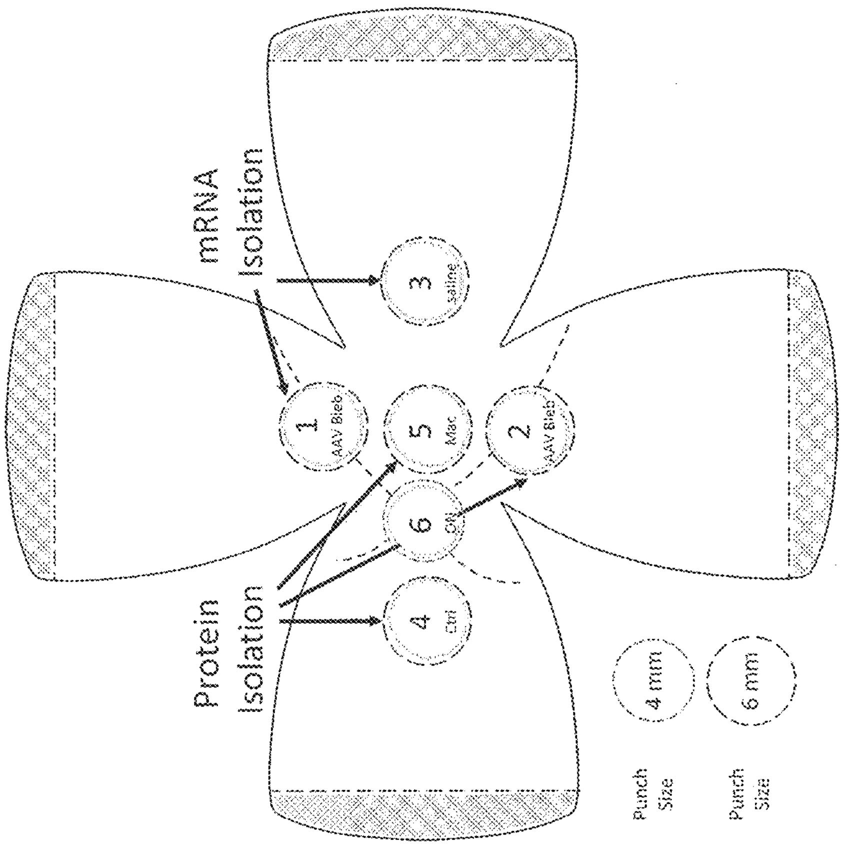

FIG. 18 shows the dissection strategy and tissue collection for OD eye.

Figure 19:
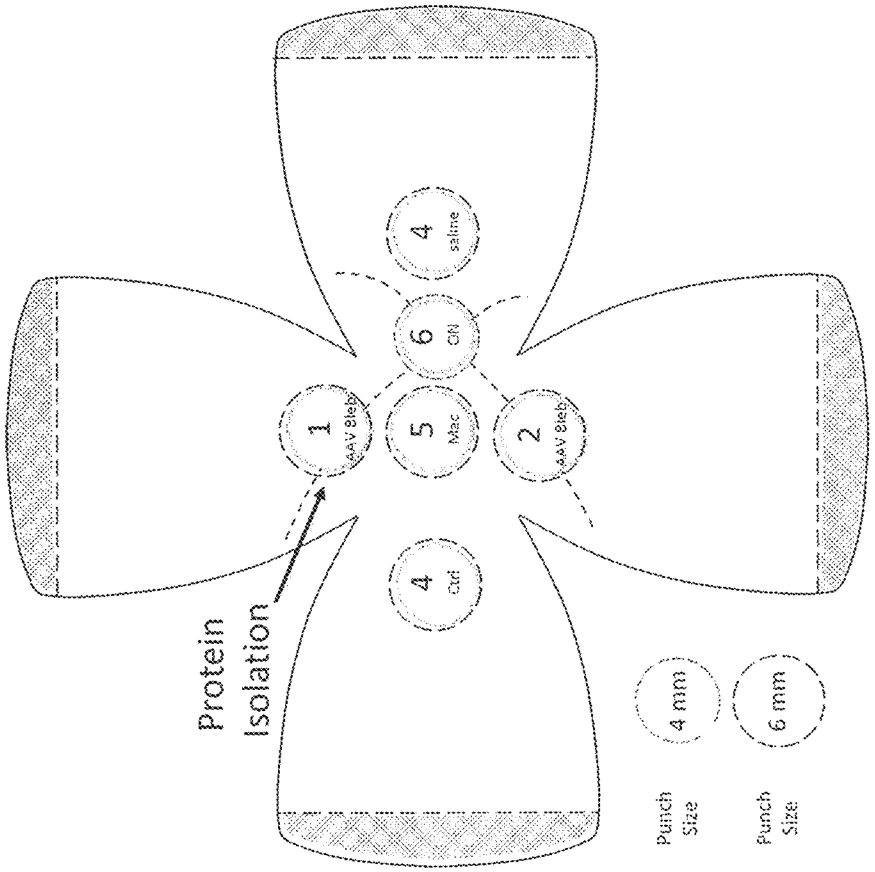

FIG. 19 shows the dissection strategy and tissue collection for OS eye.

Figure 20:
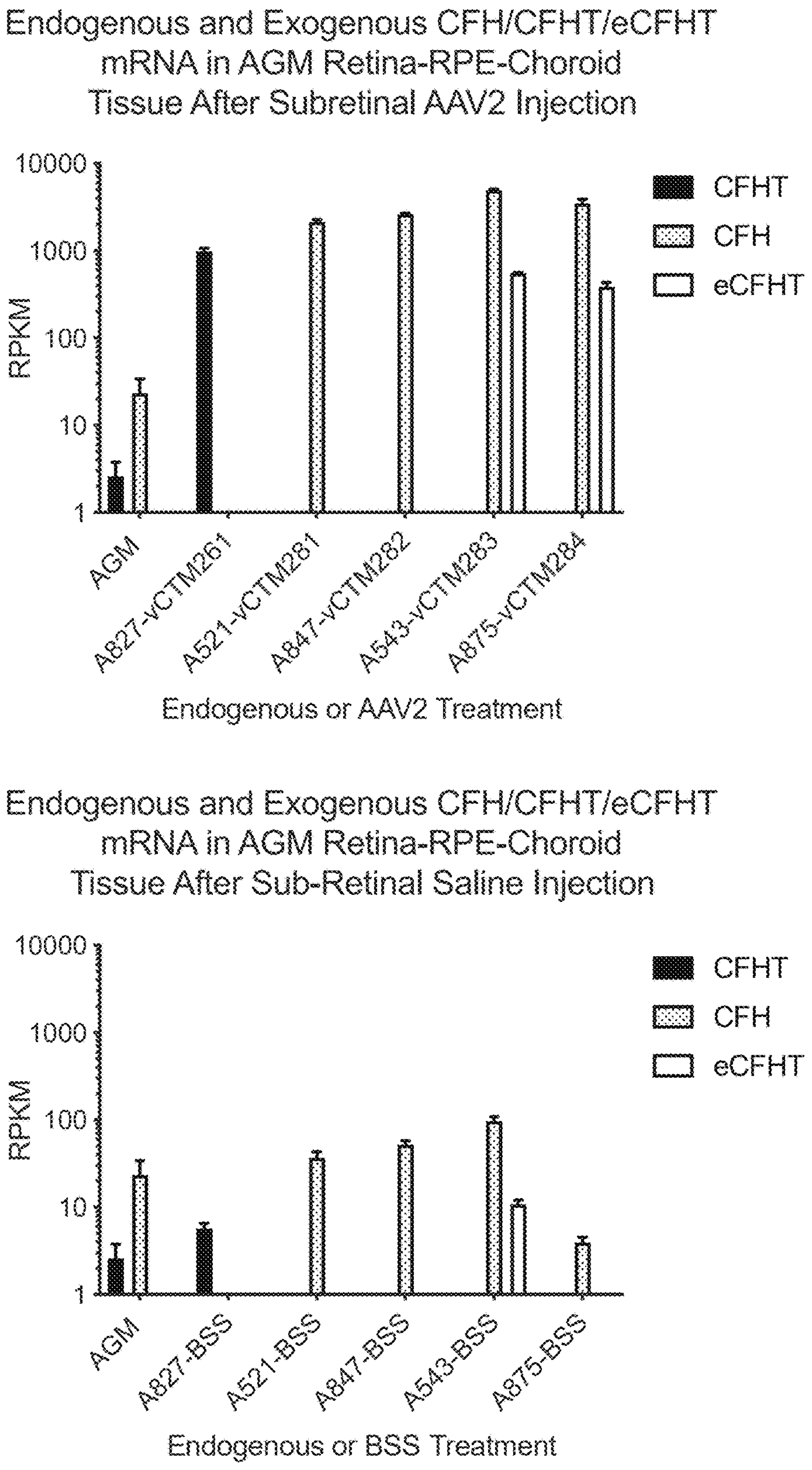

FIG. 20 shows normalized CFH/CFHT RPKM reads counts for endogenous African green monkey (AGM) retina-RPE-choroid tissue. Bleb read counts for CFHT, CFH and eCFHT after subretinal delivery of rAAV2 (top panel) and saline (bottom panel) treated eyes.

Figure 21:
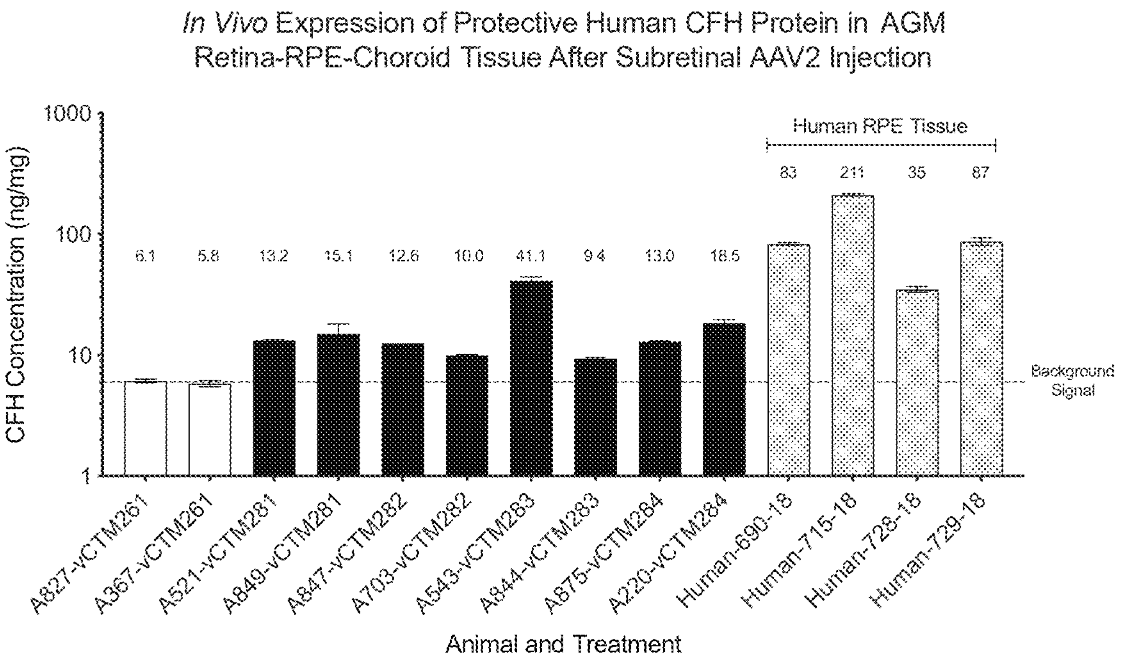
Figure 21:
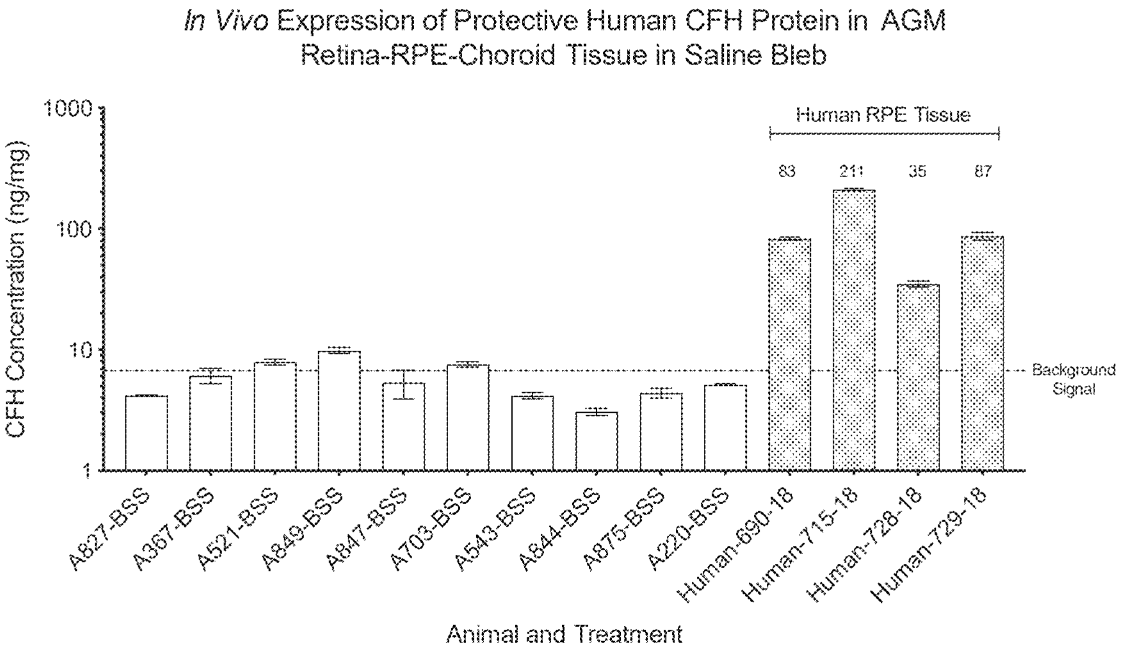

FIG. 21 shows human CFH protein concentration, detected by ELISA, in AGM retina-RPE-choroid (RRC) tissue isolated from rAAV2 bleb #2 (top) and nasal control #4 punch (bottom). Punches from all 10 treated monkeys are shown with average, standard deviation and background signal for the CFH ELISA (dotted line). Four human donor RRC samples are also shown with average and standard deviation for comparison. Concentration of CFH protein detected from RRC tissue is shown above bars (top) and estimated concentration of RPE-specific CFH protein inside the hashed region.

Figure 22:
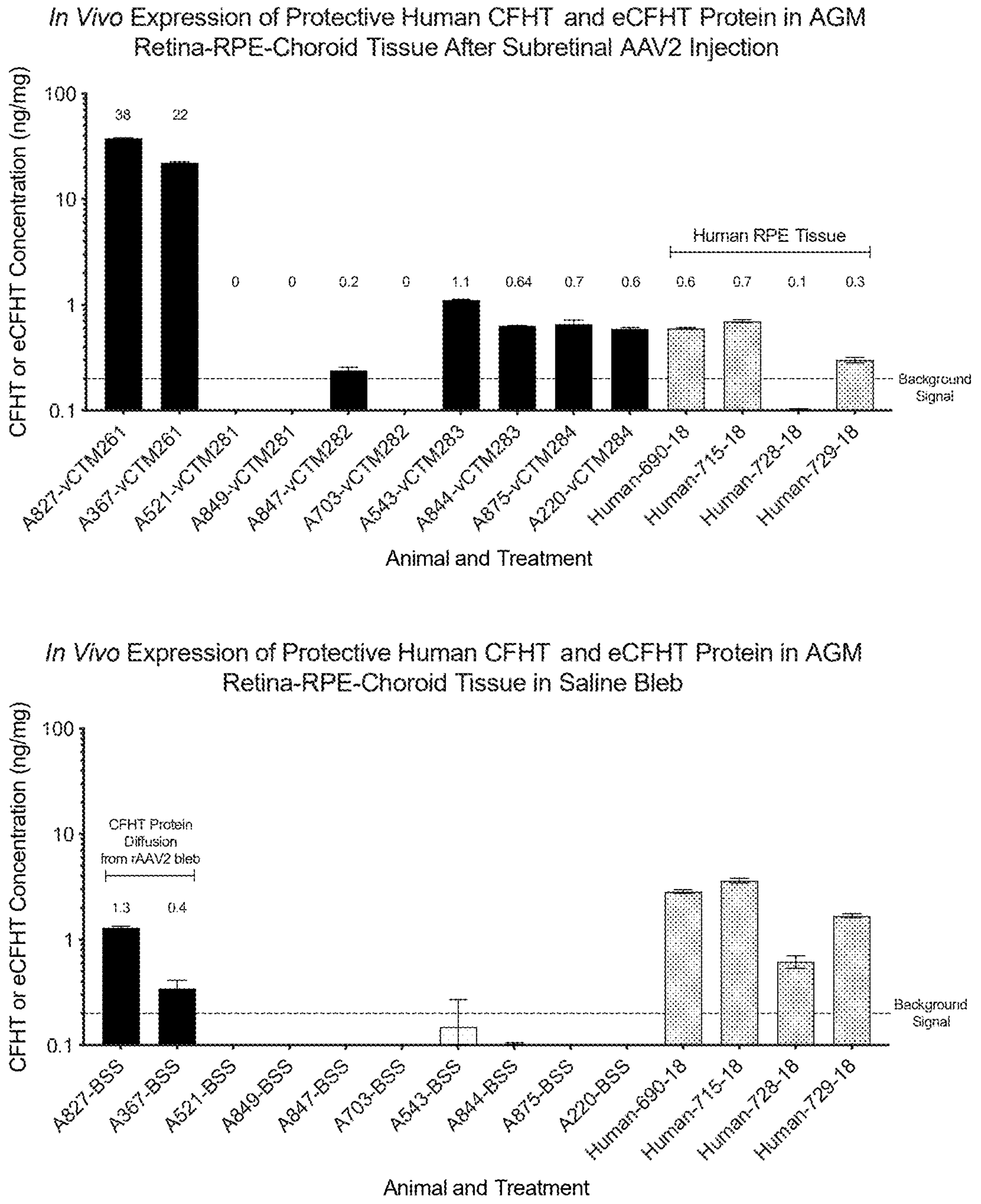

FIG. 22 shows human CFHT protein concentration, detected by ELISA, in AGM retina-RPE-choroid (RRC) tissue isolated from rAAV2 bleb #2 (top) and nasal control #4 punch (bottom). Punches from all 10 treated monkeys are shown with average, standard deviation and background signal for the CFHT ELISA. Four human donor RRC samples are also shown with average and standard deviation for comparison. Concentration of CFHT protein detected from RRC tissue is shown above the bars (top) and estimated concentration of RPE-specific CFH protein inside the bars.

Figure 23:
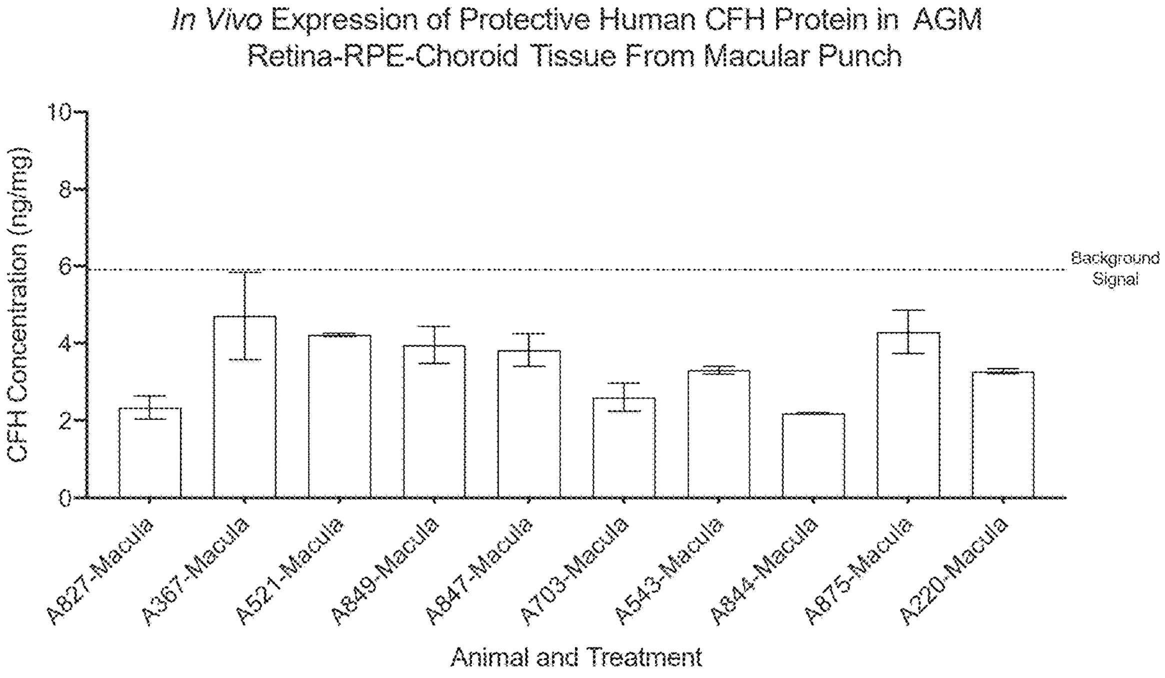
Figure 23:
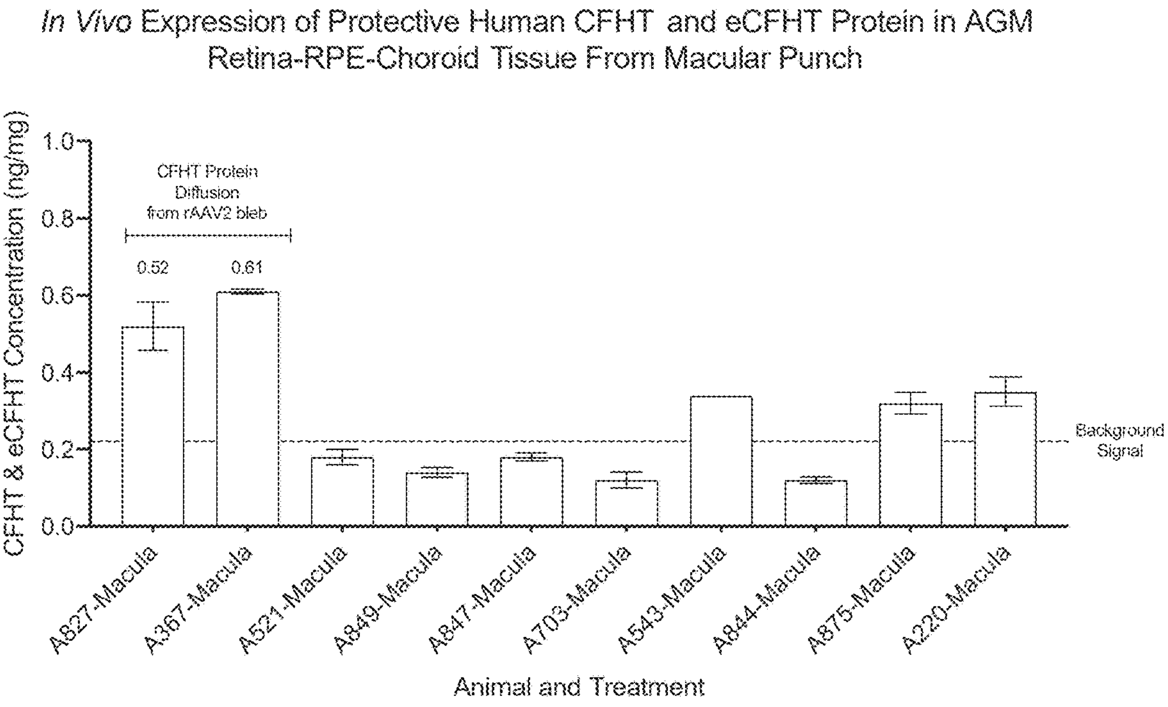

FIG. 23 ELISA detection of exogenous protective human CFH (top) and CFHT (bottom) protein concentration in AGM retina-RPE-choroid (RRC) tissue isolated from macula #5 punch. Punches from all 10 treated monkeys are shown with average, standard deviation and typical background signal for CFH and CFHT ELISA formats (dotted line).

Figure 24:
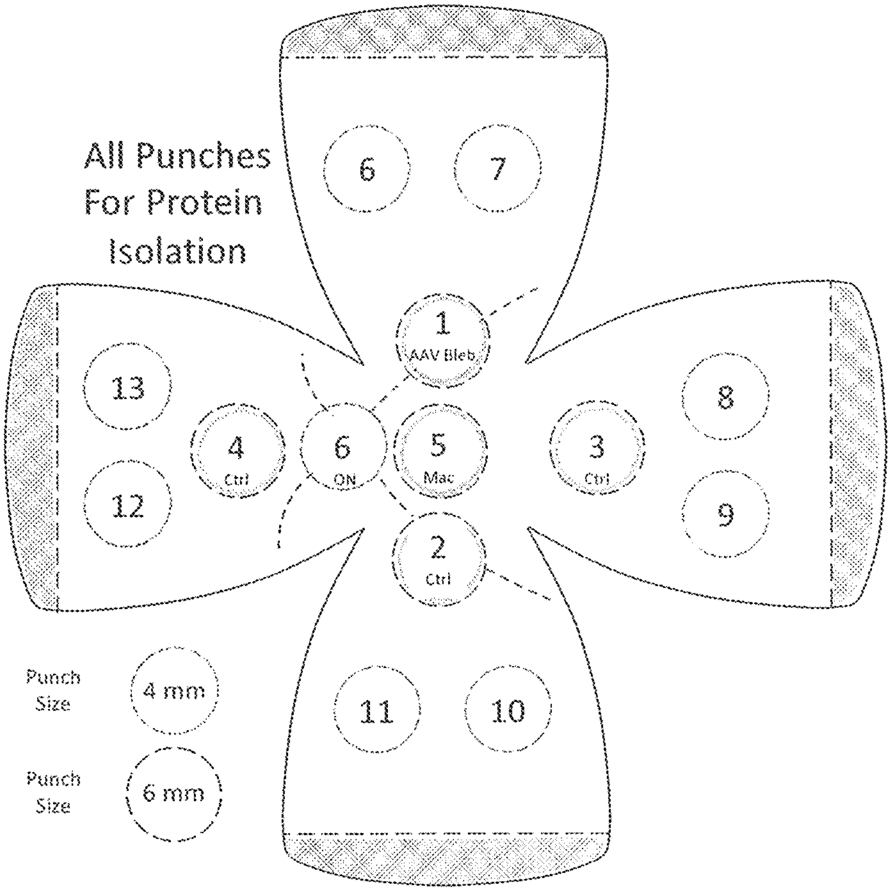

FIG. 24 shows a schematic of AGM eye with location and number of retinal-RPE-choroid (RRC) punches collected. OS and OD eyes were treated and processed similarly.

Figure 25:
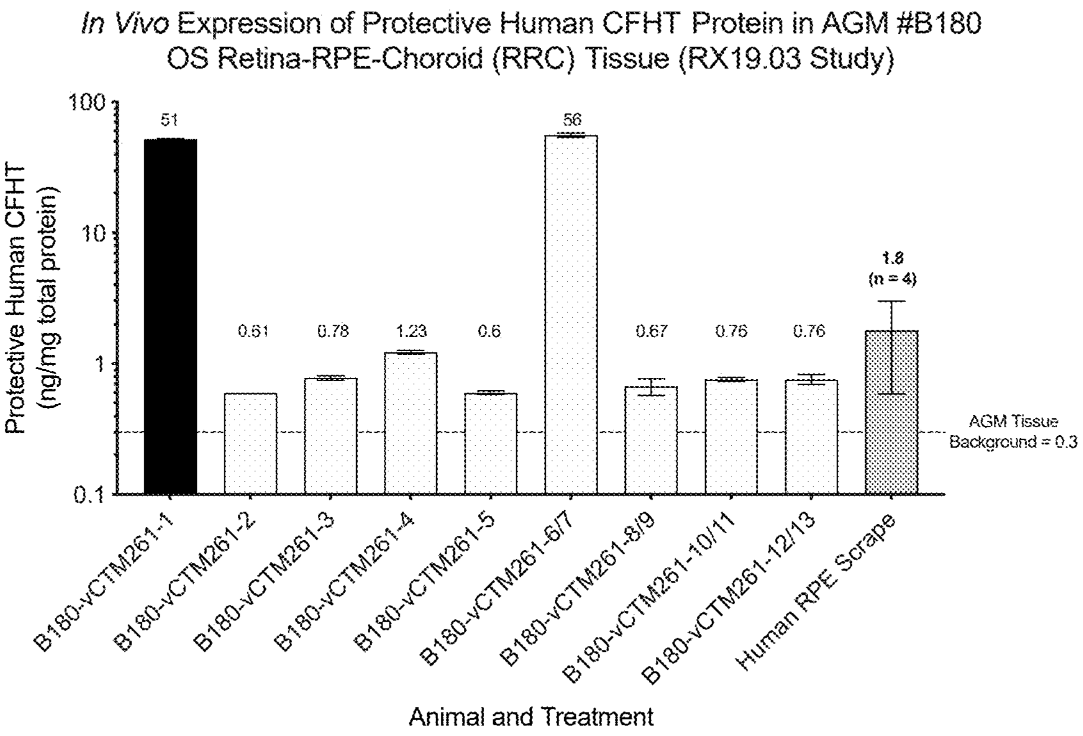
Figure 25:
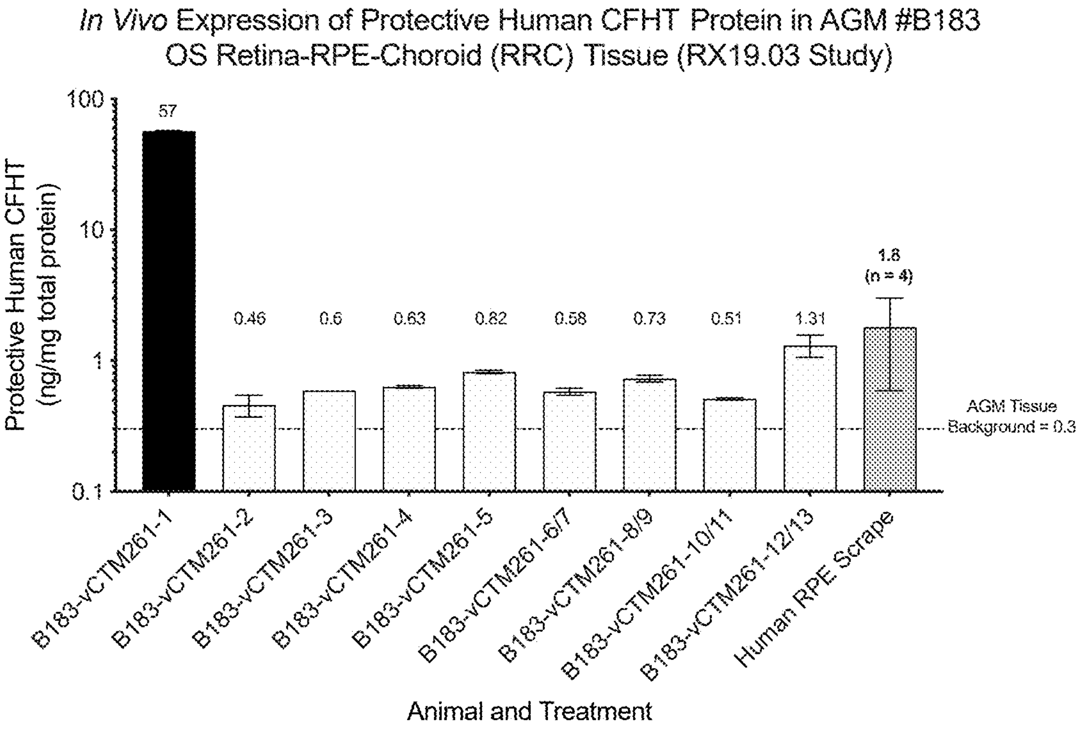

FIG. 25 shows CFHT ELISA results from retinal-RPE-choroid (RRC) tissue expression of AAV2 delivered CFHT protein using vCTM261. The top panel is animal B180 and the bottom panel is B183.

Figure 26:
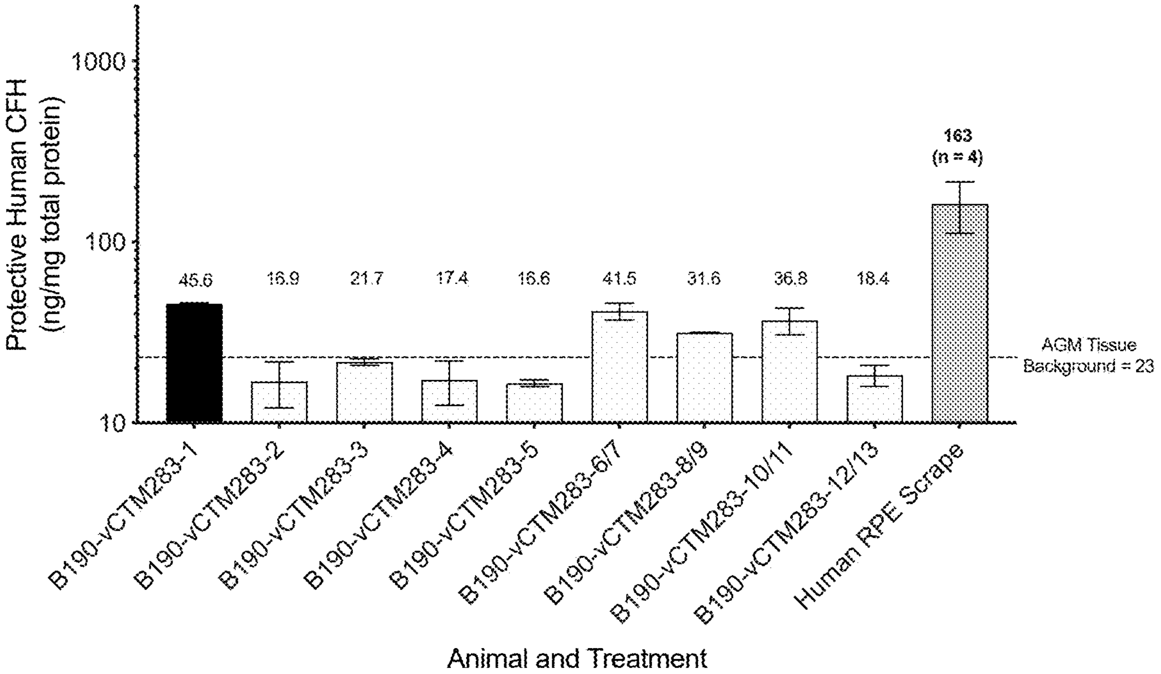
Figure 26:
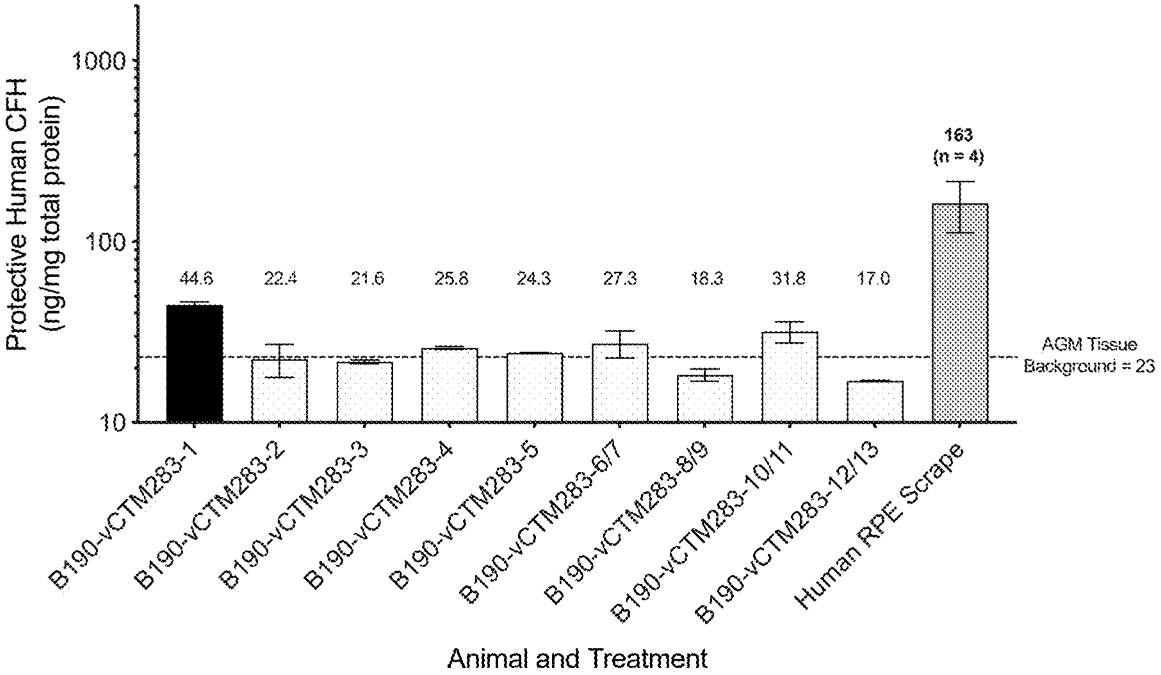

FIG. 26 shows CFH ELISA results for retinal-RPE-choroid (RRC) tissue expression of AAV2 delivered CFH and engineered CFHT protein using vCTM283. Top panel is animal B190 and bottom panel is B193.

Figure 27:
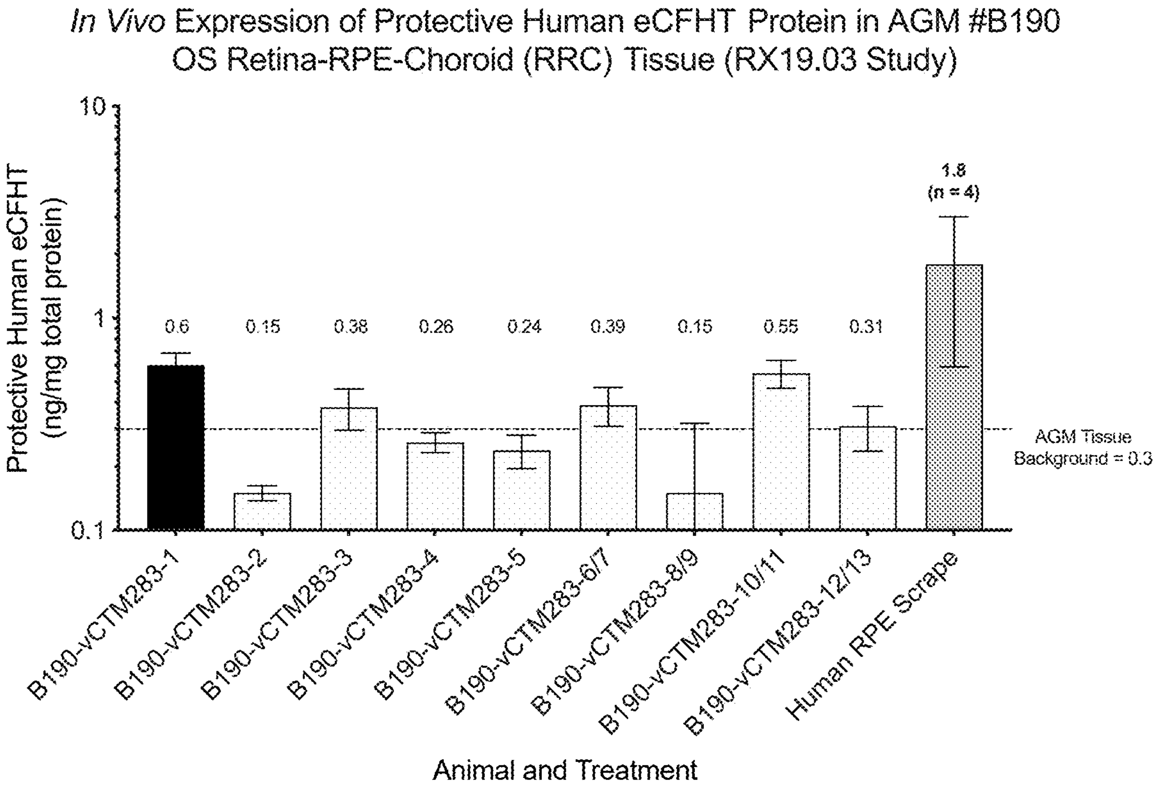
Figure 27:
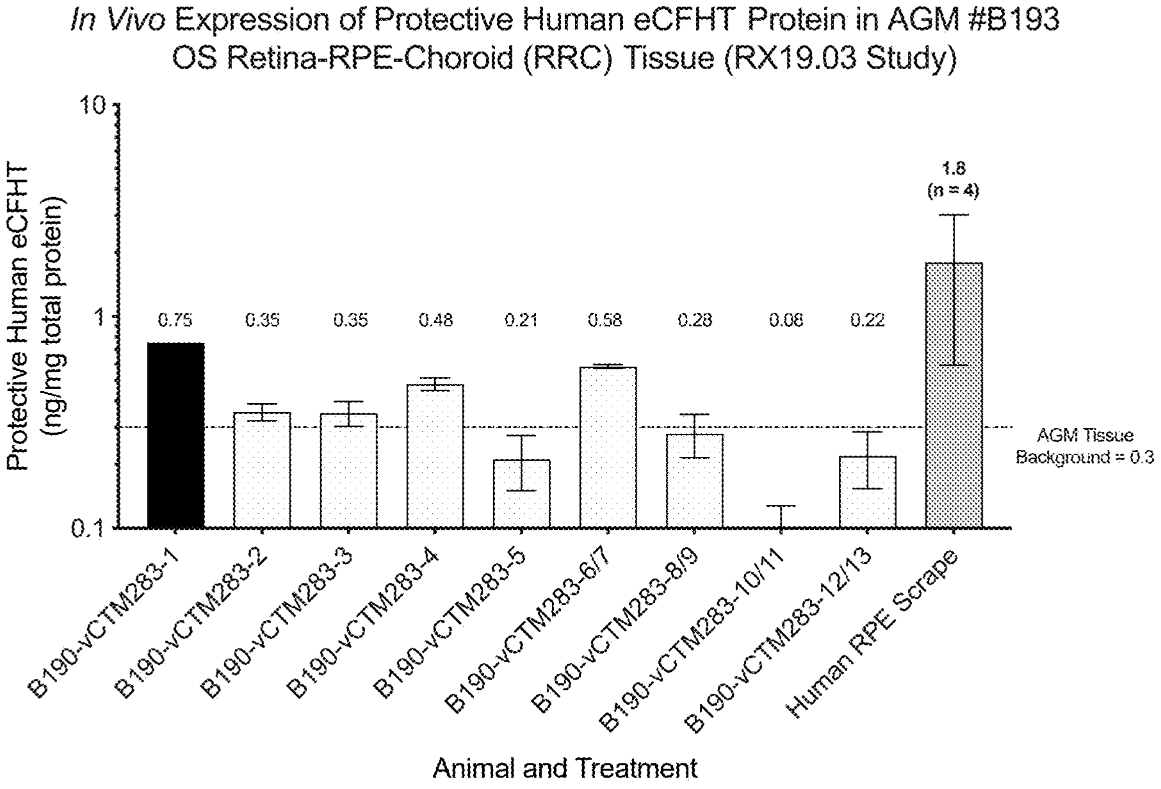

FIG. 27 shows eCFHT ELISA results for retinal-RPE-choroid (RRC) tissue expression of AAV2 delivered CFH and engineered CFHT protein using vCTM283. The top panel is animal B190 and the bottom panel is B193.

DETAILED DESCRIPTION OF THE INVENTION

1. Definitions & Conventions

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

As is discussed herein below, the human complement factor H gene is located on Chromosome 1 and encodes two proteins: A full-length complement factor H protein and a truncated complement factor H protein. As discussed hereinbelow, the Applicant has also designed and expressed a synthetic variant of the truncated complement factor H protein. For purposes of clarity the following conventions are used in this disclosure:

- "CFH" refers to the naturally occurring full-length form of human complement factor H protein, variants thereof, nucleic acid sequences encoding CFH protein, and expression systems for expressing CFH protein;
- "CFHT" refers to the naturally occurring truncated form of human complement factor H protein, variants thereof, nucleic acid sequences encoding CFHT protein and expression systems for expressing CFHT protein. The sequence at the carboxy terminus of naturally occurring CFHT is "CIRVSFTL" [SEQ ID NO:24].
- "CFH/T" refers to an expression system (e.g., a transgene and operably linked promoter) for co-expressing CFH and CFHT proteins;
- "eCFHT" refers to a non-naturally occurring truncated form of complement factor H protein comprising the sequence CIRVSKSFTL [SEQ ID NO:25] at the carboxy-terminus of the protein.
- "eCFH/T" refers to recombinant nucleic acids and expression systems (polynucleotide constructs) in which mRNAs transcripts encoding CFH and eCFHT are transcribed under control of a single promoter as a pre-mRNA. Alternate splicing of the pre-mRNA produces mRNAs encoding for CFH and eCFHT which are coexpressed to produce both proteins. In some embodiments eCFH/T transgene comprises SEQ ID NO:5.
- "FH" (or Factor H) refers generically to sequences and expression systems encoding CFH protein alone, CFHT protein alone, and CFH protein along with either of CFHT protein or eCFHT protein, and includes CFH, CFHT, eCFHT and eCFH/T, as will be apparent from context.

CFH [SEQ ID NO:2], CFHT [SEQ ID NO:4], and eCFHT [SEQ ID NO:6], are translated preproteins that comprise a 18 residue signal peptide [SEQ ID NO:23] which is cleaved to produce mature CFH [SEQ ID NO:20], CFHT [SEQ ID NO:21], eCFHT [SEQ ID NO:22]. Each reference herein to a preprotein sequence, unless otherwise clear from context, should be read as a recitation of both the preprotein and the mature protein sequences.

Selected CFH sequences are described below:

| SEQ ID Sequence length | | | |
|---|---|---|---|
| DNA | Protein | Mature Protein | Description |
| 1<br>3696n | 2<br>1231aa | 20<br>1213aa | CFH -- Naturally occurring full-length. The mature protein comprises residues 19-1231 of SEQ ID NO: 2. |
| 3<br>1350n | 4<br>449aa | 21<br>431aa | CFHT -- Naturally occurring truncated ending CIRVSFTL. The mature protein comprises residues 19-1449 of SEQ ID NO: 4. |
| | 6<br>451aa | 22<br>433aa | eCFHT - Protein -- Non-naturally occurring truncated ending in CIRVSKSFTL. The mature protein comprises residues 19-451 of SEQ ID NO: 6. |
| 5<br>3860n | | | eCFH/T -- DNA -- encodes naturally full-length CFH and engineered truncated CFHT (e.g., ending in CIRVSKSFTL). SEQ ID NO: 5 = V4.2. |

In the scientific literature the full-length CFH form is also referred to as Factor H, ARMS1, HF1, HF2 or HF. The truncated (CFHT) form is also referred to as Factor H Like-1 (FHL-1). Unless otherwise indicated, FH protein sequences are human sequences or variants thereof. CFH/T is used herein as a generic term for non-naturally occurring construct expressing both full length and any version of truncated (encodes, e.g., SEQ ID Nos:2+6 or 2+4 or 2+v4.0, 4.1, 4.3).

It will be appreciated that the terminology above is not intended to be limiting, and that in each case above in which a sequence identifier is recited it is contemplated that variants (such as substantially identical variants) may also be used.

As used herein the term "polynucleotide construct" refers to a recombinant nucleic acid sequence comprising one or more protein-encoding nucleic acid sequences operably linked to one or more promoters and optionally other specified components.

As used herein the term, "transgene" refers to a recombinant polynucleotide construct that can be introduced into a cell using a gene therapy vector, to result in expression in the cell of one or more proteins. As discussed below, exemplary FH transgenes of the invention comprise a sequence encoding CFH, CFHT, eCFHT, or a combination of full-length and truncated forms. As used herein, a transgene may include regulatory sequences controlling expression of the encoded protein(s) (for example, one or more of promoters, enhancers, terminator sequences, polyadenylation sequences, and the like), mRNA stability sequences (e.g. Woodchuck Hepatitis Virus Posttranscriptional Regulatory Element; WPRE), sequences that allow for internal ribosome entry sites (IRES) of bicistronic mRNA, sequences necessary for episome maintenance (e.g., ITRs and LTRs), sequences that avoid or inhibit viral recognition by Toll-like or RIG-like receptors (e.g. TLR-7, -8, -9, MDA-5, RIG-I and/or DAI) and/or sequences necessary for transduction into cells.

As used herein, "gene therapy vector" refers to virus-derived sequence elements used to introduce a transgene into a cell.

As used herein, "a viral vector" refers to a gene therapy vector including capsid proteins, used to deliver a transgene to a cell.

As used herein, the terms "promoter" and "enhancer promoter" refers to a DNA sequence capable of controlling (e.g., increasing) the expression of a coding sequence or functional RNA. A promoter may include a minimal promoter (a short DNA sequence comprised of a TATA-box and other sequences that serve to specify the site of transcription initiation). An enhancer sequence (e.g., an upstream enhancer sequence) is a regulatory element that can interact with a promoter to control (e.g., increase) the expression of a coding sequence or functional RNA. As used herein, reference to a "promoter" may include an enhancer sequence. An enhancer does not need to be contiguous with a promoter or coding sequence with which it interacts.

Promoters, enhancers and other regulatory sequences are "operably linked" to a transgene when they affect to the expression or stability of the transgene or a transgene product (e.g., mRNA or protein).

As used herein, the terms "introduce" or "introduced," in the context of gene therapy refers to administering a composition comprising a polynucleotide (DNA) encoding a Factor H (FH) polypeptide to a cell, tissue or organ of a patient under conditions in which polynucleotide enters cells and is expressed in the cells to produce proteins. Polynucleotides may be introduced as naked DNA, using a viral (e.g., AAV2) vector, using a non-viral vector system, or by other methods.

The term "corresponds to" and grammatical equivalents is used herein to refer to positions in similar or homologous protein or nucleotide sequences, whether the exact position is identical or different from the molecule to which the similarity or homology is measured. For example, given a first protein 100 residues in length and a second protein that that is identical to the first protein except for a deletion of 5 amino acids at the amino terminus, position 12 of the first protein will "correspond" to position 7 of the second protein.

"Adeno-associated virus 2 (AAV2)" and "recombinant Adeno-associated virus 2 (rAAV2) are used equivalently. Exemplary AAV2 vectors are derived from the adeno-associated virus 2 genome and are described extensively in the scientific literature. See, e.g., Srivastava et al., 1983, *J. Virol.* 45:555-564, incorporated herein by reference and other references cited herein below.

"Lentivirus," as used herein refers to a gene therapy vector (lentiviral vector) that may be used to transduce a transgene into a cell. See, e.g., Keeker et al., 2017, *Clin Transl Sci.* 10:242-248, incorporated herein by reference and other references cited herein below.

The terms "identical" or percent "identity," in the context of two or more nucleic acids or polypeptide sequences, refer to two or more sequences or subsequences that are the same ("identical") or have a specified percentage of amino acid residues or nucleotides that are the same (i.e., at least about 70% identity, at least about 75% identity, at least about 80% identity, at least about 90% identity, preferably at least about 91%, 92%, 93%, 94%, 95%, 96%, 97%, 98%, 99%, or higher identity) when aligned over the entire sequence of a specified region, when compared and aligned for maximum correspondence over a comparison window or designated region as measured by manual alignment and visual inspection or using a BLAST or BLAST 2.0 sequence comparison algorithms with default parameters described below (see, e.g., NCBI web site ncbi.nlm.nih.gov/BLAST/ or the like)). Such sequences are then said to be "substantially identical."

As described below, the preferred algorithms can account for gaps and the like. Preferably, identity exists over a region that is at least about 25 amino acids or nucleotides in length, or more preferably over a region that is 50-100 or more amino acids or nucleotides in length. For sequence comparison, typically one sequence acts as a reference sequence, to which test sequences are compared. In some approaches a percentage identity is determined in relation to the full length of a reference sequence selected from SEQ ID NOs:2, 4, 6, or 20-25 (amino acid sequences) or SEQ ID NOs:1, 3, 5, 8-19, 26-29, or 34-37 (nucleotide sequences). When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters. A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Moth.* 2:482 (1981), by the homology alignment algorithm of Needleman & Wunsch, *J. Mol. Biol.* 48:443 (1970), by the search for similarity method of Pearson & Lipman, Proc. *Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)). An algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., J. Mol. Biol. 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (www.ncbi.nlm.nih.gov/). This algorithm involves first identifying high scoring sequence pairs (HSPs) by identifying short words of length within the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Variants" applies to both amino acid and nucleic acid sequences. As to non-coding nucleotide sequences (e.g., sequences of regulatory elements such as promoters, enhancers, polyadenylation signals and the like) it is well known that a sequence variation is tolerated without a diminution of function (e.g., without loss of promoter function). A variant sequence is typically at last 80% identical to the reference sequence, sometimes at least about 85% identical, sometimes at least about 90% identical, at least about 91%, 92%, 93%, 94%, 95%, 96%, 97%, 98%, 99% identical and retains the function of the reference sequence.

"Conservatively modified variants" applies to both amino acid and nucleic acid sequences. As to amino acid sequences, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. The following six groups each contain amino acids that are conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W).

Numerous "polymorphic forms" of human FH proteins are known. In some embodiments the FH transgenes of the invention express proteins with one or more polymorphic variations relative to the reference sequences provided herein. It will be apparent to those of skill in the art that certain polymorphisms (e.g., R1210C) are associated with risk of disease, especially AMD, and are therefore detrimental in humans while others are non-detrimental. In some embodiments the transgenes of the invention encode variant FH proteins comprising one or more non-detrimental polymorphisms.

As used herein the deletion in the CFHR3 and CFHR1 genes associated with reduced risk of developing AMD may be referred to as "CFHR3/1 deletion" or, equivalently, "CFHR3,1 deletion."

"Bruch's membrane" refers to a layer of extracellular matrix (ECM) under between the human retinal pigment epithelium and choriocapillaris.

"Drusen" are small focal extracellular deposits comprising lipids, fluid, a variety of proteins including complement pathway-related proteins, located between the RPE basal lamina and Bruch's membrane. Drusen are visible ophthalmoscopically as white/yellow dots and can be detected using a variety of art-known methods including those described in Wu et al., 2015, "Fundus Autofluorescence Characteristics of Nascent Geographic Atrophy in Age-Related Macular Degeneration" *Invest Ophthalmol Vis Sci.* 56:1546-52 and in References 1-8 of that reference. As used herein, the terms "small drusen" and "small hard drusen" refer to distinct drusen with a diameter less than about 63 μm. The terms "large drusen," "soft drusen," and "large soft drusen" refer to drusen with a diameter greater than about 125 μm, which are often clustered. Drusen with a diameter between 63 and 125 μm can be referred to as "intermediate drusen."

As used herein, the term "endogenous" refers to a native CFH gene in its natural location in the genome or pre-mRNA, mRNA or protein expressed from an endogenous gene.

"ARMS2" refers to the AMD susceptibility 2 gene.

"HTRA1" refers to the HtrA serine peptidase 1 gene.

"Macula" has its normal meaning in the art and is an oval-shaped pigmented area near the center of the retina of the human eye, having a typical diameter of around 5.5 mm.

"Fovea" or "fovea centralis" has its usual meaning in the art and refers to has its normal meaning in the art and refers to a small, central pit composed of closely packed cones in the eye. It is located in the center of the macula lutea of the retina. The diameter of the fovea in human adults is about 1.5 mm.

The term "treatment" or any grammatical variation thereof (e.g., treat, treating, treatment, etc.), as used herein, includes but is not limited to, alleviating a symptom of a disease or condition; and/or reducing, suppressing, inhibiting, lessening, ameliorating or affecting the progression, severity, and/or scope of a disease or condition.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

2. Overview of Chromosome 1—and Chromosome 10-Directed AMD

Age-related macular degeneration (AMD) is progressive, degenerative chorioretinal degenerative disease that affects the central region of the retina known as the macula. AMD is commonly perceived as a single disease that can progress from early stage disease to late stage "wet AMD" or "dry/atrophic AMD." See Toomey et al., 2018, "Complement Factor H in Amd: Bridging Genetic Associations and Pathobiology" *Progress in Retinal and Eye Research* 62:38-57, incorporated herein by reference. Dry AMD is characterized by the development of drusen and retinal pigment epithelial (RPE) changes early in the disease course, and with loss of RPE and associated severe vision loss in advanced disease. Wet AMD is characterized by choroidal neovascularization (CNV) causing central vision loss from macular exudation.

Based on extensive genotyping studies of AMD patients it is now understood that AMD includes two distinct biological diseases: Chromosome 1-directed AMD (or "Chr 1 AMD"), which results from dysregulation of the complement system, including complement factor H dysregulation, and chromosome 10-directed AMD (or "Chr 10 AMD"), which is associated with genetic lesions in chromosomal region 10q26, which harbors the ARMS2 and HTRA1 genes. See Keenan et al, 2015, "Assessment of Proteins Associated with Complement Activation and Inflammation in Maculae of Human Donors Homozygous Risk at Chromosome 1 CFH-TO-F13B" *Invest Ophthalmol Vis Sci.* 56:487- 79; Hageman, 2015, "Methods of Predicting the Development of Amd Based on Chromosome 1 AND Chromosome 10" US Pat. Pub. 2015/0211065, both incorporated herein by reference. Risk variants/haplotypes in chromosome 1 and chromosome 10 loci together account for approximately 95 percent of AMD risk in Caucasian cohorts. As discussed herein below, an individual may be identified, based on genetic factors alone, as being at elevated risk for developing Chromosome 1-directed AMD and/or Chromosome 10-directed AMD.

The clinical phenotypes of Chr 1 AMD and Chr 10 AMD are also distinct. Chr 1 AMD patients primarily display "occult" disease with mild or no abnormal blood vessels (choroidal neovascularization, or CNV) growing under the retina and macula. Chr 1 AMD patients have large soft drusen (SD) and pigment epithelium detachment (PED), subretinal and sub-RPE fluid, geographic atrophy (GA) secondary to "atrophic" PEDs, a slow GA growth rate, and thick retina. In contrast, Chr 10 AMD patients display classic CNV and retinal angiomatous proliferation (RAP), often resulting in severe, rapid visual loss. They have few drusen (drusen are small and hard), intra-retinal fluid (cysts), a fast GA growth rate, and retinal/choroidal thinning.

Chr1-directed AMD is characterized by significantly higher levels of total MAC (C5b-9) at the RPE-choroid interface, as compared to levels at the RPE-choroid interface in homozygous CFH protective donors. Membrane-intercalated—as compared to soluble—levels of MAC are significantly higher in RPE cell membranes (~10:1), as compared to choroidal cell membranes (~1:10), leading to exacerbated RPE dysfunction and death. These data suggest that the basal surface of the RPE is the primary site of Chr1-directed AMD pathology and that risk CFH/FHL-1 variant proteins are not appropriately regulating complement activation at this interface. These data suggest that protective forms of CFH and/or CFHT should be administered to the basal RPE region.

The polynucleotide constructs and vectors disclosed herein encoding protective FH proteins prevent or ameliorate AMD or AMD development in patients with Chromosome 1-directed disease or risk of developing Chromosome 1-directed disease, including patients with risk factors for both Chromosome 1-directed disease and Chromosome 10-directed disease.

3. Patients with Chromosome 1-Directed Disease Risk and/or Chromosome 10-Directed Disease Risk As noted above, the polynucleotide constructs and vectors disclosed herein encoding protective FH proteins prevent or ameliorate AMD or AMD development in patients with Chromosome 1-directed disease or risk of developing Chromosome 1-directed disease. In some approaches the patient has risk factors for both Chromosome 1-directed disease and Chromosome 10-directed disease and may have signs or symptoms for one or both diseases.

Figure 1A:
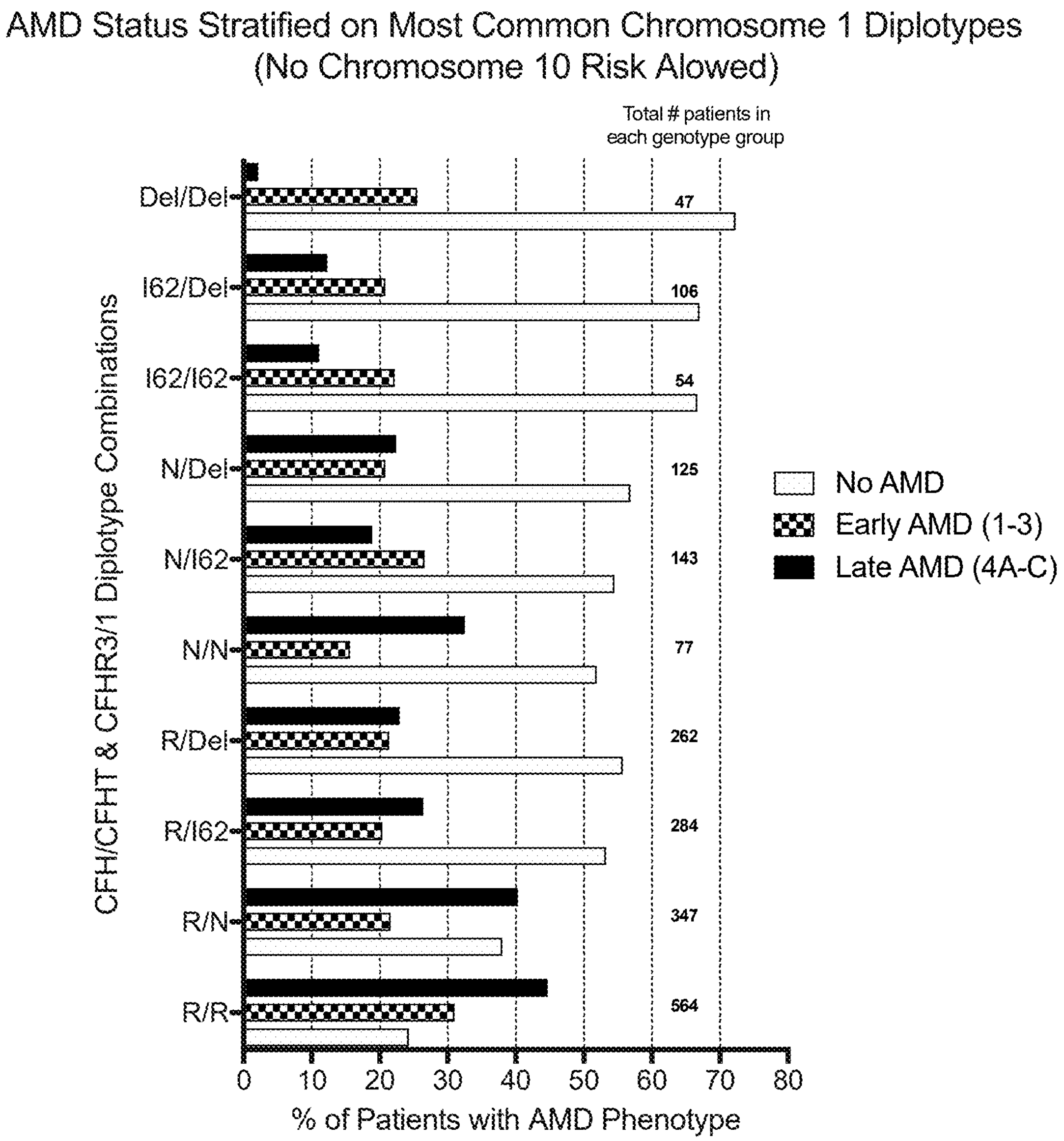
FIG. 1A shows AMD status stratified on the most common chromosome 1 diplotypes (in individuals with no chromosome 10 risk).
Figure 1B:
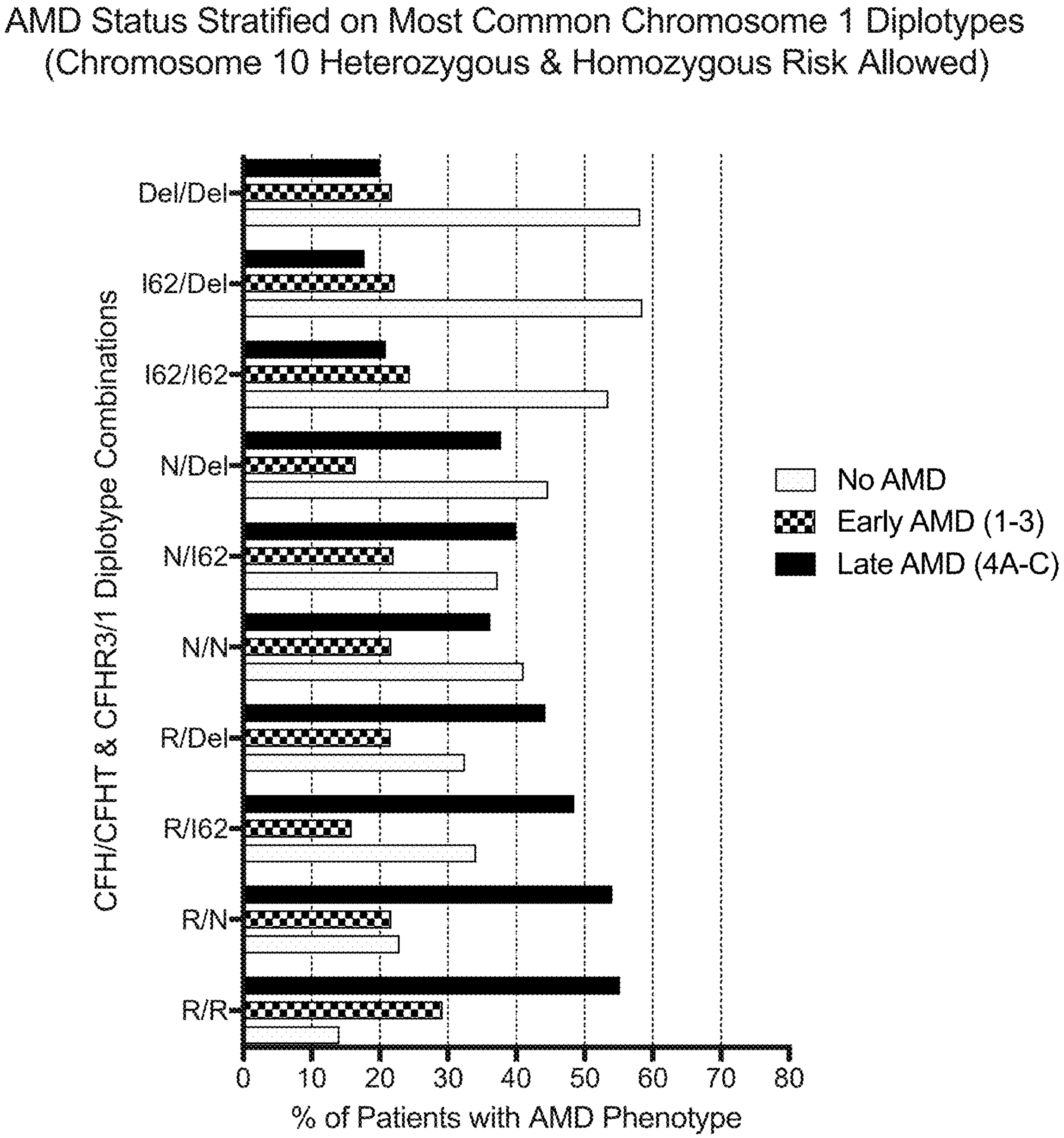
FIG. 1B shows AMD status stratified on the most common chromosome 1 diplotypes (chromosome 10 risk heterozygous and homozygous risk allowed).

As described in EXAMPLE 1, below, we have performed extensive genetic analyses of individuals at risk for developing Chromosome 1-directed AMD. TABLE 15 identifies 30 genetically defined groups of individuals groups according to genetic risk of developing AMD also see TABLE 16). Risk assessment is based on alleles present in or near the CFH locus (rs800292, rs1061170, and rs12144939/CFHR3/1 deletion) (see Hageman, U.S. Pat. No. 7,867,727 for a discussion of the CFHR ⅓ deletion associated with reduced risk of developing AMD) and in the Chromosome 10-directed locus (rs10490924). See FIGS. 1A and 1B show common chromosome 1 diplotypes in individuals with and without Chromosome 10 risk. As discussed below, a combination of genetic and phenotypic traits can be used to identify candidates for CFH gene therapy as well as the timing and course of treatment.

TABLE 1

Common AMD Haplotypes

| | CFH/CFHT Alleles | | | CFHR3/1 |
|---|---|---|---|---|
| | 62 | 402 | *936 | Status |
| Risk | V | H | E | Present |
| Neutral (Neu) | V | Y | D | Present |
| I62 | I | Y | E | Present |
| 3,1 Deletion (Del) | V | Y | E | Absent |

*Present in CFH protein only

In some embodiments a gene therapy treatment as disclosed herein is administered to a patient with elevated AMD risk defined by a chromosome 1 risk allele profile with no chromosome 10 risk. Individuals with a chromosome 1 risk allele profile with no chromosome 10 risk profile can be referred to as having "Pure Chromosome 1 Risk ("Pure Chr 1 risk")." Individuals with Pure Chr 1 risk exhibit significantly higher levels of the C3, C5b-9 membrane attack complex (MAC) and other complement components at the RPE/choroid interface and significantly higher levels of C5b-9 are exhibited in the RPE, sub-RPE space, Bruch's membrane, choriocapillaris (CC) and CC septa as compared to individuals homozygous for the protective I62/Y402 alleles. See Keenan et al, 2015, Assessment of Proteins Associated with Complement Activation and Inflammation in Maculae of Human Donors Homozygous Risk at Chromosome 1 CFH-TO-F13B, *Invest Ophthalmol Vis Sci.* 56:487-79. Moreover, significant amounts of C5b-9 are intercalated into RPE, and to a lesser extent, choroidal cell membranes. It is expected that treatment of such individuals according to the present invention will prevent, slow progression of, reverse or ameliorate symptoms and signs of Chromosome 1-directed disease.

In some approaches, a patient with a combination of both Chr 1 and Chr 10 risk factors is treated with the gene therapy of the present invention to prevent slow progression of, reverse or ameliorate symptoms and signs of Chromosome 1-directed disease.

In some approaches, a patient with a combination of both Chr 1 and Chr 10 risk factors is treated with the gene therapy of the present invention to prevent or ameliorate progression of symptoms and signs of Chromosome 1-directed disease, and a second agent is administered to the patient to prevent or ameliorate progression of Chr 10-directed AMD.

In some approaches the subject receiving therapy has a genetic profile shown in TABLE 15. In some approaches the subject receiving therapy has a genetic profile selected from those in TABLE 16. TABLE 2, below, provides a subset of risk profiles shown in TABLE 15.

TABLE 2

EXEMPLARY AMD RISK PROFILES

| | AMD Genetic Status | | AMD |
|---|---|---|---|
| Group | Chr 1 | Chr 10 | Odds Ratio |
| G1 | Risk/Risk | No Risk | 8.3 |
| G2 | Risk/Neut | No Risk | 4.5 |
| G3 | Risk/I62 | No Risk | 2.2 |
| G4 | Risk/3,1 del | No Risk | 2.1 |
| G11 | Risk/Risk | Het Risk | 19 |
| G12 | Risk/Neut | Het Risk | 9.7 |
| G13 | Risk/I62 | Het Risk | 5.7 |
| G14 | Risk/3,1 del | Het Risk | 5.7 |
| G21 | Risk/Risk | Homo Risk | 47 |
| G22 | Risk/Neut | Homo Risk | 41.4 |
| G23 | Risk/I62 | Homo Risk | 17.1 |
| G24 | Risk/3,1 del | Homo Risk | 22.3 |

In some embodiments the patient has a genetic profile selected from the group consisting of G1, G2, G3, G4, G11, G12, G13, G14, G21, G22, G23, and G24.

In some embodiments the patient has a genetic profile selected from the group consisting of G1, G2, G11, G12, G13, G14, G21, G22, G23, and G24.

In some embodiments the patient has a genetic profile selected from the group consisting of G1, G11, G12, G21, G22, G23, and G24.

In some embodiments the patient has a genetic profile selected from the group consisting of G11, G21, G22, G23, and G24.

In some embodiments the patient has a genetic profile G1. In some embodiments the patient has a genetic profile G2. In some embodiments the patient has a genetic profile G3. In some embodiments the patient has a genetic profile G4. In some embodiments the patient has a genetic profile G2. In some embodiments the patient has a genetic profile G13. In some embodiments the patient has a genetic profile G14. In some embodiments the patient has a genetic profile G1. In some embodiments the patient has a genetic profile G12. In some embodiments the patient has a genetic profile G11. In some embodiments the patient has a genetic profile G23. In some embodiments the patient has a genetic profile G24. In some embodiments the patient has a genetic profile G21. In some embodiments the patient has a genetic profile G22.

The genotypes (or "genetic profile) of a subject can be determined using art known methods including SNP analysis (e.g., using qPCR), protein analysis (e.g., using antibodies, mass spectrometry, activity assays, and the like), or whole exome/genome sequencing. It will be appreciated that, although TABLE 15 shows 30 genetic profiles, it is not necessary to actually assay or directly determine each SNP or other polymorphism to assign an individual to one of the groups G1-G30. For illustration, rs1061147 (A307A), a synonymous SNP in the FH gene, is in linkage disequilibrium with rs1061170. Thus, rs1061147 could be part of a panel assayed to identify Pure CHR1 risk patients.

In some embodiments a gene therapy treatment as disclosed herein is administered to a patient with elevated AMD risk defined by a chromosome 1 risk allele profile and a chromosome 10 risk allele. PCT patent publication Application WO 2014/043558; U.S. Pat. No. 7,745,389, Keenan et al, 2015, supra, each of which is incorporated herein by reference for all purposes, provide detailed descriptions of genetic markers on chromosome 1 and 10 that may be used to identify those at risk for developing Chr 1 and/or Chr 10 AMD. Persons of ordinary skill in the art guided by these and other publications, will have a variety of methods to identify patients heterozygous or homozygous for chromosome 1 risk factors (or risk haplotypes); and will be able to identify the subsets of such patients who are neither heterozygous nor homozygous for chromosome 10 risk factors (or risk haplotypes) (see EXAMPLE 1).

4. Protective CFH Transgenes and Proteins

4.1. Factor H Properties

Complement Factor H (FH) is a multifunctional protein that is a key regulator of the complement system. See Zipfel, "Complement Factor H: Physiology and Pathophysiology" *Semin Thromb Hemost.* 27:191-199, 2001. Biological activities of Factor H include: (1) binding to C-reactive protein (CRP) and pentraxin 3 (PTX3); (2) binding to C3b; (3) binding to heparin; (4) binding to sialic acid; (5) binding to all 'self' cell surfaces; (6) binding to cellular integrin receptors; (7) binding to pathogens, including microbes; (8) all 'self' extracellular matrices; (9) binding to adrenomedulin, (10) binding to oxidized lipids and proteins; (11) binding to cellular debris; (12) binding to CFI; (13) binding to C3 convertases; and (12) C3b co-factor activity. Binding and activity assays for Factor H activities are well known and include those described in herein below and in Hageman "Methods for Treatment of Age-Related Macular Degeneration" U.S. Pat. No. 7,745,389, 2005, sometimes referred to hereinafter as "Hageman '389."

Figure 2:
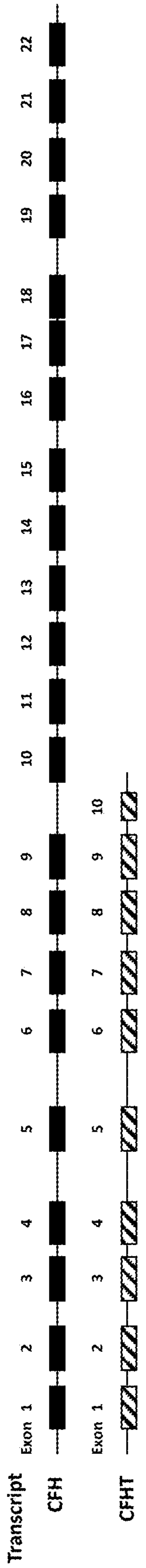
FIG. 2 shows the exon/intron structure of human Complement Factor H transcripts.

The Factor H gene sequence (150,626 bases in length) is provided as GenBank accession number AL049744. As a result of an alternative splicing process, the FH gene encodes two different proteins: A 1231 amino acid "full-length" CFH protein (referred to as "CFH") and a 449 amino acid protein "truncated" CFH protein" (referred to as "CFHT"). The CFH polypeptide is encoded by exons 1-22 of the FH gene, including a 18 amino acid signal peptide. CFHT is an alternatively spliced transcript encoded by exons 1-9 and a unique exon located within intron 9 of the FH gene. See FIG. 2. The first 445 amino acids of CFH and CFHT are identical, with CFHT having a unique 4 amino acid sequence (SFTL) at the C-terminus.

Mature CFH is a glycoprotein with an approximate molecular weight of 155 kDa. The CFHT polypeptide has an approximate molecular weight of 45-50 kDa (U.S. Patent Application Pub. 2017/0369543, SEQ ID NO:4).

The 3,926 base sequence of the human CFH cDNA is provided in U.S. Patent Application Pub. 2017/0369543 A1, SEQ ID NO:1 (GenBank accession number Y00716). The Factor H polypeptide encoded by this cDNA is shown in U.S. Patent Application Pub. 2017/0369543 A1, SEQ ID NO:2 (GenBank accession number Y00716). Also see Ripoche et al., 1988, "The Complete Amino Acid Sequence of Human Complement Factor H" Biochem J 249:593-602 (showing a H402 variant). The cDNA and amino acid sequences for human CFHT (FHL-1) are found in the EMBL/GenBank Data Libraries under accession numbers Y00716 and X07523, respectively. The 1658 base nucleotide sequence of the reference form of CFHT is provided in U.S. Patent Application Pub. 2017/0369543 as SEQ ID NO:3 (GenBank accession number X07523), and the CFHT polypeptide sequence is provided in U.S. Patent Application Pub. 2017/0369543 A1 as SEQ ID NO:4 (GenBank accession number X07523).

CFH and CFHT are the only fluid phase regulators of the alternative complement pathway (AP). CFH is expressed in RPE. CFH protein levels are approximately 25% higher in Chr 1 non-risk individuals, and 10% higher in individuals with the I62-tagged haplotype, as compared to Pure Chr 1 risk patients (see TABLES 3-6). A major established role of CFH—and to a lesser extent CFHT—is its ability to discriminate between activation of the AP on self versus non-self, protecting self (both cellular and extracellular) by regulating the subsequent activation of C3b and tissue destruction mediated by C3a, C5a and MAC (membrane attack complex). CFH contains two regions that bind C3b and three regions that bind cell surface glycosaminoglycans (GAG) and sialic acid associated with 'self' surfaces. In contrast, CFHT contains only one C3b and one GAG binding site. Thus, the additional binding sites and higher expression of CFH protein suggests it is the major AP regulator with CFHT playing a lesser regulatory role in many tissues. As with the full-length forms of protective CFH, complement activity and ligand binding (C3b, CRP and oxidized proteins) are, in general, more robust with the protective versions of CFHT protein (see TABLES 7-8).

4.2. Protective Factor H Alleles

As described by Gregory S. Hageman in 2005, two common nonsynonymous polymorphisms in the CFH gene are associated with risk of developing AMD. See Hageman U.S. Pat. No. 7,745,389. Broadly speaking, individuals homozygous for CFH alleles encoding isoleucine at position 62 and tyrosine at position 402 (a "protective" allele) are less likely to develop AMD than individuals homozygous for CFH with valine at position 62 and tyrosine at position 402 (a "neutral" allele), who are in turn less likely than individuals homozygous for CFH with valine at position 62 and histidine at position 402 (a "risk" allele) (now understood as Chromosome 1-directed AMD). A less common polymorphism exists at position 1210 and individuals with cysteine at this position rather than arginine have a high likelihood of developing AMD.

Hageman U.S. Pat. No. 7,745,389 also described that a "protective" FH protein (encoded by the protective allele) comprising isoleucine at position 62, tyrosine at position Y402, and, in full-length CFH, arginine at position 1210, could be administered to a patient with, or at risk of developing, AMD to prevent or ameliorate disease development. Hageman '389 taught that protective FH could be administered to a patient as a recombinant or purified protein (delivered systemically or to the eye) or could be delivered using gene therapy, or by other methods.

Recent genetic analysis has been carried out in patients who are homozygous risk at chromosome 1, but without any risk alleles at chromosome 10 ("Pure Chr 1 risk"). As described in Example 1, over 2,000 genotyped and phenotyped individuals derived from 8,000 samples showed that Pure Chr 1 risk patients with a risk allele (V62, H402) on one chromosome are protected from AMD when they carry a protective FH allele (I62, Y402) or even a neutral FH allele (V62, Y402) on the other chromosome. These findings provide additional biological support for the protective role of protective FH in patients, and suggest that delivery of functional FH (especially protective FH) to ocular tissue can protect individuals, such as those carrying one or two copies of a chromosome 1 risk allele, from progression to late-stage AMD or slow the progression of the disease.

Figure 3:
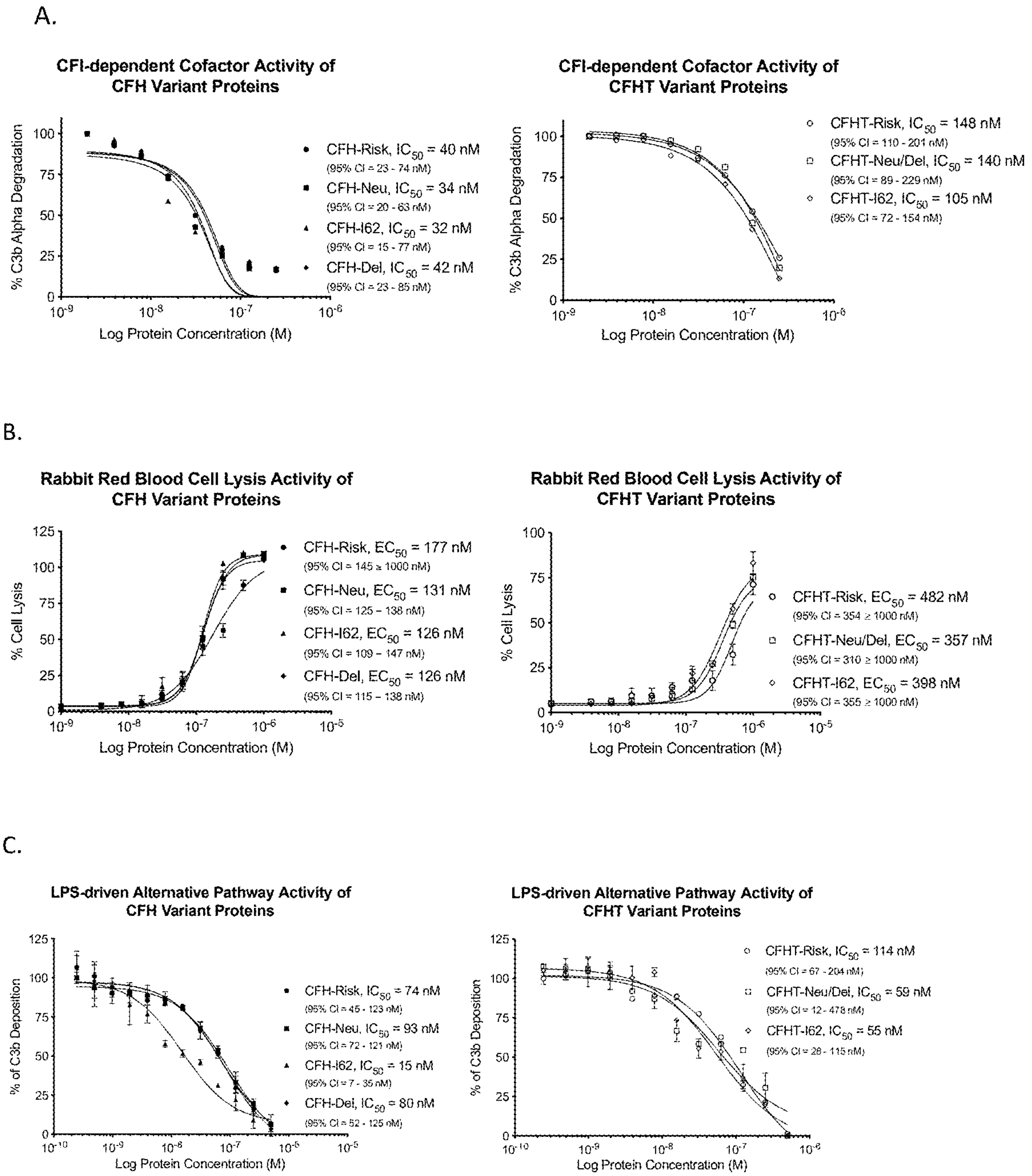
FIG. 3A-3C: Ligand binding and fluid phase activity profiles of CFH family protein variants.

Without intending to be bound by a particular mechanism, protective CFH-I62-Y402-E936 and protective CFHT-I62-Y402 are more active than corresponding CFH and CFHT risk, neutral and deletion proteins in certain in vitro assays, including binding to C3b, MDA and CRP (See TABLE 9), CFI-dependent co-factor activity (C3b cleavage), LPS-driven C3b deposition, and rabbit erythrocyte hemolysis assays (FIG. 3A-3C). Without intending to be bound by a particular mechanism this difference in activity and binding may contribute to the protective effect. See TABLES 7-10, examples below, and Laine et al., 2007, "Y402H Polymorphism of Complement Factor H Affects Binding Affinity to C-Reactive Protein," *J Immunol.* 178(6):3831-6).

TABLE 10

CFH and CFHT mRNA Expression in Various Tissues

| | RPE-Choroid *Probe Intensity | | Retina *Probe Intensity | | Human Tissue (RPKM) |
|---|---|---|---|---|---|
| Target and Tissue | Mac | XMac | Mac | XMac | **Mixed |
| CFH-protection | 995 | 881 | 67 | 60 | 19143 |
| CFH-risk | 975 | 880 | 69 | 54 | 3311 |
| CFHT-protection | 603 | 920 | 28 | 26 | 22 |
| CFHT-risk | 597 | 915 | 33 | 28 | 929 |

*Arbitrary units.

**Genotype-Tissue Expression (GTEx) results from adipose, tibial artery, tibial nerve, skin, lung. "RPKM" is Reads Per Kilobase of transcript, per Million mapped reads.

TABLE 4

Plasma CFH and CFHT Protein Concentrations in Patients with AMD Protective and Risk Genotypes

| | Plasma Concentration | |
|---|---|---|
| Target Protein | Median (μg/ml) | 95% CI (μg/ml) |
| CFH-protection | 227 | 232-272 |
| CFH-risk | 250 | 212-271 |
| CFHT-protection | 1 | 1.005-1.175 |
| CFHT-risk | 0.97 | 0.8765-1.059 |

TABLE 5

CFH and CFHT Protein Concentrations in Macular and Extramacular RPE, Choroid and Retina

| | RPE | | Choroid | | Retina | |
|---|---|---|---|---|---|---|
| Target Protein | Mac | XMac | Mac | XMac | Mac | XMac |
| CFH (ng/mg) | 496 | 310 | 1020 | 868 | 34.1 | 31 |
| CFHT (ng/mg) | 9.5 | 8.5 | 30 | 6 | 0.5 | 2.5 |

TABLE 6

CFH:CFHT mRNA and Protein Ratios (Calculated from data in TABLES 3-5)

| | CFH/CFHT Ratios | | | | | | | | | |
|---|---|---|---|---|---|---|---|---|---|---|
| | RPE + Choroid | | RPE Only | | Choroid Only | | Retina | | Human Tissue | |
| Protein Ratios | Mac | XMac | Mac | XMac | Mac | XMac | Mac | XMac | Mixed | Plasma |
| Mixed genotype | | | 52 | 36 | 34 | 145 | 68 | 12 | | |
| Protection Only | | | | | | | | | | 227 |
| Risk Only | | | | | | | | | | 258 |
| | | | | | mRNA Ratios | | | | | |
| Protection | 1.65 | 0.96 | | | | | 2.39 | 2.31 | 870 | |
| Risk | 1.63 | 0.96 | | | | | 2.1 | 1.93 | 3.56 | |

TABLE 7

Summary of Protective CFH and CFHT Protein Activities in Binding and Functional Assays

| Protective Protein | Protective Variants and C-Terminal | Binding Affinity $K_D$ (nM ± SD) | | | Functional Assay ($IC_{50}$ or $EC_{50}$ nM) | | |
|---|---|---|---|---|---|---|---|
| Name | Sequence | C3b | CRP | MDA | LPS | Cofactor* | RBC Lysis |
| CFH | I62-Y402-E936 | 141 | 127 ± 11 | 222 ± 13 | 12.4 | 9.2 | 258 |
| CFHT | I62-Y402-SFTL | 717 | 14.3 ± 0.1 | 219 ± 17 | 15.9 | 31.2 | 701 |
| eCFHT-SK | I62-Y402-SKSFTL | 478 | 13.7 ± 2.5 | 290 ± 1 | 19.1 | 37.0 | 801 |
| eCFHT-SE | I62-Y402-SESFTL | 938 | 25.3 ± 0.6 | 305 ± 1 | 25.4 | 89.7 | 795 |

*$IC_{50}$ value for iC3b 43-kDa band appearance.

TABLE 8

| CFH and CFHT Protein Activity and Binding Ranking from Best (1) to Worst (6): Protection Score | | | | | | | |
|---|---|---|---|---|---|---|---|
| | Binding Affinity Rank | | | Functional Assay Rank | | | Binding and Activity |
| Protein Variant | C3b | CRP | MDA | LPS | Co-factor | RBC Lysis | Score |
| CFH-Protection | 1 | 4 | 2 | 1 | 1 | 1 | 10 |
| CFH-Risk | 2 | 6 | 6 | 5 | 2 | 2 | 23 |
| CFHT-Protection | 4 | 2 | 1 | 2 | 3 | 3 | 15 |
| CFHT-Risk | 5 | 5 | 5 | 6 | 6 | 4 | 31 |
| eCFHT-SK | 3 | 1 | 3 | 3 | 4 | 6 | 20 |
| eCFHT-SE | 6 | 3 | 4 | 4 | 5 | 5 | 27 |

TABLE 9

| Binding to C3b, MDA and CRP | | | | | | | |
|---|---|---|---|---|---|---|---|
| | | Relative C3b-Binding | | Relative MDA-Binding | | Relative CRP-Binding | |
| Protein Variant | Detection Antibody | Binding Potential | % FH-Risk | Binding Potential | % FH-Risk | Binding Potential | % FH-Risk |
| CFH-Risk | AbCam | 22 | 100% | 30 | 100% | 1 | 100% |
| CFH-Neu | (OX-24; | 29 | 134% | 39 | 130% | 14 | 956% |
| CFH-I62 | #Ab112197) | 29 | 133% | 75 | 251% | 10 | 656% |
| CFH-Del | | 24 | 107% | 43 | 145% | 14 | 972% |
| CFHT-Risk | | 2 | 10% | 10 | 35% | 2 | 131% |
| CFHT-Neu/Del | | 3 | 15% | 28 | 94% | 101 | 6874% |
| CFHT-I62 | | 4 | 17% | 32 | 107% | 87 | 5900% |

4.3. Factor H Transgenes for Treatment or Prevention of Chromosome 1 Directed Disease In this section we describe protective FH transgenes that may be delivered to the eye of a person with, or at risk of developing, Chr 1 directed AMD. Expression and delivery systems for introducing the FH transgene(s) into the eye are described below in Section 5.

We have compared the relative binding affinity and alternative complement pathway activity of risk and protective versions of CFH and CFHT proteins (CFH-I62-Y402-E936, CFH-V62-H402-E936, CFHT-I62-Y402 (eCFHT-SK and eCFHT-SE), CFHT-V62-H402 protein variants). In brief, the protective versions of both CFH and CFHT have stronger binding affinity and better negative regulatory activity of alternative complement pathway than neutral and risk protein variants. In addition, full-length CFH activity is typically better (~30-300%) in most assays, except CRP binding; in which CFHT has ~10-fold better binding affinity. Overall, protective CFH and CFHT proteins perform better than risk versions and eCFHT-SK is similar to protective CFHT-I62-Y402 protein in all assays tested to date. See TABLES 6, 8 and 9.

The gene therapy vectors of the present invention generally comprise transgenes encoding protective forms of FH with isoleucine at 62 (I62) and tyrosine at 402 (Y402). The full-length protective CFH protein generally has arginine at position 1210 (cysteine at 1210 is associated with high risk of developing AMD) and generally has glutamic acid at position 936 (E936). CFH variants with aspartic acid at position 936 (D936) are also contemplated. E936 and D936 are common variants of CFH. Glutamic acid at position 936 is found the protective I62 form of CFH, and is also linked to a deletion at the Complement Factor H Related 1/Complement Factor H Related 3 locus (CFHR3/1 deletion) that is associated with reduced AMD risk. See Hageman U.S. Pat. No. 7,867,727 and Hughes et al., 2006, Nat. Genet. 3:1173-77. It will be appreciated that the 936 and 1210 position are not present in the truncated CFHT protein. In some embodiments, gene therapy vectors of the present invention comprise truncated CFH with isoleucine at position 62 (I62) and tyrosine at position 402 (Y402).

It will be understood that, when referring to protective FH proteins, in addition to CFH and CFHT proteins identified by sequence, it is also contemplated that variants of the protective FH proteins including substantially identical variants, conservatively substituted variants, and polymorphic forms variants may be used. See Section 4.3.5 below.

Multiple approaches are contemplated for gene therapy directed to Chromosome-1 directed AMD. Approaches include:

(a) Gene therapy using a transgene encoding full-length CFH;

(b) Gene therapy using a transgene(s) encoding full-length and truncated CFH;

(c) Gene therapy using a transgene encoding truncated CFHT.

In an aspect, the invention is directed to treating patients with, or at risk of developing, Chr 1 directed AMD by administering a gene therapy vector to the eye(s) of the patient, where the vector expresses a transgene encoding a full-length protective CFH or a variant thereof. In some embodiments the CFH transgene encodes the full-length CFH protein sequence provided in TABLE 33B (SEQ ID NO:2). In some embodiments the CFH transgene encodes the full-length CFH protein sequence comprising SEQ ID NO:20. In some embodiments the CFH transgene comprises SEQ ID NO:1.

Figure 4:
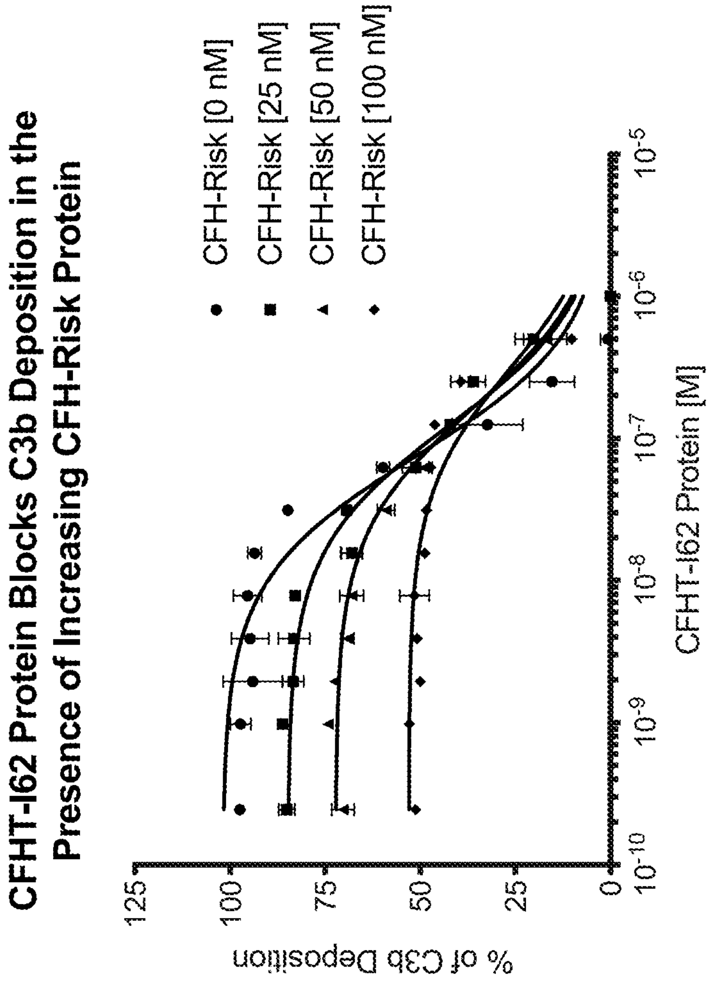
FIG. 4. Protective CFHT blocks C3b deposition in the presence of increasing levels of CFH-risk protein. LPS-dependent AP activity for 0, 25, 50 or 100 nM CFH-risk protein in the presence of increasing amounts of protective CFHT-I62 protein.

Although the functional role of CFHT in normal complement regulation has been less clear than that of CFH, we believe that expression of CFHT is required or sufficient for maximal therapeutic benefit to patients with, or at risk of developing, Chromosome 1-directed AMD. We note that the two strongest AMD protection-associated SNPs are found in both CFH and CFHT proteins. Further, as discussed in Example 7, below, and without intending to be bound by a particular mechanism, we have determined that protective CFHT-I62 protein can augment CFH-Risk protein deficits in in vitro assays. See Examples 1 and 7, and FIG. 4. In addition, as discussed in Example 6, below, we have discovered that surprisingly CFHT protein produced in transfected RPE migrates a significant distance away from the bleb providing additional therapeutic benefits including reduced damage to the macula and fovea during administration of the therapeutic agent.

4.3.1. Coadministered and Coexpressed Protective CFH and CFHT Transgene

As noted above, in one approach gene therapy delivers a transgene(s) encoding both full-length and truncated CFH. In one approach CFH- and CFHT-encoding sequences are codelivered and coexpressed (e.g., encoded in the same transgene). In one embodiment the CFH and CFHT encoding sequences are under control of a single promoter.

In an aspect, the invention is directed to treating patients with, or at risk of developing, Chr 1 directed AMD by administering a gene therapy vector to the eye(s) of the patient, where the vector expresses a transgene encoding both CFH and CFHT. We designed and tested expression constructs that produce CFH and CFHT protective proteins from an engineered construct by incorporating a synthetic intron and poly A signal. Both a full-length CFH and CFHT transcript are generated from these constructs, as determined by RT-PCR and protein analysis. Advantageously, expression of both splice variants tracks the natural biology of the Complement Factor H system. However, the combined size of CFH and CFHT coding sequences is a barrier to this gene therapy due to the limited capacity of vectors such as AAV2.

We have overcome this barrier by engineering a transgene (eCFH/T) that, when expressed in human cells, produces both CFH and eCFHT proteins as a result of alternative splicing. Using a novel strategy we designed transgenes with functional intron splice donor and acceptor regions. See EXAMPLE 3. In some embodiments the CFH transgene comprises SEQ ID NO:3. In one approach the nucleotide sequence for the eCFH/T transgene is provided as SEQ ID NO:5. Nucleotides 1-1335 of SEQ ID NO:5 encode amino acids 1-445 of both CFH and eCFHT. Nucleotides 1336-1356 contain a functional intron splice donor region that encodes two amino acids (SK) followed by the C-terminal SFTL tail. Nucleotides 1357-1478 encode an SV40 poly A tail for eCFHT mRNA stability, followed by another intron containing sequence with a branch site and splice acceptor site for faithful intron removal (nucleotides 1479-1500). When splicing occurs and the 165 nucleotide long intron is removed, nucleotide 1336 and nucleotides 1501 are spliced together to encode amino acids 446-1231 of the full-length CFH polypeptide.

Due to constraints of including an optimal splice donor in these small synthetic introns, the CFHT protein includes two extra amino acids prior to the C-terminal SFTL tail. Therefore, to test if the extra two amino acids (SE and SK) influence protein activity, we purified his-tagged eCFHT-SE (eCFHT) and eCFHT-SK recombinant proteins to test in various alternative pathway relevant assays. The non-native eCFHT-SE and eCFHT-SK proteins are compared to similarly purified protective versions of native CFH and CFHT proteins.

In one aspect, the invention is directed to treating patients with, or at risk of developing, Chr 1-directed AMD by administering a gene therapy vector to the eye(s) of the patient, where the vector expresses a transgene encoding CFHT comprising the carboxy-terminal sequence CIRVSKSFTL (eCFHT) [SEQ ID NO:6]. In some embodiments the CFH transgene comprises SEQ ID NO:5. In preferred embodiments the eCFHT transgene encodes the eCFH/CFHT protein sequence of SEQ ID NO:6 or a protein comprising residues 19-451 of SEQ ID NO:6.

Figure 8:
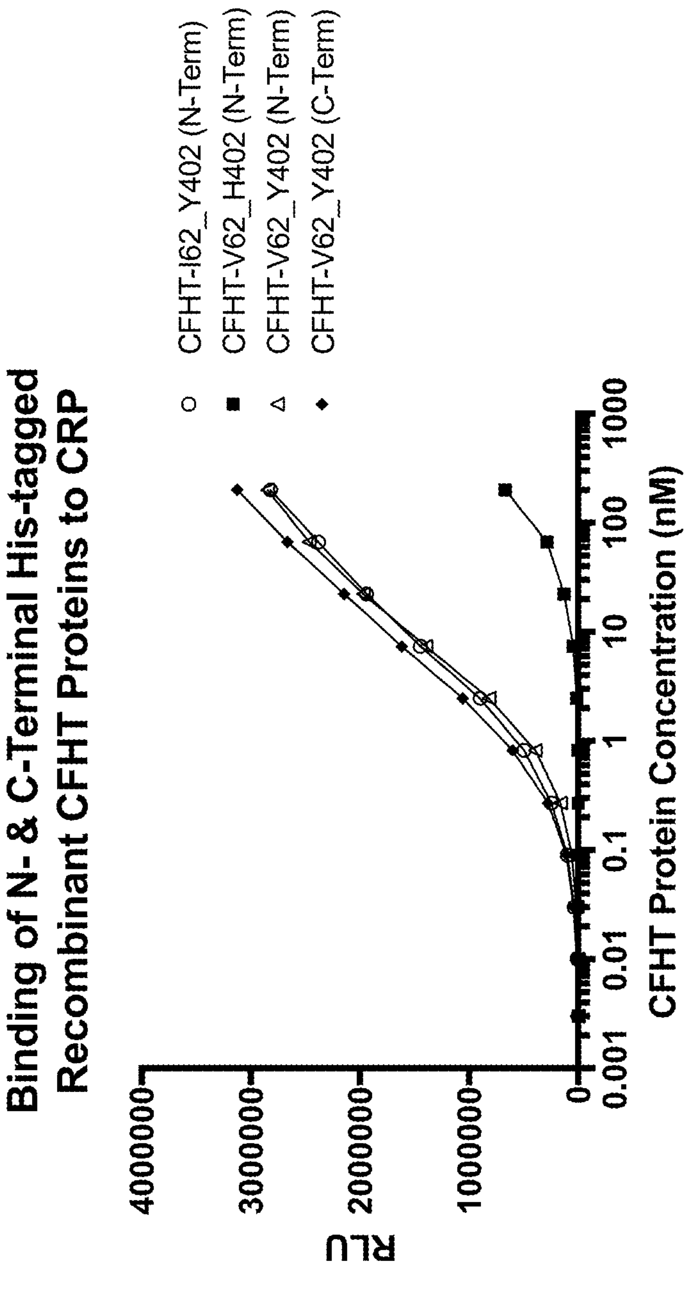
FIG. 8 shows binding of CRP by various forms of CFHT as assessed using N- and C-terminal His-tagged recombinant CFHT protein.

4.3.2. Activity and Binding Properties of FH Forms Including Protective Engineered eCFHT-SE and eCFHT-SK Proteins The eCFH/T constructs developed for AAV delivery of protective proteins, generates native CFH and non-native CFHT protein that terminate in either SESFTL or SKSFTL, depending on the intron sequence used. Native CFHT protein has a C-terminus that ends in SFTL. To determine if the modified eCFHT-SE and eCFHT-SK proteins function similarly to native CFHT we purified His-tagged protective eCFHT-SK and eCFHT-SE recombinant protein from HEK293 cells and compared to His-tagged protective CFH-I62-Y402-E936 and CFHT-I62-Y402 proteins. We tested both binding activity in plate-based assays to determine binding affinity (e.g. KD for C3b, CRP and MDA-LDL ligands) and several functional assays (e.g. LPS-dependent alternative pathway regulation, CFI-dependent cofactor activity and rabbit erythrocyte cell lysis control). See FIG. 8.

Protective CFH-I62-Y402-E936 binds more strongly to C3b than protective CFHT-I62-Y402, 141.2 versus 717.7 nM. The eCFHT proteins, show similar C3b binding affinity; with protective eCFHT-SK protein modestly better than both native CFHT and eCFHT-SE protein (477.6 nM verse 717.7 and 938.1 nM). As demonstrated below, CFHT protein has about 10-fold better binding affinity to monomeric CRP. Again, we show protective CFHT-I62-Y402-E936 binds more strongly to CRP than protective CFH-I62-Y402-E936 (14.3 nM versus 127 nM) and eCFHT-SK and eCFHT-SE protective proteins also robustly bind to CRP. As with C3b binding, the eCFHT-SK protein (KD=13.7 nM) is modestly better than eCFHT-SE protein (KD=25.3 nM) when tested in these plate-based CRP binding assays. The final assay compared binding affinities of all protective proteins to MDA-modified LDL particles. Protective CFH-I62-Y402-E936 and CFHT-I62-Y402 have similar binding affinities (KD ~220 nM) while eCFHT-SK and eCFHT-SE encoded engineered proteins have a slightly reduced binding affinity (KD ~300 nM) to MDA adducts.

To compare functional activity of protective CFH-I62-Y402-E936 and CFHT proteins we first assayed the effect of recombinant proteins on deposition of C3b on microtiter plates following complement activation via the alternative pathway (AP). Proteins were added to human serum (12.5% final serum concentration), which was then exposed to LPS-coated microtiter plates to initiate AP activation. Deposition of C3b/iC3b was detected as a measure of alternative pathway complement activation. Both protective eCFHT-SE and eCFHT-SK can prevent C3b deposition, with an IC50 of 25.4 nM and 19.1 nM, respectively. The ability of both proteins to block LPS-dependent C3b deposition are similar to protective CFH-I62-Y402-E936 and CFHT-I62-Y402 proteins (IC50=12.4 and 15.9 nM, respectively). Both risk versions of CFH and CFHT are less active (IC50=25.9 and 26.7 nM, respectively).

Next, CFI-dependent cofactor assays were implemented using protective eCFHT-SE and eCFHT-SK proteins. The eCFHT-SK protein exhibits strong cofactor activity that is similar to protective CFHT-I62-Y402 recombinant protein (IC50=37 and 31.2 nM, respectively). There is degradation of the C3b alpha-chain and appearance of degradation products at 43 kDa and 68 kDa iC3b with all protein preps, as determined by SDS-PAGE. In order to more accurately quantify cofactor activity of eCFHT-SE and eCFHT-SK and compare to native protective CFH-I62-Y402-E936 and CFHT-I62-Y402 proteins, the intensity of alpha-chain, beta-chain, as well as iC3b 68-kDa and 43-kDa fragments were determined by densitometry analysis and plotted using Prism software. The semi-quantitative densitometry analysis further confirms our finding that protective eCFHT-SK has strong CFI-dependent cofactor activity in the presence of C3b. And, as shown above for ligand binding activities, eCFHT-SK engineered protein is more similar to native protective CFHT-I62-Y402 than CFHT-SE protein.

Lastly, we monitor recombinant protein activities in cell lysis assay using rabbit erythrocytes and normal human serum (NHS). Protective CFH-I62-Y402-E936 controls lysis better than protective CFHT-I62-Y402 by about 3-fold and both engineered eCFHT-SE and eCFHT-SK are similar to native protective CFHT-I62-Y402 protein (EC50=795, 801 nM and 701 nM, respectively). Risk versions of both CFH and CFHT are less active than the protective protein counterparts.

In summary, the protective engineered eCFHT-SE and eCFHT-SK proteins are nearly identical to the native protective CFHT-I62-Y402 protein in all assays tested to date (see TABLE 7). A slight advantage is detected with eCFHT-SK over eCFHT-SE in several assays and overall may replace native protective CFHT protein. An activity and binding score based on the relative ability of proteins to control several alternative complement functions is provided in TABLE 8. In summary, these results suggest that AAV virus that express protective CFH, CFHT or co-expressed protective CFH and eCFHT (i.e., eCFHT-SK) will have therapeutically beneficial alternative complement pathway activity and prevent or delay progression of age-related macular degeneration in individuals with Chromosome 1-directed AMD risk.

4.3.3. CFH/CFHT Expression Ratio

Figure 5:
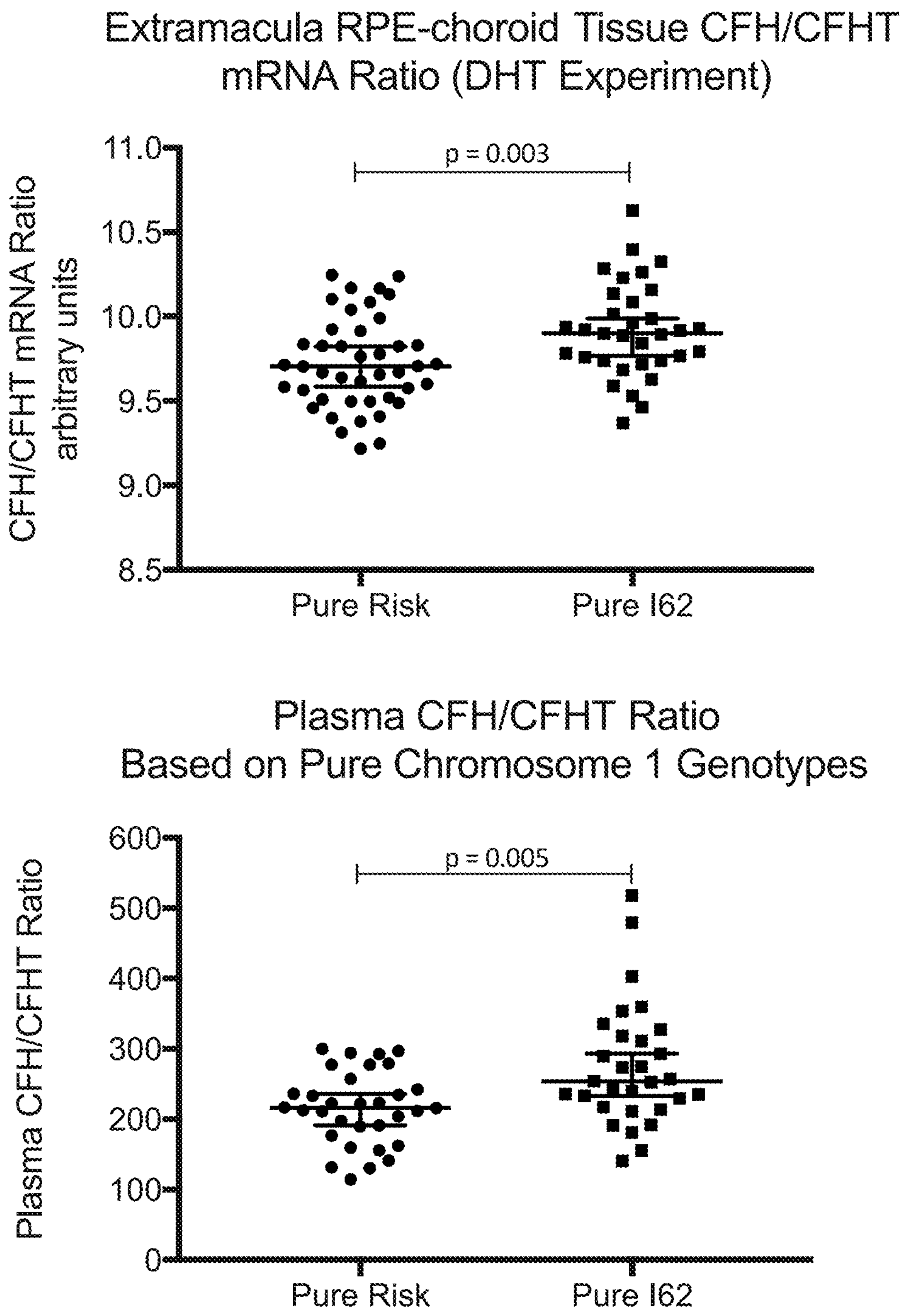
FIG. 5 shows ratios of CFH/CFHT mRNA in extramacular RPE-choroid tissue top) and shows ratios of CFH/CFHT protein in plasma.

We determined the CFH/CFHT Expression Ratio in normal tissue. We used this to identify a target ratio for the gene therapy methods of the invention. As shown in TABLES 2-5 and FIG. 5, different CFH/CFHT ratios are associated with risk and protective genotypes. See Example 4 for methods used in the studies described in this section.

The ratio of plasma CFH protein to CFHT protein is significantly different between risk and I62 protection (p=0.005) patients. This suggests that AMD-specific chromosome 1 genotypes influence the relative amounts of full-length CFH transcript to alternatively spliced CFHT transcript with I62 protection genotype favoring more CFH than CFHT and the risk genotype producing more CFHT than CFH.

In one approach, the ratio of CFH protein/CFHT protein in macular and extramacular RPE that results from expression of an engineered eCFH/T transgene is in a range similar to that found in RPE cells as summarized above. In one approach the expression of CFH and CFHT from a transgene results in a CFH to CFHT protein ratio of approximately 10:1 to 150:1. In some embodiments, CFH and CFHT proteins are expressed at protective tissue ratios (~10 to 100-fold more CFH than CFHT) in RPE tissue using an AAV delivery system. In some embodiments the eCFH/T transgene results ~10 to 16-fold higher ratio of CFH over CFHT (or eCFHT) protein.

4.3.4. Expression of Exogenous Protective CFHT in the Absence of Expression of Exogenous CFH In another embodiment, cells are transduced only with CFHT encoding sequence, so that exogenous CFHT transgene is expressed in the absence of expression of exogenous CFH. We believe that CFHT is effective for treatment or prevention of AMD when expressed in the appropriate tissues at therapeutically effective levels. In an approach, the invention is directed to treating patients with, or at risk of developing, Chr 1-directed AMD by administering a gene therapy vector to the eye(s) of the patient, where the vector expresses a transgene encoding truncated FH (CFHT) or a variant thereof. In one example, the CFHT transgene encodes the CFHT protein sequence provided in TABLE 33D (SEQ ID NO:4). In some embodiments the CFHT transgene encodes the CFHT protein sequence comprising SEQ ID NO:21.

In one therapeutic approach, expression of exogenous CFHT, in the absence of exogenous CFH expression, provides therapeutic benefit to a patient. As described herein below, expressed CFHT at high levels in transfected cells including cell culture and primate RPE. See, e.g., Example 5. Further, we have determined that in in vitro assays, protective CFHT blocks C3b deposition in the presence of CFH-risk protein. See, e.g., Example 5. Still further, we have determined that CFHT produced from AAV2 injected subretinally in extramacular regions (bleb) will migrate from these extramacular regions to the macula and other positions remote from the injection site.

Without intending to be bound by a particular mechanism, we conclude CFHT likely plays an important role in regions of tissues where diffusion is restrictive. Thus, one unique feature of CFHT is its smaller size, which allows it to diffuse passively through regions such as Bruch's membrane. Another feature that is unique to CFHT is the presence of a C-terminal SFTL tail that is not present on CFH. Although the precise function of this region of CFHT has not been fully established, Swinkels et al. have suggested it may impart an increased binding affinity of CFHT to monomeric, inflammatory C-reactive protein (CRP) and PTX3 (Swinkels et al., 2018 "C-Reactive Protein and Pentraxin-3 Binding of Factor H-like Protein 1 Differs from Complement Factor H: Implications for Retinal Inflammation" *Scientific Reports* 8:1643; also see Clark et al., 2017, "Bruch's Membrane Compartmentalizes Complement Regulation in the Eye with Implications for Therapeutic Design in Age-Related Macular Degeneration" Front Immunol. 8:1778, and Clark et al., 2014, "Identification of Factor H-Like Protein 1 AS THE Predominant Complement Regulator in Bruch's Membrane: Implications for Age-Related Macular Degeneration" Journal of Immunology 193(10):4962-4970, each incorporated by reference). Our data suggest that the SFTL tail alone does not mediate this binding, however it is clear that protective CFHT has an approximate 10-fold higher binding affinity for CRP than does protective CFH (see TABLES 6-7), whereas the risk forms of both CFH and CFHT exhibit extremely low, if any, affinity for CRP. Moreover, both CFH and CFHT possess a single RGD motif. We have shown that this motif is better exposed in CFHT, which may allow for more robust binding to cell surface-associated integrins.

Treatment with protective CFHT alone (without exogenous CFH expression) results in therapeutic benefit not achieved by treatment using the full-length CFH. Without intending to be bound by a particular mechanism, we believe CFHT is a major alternative complement negative regulatory protein in Bruch's membrane. Bruch's membrane is a major site of AMD disease pathogenesis and is the site where drusen form. We have discovered that CFHT protein secreted by RPE cells transfected with a CFHT-encoding transgene express can passively diffuse through Bruch's membrane into the choroid and can migrate laterally away from the transfected cells. See EXAMPLE 5. CFHT is largely bound to Bruch's membrane through interactions with heparin sulfate and this binding is reduced by the common 402H form associated with an increased risk of AMD. Without intending to be bound by a particular mechanism, we believe that, surprisingly, CFHT secreted from the RPE can migrate laterally in the choroidal space of the primate eye. Surprisingly, we have observed that CFHT can laterally migrate for significant distances (e.g., more than 10 mm from the site of transgene injection). This discovery has profound ramifications for clinical practice, as discussed herein below.

4.3.5. Variants of Protective FH Proteins Including Substantially Identical Variants, Conservatively Substituted Variants, and Polymorphic Forms Variants Preferred CFH, CFHT and eCFHT amino acid sequences are provided in TABLE 33B (SEQ ID NO:2), TABLE 33D (SEQ ID NO:4), and TABLE 33F (SEQ ID NO:6) respectively. However, it is contemplated that the proteins with different sequence may be used. In some embodiments, for example, a FH protein used in the present invention comprises aspartic acid (D) rather than glutamic acid (E) at position 936. See Kerr et al., 2017, "Disease-Linked Mutations in Factor H Reveal Pivotal Role of Cofactor Activity in Self Surface-Selective" *J Biol Chem.* 292:13345-60. The signal peptide of the protective proteins may be modified or replaced with a heterologous signal peptide. Thus, although exemplary CFH, CFHT, and eCFH/T sequences are provided in TABLE 33A (SEQ ID NO:1), TABLE 33C (SEQ ID NO:3), and TABLE 33E (SEQ ID NO:5) respectively, transgenes encoding different FH sequences may be used, including, transgenes encoding substantially identical variants, conservatively substituted variants, and polymorphic variants of polypeptides described herein.

Other FH proteins may have sequences substantially identical to SEQ ID NO:2, 4 or 6 (or SEQ ID NO:20, 21 or 22). In one approach a transgene is used that encodes a protective FH protein with least about 90% identity, preferably 91%, 92%, 93%, 94%, 95%, 96%, 97%, 98%, 99%, or higher identity to SEQ ID NO:2, 4 or 6 (or SEQ ID NO:20, 21 or 22). In one approach the transgene encodes SEQ ID NO:20, 21 or 22, or a substantially identical variant, with a nonnaturally occurring signal peptide sequence at the amino terminus. In one approach, the transgene encodes a protective FH protein that is a conservatively modified variant of SEQ ID NO:2, 4 or 6 (or SEQ ID NO:20, 21 or 22). In one approach, the transgene encodes a protective FH protein that is a polymorphic variant of SEQ ID NO:2, 4 or 6 (or SEQ ID NO:20, 21 or 22). In some embodiments the substantially identical or conservatively substituted protective variant binds C3b at least 90% equally as well as or close to the reference protein with SEQ ID NO:2, 4 or 6 (or SEQ ID NO:20, 21 or 22). In some embodiments the substantially identical or conservatively substituted protective variant binds C3b at least 90% more avidly than the reference protein with SEQ ID NO:2, 4 or 6 (or SEQ ID NO:20, 21 or 22). Interactions between C3b and CFH proteins can be analyzed by art known methods including surface resonance using a Biacore 3000 system (Biacore AB, Uppsala, Sweden), as described in Manuelian et al., 2003, Mutations in Complement Factor H Reduce Binding Affinity to C3B AND Heparin and Surface Attachment to Endothelial Cells in Hemolytic Uremic Syndrome. *J Clin Invest* 111, 1181-90). In one approach, C3b (CalBiochem, Inc), is coupled using standard amine-coupling to flow cells of a sensor chip (Carboxylated Dextran Chip CM5, Biacore AB, Uppsala, Sweden). Two cells are activated and C3b (50 micrograms/ml, dialyzed against 10 mM acetate buffer, pH 5.0) is injected into one flow cell until a level of coupling corresponding to 4000 resonance units is reached. Unreacted groups are inactivated using ethanolamine-HCl. The other cell is prepared as a reference cell by injecting the coupling buffer without C3b. Before each binding assay, flow cells will be washed thoroughly by two injections of 2 M NaCl in 10 mM acetate buffer, pH 4.6 and running buffer (PBS, pH 7.4). The Factor H protein is injected into the flow cell coupled with C3b or into the control cell at a flow rate of 5 ul/min at 25° C. Binding of Factor H to C3b is quantified by measuring resonance units over time, as described in Manuelian et al., 2003, supra. The variant protein may also have other activities characteristic of the reference protein including binding CRP, binding endothelial cell surfaces, cofactor activity in fluid phase, or heparin binding. Binding and activity assays are well known in the art and include those described in Hageman U.S. Pat. No. 7,745,389.

In one embodiment, CFH, CFHT, and eCFH/T transgenes have nucleotide sequences of SEQ ID NOs: 1, 3 and 5. These transgene sequences were engineered using a GeneOptimizer algorithm to optimize expression of the encoded protein in human cells. See Raab et al., 2010, "The GeneOptimizer Algorithm: Using a Sliding Window Approach to Cope with the Vast Sequence Space in Multiparameter DNA Sequence Optimization" *Syst Synth Biol* 4:215. However, it is contemplated that the transgene sequences may be varied. A transgene for use in the present invention may differ from SEQ ID NOs: 1, 3 and 5 provided they encode a CFH, CFHT and/or eCFHT protein(s) that retains complement component 3b (C3b) binding activity and has (i) at least 90% amino acid sequence identity to the amino acid sequence of SEQ ID NO:2, with the proviso that residue 62 is isoleucine, residue 402 is tyrosine, and residue 1210 not cysteine and preferably is arginine and/or (ii) at least 90% amino acid sequence identity to the amino acid sequence of SEQ ID NO:4, with the proviso that residue 62 is isoleucine and residue 402 is tyrosine. In other embodiments the protein encoded by the transgene is at least about 90% identity, preferably at least about 91%, 92%, 93%, 94%, 95%, 96%, 97%, 98%, 99%, or higher identity to SEQ ID NO:2, 4, 7, 20, 21 or 22. In preferred embodiments a CFH, CFHT, eCFHT or eCFH/T transgene encodes a protein that retains the following additional activities of CFH: (1) binding to monomeric C-reactive protein (CRP); (2) binding to heparin; (3) binding to sialic acid; (4) binding to cell surfaces; (5) binding to cellular integrin receptors; (6) erythrocyte lysis assay; (7) LPS-driven C3B deposition; (8) binding to C3b; (9) binding to MDA-modified lipids and proteins; and (10) C3b cofactor activity. Malondialdehyde (MDA) is a byproduct of lipid peroxidation that can modify DNA and proteins.

Expression and Delivery Systems

Gene therapy according to the present invention makes use of an expression system (or expression cassette) including a FH transgene (e.g., CFH, CFHT or eCFH/T transgenes) and associated regulatory sequences and delivery vector system (e.g. a recombinant adeno-associated viral vector) to introduce the expression system into target cells (e.g., retinal pigment epithelial cells). Without intending to be bound by a particular mechanism, therapeutically effective FH gene therapy requires that the expression and delivery systems work together to produce an appropriate level of FH protein in the appropriate tissue. According to the present invention FH protein may be produced in and secreted from RPE cells. The large size of the CFH gene, CFH mRNA and CFH protein presented significant challenges in our attempts to achieve appropriate expression. In particular, coexpressing full-length and truncated FH presented significant challenges.

For general reviews related to gene therapy, including descriptions of expression and delivery systems see Moore et al., 2017, "Gene Therapy for Age-Related Macular Degeneration" Expert *Opinion on Biological Therapy* 17:10: 1235-1244; Aponte-Ubillus et al., 2018, "Molecular Design for Recombinant Adeno-Associated Virus (rAAV) Vector Production" *Applied microbiology and biotechnology* 102.3:1045-1054; Ochakovski et al., 2017, "Retinal Gene Therapy: Surgical Vector Delivery in the Translation to Clinical Trials" *Frontiers in Neuroscience* 11; Schön et al., 2015, "Retinal Gene Delivery by Adeno-Associated Virus (AAV) Vectors: Strategies and Applications" *European Journal of Pharmaceutics and Biopharmaceutics* 95:343-352; Naso et al., 2017, "Adeno-Associated Virus (AAV) AS A Vector for Gene Therapy" BioDrugs 31:317; Dunbar et al., 2018, "Gene Therapy Comes of Age" *Science* 359:6372; Penaud-Budloo et al., 2018., "Pharmacology of Recombinant Adeno-Associated Virus Production" *Molecular Therapy: Methods & Clinical Development* 8:166-180; each of which is incorporated by reference for all purposes.

4.4. Expression System

Regulatory sequences for transgene expression include nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, enhancers, translation leader sequences, introns, splicing and polyadenylation signals and transcription termination sequences; sequences that enhance translation efficiency (e.g., Kozak consensus sequence) and sequences that enhance protein stability. As discussed above, in preferred embodiments codon choice in the protein coding portions of the transgene sequence are optimized for expression in human cells.

According to the invention, it is desirable that the CFH/CFHT protein(s) is expressed, preferably at high levels, by RPE cells. As described in EXAMPLES 2, 3 and 5, below, we prepared and tested numerous expression systems for expression CFH, CFHT and eCFH/T transgenes in established and primary cell lines. For these assays we used both pcDNA3.1 based reporters and AAV2 vector in which transgene expression is controlled by an operably linked promoter or enhancer/promoter. Following several rounds of screening, several specific combinations of promoters and regulatory elements were tested for the ability to drive expression of a reporter gene in several established and primary cell lines: sctmCBA; CFH; BEST1-EP-454; RPE65-EP-419; RPE65-EP-415; VMD2; smCBA; and CBA. In some cases, a proprietary enhancer/promoter system was used. Generally, the promoter/enhancers were shortened versions of the human endogenous RPE-specific enhancer promoter sequences (e.g. RPE65 and BEST1). As shown in the Examples and TABLE 11, high expression levels were observed in human adult and fetal RPE cells using certain promoter/enhancer/polyA combinations delivered using rAAV2. TABLE 12 also describes selected constructs that may be used.

In some embodiments the protective transgene is the CFHT truncated form comprising I62-Y402. In one approach expression of the CFHT protein is driven by a promoter selected from CBA [e.g., SEQ ID NO: 13], smCBA [e.g., SEQ ID NO:7], VMD2 [e.g., Table 34N], BEST1-EP-454 [e.g., SEQ ID NO: 8], RPE65-EP-419 [e.g., SEQ ID NO:10], RPE65-EP-415 [e.g., SEQ ID NO:9], or sctmCBA [e.g., SEQ ID NO: 14]. In some embodiments the polyadenylation sequence is bGH. In one embodiment the promoter is CBA and the polyadenylation sequence is bGH. In one embodiment the promoter is smCBA and the polyadenylation sequence is bGH.

In some embodiments the protective transgene is the engineered CFH form comprising I62-Y402-E936. In one approach expression of the CFH protein is driven by a promoter selected from BEST1-EP-454; RPE65-EP-415; smCBA; CBA; RPE65-EP-419; sctmCBA; or VMD2. In some embodiments the polyadenylation sequence is bGH. In some embodiments the polyadenylation sequence is HSV TK. In some embodiments the promoter is BEST1-EP-454 and the polyadenylation sequence is HSV TK. In some embodiments the promoter is RPE65-EP-415 and the polyadenylation sequence is HSV TK. In some embodiments the promoter is smCBA and the polyadenylation sequence is HSV TK.

In some embodiments the protective transgene is the full-length CFH form CFH (I62-Y402-E936 coexpressed with CFHT or eCFHT (I62-Y402) (e.g., eCFH/T). In one approach expression of the eCFH/T coding sequence is driven by a promoter selected from BEST1-EP-454; RPE65-EP-415; RPE65-EP-419; sctmCBA; smCBA; and VMD2. In some embodiments the polyadenylation sequence is bGH. In some embodiments the polyadenylation sequence is HSV TK. In one approach expression of the eCFH/T coding sequence is driven by BEST1-EP-454 and the polyadenylation sequence is HSV TK. In one approach expression of the eCFH/T coding sequence is driven by RPE65-EP-415 and the polyadenylation sequence is HSV TK. In one approach expression of the eCFH/T coding sequence is driven by smCBA and the polyadenylation sequence is HSV TK. In one approach expression of the eCFH/T coding sequence is driven by RPE65-EP-419 and the polyadenylation sequence is HSV TK.

In some embodiments the protective transgene encodes CFHT operably linked to a CBA enhancer promoter and a polyadenylation sequence. In some embodiments the polydenylation sequence is a Bovine Growth Factor (bGH) polyadenylation sequence. In some embodiments the transgene is contained in a rAAV2 expression vector.

In some embodiments the protective transgene encodes CFH operably linked to a BEST1-EP-454 enhancer promoter and a polydenylation sequence. In some embodiments the polydenylation sequence is a HSV Thymidine Kinase (TK) polyadenylation sequence. In some embodiments the transgene is contained in a rAAV2 expression vector.

In some embodiments the protective transgene encodes CFH operably linked to a RPE65-EP-415 enhancer promoter and a polydenylation sequence. In some embodiments the polydenylation sequence is a HSV Thymidine Kinase (TK) polyadenylation sequence. In some embodiments the transgene is contained in a rAAV2 expression vector.

In some embodiments the protective transgene is eCFHT operably linked to a BEST1-EP-454 enhancer promoter or a RPE65-EP-415 enhancer promoter and a polydenylation sequence. In some embodiments the polydenylation sequence is a HSV Thymidine Kinase (TK) polyadenylation sequence. In some embodiments the eCFH/T is v4.0, v4.1, or v4.3. In some embodiments the eCFH/T is v4.2. In some embodiments the transgene is contained in a rAAV2 expression vector.

4.1. Transgene Organization

In general transgenes of the invention comprised the elements and arrangement:

(5'-A)-(B)-(C)-(D)-(3'A)

where A is an ITR sequence, B is a promoter or promoter-enhancer sequence, C is a Factor H encoding sequence, and D is a polyadenylation sequence.

5.2.1 [A] Inverted Terminal Repeats (ITR)

Transgenes delivered by AAVs particles are flanked by ITRs (inverted terminal repeats) required for genome replication and packaging. In some embodiments, the Right ITR is the identical reverse complement of the Left ITR (so that a single 5'-3' nucleotide sequence can define both ITRs). A certain degree of mismatch between the left and right ITRs is tolerated. Various ITRs are known and are suitable for use with AAV2. In one preferred embodiment the ITR is SEQ ID NO:18 (and its reverse complement). In another preferred embodiment the ITR is SEQ ID NO:125 (and its reverse complement).

5.2.2 [B] Promoter and Enhancer Elements

Suitable promoters include promoters derived (e.g., by truncation) from the RPE65-750 base promoter (SEQ ID NO:17), such as the RPE-415 promoter (SEQ ID NO:9) which is shown in combination with the EP promoter as RPE65-EP-415 (SEQ ID NO:9) and RPE65-419 which is shown in combination with the EP promoter as RPE65-EP-419 (SEQ ID NO:10).

Exemplary promoter and enhancer nucleotide sequences are provided as SEQ ID NOs: 8-17 and 27 ("promoter/enhancer sequences"). It will be understood by those of skill in the art that regulatory (promoter/enhancer) sequences can tolerate a certain degree of variation whilst retaining the regulatory property. In certain embodiments described herein in which a promoter/enhancer is called out, a substantially identical sequence (e.g., a sequence with at least about 90% identity, preferably at least about 91%, 92%, 93%, 94%, 95%, 96%, 97%, 98%, 99% nucleotide identity over the entire promoter/enhancer sequence) is contemplated as a suitable substitute for the exemplified sequence. As is well known in the art, variation is tolerated in the relationship (e.g., distance and orientation) between enhancers and promoters.

5.2.2.1 CBA

In one approach a CBA (chicken beta-actin) promoter is used to drive expression of the FN protein in the AAV2 transgene. An exemplary CBA promoter has a sequence of SEQ NO: 13, or is a variant thereof with at least about 90% or 95% sequence identity to SEQ ID NO:13. In one embodiment, the CBA promoter includes a CMV enhancer sequence (approx. nucleotides 1-305 of SEQ ID NO:13), the beta actin promoter (approx nucleotides 306-587), a spacer (approx nucleotides 588-589), a chicken b-actin intron (approx nucleotides 590-1560), an intron acceptor b-globin (approx nucleotides 1561-1603) and a beta globin exon 3 (approx nucleotides 1604-1657).

In one embodiment A is SEQ ID NO:18 or 125, B is the CBA promoter as described above (e.g., SEQ ID NO:13, C encodes protective CFHT (e.g., SEQ ID NO:3), D is the bGH polyadenylation site (e.g., SEQ ID NO:29) or HSV TK polyadenylation site (e.g. SEQ ID NO:28).

In one embodiment A is SEQ ID NO:18, B is the CBA promoter as described above (e.g., SEQ ID NO:13, C encodes protective CFHT (e.g., SEQ ID NO:3), D is the bGH polyadenylation site (e.g. SEQ ID NO:29).

In one embodiment A is SEQ ID NO:125, B is the CBA promoter as described above (e.g., SEQ ID NO:13), C encodes protective CFHT (e.g., SEQ ID NO:3), D is the bGH polyadenylation site (e.g. SEQ ID NO:29).

5.2.2.2 smCBA Promoter

In one approach a smCBA (small modified chicken beta-actin) promoter is used to drive expression of the FN protein in the AAV2 transgene. See U.S. Pat. No. 8,298,818. An exemplary smCBA promoter has a sequence of SEQ NO: 12, or is a variant thereof with at least about 90% or 95% sequence identity to SEQ ID NO:12. In one embodiment, the smCBA promoter includes a CMV enhancer sequence (approx. nucleotides 1-363 of SEQ ID NO:12), the beta actin promoter (approx nucleotides 364-645), a spacer (approx nucleotides 646-647), a chicken b-actin intron (approx nucleotides 648-850), an intron acceptor b-globin (approx nucleotides 851-893) and a beta globin exon 3 (approx nucleotides 894-939).

5.2.2.3 sctmCBA Promoter

In one approach a sctmCBA promoter is used to drive expression of the FN protein in the AAV2 transgene. An exemplary smCBA promoter has a sequence of SEQ NO: 14, or is a variant thereof with at least about 90% or 95% sequence identity to SEQ ID NO:14. In one embodiment, the smCBA promoter includes a CMV enhancer sequence (approx. nucleotides 1-302 of SEQ ID NO:14), the beta actin promoter (approx nucleotides 303-584), a spacer (approx nucleotides 585-586), and a truncated chicken b-actin intron (approx nucleotides 648-850).

5.2.2.4 BEST1

In one approach a BEST1-EP-454 promoter is used having a sequence of SEQ NO:8, or is a variant thereof with at least about 90% or 95% sequence identity to SEQ ID NO:8.

5.2.2.5 VMD2 Promoter

In one approach a VMD2 promoter is used. VMD2 has 680 bases from BEST1-743 [SEQ ID NO:11] and a 97 base 3' enhancer sequence from SV40 intron. See TABLE 34N and US Patent Publication US 2016/0369299. In one approach a variant of VMD2 with at least about 90% or 95% sequence identity to the sequence of TABLE 34N is used.

5.2.2.6 RPE65 Promoter

In one approach a truncated RPE65 promoter is used. The promoter may be the RPE65-EP-415 promoter having a sequence of SEQ NO: 9, or is a variant thereof with at least about 90% or 95% sequence identity to SEQ ID NO:9. The promoter may be the RPE65-EP-419 promoter having a sequence of SEQ NO:10, or is a variant thereof with at least about 90% or 95% sequence identity to SEQ ID NO:10.

5.2.2.7 Enhancers

Enhancers include sequence derived from the CMV enhancer, e.g., the 304 n "EP" enhancer (SEQ ID NO: 7) or a substantially identical variant thereof (e.g., with at least about 90% or 95% sequence identity to SEQ ID NO:7.

5.2.3 [C]. CFH Coding Sequence

The Factor H encoding sequences are as described herein.

5.2.4 [D]. Polyadenylation Sequences

Exemplary polyadenylation sequences include sequences derived from the bovine Growth Hormone bGH polyadenylation signal (e.g., SEQ ID NO:29); sequences derived from the HSV Thymidine Kinase polyadenylation signal (e.g., SEQ ID NO:28); and sequences derived from the SV40 polyadenylation signal (e.g., SEQ ID NO:26).

TABLE 11

| AAV2 Constructs | | | | | | | | | | | | |
|---|---|---|---|---|---|---|---|---|---|---|---|---|
| | | AAV2 Enhancer/Promoter/Poly A Elements | | | AAV2 Size and Titer | | | Transient Transfection Results | | AAV2 Transduction Results | | |
| Protective Transgene | pCTM # | Promoter Name | Promoter Size (bp)* | Poly A Name | Poly A Size (bp) | ITR to ITR Size (bp) | Viral Concentration (vg/ml) | RPE7 Cells | Fetal RPE Cells | RPE7 Cells | COS7 Cells | Fetal RPE Cells |
| | | | | | | | | Fold protective protein above endogenous | | | | |
| CFHT (I62-Y402) | 261 | CBA | 1768 | bGH | 225 | 3700 | 5.43E+12 | 45.9 | 37.6 | >100 | 1728 | 34.4 |
| | 259 | smCBA | 1000 | bGH | 225 | 2932 | 5.85E+12 | 30.5 | 34.4 | 275 | 174 | 14.2 |
| | 257 | VMD2 | 838 | bGH | 225 | 2793 | 5.54E+12 | | | | | 2 |
| | 248 | BEST1-EP-454 | 515 | bGH | 225 | 2477 | | 15.6 | 9.4 | | | |
| | 251 | RPE65-EP-419 | 480 | bGH | 225 | 2412 | | 15.1 | 17.1 | | | |
| | 254 | RPE65-EP-415 | 476 | bGH | 225 | 2408 | | 19.7 | 22.4 | | | |
| | 246 | sctmCBA | 797 | bGH | 225 | 2729 | | 39.4 | 46.1 | | | |
| CFH (I62-Y402-E936) | 281 | BEST1-EP-454 | 515 | HSV TK | 84 | 4656 | 3.05E+12 | 4.6 | 1 | 4.9 | 93 | 3.8 |
| | 282 | RPE65-EP-415 | 476 | HSV TK | 84 | 4563 | 2.89E+12 | 7.2 | 1 | 16 | 125 | 1 |
| | 273 | smCBA | 1000 | HSV TK | 84 | 5066 | 5.72E+12 | 34.4 | | 5.3 | 68 | 1.5 |
| | 267 | VMD2 | 838 | HSV TK | 84 | 4927 | 6.03E+12 | | | | | 1.2 |
| | 260 | CBA | 1768 | bGH | 296 | 6046 | | 83 | 4 | | | |
| | 258 | smCBA | 1000 | bGH | 296 | 5277 | 4.68E+12 | 64.7 | 2 | 1 | 1.2 | 2.1 |
| | 285 | RPE65-EP-419 | 480 | HSV TK | 84 | 4627 | | 3.8 | 1 | | | |
| | 266 | sctmCBA | 797 | HSV TK | 225 | 4955 | | | | | | |
| | 256 | VMD2 | 838 | bGH | 225 | 5138 | 6.52E+12 | | | | | 1.5 |
| | | | | | | | | Fold protective CFH, eCFHT protein above endogenous | | | | |
| eCFH/T (I62-Y402-E936/I62-Y402) | 283 | BEST1-EP-454 | 515 | HSV TK | 84 | 4819 | 2.67E+12 | | 52.5, 29.7 | 12, 2.7 | 119, 2.3 | 1.2, 4.3 |
| | 284 | RPE65-EP-415 | 476 | HSV TK | 84 | 4727 | 3.11E+12 | | 51.2, 50 | 7, 1.7 | 84, 1.7 | 1.3, 2.8 |
| | 271 | smCBA | 1000 | HSV TK | 84 | 5229 | 3.88E+12 | 33, 2 | | 2, 1.3 | 13, 1.3 | 0.8, 0.8 |
| | 268 | VMD2 | 838 | HSV TK | 84 | 5092 | 3.30E+12 | | | | | 1.3, 1.2 |
| | 286 | RPE65-EP-419 | 480 | HSV TK | 84 | 4790 | | | 35.2, 45.6 | | | |
| | 272 | sctmCBA | 797 | bGH | 225 | 5259 | | | | | | |
| | 270 | smCBA | 1000 | bGH | 225 | 5581 | | | | | | |
| | 269 | VMD2 | 838 | bGH | 225 | 5442 | | | | | | |

*Promoter sequence also includes nucleotides that remain during genetic engineering of plasmid

TABLE 12

| AAV2 Constructs | | | | | |
|---|---|---|---|---|---|
| | Transgene Name | Name | Promoter | Enhancer | pA Signal |
| i | CFH | BEST1-EP-454 | Bestrophin-1 | CMV I/E | HSV TK |
| ii | (I62-Y402-E936) | RPE65-EP-415 | RPE65 | CMV I/E | |
| iii | | VMD2 | Vitelliform macular dystrophy | | |
| iv | | smCBA | Small CMV-Chicken beta-actin | CMV I/E | |
| v | CFHT | VMD2 | Vitelliform macular dystrophy | | bGH |
| vi | (I62-Y402) | smCBA | Small CMV-Chicken beta-actin | CMV I/E | |
| vii | | CBA | Large CMV-Chicken beta-actin | CMV I/E | |
| viii | Engineered | BEST1-EP-454 | Bestrophin-1 | CMV I/E | HSV TK |

TABLE 12-continued

| | AAV2 Constructs | | | | |
|---|---|---|---|---|---|
| | Transgene Name | Name | Promoter | Enhancer | pA Signal |
| ix | CFH/T (eCFH/T) | RPE65-EP-415 | RPE65 | CMV I/E | |
| x | (I62-Y402; | VMD2 | Vitelliform macular dystrophy | | |
| xi | I62-Y402-E936) | smCBA | Small CMV-Chicken beta-actin | CMV I/E | |

For example and not limitation, other promoters or modified promoters—including natural and synthetic—suitable for controlling expression of the therapeutic products include, but are not limited to UBC, GUSB, NSE, synapsin, MeCP2, GFAP, PAI1, ICAM, flt-1, and CFTR (see Papadakis et al 2004; Promoters and Control Elements: Designing Expression Cassettes for Gene Therapy in *Current Gene Therapy,* 2004, 4, 89-113; Gray & Samulski 2011; Vector Design and Considerations for Cns Applications in Gene Vector Design and Application to Treat Nervous System Disorders, ed. J. Glorioso (Washington, Dc: Society for Neuroscience), 1-9.; Trapani et al 2014; Vector Platforms for Gene Therapy of Inherited Retinopathies Progress in Retinal and Eye Research 43 (2014) 108e128; Powell and Gray 2015). Viral Expression Cassette Elements to Enhance Transgene Target Specificity and Expression in Gene Therapy *Discov Med.* 2015 Jan. 19(102): 49-57, each incorporated herein by reference).

For example and not limitation, enhancers that may be used in embodiments of the invention include but are not limited to: an SV40 enhancer, a cytomegalovirus (CMV) enhancer, an elongation factor 1 (EF1) enhancer, yeast enhancers, viral gene enhancers, and the like. Termination control region may comprise or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

5.3. Exemplary Viral- and Non-Viral Vectors

In one approach, the FH transgene is delivered to the RPE using an rAAV2 system that is capable of transducing RPE cells at high efficiency. In addition to AAV2, other adeno-associated virus-based vectors include AAV1, AAV2, AAV3, AAV4, AAV5, AAV6, AAV7, AAV8, AAV9, AAV10, AAV11 and pseudotyped AAV.

For packaging a transgene into virions, the ITRs are the only AAV components required in cis in the same construct as the transgene. The cap and rep genes can be supplied in trans. Accordingly, DNA constructs can be designed so that the AAV ITRs flank the coding sequence for the anti-pathogen construct (or subunits thereof, or subunits thereof fused to a dimerizable domain which is part of a regulatable promoter), thus defining the region to be amplified and packaged—the only design constraint being the upper limit of the size of the DNA to be packaged (approximately 4.5 kb).

In addition to AAV vectors, other viral vectors that may be used include, but are not limited to, retroviruses, adenoviruses (AdV), lentiviruses, pox viruses, alphaviruses, and herpes viruses. See e.g., Keeler et al., 2017, "Gene Therapy 2017: Progress and Future Directions" *Clin Transl Sci* (2017) 10, 242-248, incorporated by reference.

Viral vectors (e.g., rAAV2, lentiviral vectors) containing expression cassettes with CFH transgenes may be produced, collected and purified using art-known methods (including methods described in publications cited herein). For AAV methods see Zolotukin et al., 2002, Production and Purification of Serotype 1, 2, and 5 Recombinant Adeno-Associated Viral Vectors" *Methods* 28:158-167; Aponte-Ubillus et al., 2018; Naso et al., 2017; and Penaud-Budloo et al., 2018; all incorporated by reference and cited above.

Non-viral delivery systems may be used, including gene delivery means and methods such direct naked nucleic acid injection, nucleic acid condensing peptides and non-peptides, cationic liposomes and encapsulation in liposomes. In one approach, virus-like particles, or VLPs, can be used to deliver a transgene to RPE or other cells. See Itaka and Kataoka, 2009, "Recent development of nonviral gene delivery systems with virus-like structures and mechanisms," *Eur J Pharma and Biopharma* 71:475-483.

5. 6. Therapeutic Strategy for Delivering Protective Protein

By studying patient populations representing 'pure risk' in Chr 1-directed disease, striking observations have been made about the development and progression of Chr 1-directed disease. We have observed that the presence of drusen, and particularly, the formation of large drusen/pigment epithelial detachments is strongly associated with Chr 1-directed disease and that these phenotypic biomarkers are critically useful in assessing the risk of progression of disease to Geographic Atrophy (GA).

We have developed a therapeutic strategy for delivering a protective protein via AAV gene therapy to treat Chr 1 AMD risk patients with the goal of preventing cell death that results in the breakdown of the retinal pigment epithelium. This strategy allows CFH mediated disease to be arrested by slowing or reversing the formation of drusen (initially small drusen, but also retinal pigment epithelial detachments that form larger drusen, and ultimately progression to geographic atrophy), depending on when the intervention is provided to the patient. The strategy takes into account our understanding of (1) the genetic profiles associated with Chromosome 1 Directed Disease risk, (2) the amplification of Chromosome 1-Directed Disease risk by certain Chromosome 10-Directed Disease risk genetic profiles, and (3) the progression of disease associated with Chromosome 1, or Chromosome 1 and 10 combined, genetic risk factors allows us to administer treatment to patients at specific disease stages to result in the best treatment outcome. By considering a patient's genetic risk (Chr 1 and Chr 1/10) in combination with biomarkers we propose a mechanism for determining the most appropriate stage in a given patent for treatment. As used herein, signs and symptoms indicative of the presence or progression of Chromosome 1-Directed Disease are referred to as "biomarkers" or "phenotype" or "phenotypic stage."

In one aspect we propose that the optimal phenotypic stage for treatment with the methods disclosed herein vary with the patient's genetic profile, and that, in some embodiments, patients at higher genetic risk a will be treated at an earlier stage than a patient with a similar phenotype and a lower genetic risk.

Potential treatment candidates may be assessed in various ways. Initially they are assessed by genotyping to determine their individual genetics and associated risk of disease. In addition, they may be assessed via a clinical exam, including:

Imaging and morphological assessments (for example and including but not limited to, color fundus photography, SD-OCT and confocal scanning laser ophthalmoscopy (for example Spectralis system), including near infrared reflectance (NIR), Blue-light Autofluorescence, Green-light Autofluorescence, Fluorescein angiography);

Functional testing (for example and including but not limited to visual acuity, best corrected visual acuity (BCVA using ETDRS chart), Low luminance BCVA (LLVA, using neutral density filter with ETDRS chart) Reading speed (monocular/binocular), Microperimetry (MAIA) including fixation stability, Dark-adapted microperimetry (S-MAIA): scotopic and mesopic microperimetry sensitivity, and multifocal ERG.

Additional indicators include a combination of morphological and functional information (vision, reading speed, low light vision, fixation, electroretinogram, etc.).

Additionally, patients may be assessed based on a number of phenotypic and blood-derived biomarkers. We have discovered that administering FH transgenes of the invention provides benefit to patents when administered in particular phenotypic windows defined by changes in the anatomy of the eye and appearance or changes in levels of certain biomarkers including, without limitation: the volume of individual drusen (including drusen height, distance to outer limiting membrane, transmission defect/hyper-transmission (loss of RPE), presence of pigmentary changes, and hypopigmentation; overall drusen volume, the number and volume of soft drusen (SD) and pigment epithelium detachment (PED).

Figure 6:
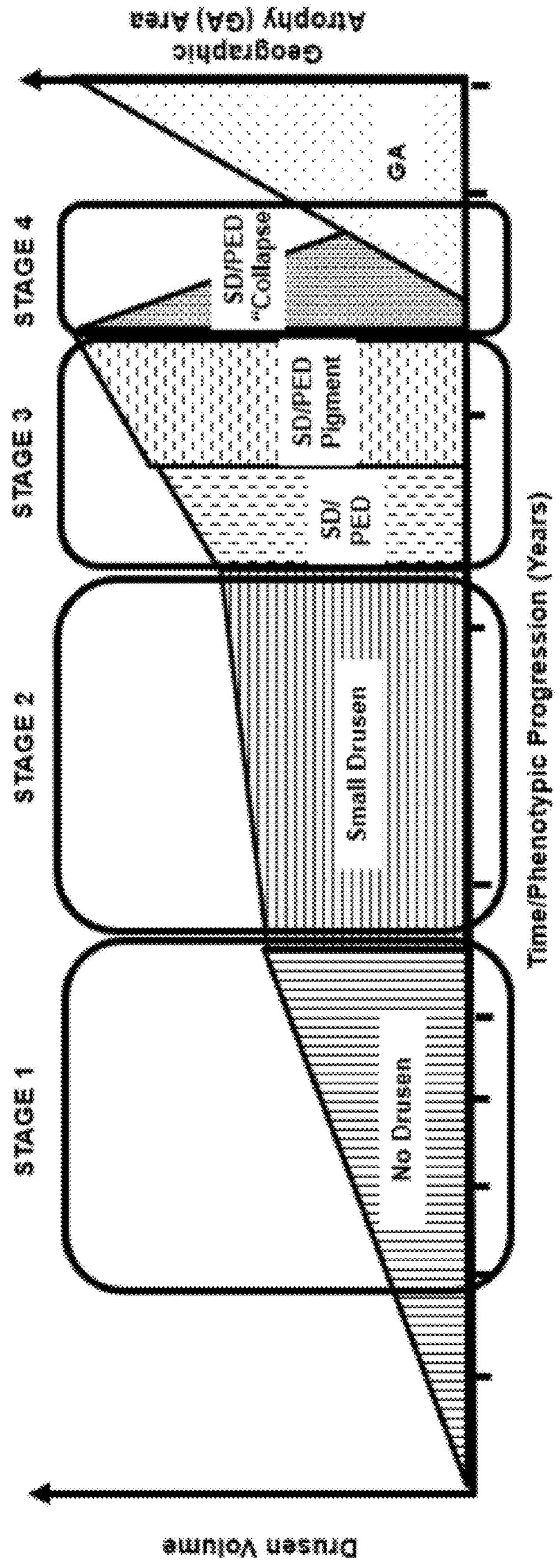
FIG. 6 illustrates the phenotypic progression of Chromosome 1-directed AMD and shows multiple stages of AMD phenotypic progression including exemplary phenotypic stages for administration of the gene therapy vectors of the invention. The four stages denoted with boxes are, from right to left: no drusen, small drusen, soft drusen (SD), Pigment epithelial detachment (PED), SD/PED with RPE pigment, SD/PED collapse, and Geographic Atrophy (GA) and abortive GA.

Patients with genetic risk of developing CFH dysregulation syndrome and ultimately AMD, develop phenotypic changes over time. The phenotypic changes are represented in FIG. 6. FIG. 6 is a depiction of the natural history of AMD development and progression, and depicts various stages where a patient may undergo treatment depending on their genetic risk, phenotypic presentation, and clinical assessment. FIG. 6 shows the progression of disease (phenotypic presentation, and clinical assessment) over time (age in decades, starting at birth and progressing to age 90-100). Progression includes no perceptible evidence of morphological change ("no drusen"), through the formation of "small drusen," to more advanced manifestations of the disease where there is evidence of detachment of the pigment epithelium (PED), drusen becomes larger (soft drusen) and pigmentary changes in the retina occur (resulting from migration of pigment into the retina in the area of the large drusen). Ultimately these larger drusen "collapse" and result in the formation or atrophic regions of retina (geographic atrophy), lacking photoreceptors or other viable retinal structures.

Notably we have also discovered that large drusen, a biomarker unique to CFH dysregulation, can guide in selecting the timing of intervention. Soft drusen (SD) in early AMD, coupled with genetic information, provides a robust treatment biomarker. Soft drusen provides a unique biomarker indicating an enhanced risk for Chr 1-directed AMD and a possible advance to atrophy and vision loss over time.

Drusen volume can be characterized accurately and mapped over time with existing imaging techniques (e.g., spectral domain optical coherence tomography, or SD-OCT), to predict progression prior to vision loss (Schlanitz et al., 2017, "Drusen Volume Development Over Time and its Relevance to the Course of Age-Related Macular Degeneration" *Br J Ophtholmol* 101:198-203, Schlanitz et al., 2017, *Ophthalmology* 124:1718-1722; both incorporated herein by reference). In addition, the ability to characterize drusen volume makes therapeutic intervention possible early in the AMD disease progression based on genotypic and phenotypic characterization. In addition, a change in drusen volume can be used to follow the course of the disease and to help determine whether treatment is beneficial to patients.

Other phenotypic characteristics used in assessment of patient suitability for treatment (in addition to the genotypic characteristics described above) include: GA less than or equal to 2 disc areas (<5 mm$^2$), visual acuity lower than 20/70, large soft drusen (SD) with a volume above a specified threshold, and/or pigment epithelium detachment (PED). Exemplary morphological findings that may be used to assess when to treat a particular patient that presents with risk of CFH mediated macular degeneration include those in TABLE 13.

TABLE 13

| | CHROMOSOME 1-DIRECTED DISEASE BIOMARKERS (SIGNS AND SYMPTOMS) |
|---|---|
| 1 | At least one >63 μm diameter druse in at least one eye within 3000 μm of foveal center |
| 2 | Multiple 65 μm diameter drusen or larger, or at least one druse 125 μm diameter or larger |
| 3 | Evidence of retinal pigmentation in region of drusen |
| 4 | Retinal thickness characteristic of Chr 1-directed disease (total and individual layers: ONL, RPE). Chr 1 patients have retinas that are ~30-50 um thicker than those of Chr 10 patients in the macula |
| 5 | Evidence of disruption of retinal layers |
| 6 | Reflectivity of drusen and ONL |
| 7 | Transmission defect/hyper-transmission (evidence of loss of RPE, hypopigmentation on OCT) |
| 8 | Presence of hyperpigmentary changes |

In a related embodiment, FIG. 6, discussed above, identifies four phenotypically defined stages of AMD progression and these stages may also be used to assess when to treat a particular patient. The time (or stage) at which a patient receives treatment as described herein can also be described with reference to FIG. 6. For example, a patient may be treated at one of stages 1-4. The patient may be homozygous or heterozygous for a Chromosome 1 risk allele. In some embodiments, the patent does not carry a Chromosome 10 risk allele. In one approach a patient in Stage 1 (asymptomatic) receives treatment. In one approach a patient in Stage 2 (small drusen) receives treatment. In one approach a patient in Stage 3 (soft drusen and pigment epithelial detachment) receives treatment. In one approach a patient in Stage 4 (soft drusen and pigment epithelial collapse) receives treatment. In yet another related approach, TABLE 14 identifies stages (A)-(E) which may be used to assess when to treat a particular patient. In a related embodiment, In one aspect the invention provides a method for determining whether a patient is a candidate for FH gene therapy. The same method can be applied to other types of treatment for Chr 1 directed ocular diseases. In one approach the method comprises:

a) Determining a chromosome 1 risk profile for a patient;

b) Determining a chromosome 10 risk profile for the patient;

c) Assigning an AMD risk profile for the patient based on (a) and (b);

d) Determining a chromosome 1 disease stage for the patient.

e) Determining whether the patient is a candidate for treatment based on (a), (c) and (d).

According to this approach, patients at higher genetic risk are treated earlier than patients with lower genetic risk. For example, a patient with a low number of small drusen may not be treated if the patient has low genetic risk but treatment may be initiated for a patient with a low number of small drusen and high genetic risk. Step (c), assigning an AMD risk profile for the patient may be carried out by referring to TABLE 15 (or updates thereof), based on calculated Odds Ratios (which may vary by ethnicity). Thus, a patient with higher AMD risk profile (i.e., at greater risk) may receive treatment at an earlier disease stage than a patient with a lower AMD risk profile. Counter-intuitively, we contemplate treatment of patients prior to the appearance of signs or symptoms of Chr 1-directed AMD (e.g., no appearance of drusen), particularly patients at high genetic risk (e.g., patients with a G21 or G22 risk profile).

Using TABLE 14 below, for illustration and not limitation, a patient with a G21 (high) AMD risk profile would be a candidate for gene therapy even if asymptomatic while a patient at G4 (low) AMD risk profile would not be a candidate for gene therapy if asymptomatic, but would be a candidate if soft drusen is detected. An AMD risk profile can be determined by known methods including, but not limited to, SNP and deletion analysis as summarized in TABLES 1, 15 and 16.

For example and not for limitation, TABLE 15 below illustrates 60 combinations of genetic profiles and biomarkers (signs and symptoms) that may be used to control timing of therapy to a patient. For example, a patient with a G4 genetic risk profile and observable pigment epithelial collapse (lower genetic risk and more significant phenotype indicative of Chr 10-directed AMD development). As another example, the upper right cell in the table refers to treatment of a patient with a G21 genetic risk profile who is asymptomatic as defined below (higher genetic risk and no phenotype indicative of Chr 10-directed AMD development). It is contemplated that individuals with each of the risk profiles shown in TABLE 15 may receive gene therapy treatment (initial administration of the gene therapy vectors of the invention) at any of the phenotypic stages (A)-(E). A patient who has received an initial treatment (at a given disease development stage) may receive subsequent treatment at later stages.

Time of Administration Based on Appearance of Signs and Symptoms:

A) Asymptomatic (no drusen).

B) Small drusen (at least one >63 μm druse in at least one eye within 3000 um of foveal center) and none of C-E.

C) Soft drusen (multiple 65 μm drusen or larger, or at least one druse 125 μm or larger) and none of D-E.

D) Evidence of retinal pigmentation in region of drusen and not E.

E) Pigment epithelial collapse.

TABLE 14

| | Genetic profile | | | Phenotype | | | | |
|---|---|---|---|---|---|---|---|---|
| Dip | Chromosome 1 | Chromosome 10 | Odds Ratio | A | B | C | D | E |
| G21 | Risk/Risk | Homo Risk | 47 | + | + | + | + | + |
| G22 | Risk/Neut | Homo Risk | 41.4 | + | + | + | + | + |
| G24 | Risk/3,1 del | Homo Risk | 22.3 | + | + | + | + | + |
| G11 | Risk/Risk | Het Risk | 19 | | + | + | + | + |
| G23 | Risk/I62 | Homo Risk | 17.1 | | + | + | + | + |
| G12 | Risk/Neut | Het Risk | 9.7 | | | + | + | + |
| G1 | Risk/Risk | No Risk | 8.3 | | | + | + | + |
| G13 | Risk/I62 | Het Risk | 5.7 | | | + | + | + |
| G14 | Risk/3,1 del | Het Risk | 5.7 | | | + | + | + |
| G2 | Risk/Neut | No Risk | 4.5 | | | + | + | + |
| G3 | Risk/I62 | No Risk | 2.2 | | | + | + | + |
| G4 | Risk/3,1 del | No Risk | 2.1 | | | + | + | + |

The therapeutic method of the invention may also be administered to provide benefit in individuals with rare CFH (and other complement genes) early-onset AMD-associated mutations including but not limited to, CFH R1210C, R53C, and D90G).

6. 7. Administration Methodology and Dose

As summarized above, aspects of the invention include methods of administering a FH-encoding polynucleotide construct, typically in the form of a viral particle, to a subject in need of treatment. As such, aspects of the invention include contacting the subject with a viral vector, e.g., as described above, under conditions by which expression of protective FH in the subject results in a beneficial effect on one or more aspects of the subject's health. The invention is not limited to a particular site or method of administration. For example, for illustration and not limitation, gene therapy vectors may be administered by systemic administration (e.g., intravenous injection or infusion), local injection or infusion (e.g., subretinal injection, ocular administration, transscleral administration), by use of an osmotic pump, by application (e.g., eye drops) and by other means for treatment of AMD. It is contemplated that transgenes of the invention may be introduced into, and expressed in, a variety of cell types including retinal cell types, such as rods, cones, RPE, and ganglion cells, and choroidal cells. Gene therapy vectors of the invention may also be administered intravitreally, intravascularly, extraocularly, or to the choroid.

AAV or other vectors comprising an FH transgene may be suspended in a physiologically compatible carrier for administration to a human. Suitable carriers may be readily selected by one of skill in the art in view of the route of delivery. For example, one suitable carrier includes saline, which may be formulated with a variety of buffering solutions (e.g., phosphate buffered saline).

6.1. Ocular Administration

6.1.1. Subretinal Injection

Introduction of protective CFH, eCFH/T and/or CFHT-only alternative complement pathway regulator proteins at the level of the RPE-choroid interface provides better control of complement regulation during early stages of Chromosome 1-directed AMD and prevents blindness associated with late stage geographic atrophy and choroidal neovascularization. This approach reestablishes proper control of the alternative complement pathway caused by common AMD risk-associated CFH polymorphisms (e.g. Y402H). Administration of the gene therapy vector is preferably subretinal injection creates a bleb or blister under the retina. The size of the bleb is related to the volume injected, with a larger volume resulting in a larger bleb. Viral vector is delivered directly to the region of the retina under the bleb and RPE cells in this area are transduced. That is, subretinal injection produces a 'bleb' which can be understood to define the zone of delivery of vector. RPE cells within boundary or margin of the bleb may be referred to as "under the bleb." See Hsu et al., 2018, "Volumetric Measurement of Subretinal Blebs Using Microscope-Integrated Optical Coherence Tomography," Transl Vis Sci Technol. 7(2):19. One way to introduce the vectors is by subretinal injection of viral particles in the extramacular quadrant, remote from SD/PED, to create a subretinal "bleb" and transfect the surrounding region of the retina. See Xue et al., "Technique of Retinal Gene Therapy: Delivery of Viral Vector into the Subretinal Space" Eye 31:1308-1316, 2017. Also see Moore et al. 2017, Ochakovski et al. 2017, Schön et al. 2015, supra.

A bleb may be generally hemispherical and characterized by a bleb margin (boundary) that defines the region inside the bleb (containing injectate) and the region outside the bleb. The bleb may be characterized as having an approximately circular cross section with a circumference, a center, and a radius.

In alternative embodiments, the gene therapy vector is administered via intravitreal injection, choroidal, transcleral, intravascular, or by other routes.

6.1.2. Bleb Placement and Size

Placement of a bleb(s) affects distribution of the therapeutic agent. For example, one or more blebs can be created in one quadrant or multiple quadrants of the eye to ensure sufficient distribution of the therapeutic agent and/or blebs can be placed in diseased regions (e.g., where drusen is present). According to the present invention, when the gene therapy vector encodes CFHT (whether alone or expressed with CFH) bleb placement is informed by the discovery that CFHT expressed in RPE cells in a subretinal bleb can migrate to other areas of the eye. See Example 6.

As discussed herein (e.g., Section 14) in preclinical studies in African Green Monkeys (AGM) we have observed migration of CFHT from a primary rAAV2 bleb location superior of the macula to both nasal and macular regions of the eye of treated African Green Monkeys. Without intending to be bound by a particular mechanism, our observations are consistent with a mechanism in which CFHT protein expressed by transduced cells in the bleb region crosses Bruch's membrane and enters the choriocapillaris to gain access to other regions of the eye. Based, in part, on this discovery we have determined that CFHT protein can be delivered to the primate (e.g., human) macula from an injection outside the macula. In this case cells in the bleb regions will produce and secrete CFHT protein, the CFHT protein will diffuse across Bruch's membrane and enter the choriocapillaris to gain access by "lateral diffusion" to other regions of the eye. Once on the choriod side, protective CFHT protein can control complement defects on endothelial cells and is expected to cross Bruch's membrane again to control complement in the sub-RPE space. Without intending to be limited to a particular mechanism, protective CFHT protein produced by RPE cells under the extramacular bleb) can act locally to control alternative complement pathway (sub-RPE space) as well as cross Bruch's membrane to act on choroidal endothelial cells both locally (under extramacular bleb) as well as to other regions of the eye, including the macula. CFHT protein that has migrated to other regions of the eye and macular choroidal space has the ability to once again diffuse across Bruch's membrane to act in the sub-RPE space to control alternative complement pathway. One result is that the alternative complement pathway is controlled in both the RPE (e.g., sub-RPE space) and choroid tissue (e.g., choriocapillary compartment).

In AGM experiments migration of ~4-7 mm from the bleb margin was observed. The lateral migration of CFHT means that subretinal injections outside the macula can be used to deliver CFHT into the macular area. Likewise, subretinal injections outside the macula can be used to deliver CFHT to the fovea. In some cases, injections may be made within the macula, but outside the fovea, to deliver CFHT protein to the macula and fovea. Additionally, the lateral migration suggests that a single or small number of injections could deliver CFHT to a larger area of the eye than achievable without migration.

The advantages of injection outside the macula will be apparent to those of ordinary skill in the art. Thus, in one aspect the invention involves delivery of vector by a subretinal injection that is not an injection into the macula. In one approach, the center of the vector-containing bleb is outside the macula. In one approach, the bleb margin is outside the macula. In one approach, the bleb margin is at least 1 mm, at least 2 mm, at least 3 mm, at least 4 mm, at least 5 mm at least 6 mm, at least 7 mm, at least 8 mm, at least 9 mm, or at least 1 cm from the macula. In one approach, the bleb margin is at least 1 to 5 mm, 1-10 mm, 4 to 20 mm, e.g., 5 to 20 mm, 5 to 15 mm, e.g., 10-15 mm from the macula. In one approach the center-to-center distance from the center of a bleb to the center of the macula is at least 10 mm, such as at least 15 mm, at least 20 mm or at least 25 mm.

In one approach, the bleb margin is outside the fovea. In one approach, the bleb margin is at least 1 mm, at least 2 mm, at least 3 mm, at least 4 mm, at least 5 mm at least 6 mm, at least 7 mm, at least 8 mm, at least 9 mm, or at least 1 cm from the fovea. In one approach, the bleb margin is at least 1 to 20 mm, e.g., 1 to 5 mm, 1-10 mm, 5 to 20 mm, 5 to 15 mm from the fovea. In one approach the center-to-center distance from the center of a bleb to the center of the fovea is at least 10 mm, such as at least 15 mm, at least 20 mm or at least 25 mm.

Bleb size is related to the volume of injectate. Generally, the volume of injectate is from 25 to 300 microliters, usually 25 to 200 microliters, often 50-100 microliters, and often 100-200 microliters.

6.2. Dose

It is to be noted that dosage values may vary with the severity of the condition. It is to be further understood that for any particular subject, specific dosage regimens can be adjusted over time according to the individual need and the professional judgment of the person administering or supervising the administration of the compositions, and that dosage ranges set forth herein are exemplary only and are not intended to limit the scope or practice of the claimed composition.

The amount of vector administered will be an "effective amount" or a "therapeutically effective amount," i.e., an amount that is effective, at dosages and for periods of time necessary, to achieve a desired result. A desired result would include an improvement in CFH and/or CFHT activity in a target cell (e.g., an RPE cell) or a detectable improvement in a symptom associated with CFH and/or CFHT dysfunction, including without limitation an improvement in AMD symptoms or signs, preferably a statistically significant improvement. Alternatively, if the pharmaceutical composition is used prophylactically, a desired result would include a demonstrable prevention of one or more symptoms of CFH and/or CFHT dysfunction, including without limitation, a symptom or sign of AMD, preferably a statistically significant prevention. A therapeutically effective amount of such a composition may vary according to factors such as the disease state, age, sex, and weight of the individual, or the ability of the viral vector to elicit a desired response in the individual. Dosage regimens may be adjusted to provide the optimum response. A therapeutically effective amount is also one in which any toxic or detrimental effects of the viral vector are outweighed by the therapeutically beneficial effects. The amount of viral vector in the composition may vary according to factors such as the disease state, age, sex, and weight of the individual.

Dosage regimens may be adjusted to provide the optimum therapeutic response. For example, a single bolus may be administered, several divided doses may be administered over time or the dose may be proportionally reduced or increased as indicated by the exigencies of the therapeutic situation. A preferred human dosage may be $10^9$ to $10^{13}$ AAV genomes per injection in a volume of 100-300 μl per subretinal bleb. More than one bleb may be created per eye. Multiple AAV2 treatments, non-AAV2 virus-based, nanoparticle, or other approaches may be administered in any given individual over a lifetime.

7. Cell Therapy

Cell therapy is also contemplated. In one approach a cell or cells are transformed ex-vivo with a polynucleotide construct comprising a Factor H gene described herein and an operably linked promoter, and optionally other regulatory elements, and transformed cells or progeny of transformed cells are administered to a patient, e.g., systemically or by ocular injection. Exemplary cells for use in cell therapy include stem cells, RPE cells, and macrophages.

8. Treatment Outcome

CFH/CFHT gene therapy in a suitable patient, including treatment of an individual at risk of developing AMD or in early stages of the disease, can stabilize, ameliorate or reverse a symptom or sign of AMD in the patient. For example and without limitation, providing protective FH protein (e.g., CFH, CFHT, or eCFHT) to patients that are heterozygous or homozygous for a Chr 1 risk allele can stabilize and/or slow or even reverse the progression of the disease, as demonstrated by various ocular biomarkers. In one approach the primary desired treatment outcome in a patient treated with FH gene therapy is a reduction in total drusen and/or PED volumes, volume of individual drusen/PED (including drusen height, distance to outer limiting membrane, transmission defect/hyper-transmission [loss of RPE], presence of pigmentary changes, and hypopigmentation; overall drusen volume, the number and volume of small drusen (SD)/pigment epithelium detachment (PED), presence and extent of geographic atrophy (GA lesion size and growth), and areas of new GA. Often the reduction or relative improvement is by a factor of at least about 10%, preferably by at least about 25%, more preferably by at least about 50%. Improvements of functional measures, including without limitation: visual acuity (Early Treatment Diabetic Retinopathy Study, or ETDRS); best corrected visual acuity (or BCVA); microperimetry (macular integrity assessment, or MAIA); dark adaptation; reading speed; visual evoked potential (VEP); and multifocal electroretinography (mfERG), are contemplated. Other biomarkers indicative of stabilization, slowing, or reversing AMD progression including without limitation: BCVA Change; Area of GA Change (square root transformation or otherwise); Fixation; Reading Speed; % New Areas of GA; Photoreceptor Height; Individual Druse Characteristics.

9. Pharmaceutical Compositions

Another aspect of the invention pertains to pharmaceutical compositions of the vectors of the invention. In one embodiment, the composition includes an effective amount of a vector and a pharmaceutically acceptable carrier.

10. Unit Dose Form

Sterile injectable solutions can be prepared by incorporating a vector, e.g., a viral vector, in the required amount, optionally with a diluent or excipient suitable for injection into a human patient. Provided are unit dosage forms such as a single use, pre-filled syringes or other injection device, with sufficient AAV particles for a single administration to a patient.

11. Therapy for Other Chromosome 1-Directed Diseases

In some embodiments, transgenes described herein for treatment of AMD may be used in treatment of other complement-related diseases and/or may be targeted to non-ocular including, for illustration, kidney podocyte or epithelial cells for treatment of IgA nephropathy), coronary artery disease (CAD), coronary artery calcification (CAC; Agaston scores), aortic artery calcification (AAC; Agaston scores), appendicitis, tonsillitis, cholecystitis, periodontitis, nephritis, and IgA nephropathy. It will be understood that the polynucleotide constructs described herein find use for treatment of any condition associated with Chr 1 risk alleles (Complement Factor H Dysregulation). For some conditions systemic administration of the vectors may be appropriate.

12. Method of Treatment

In one aspect the invention provides a method for preventing, slowing progression of, reversing or ameliorating symptoms and signs of Chromosome 1-directed disease in a patient comprising (1) determining a genetic profile of the patient; (2) determining a biomarker of the patient; (3) administering a gene therapy vector comprising a polynucleotide sequence that encodes a protective Factor H polypeptide selected from (a) full length CFH polypeptide; (b) truncated CFH polypeptide; (c) a variant of truncated CFH polypeptide comprising an amino-terminal sequence CIRVSKSFTL; (d) both full length CFH polypeptide and truncated CFH polypeptide; and (e) both full length CFH polypeptide and a variant of truncated CFH polypeptide comprising a carboxy-terminal sequence CIRVSKSFTL; with the proviso that the Factor H polypeptide of (a)-(c) or the Factor H polypeptides of (d)-(e) comprise isoleucine (I) at position 62 and tyrosine (Y) at position 402; and a promoter operably linked to the polynucleotide sequence (optionally, with the proviso that the promoter is not the complement Factor H gene promoter); wherein introduction of the polynucleotide construct into a mammalian cell results in expression of the protective Factor H polypeptide(s).

In some cases the genetic risk profile is selected from G1 to G30 as defined in TABLE 11. In some embodiments the patient's genetic profile is selected from G4, G2, G13, G14, G1, G12, G11, G23, G24, G21, or G22. In some embodiments the genetic profile is G11, G23, G24, G21, or G22.

In some embodiments, the patients phenotype defined by biomarkers and signs identified in TABLE 14. In some embodiments the patient is has no symptoms of AMD (i.e. asymptomatic). In some embodiments, at the time of first administration of the administering a gene therapy vector patient does not exhibit (i) drusen, or does not exhibit (ii) small drusen, or does not exhibit (iii) soft drusen (SD), or does not exhibit (iv) pigment epithelial detachment (PED), or does not exhibit (v) SD/PED with RPE pigment, or does not exhibit (vi) SD/PED collapse, or does not exhibit (vii) Geographic Atrophy (GA).

13. Examples

13.1. Example 1. A Protective Allele Reduces Risk Even in the Presence of a Risk Allele We performed extensive genetic analyses of "Pure Chr 1 risk" individuals (i.e., individuals that are heterozygous (G2-G4 in TABLES 2 and 15) or homozygous (G1 in TABLES 2 and 15) for AMD risk factors (SNPs/variants; haplotypes) on chromosome 1, but have no AMD risk factors (SNPs/variants; haplotypes) on chromosome 10. Heterozygous Chr 1 risk individuals can carry (i) one risk allele and (ii) a second allele that is either neutral, I62-tagged protective, or CFHR3/1 deletion-tagged protective (G2-G4 in TABLES 2 and 15). Risk, neutral and protective alleles can oftentimes be tagged by individual SNPs/variants, and also by specific combinations of SNPs/variants (haplotypes). The number of SNPs/variants that define any given haplotype can vary between 2 and to greater than 50. See Hageman et al., 2005 "A common haplotype in the complement regulatory gene factor H (HF1/CFH) predisposes individuals to age-related macular degeneration," *Proc Natl Acad Sci USA,* 102(20), 7227-32; Hageman et al., 2006, "Extended Haplotypes in the Complement Factor H (Cfh) AND Cfh-Related (Cfhr) Family of Genes Protect Against Age-Related Macular Degeneration: Characterization, Ethnic Distribution and Evolutionary Implications," *Ann Med,* 38(8), 592-604; U.S. Pat. Nos. 7,745,389, 8,088,579 and 8,497,350; and US Publication US2018155788.

One study of 2,009 genotyped and phenotyped individuals (derived from 8,000 total individuals) and employing 4-SNP haplotypes demonstrate the novel finding that such Pure Chr 1 risk patients are protected against the development of AMD when they carry a protective CFH allele or even a neutral CFH allele, in the presence of a risk allele (G2-G4 in TABLES 2 and 15). For Pure Chr 1 risk individuals, the risk of developing late-stage AMD is directly impacted by the diplotype pairing of risk (R), neutral (N) or protective (P; I62/3,1 Del) alleles. Individuals with two copies of a risk allele (V62-H402/V62-H402) have an Odds Ratio (OR) of 8.3; individuals with one copy of a neutral allele (V62-Y402) together with one copy of a risk allele (V62-H402)/lowers the OR to 4.5; and individuals with and one copy of a protective allele together with one copy of a risk allele lowers the OR to 2.2. (I62-Y402/V62-H402). This unexpected result strongly suggests that it is only necessary to have some fully functional (protective or neutral) CFH present—even in the presence of some risk protein—to provide for appropriate regulation of the alternative complement cascade, thereby decreasing the risk of developing Chr 1-directed AMD and other co-segregating diseases.

Table 16 shows diplotypes association with Early or Late AMD. This information can also be used to identify patients for treatment based on a genetic risk profile and phenotype.

TABLE 15

GENOTYPE GROUPS (BASED ON 4 SNPS) AND ASSOCIATED AMD ODDS RATIOS

| AMD Genetic Status | | | | AMD | | rs800292 CFH I62 (A) | rs1061170 CFH Y402 (T) | rs12144939 CFHR3,1 Del (T) | rs10490924 ARMS2 No Risk (G) |
|---|---|---|---|---|---|---|---|---|---|
| Group | Chr 1 | Chr 10 | CFHR3,1 (# Copies) | Odds Ratio | CFH Protein Status | CFH V62 (G) | CFH H402 (C) | CFHR3,1 No Del (G) | ARMS2 Risk (T) |
| G1 | Risk/Risk | No Risk | 2 | 8.3 | VV62, HH402, EE936 | GG | CC | GG | GG |
| G2 | Risk/Neut | No Risk | 2 | 4.5 | VV62, YH402, ED936 | GG | CT | GG | GG |
| G3 | Risk/I62 | No Risk | 2 | 2.2 | IV62, YH402, EE936 | AG | CT | GG | GG |
| G4 | Risk/3,1 del | No Risk | 1 | 2.1 | VV62, YH402, EE936 | GG | CT | GT | GG |
| G5 | Neut/Neut | No Risk | 2 | 2.7 | VV62, YY402, DD936 | GG | TT | GG | GG |
| G6 | Neut/I62 | No Risk | 2 | 2.1 | IV62, YY402, ED936 | AG | TT | GG | GG |
| G7 | Neut/3,1 del | No Risk | 1 | 1.8 | VV62, YY402, ED936 | GG | TT | GT | GG |
| G8 | I62/I62 | No Risk | 2 | 1.2 | II62, YY402, EE936 | AA | TT | GG | GG |
| G9 | I62/3,1 del | No Risk | 1 | 1.4 | IV62, YY402, EE936 | AG | TT | GT | GG |
| G10 | 3,1 del/3,1 del | No Risk | 0 | 1.0 (ref) | VV62, YY402, EE936 | GG | TT | TT | GG |
| G11 | Risk/Risk | Het Risk | 2 | 19.0 | VV62, HH402, EE936 | GG | CC | GG | GT |
| G12 | Risk/Neut | Het Risk | 2 | 9.7 | VV62, YH402, ED936 | GG | CT | GG | GT |
| G13 | Risk/I62 | Het Risk | 2 | 5.7 | IV62, YH402, EE936 | AG | CT | GG | GT |
| G14 | Risk/3,1 del | Het Risk | 1 | 5.7 | VV62, YH402, EE936 | GG | CT | GT | GT |
| G15 | Neut/Neut | Het Risk | 2 | 7.7 | VV62, YY402, DD936 | GG | TT | GG | GT |
| G16 | Neut/I62 | Het Risk | 2 | 3.6 | IV62, YY402, ED936 | AG | TT | GG | GT |
| G17 | Neut/3,1 del | Het Risk | 1 | 3.5 | VV62, YY402, ED936 | GG | TT | GT | GT |
| G18 | I62/I62 | Het Risk | 2 | 3.1 | II62, YY402, EE936 | AA | TT | GG | GT |
| G19 | I62/3,1 del | Het Risk | 1 | 1.6 | IV62, YY402, EE936 | AG | TT | GT | GT |
| G20 | 3,1 del/3,1 del | Het Risk | 0 | 3.4 | VV62, YY402, EE936 | GG | TT | TT | GT |
| G21 | Risk/Risk | Homo Risk | 2 | 47.0 | VV62, HH402, EE936 | GG | CC | GG | TT |
| G22 | Risk/Neut | Homo Risk | 2 | 41.4 | VV62, YH402, ED936 | GG | CT | GG | TT |
| G23 | Risk/I62 | Homo Risk | 2 | 17.1 | IV62, YH402, EE936 | AG | CT | GG | TT |
| G24 | Risk/3,1 del | Homo Risk | 1 | 22.3 | VV62, YH402, EE936 | GG | CT | GT | TT |

TABLE 15-continued

GENOTYPE GROUPS (BASED ON 4 SNPS) AND ASSOCIATED AMD ODDS RATIOS

| AMD Genetic Status | | | | AMD | | rs800292 CFH I62 (A) | rs1061170 CFH Y402 (T) | rs12144939 CFHR3,1 Del (T) | rs10490924 ARMS2 No Risk (G) |
|---|---|---|---|---|---|---|---|---|---|
| Group | Chr 1 | Chr 10 | CFHR3,1 (# Copies) | Odds Ratio | CFH Protein Status | CFH V62 (G) | CFH H402 (C) | CFHR3,1 No Del (G) | ARMS2 Risk (T) |
| G25 | Neut/Neut | Homo Risk | 2 | 28.8 | VV62, YY402, DD936 | GG | TT | GG | TT |
| G26 | Neut/I62 | Homo Risk | 2 | 17.2 | IV62, YY402, ED936 | AG | TT | GG | TT |
| G27 | Neut/3,1 del | Homo Risk | 1 | 46.0 | VV62, YY402, ED936 | GG | TT | GT | TT |
| G28 | I62/I62 | Homo Risk | 2 | 5.0 | II62, YY402, EE936 | AA | TT | GG | TT |
| G29 | I62/3,1 del | Homo Risk | 1 | 9.3 | IV62, YY402, EE936 | AG | TT | GT | TT |
| G30 | 3,1 del/3,1 del | Homo Risk | 0 | 1.6 | W62, YY402, EE936 | GG | TT | TT | TT |

TABLE 16

AMD Genetic Status (Diplotype Combinations As A Percentage Of The Total Utah/Iowa/Melbourne Cohort, As A Percentage Of AMD Patients In The Cohort And As A Percentage Of Each AMD Subgroup).

| | Risk/Risk | Risk/Neut | Risk/I62 | Risk/3,1 | Neut/Neut | Neut/I62 | Neut/3,1 | I62/I62 | I62/3,1 | 3,1/3,1 | total |
|---|---|---|---|---|---|---|---|---|---|---|---|
| As a percentage of total combined cohort (n = 5256): No Risk at Chromosome 10 | | | | | | | | | | | |
| Controls (0, 1a) | 2.9% | 2.9% | 3.7% | 3.1% | 1.0% | 1.9% | 1.7% | 1.0% | 1.8% | 0.7% | 20.6% |
| Early AMD (1b-3) | 3.6% | 1.7% | 1.2% | 1.2% | 0.4% | 0.8% | 0.5% | 0.3% | 0.5% | 0.2% | 10.3% |
| Late AMD (4a-4c) | 4.9% | 3.0% | 1.7% | 1.3% | 0.5% | 0.6% | 0.6% | 0.2% | 0.4% | 0.0% | 13.2% |
| | Risk/Risk | Risk/Neutral | Risk/I62V | Risk/3,1 | Neut/Neut | Neut/I62 | Neut/3,1 | I62/I62 | I62/3,1 | 3,1/3,1 | total |
| Heterozygous Risk at Chromosome 10 | | | | | | | | | | | |
| Controls (0, 1a) | 1.3% | 1.7% | 1.8% | 1.5% | 0.4% | 1.2% | 0.9% | 0.6% | 1.1% | 0.3% | 11.0% |
| Early AMD (1b-3) | 2.3% | 1.5% | 1.0% | 1.1% | 0.4% | 0.6% | 0.3% | 0.3% | 0.3% | 0.2% | 7.8% |
| Late AMD (4a-4c) | 6.8% | 4.5% | 2.8% | 2.1% | 0.8% | 1.0% | 0.8% | 0.4% | 0.3% | 0.2% | 19.7% |
| Homozygous Risk at Chromosome 10 | | | | | | | | | | | |
| Controls (0, 1a) | 0.2% | 0.2% | 0.3% | 0.2% | 0.1% | 0.1% | 0.0% | 0.1% | 0.1% | 0.1% | 1.4% |
| Early AMD (1b-3) | 0.5% | 0.5% | 0.4% | 0.3% | 0.1% | 0.2% | 0.1% | 0.1% | 0.2% | 0.0% | 2.4% |
| Late AMD (4a-4c) | 2.1% | 1.8% | 1.4% | 1.2% | 0.5% | 0.6% | 0.5% | 0.1% | 0.2% | 0.1% | 8.4% |
| As a percentage of AMD patients in combined cohort (n = 3401): No Risk at Chromosome 10 | | | | | | | | | | | |
| Early AMD (1b-3) | 5.5% | 2.6% | 1.9% | 1.8% | 0.6% | 1.2% | 0.8% | 0.4% | 0.8% | 0.4% | 16.0% |
| Late AMD (4a-4c) | 7.6% | 4.6% | 2.7% | 2.0% | 0.8% | 1.0% | 0.9% | 0.2% | 0.6% | 0.0% | 20.5% |
| 4a + 4c | 2.0% | 1.1% | 0.5% | 0.4% | 0.1% | 0.2% | 0.3% | 0.1% | 0.2% | 0.0% | 5.0% |
| 1b only | 0.1% | 0.3% | 0.2% | 0.2% | 0.0% | 0.1% | 0.1% | 0.1% | 0.1% | 0.0% | 1.3% |
| 2a-3 | 5.4% | 2.3% | 1.6% | 1.6% | 0.6% | 1.1% | 0.7% | 0.3% | 0.7% | 0.4% | 14.6% |
| Heterozygous Risk at Chromosome 10 | | | | | | | | | | | |
| Early AMD (1b-3) | 3.5% | 2.3% | 1.5% | 1.8% | 0.6% | 0.9% | 0.5% | 0.4% | 0.4% | 0.3% | 12.1% |
| Late AMD (4a-4c) | 10.4% | 6.9% | 4.3% | 3.3% | 1.3% | 1.6% | 1.3% | 0.6% | 0.5% | 0.2% | 30.5% |
| 4a + 4c | 2.8% | 1.5% | 1.1% | 0.8% | 0.3% | 0.2% | 0.3% | 0.1% | 0.1% | 0.0% | 7.2% |
| 1b only | 0.2% | 0.0% | 0.1% | 0.1% | 0.1% | 0.1% | 0.0% | 0.1% | 0.0% | 0.1% | 0.7% |
| 2a-3 | 3.3% | 2.3% | 1.4% | 1.6% | 0.5% | 0.8% | 0.5% | 0.4% | 0.4% | 0.2% | 11.3% |
| Homozygous Risk at Chromosome 10 | | | | | | | | | | | |
| Early AMD (1b-3) | 0.8% | 0.8% | 0.7% | 0.5% | 0.1% | 0.2% | 0.1% | 0.1% | 0.3% | 0.0% | 3.6% |
| Late AMD (4a-4c) | 3.2% | 2.7% | 2.2% | 1.9% | 0.8% | 0.9% | 0.8% | 0.1% | 0.3% | 0.1% | 13.0% |
| 4a + 4c | 0.94% | 0.71% | 0.41% | 0.38% | 0.26% | 0.18% | 0.06% | 0.03% | 0.12% | 0.00% | 3.1% |
| 1b only | 0.00% | 0.06% | 0.03% | 0.06% | 0.00% | 0.03% | 0.00% | 0.06% | 0.03% | 0.00% | 0.3% |
| 2a-3 | 0.76% | 0.74% | 0.65% | 0.44% | 0.09% | 0.21% | 0.15% | 0.09% | 0.24% | 0.03% | 3.4% |

13.2. Example 2. Promoter Activity in RPE Cells

We tested a large number of promoter candidates using a luciferase reporter system and transient transfection using the following human immortalized cell types: HEK293 (ATCC # CRL-1573), A549 (ATCC # CRL-185), RPE1 (ATCC # CRL-4000), COS-7 (ATCC # CRL-1651), RPE7 (Sigma 09061602) and human undifferentiated fetal RPE cells (ScienCell #6540).

13.2.1. Designing RPE-Specific RPE65 and BEST1 Promoters for AAV Gene Therapy Vectors

13.2.2. Rationale

We compared the strength of RPE65-750 (SEQ ID:17), BEST1-723 (SEQ ID:11) and CFH (SEQ ID:15) promoter elements in immortalized cell lines and determined that promoter activity was not sufficient for robust transgene expression. Therefore, we continue to identify optimal promoter enhancer regions from RPE65 and BEST1 promoter sequences for RPE-specific gene expression. Identification of small (≤500-bp) RPE-specific promoter elements that can drive high level expression of protective CFH, CFHT and engineered CFHT (eCFH/T) are essential for our chromosome 1-directed AMD therapeutic program.

13.2.3. Methods

RPE65 and BEST1 Promoter Cloning

The RPE65-750 was used as template for PCR with combinations of RPE65-750 specific forward and reverse primers (TABLE 17A). The BEST1-723 (GeneArt construct #17ABUNXP) was used as template for PCR with combinations of BEST1 promoter specific forward and reverse primers (TABLE 17B). PCR analysis was performed using Platinum PCR SuperMix (ThermoFisher, Cat. #11306-016) following manufacturer's instructions. All 70 RPE65 and 59 BEST1 PCR products were purified using QIAquick PCR Purification kit (Qiagen Cat. #28106). Purified PCR fragments were digested with XhoI and BamHI (built in to the primers) and cleaned up with QIAquick PCR Purification kit. These promoter inserts were then cloned into XhoI and BglII sites upstream of firefly luciferase construct pGL4.10 [Luc2] (Promega, Cat. # E665A) and verified by DNA sequencing and restriction digestion. In another approach, BEST1 promoter sequences were synthesized by GeneArt (ThermoFisher) that included CEBP alpha and E-box elements identified to be important for RPE-specific expression of BEST1 mRNA (Esumi, N., et. al., JBC; 2004:19064-19073). The BEST1-V1 (#17AAUYRP), BEST1-V2 (#17AAUYQP) and BEST1-V3 (#17AAUYPP) plasmids were digested with XhoI and BglII and the 192, 107 and 144 nucleotide promoters, respectively, were cloned upstream of firefly luciferase pGL4.10[Luc2] (Promega, Cat. # E665A) and verified by DNA sequencing and restriction digestion.

TABLE 17A

PCR primers for RPE65 promoter cloning

| Primer Name | RPE65 Specific Primer Sequence | SEQ ID NO: |
|---|---|---|
| pRPE65_F_2 | CAAATAAAGCCAAGCATCAGGG | 86 |
| pRPE65_F_4 | TCTCAGAGTGCCAAACATATACC | 87 |
| pRPE65_F_5 | CAGGCATTAGTGACAAGCAAAG | 88 |
| pRPE65_F_6 | GAAGGATTGAGGTCTCTGGAAA | 89 |
| pRPE65_F_7 | GAGAATGAAGGCACAGAGGTATT | 90 |
| pRPE65_F_10 | GAGGGTTAGAGGTGCACAAT | 91 |
| pRPE65_F_14 | CCCACCTAGCTCCTTTCTTTC | 92 |
| pRPE65_F_25 | AACCTGGTTGGAAGAATATTGG | 93 |
| pRPE65_F_26 | AGAGAATGGTGCCAAGGT | 94 |
| pRPE65_F_27 | CTTCTCCAATCTTAGCACTAATCAA | 95 |
| pRPE65_F_28 | CTGGTTCATAGGTGGTATGTAATAGA | 96 |
| pRPE65_F_30 | CAGAGTTATAAGATCTGTGAAGACA | 97 |
| pRPE65_R_8 | CCAAGGAGAATGAGAACAGATTAGA | 98 |
| pRPE65_R_9 | ACTGCAGAATGAAGAAGGAA | 99 |
| pRPE65_R_11 | TATTGTCCCTGTCCCTGTCT | 100 |
| pRPE65_R_12 | GGCTTGCTGTTCCCATAACA | 101 |
| pRPE65_R_20 | AAAGGAGTTATGGCTTTGGGA | 102 |
| pRPE65_R_25 | CCCTAATACCTCTGTGCCTT | 103 |
| pRPE65_R_26 | GGGAACAGAAGTTGCTTTCA | 104 |
| pRPE65_R_30 | CAGGCCTGAGCTGATCC | 105 |

TABLE 17B

PCR primers for BEST1 promoter cloning.

| Primer Name | BEST1 Specific Primer Sequence | SEQ ID NO: |
|---|---|---|
| pBEST1_F_4 | CCAGAAACCAGGACTGTTGA | 106 |
| pBEST1_F_5 | TGAGAGAGGAGCTGAAACCTAC | 107 |
| pBEST1_F_6 | GAAATTCCCCAGCAACACCATC | 108 |
| pBEST1_F_13 | CAATCAGAGCTCCTCGTCAG | 109 |
| pBEST1_F_15 | CCAACACCCTCCAAGAAGAAA | 110 |
| pBEST1_F_17 | CCGTTGTCTCTGAGCAGATTA | 111 |
| pBEST1_F_20 | TTAGGGAGTCAAGTGACGGC | 112 |
| pBEST1_F_22 | CCTGCCAGCCAATCACA | 113 |
| pBEST1_F_24 | AGTGCCAGCCTCTAAGAGT | 114 |
| pBEST1_F_25 | GAACACTGGTGGAGCAGAT | 115 |
| pBEST1_F_26 | CCAACAGGGCTGTCAAAGAC | 116 |
| pBEST1_F_29 | GAGAGTTCCTGGCACAGA | 117 |
| pBEST1_R_4 | TTTCTTCTTGGAGGGTGTTGG | 118 |
| pBEST1_R_19 | ACTCCCTGGGACTCTGTG | 119 |
| pBEST1_R_19x | AAATCCAGAGGCTAAAGGATCTG | 120 |

TABLE 17B-continued

| PCR primers for BEST1 promoter cloning. | | |
|---|---|---|
| Primer Name | BEST1 Specific Primer Sequence | SEQ ID NO: |
| pBEST1_R_20 | CTGTGCTGAGCTTCAACTTCTG | 121 |
| pBEST1_R_25 | CCCACGTGAGTGCTGAG | 122 |
| pBEST1_R_28 | GGTCTGGCGACTAGGCT | 123 |
| pBEST1_R_29 | AGGAGTCCTTGTCTTAGTCC | 124 |

13.2.4. Dual Luciferase Assay in RPE7 Cell Line

RPE7 cells were seeded in 96 well plate ($1\times10^4$ cells per well in 75 μl of complete culture medium). Twenty-four hours after seeding, cells were transfected with the following plasmids using Lipofectamine 3000 reagent (ThermoFisher Scientific, Cat. # L300008) with our optimized transfection protocol: 100 ng of firefly luciferase driven by RPE65-750 promoter, positive control CMV-fLuc (pCTM224) and negative control pGL4.10(Luc2) lacking a promoter element. To normalize all electroporations we also co-transfected 10 ng of *Renilla* luciferase SV40-rLuc (pCTM238). For each transfection (one well), 100 ng of firefly luciferase plasmid DNA and 10 ng of *Renilla* luciferase plasmid DNA was diluted into 5 μl of Opti-MEM medium (ThermoFisher Scientific, Cat. #31985070) containing 0.22 μl of P3000 Reagent. The 0.15 μl of Lipofectamine 3000 reagent was diluted into 5 μl of Opti-MEM medium. The diluted DNA and diluted Lipofectamine reagent were then mix and let stand at room temperature for 15 min. Finally, the 10 μl mixture was dropped onto cells. All transfection was conducted in duplicates. Twenty-four hours post-transfection, the plate was removed from the incubator and 75 μl of Dual-Glo Luciferase Reagent System (Promega, Cat. #E2920) was added to each well. Firefly luminescence was measured 10 min after reagent was added using the BioTek plate reader. Finally, 75 μl of Dual-Glo Stop & Glo Reagent was added to each well and *Renilla* luminescence was measured 10 min after reagent was added. The ratio of firefly luminescence (fLuc) to *Renilla* luminescence (rLuc) was calculated for each reporter construct. The ratio was then normalized to negative control plasmid pGL4.10(Luc2) and this relative ratio was used to compare promoter activities for each reporter construct.

13.2.5. Results and Discussion

Figure 7A:
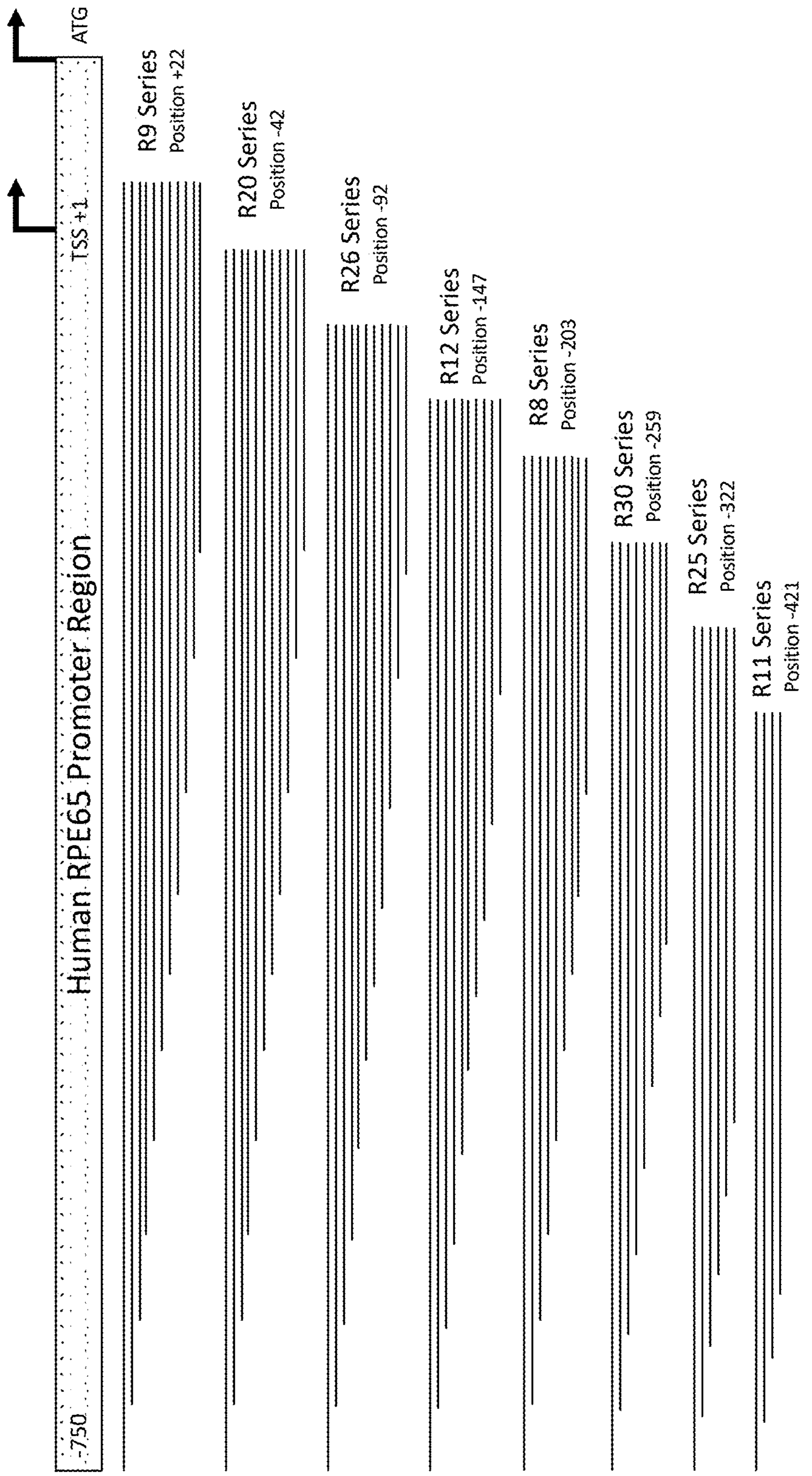
FIG. 7A is a schematic of the endogenous human RPE65 promoter and deletion fragments cloned upstream of a firefly luciferase reporter system to identify ≤500-bp transcriptional enhancer/repressor regions suitable for driving RPE-specific expression of transgenes of the invention in mammalian cells. A total of 70 RPE65 PCR fragments were cloned upstream of the firefly luciferase vector to identify RPE-specific elements. Each individual series has an identical 3' start site with position upstream of the transcriptional start site (TSS) indicated.
Figure 7B:
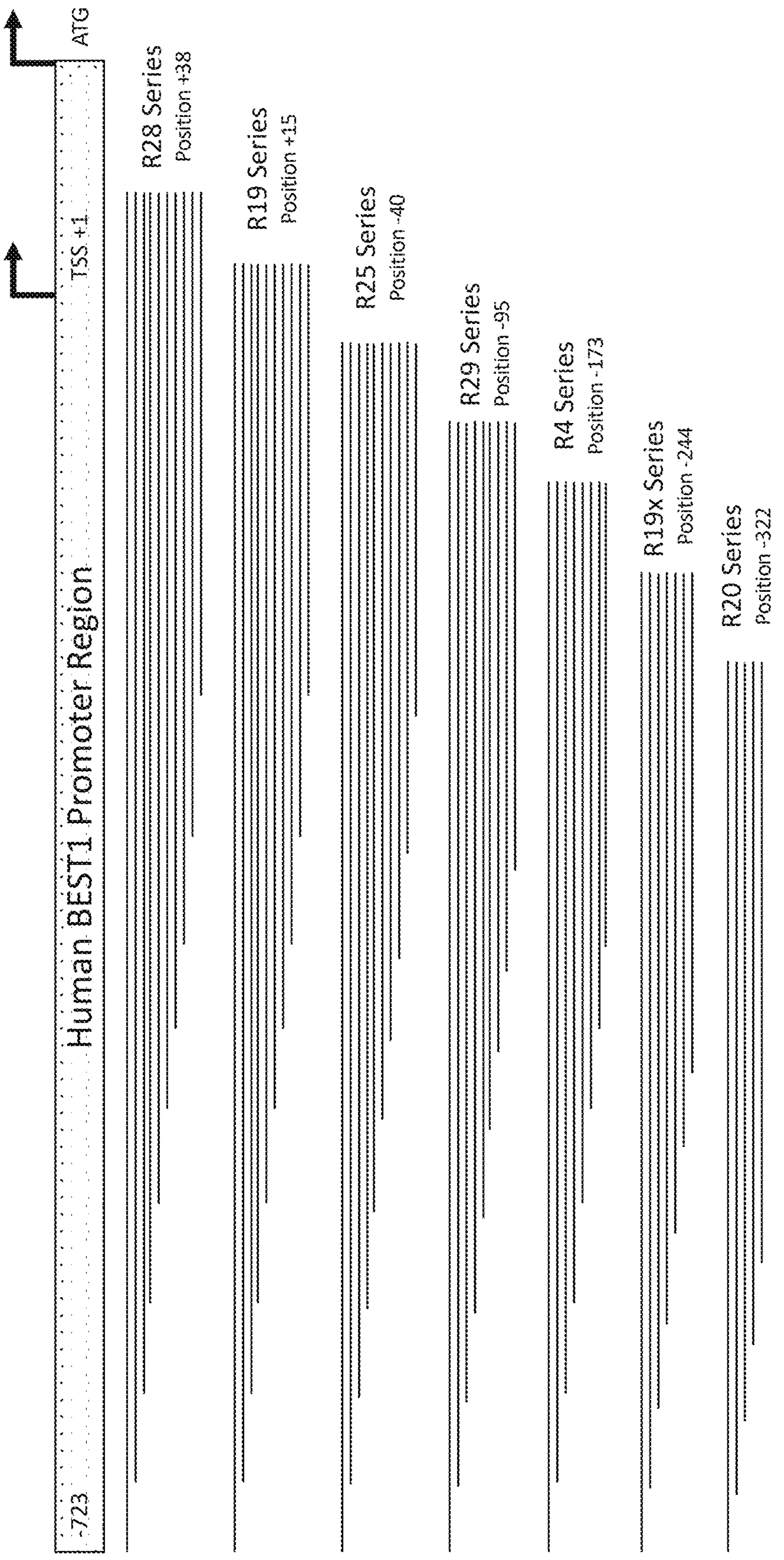
FIG. 7B is a schematic of BEST1-723 promoter fragments designed to identify transcriptional enhancer/repressor regions. A total of 59 BEST1 PCR fragments were cloned upstream of the firefly luciferase vector to identify RPE-specific elements. Each individual series has an identical 3' start site with position upstream of the transcriptional start site (TSS) indicated.

We constructed and tested several RPE65, BEST1 and CFH promoter elements in multiple RPE-derived (RPE1, ARPE19 and RPE7) and non-RPE cell lines (HEK293 and A549). Our goal was to identify small promoter elements (≤500-bp) that can direct high level expression of protective CFH and/or CFHT in an RPE-specific manner. As shown in FIG. 7A and FIG. 7B, we generated 70 promoter elements across the RPE65 promoter and 59 promoter elements across the BEST1 promoter region using PCR. The promoter elements were cloned upstream of firefly luciferase reporter. Plasmid DNAs were transfected into cells in a 96-well plate format using LipofectAmine 3000 along with *renilla* luciferase control plasmid DNA to normalize transfection variability between wells and analyzed 24-hrs post-transfection.

Selected RPE65 and BEST1 promoter activities are shown TABLE 18A and TABLE 18B. TABLE 18A shows comparison of normalized firefly luciferase expression from a subset of RPE65 promoter fragments in RPE7 cell line. Transfection was normalized to *renilla* luciferase and fold-induction is normalized to promoterless luciferase vector. TABLE 18B shows comparison of normalized firefly luciferase expression from a subset of BEST1 promoter fragments in RPE7 cell line. Transfection was normalized to *renilla* luciferase and fold-induction is normalized to promoterless luciferase vector. Overall, nine (9/70) RPE65 and six (6/59) BEST1 promoter constructs were identified that exhibited more than 5-fold higher expression than the control promoterless construct.

TABLE 18A

| RPE65 Promoter Name | Fold Normalized Induction (firefly/renilla luciferase) | |
|---|---|---|
| (number nucleotides) | Average | SD |
| Promoterless (0) | 1 | 0 |
| F2-R20 (105) | 5.1 | 0.1 |
| F6_R20 (160) | 2 | 0.4 |
| F14-R20 (204) | 2.8 | 0 |
| F26-R20 (266) | 3.9 | 0.2 |
| F7-R20 (306) | 1.6 | 0.1 |
| F28-R20 (367) | 2.7 | 0.3 |
| F30-R20 (418) | 2.9 | 0.4 |
| F27-R20 (477) | 2.1 | 0.2 |
| F10-R20 (518) | 8.4 | 0.2 |
| F25-R20 (569) | 3.3 | 0.4 |
| F5-R20 (629) | 1.7 | 0.1 |
| F4-R20 (682) | 2.6 | 0.4 |
| F6-R26 (109) | 5.4 | 0.3 |
| F14-R26 (153) | 2.8 | 0.5 |
| F26-R26 (215) | 4.7 | 0.1 |
| F7-R26 (255) | 6.5 | 0.4 |
| F28-R26 (316) | 12.3 | 0.4 |
| F30-R26 (367) | 3.8 | 0.2 |
| F27-R26 (426) | 4.4 | 0.1 |
| F10-R26 (467) | 2.7 | 0.1 |
| F25-R26 (518) | 4.6 | 0 |
| F5-R26 (578) | 3.5 | 0.2 |
| F4-R26 (631) | 7.9 | 0.3 |
| F7-R8 (146) | 8.1 | 0.3 |
| F25-R8 (409) | 5.1 | 0.2 |
| RPE65-750 | 8.1 | 0.1 |
| CMV-fLuc | 5755.4 | 48.4 |

TABLE 18B

| BEST1 Promoter Name | Fold Normalized Induction (firefly/renilla luciferase) | |
|---|---|---|
| (number nucleotides) | Average | SD |
| Promoterless (0) | 1 | 0.08 |
| F29-R19x (114) | 1.9 | 0.08 |
| F26-R19x (165) | 3.6 | 0.08 |
| F4-R19x (215) | 1.3 | 0.03 |
| F5-R19x (271) | 2.4 | 0.02 |
| F6-R19x (317) | 2.0 | 0 |
| F13-R19x (371) | 1.8 | 0.07 |
| F22-R19x (418) | 26.8 | 0.4 |
| F26-R20 (87) | 2.5 | 0.13 |
| F5-R20 (193) | 2.6 | 0.04 |
| F6-R20 (239) | 3.7 | 0.21 |
| F13-R20 (293) | 4.0 | 0.18 |
| F22-R20 (340) | 22.2 | 0.76 |
| F20-R28 (116) | 4.9 | 0.1 |
| F17-R28 (180) | 2.0 | 0 |
| F15-R28 (230) | 2.4 | 0.3 |
| F25-R28 (318) | 8.5 | 0.6 |
| F29-R28 (395) | 2.3 | 0.1 |

TABLE 18B-continued

| BEST1 Promoter Name (number nucleotides) | Fold Normalized Induction (firefly/renilla luciferase) Average | SD |
|---|---|---|
| F26-R28 (446) | 3.4 | 0.6 |
| F4-R28 (496) | 1.7 | 0.4 |
| F5-R28 (552) | 2.0 | 0.1 |
| F6-R28 (598) | 1.4 | 0.3 |
| F13-R28 (652) | 3.4 | 0.4 |
| F22-R28 (699) | 6.4 | 0.3 |
| BEST1-V3 (144) | 37.2 | 0.01 |
| CMV-fLuc | 1347.8 | 70.27 |

13.2.6. Optimizing RPE-Selective Promoters by Addition of CMV Enhancer for AAV Gene Therapy Vectors

13.2.6.1. Rationale

To increase activity of these RPE-selective promoters, we cloned a 304-bp CMV enhancer element upstream of the RPE65 and BEST1 promoter elements and compare reporter expression in RPE7, primary RPE, A549 and HEK293 cells. Inclusion of the CMV enhancer increased reporter expression up to 500-fold; and in some cases, resulted in higher expression than the CMV promoter.

13.2.7. Methods

13.2.7.1. CMV Enhancer RPE65 and BEST1 Promoter Cloning

GeneArt construct pAAV-CAG-FLEX-EGFP was used as template for PCR with CMV-Enhancer_F: CGTTACATAACTTACGGTAAATGG (SEQ ID NO:19) and CMV-Enhancer_R: CATGGTA ATAGCGATGACTAATAC (SEQ ID NO: 126). PCR amplification was performed using Platinum PCR SuperMix (ThermoFisher, Cat. #11306-016) following manufacturer's instructions. The PCR product was purified using QIAquick PCR Purification kit (Qjagen Cat. #28106) and digested with SacI and XhoI engineered into the primers and cleaned up with QIAquick PCR Purification kit. This enhancer insert was then cloned into SacI and XhoI sites upstream of the following nine RPE65 promoter clones: F10-R20, F2-R20, F4-R26, F28-R26, F7-R26, F6-R26, F25-R8, F7-R8, F30-R9 and four BEST1 promoter clones: F25-R28, F25-R4, F22-R4 and BEST1-144. All recombinants were verified by restriction digestion and DNA sequencing using reporter vector specific primers.

13.2.7.2. Dual Luciferase Assay in Primary RPE, RPE7, HEK293 and A549 Cells Primary fetal RPE (ScienCell #6540), RPE7 (Sigma Cat. #09061602), HEK293 (ATCC # CRL-1573) and A549 (ATCC # CRL-185) cells were seeded in 96-well plates at $1\times10^4$ cells per well in 75 μl of complete culture medium. Twenty-four hours after seeding, cells were transfected with plasmid DNA using Lipofectamine 3000 reagent (ThermoFisher Scientific, Cat. #L300008) with optimized transfection protocol. Briefly, 100 ng of firefly luciferase driven by various enhancer-RPE65 and enhancer-BEST1 promoters, a positive control CMV-fLuc (pCTM224) and a negative control pGL4.10 (Luc2) lacking a promoter element were tested. To normalize all electroporations we also co-transfected 10 ng of *Renilla* luciferase SV40-rLuc (pCTM238). For each transfection, 100 ng of firefly luciferase plasmid DNA and 10 ng of *Renilla* luciferase plasmid DNA were diluted into 5 μl of Opti-MEM medium (ThermoFisher Scientific, Cat. #31985070) containing 0.22 μl of P3000 Reagent. Then 0.15 μl of Lipofectamine 3000 reagent was diluted into 5 μl of Opti-MEM medium. The diluted DNA and diluted Lipofectamine reagent were then mixed and left at room temperature for 15 min. Finally, the 10 μl DNA/lipid mixture was dropped onto cells. All transfections were conducted in duplicate. Twenty-four hours post-transfection the plate was removed from the incubator and 75 μl of Dual-Glo Luciferase Reagent System (Promega, Cat. #E2920) was added to each well. Firefly luminescence was measured 10 min after reagent was added using the BioTek plate reader. Finally, 75 μl of Dual-Glo Stop & Glo Reagent was added to each well and *Renilla* luminescence was measured 10 min after reagent addition. The ratio of firefly luminescence (fLuc) to *Renilla* luminescence (rLuc) was calculated for each enhancer/promoter construct. The ratio was then normalized to negative control plasmid pGL4.10 (Luc2) and this relative ratio was used to compare promoter activities for each reporter construct.

13.2.8. Results and Discussion

Our goal is to identify small promoter elements (≤500-bp) that can direct high level expression of protective CFH and/or CFHT in an RPE-selective manner. To escalate basal promoter activity and increase protective protein expression, we cloned a 304-bp CMV enhancer element (SEQ ID NO:7) and placed it upstream of BEST1 and RPE65 minimal promoter elements that we identified in section 14.2. A total of 13 promoter elements were selected: 4 BEST1 and 9 RPE65. TABLE 19 lists several BEST1 and RPE65 minimal promoter elements used, overall enhancer/promoter size in nucleotides and final name of enhancer/promoter elements tested in RPE7, primary RPE cells, A549 and HEK293 cells.

TABLE 19

BEST1 and RPE65 enhancer/promoter constructs tested in firefly luciferase assay.

| Base Promoter | Enhancer (# nucleotides) | Promoter Name (# nucleotides) | Overall Enhancer/ Promoter Size (# nucleotides) | Final Enhancer/ Promoter Name |
|---|---|---|---|---|
| BEST1 | CMV (305) | F25-R28 (318) | 622 | BEST1-EP-628 |
| | | F25-R4 (108) | 412 | BEST1-EP-418 |
| | | F22-R4 (489) | 793 | BEST1-EP-799 |
| | | BEST1-V3 (144) | 448 | BEST1-EP-454 |
| RPE65 | | F10-R20 (518) | 822 | RPE65-EP-828 |
| | | F2-R20 (105) | 409 | RPE65-EP-415 |
| | | F4-R26 (631) | 935 | RPE65-EP-941 |
| | | F28-R26 (316) | 620 | RPE65-EP-626 |

TABLE 19-continued

BEST1 and RPE65 enhancer/promoter constructs tested in firefly luciferase assay.

| Base Promoter | Enhancer (# nucleotides) | Promoter Name (# nucleotides) | Overall Enhancer/ Promoter Size (# nucleotides) | Final Enhancer/ Promoter Name |
|---|---|---|---|---|
| | | F7-R26 (255) | 559 | RPE65-EP-565 |
| | | F6-R26 (109) | 413 | RPE65-EP-419 |
| | | F25-R8 (409) | 713 | RPE65-EP-719 |
| | | F7-R8 (146) | 450 | RPE65-EP-456 |
| | | F30-R9 (482) | 786 | RPE65-EP-792 |

Addition of the 304-bp CMV immediate/early enhancer sequence to base RPE65 and BEST1 promoter elements resulted in 50 to 500-fold increase in reporter expression, except BEST1-EP-799. As shown in TABLE 20 all enhancer/promoter containing elements express as well as CMV control in RPE7 and primary RPE cells and not as well in non-RPE cell types (e.g. HEK293 kidney and A549 lung cell lines). The overall size of the most optimal enhancer/promoter elements ranged from 415 to 792-bp. The small < 500-bp enhancer/promoter elements (RPE65-EP-415, RPE65-EP-419 and BEST1-EP-454) may be very useful for the large engineered (eCFH/T) AAV vectors since the cDNA (3921-bp) is near the maximal cargo payload for AAV packaging. In TABLE 20 transfection was normalized to *renilla* luciferase and fold-induction is compared to promoterless luciferase vector. CMV-fLuc was used as a positive control and represents high reporter expression.

TABLE 20

Comparison of firefly luciferase expression from 4 BEST1 and 9 RPE65 enhancer/promoter elements in RPE7, primary RPE, HEK293 and A549 cell lines.

| Enhancer/ | RPE7 | | Primary RPE | | HEK293 | | A549 | |
|---|---|---|---|---|---|---|---|---|
| Promoter Name | Average | SD | Average | SD | Average | SD | Average | SD |
| Promoterless | 1.0 | 0.0 | 1.0 | 0.0 | 1.0 | 0.0 | 1.0 | 0.0 |
| RPE65-EP-792 | 2865.3 | 51.5 | 814.8 | 72.3 | 475.9 | 32.7 | 968.0 | 23.4 |
| RPE65-EP-415 | 2935.0 | 90.3 | 568.2 | 45.8 | 63.1 | 2.4 | 676.4 | 18.1 |
| RPE65-EP-828 | 590.9 | 17.3 | 217.4 | 16.4 | 11.0 | 0.1 | 152.9 | 5.6 |
| RPE65-EP-941 | 644.2 | 35.2 | 233.7 | 15.6 | 16.5 | 0.0 | 172.0 | 3.0 |
| RPE65-EP-419 | 2892.1 | 71.1 | 623.8 | 16.4 | 73.6 | 1.4 | 546.5 | 2.1 |
| RPE65-EP-565 | 1085.3 | 74.3 | 545.7 | 52.0 | 30.3 | 0.1 | 343.5 | 4.3 |
| RPE65-EP-626 | 1062.2 | 48.7 | 299.2 | 3.6 | 25.7 | 0.2 | 210.9 | 10.7 |
| RPE65-EP-456 | 803.7 | 88.5 | 143.3 | 8.8 | 12.0 | 0.1 | 256.6 | 1.8 |
| RPE65-EP-719 | 351.7 | 6.7 | 100.1 | 1.0 | 8.2 | 0.1 | 151.6 | 4.5 |
| BEST1-EP-628 | 313.4 | 1.9 | 108.3 | 10.9 | 14.3 | 0.3 | 209.7 | 6.3 |
| BEST1-EP-418 | 370.9 | 8.8 | 174.4 | 12.6 | 22.5 | 0.0 | 209.0 | 3.7 |
| BEST1-EP-799 | 7.0 | 0.2 | 3.4 | 0.2 | 0.8 | 0.0 | 1.5 | 0.0 |
| BEST1-EP-454 | 1761.7 | 33.0 | 522.4 | 43.5 | 64.1 | 0.1 | 642.0 | 15.8 |
| CMV-fLuc | 2743.2 | 60.6 | 476.7 | 82.4 | 4036.4 | 102.5 | 1986.9 | 16.8 |

13.2.9. Testing Mini-Enhancer/Promoter EGFP AAV2 Constructs in RPE1 Cells

13.2.9.1. Rationale

We designed, constructed and tested several small (≤500-bp) promoter/enhancer elements using a luciferase reporter-based approach and optimized three mini-enhancer/promoters "mini-EP" (BEST1-EP-454, RPE65-EP-419 and RPE65-EP-415). In this study, we test the ability of enhancer/promoter elements to express EGFP protein after transient, lipid-based transfection and AAV2 transduction of RPE1 cells.

13.2.9.2. Methods

13.2.9.2.1. Transfection of RPE1 Cells with Mini-EP-EGFP Constructs

Figure 9A:
FIGS. 9A-C shows a schematic of mini-EP (modified enhancer-promoter) constructs (rAAV2 maps) comprising a promoter and an enhanced green fluorescent protein (EGFP) coding sequence. These constructs are examples used to test promoters for maximal RPE-specific expression and minimal promoter size for AAV-based therapeutic vectors.
Figure 9B:
Figure 9C:
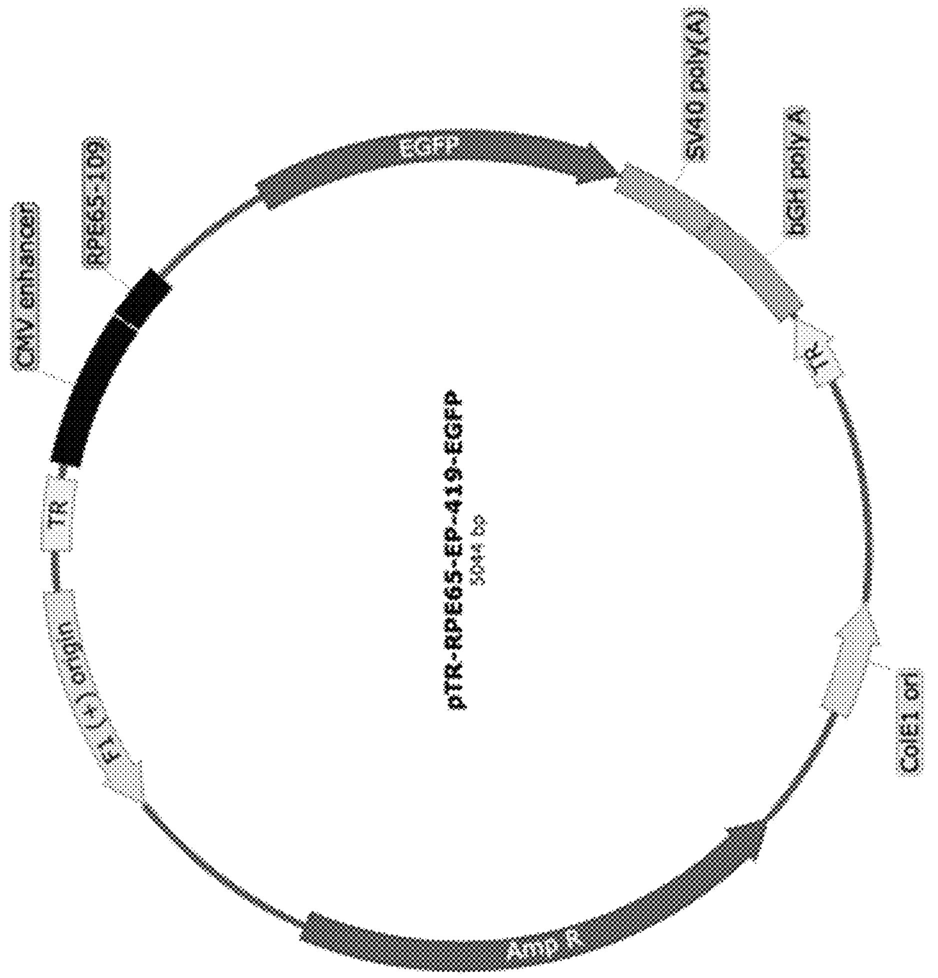

RPE1 (ATCC # CRL-4000) cells were seeded in 96-well plates at $1\times10^4$ cells per well in 100 μl of complete culture medium and 24 hours after seeding, cells were transfected with plasmid DNA using Lipofectamine 3000 reagent (ThermoFisher Scientific, Cat. #1300008). The CMV-EGFP vector was used as a positive control for EGFP expression. Briefly, 100 ng of AAV2-based plasmid DNA pTR-BEST1-EP-454-EGFP, pTR-RPE65-EP-415-EGFP), pTR-RPE65-EP-419-EGFP (see FIG. 9A-C for AAV2 maps) and pTR-CBA-EGFP were diluted in 5 μl of Opti-MEM medium (ThermoFisher Scientific, Cat. #31985070) containing 0.22 μl of P3000 Reagent. Then 0.15 μl of Lipofectamine 3000 reagent was diluted into 5 μl of Opti-MEM medium. The diluted DNA and Lipofectamine reagent were then mixed and left at room temperature for 15 min. Finally, 10 μl DNA/lipid mixture was dropped onto cells. All transfections were conducted in duplicate. EGFP signal was monitored using fluorescence microscope and photos taken using an IPhone camera.

13.2.10. Transduction of RPE1 Cells with Mini-EP-EGFP AAV2 Virus

RPE1 (ATCC # CRL-4000) cells were seeded in 96-well plates at $5\times10^3$ cells per well in 100 μl of complete culture medium containing 10% FBS. Twenty-four hours after seeding, cells were transduced with the following AAV2 particles at several MOIs ($1\times10^5$, $1\times10^6$ and $1\times10^7$) in 100 μl of culture medium containing 0.2% FBS: pTR-BEST1-EP-454-EGFP, pTR-RPE65-EP-415-EGFP, pTR-RPE65-EP-419-EGFP and pTR-CBA-EGFP as a positive control. Virus-containing medium was removed the following day and replaced with complete culture medium with 10% FBS. Medium was refreshed twice a week and EGFP signal was monitored under fluorescence microscopy.

13.2.11. Results and Discussion

Figure 10:
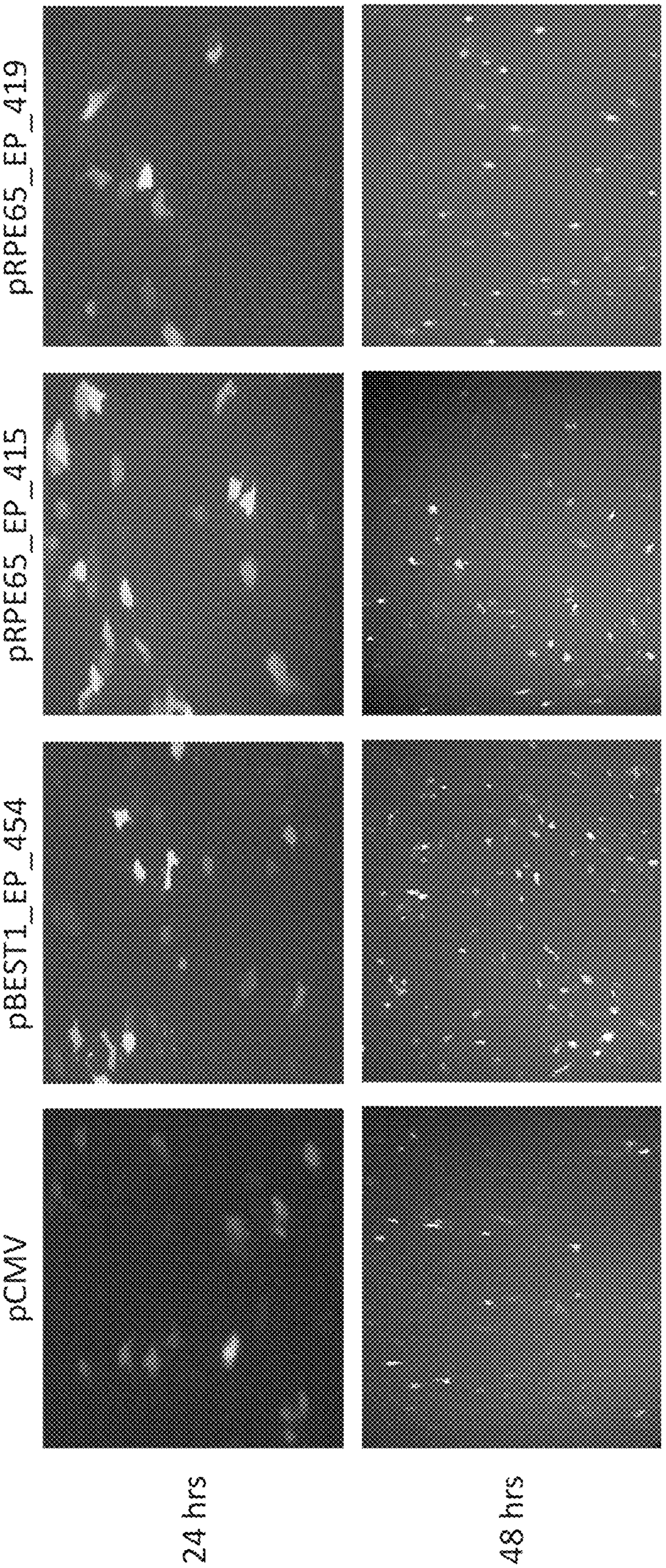
FIG. 10 shows fluorescence micrographs showing EGFP expression in RPE1 cells transiently transfected with mini-EP-EGFP constructs at indicated time points.

Using reporter assays, we identified three small enhancer promoter motifs (BEST1-EP-454, RPE65-EP-415 and RPE65-EP-419) that show strong expression of linked luciferase in a pcDNA3.1 backbone. To determine whether these mini-EPs are capable of driving protein expression in pTR-AAV based DNA constructs, we compare expression of EGFP in RPE1 cells under the control of three mini-EPs versus the strong CMV enhancer/promoter. As shown in FIG. 10, 24 hours after transfection, both BEST1-EP-454-EGFP and RPE65-EP-415-EGFP transfected cells exhibit strong EGFP signal, which is comparable to that of CMV-EGFP transfected cells. RPE65-EP-419 produces slightly lower EGFP expression and fewer EGFP-positive cells. Similar results are found at 48 hours after transfection.

To further determine the expression of EGFP protein in RPE1 cells after transduction with mini-EP-EGFP AAV2 virus, we treated cells with viral particles at various multiplicities of infection (MOI) and monitor EGFP signal by fluorescence microscopy. In general, we observe fewer EGFP positive cells in virus-transduced cells than in DNA-transfected cells; and as expected, the EGFP signal is weaker.

Figure 11:
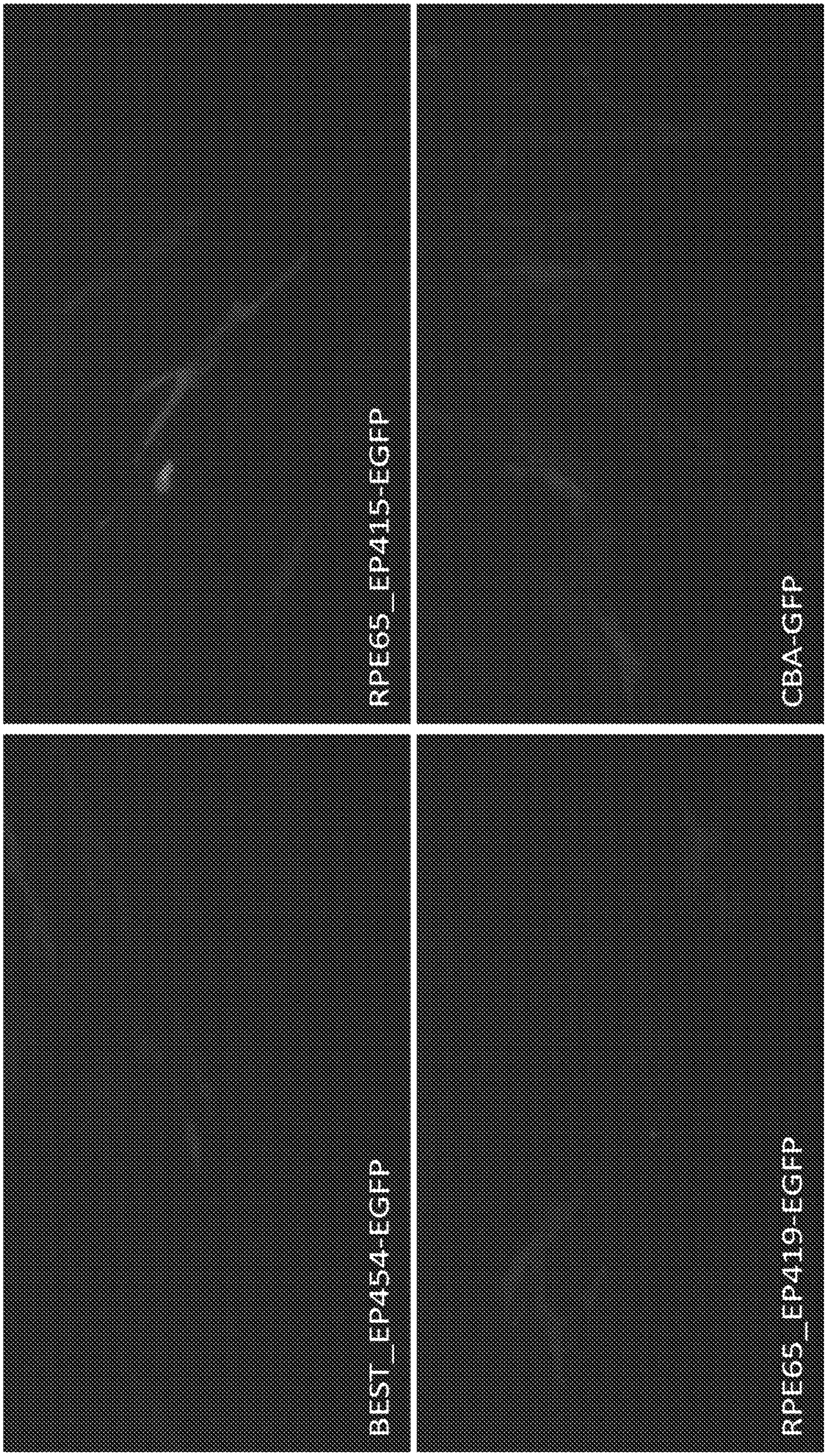
FIG. 11 shows fluorescence micrographs of EGFP expression in RPE1 cells transduced with mini-EP-EGFP AAV2 particles after 42 days in culture.

Finally, we compare long term EGFP expression of BEST1-EP-454-EGFP, RPE65-EP-415-EGFP and RPE65-EP-419-EGFP in AAV2 transduced RPE1 cells. Forty-two days post-transduction the 3 mini-EPs are showing favorable expression, comparable to CBA-EGFP transduced cells (FIG. 11). A qualitative comparison of mini-EP expression testing performed to date is shown in TABLE 21.

TABLE 21

Intensity of EGFP signal in RPE1 cells transfected with pTR-mini-EP-EGFP constructs or transduced with pTR-mini-EP-EGFP AAV2 virus at MOI of $1\times10^7$ at indicated time points.

| | EGFP Intensity | | |
|---|---|---|---|
| AAV2 Construct | Transfection (2 days) | Transduction (14 days) | Transduction (42 days) |
| pTR-BEST1-EP-454-EGFP | +++++ | ++ | ++ |
| pTR-RPE65-EP-415-EGFP | +++++ | ++ | ++ |
| pTR-RPE65-EP-419-EGFP | ++++ | + | + |
| pTR-CBA-EGFP | +++++ | +++ | +++ |

13.2.12. AAV2 Transduction of Mini-Enhancer/Promoter CFH-TK and eCFH/T-TK Constructs 13.2.12.1. Methods Large Scale Production of AAV2 Particles and RPE7 Transduction Large scale plasmid DNA isolation and AAV2 viral production were performed as described in Zolotukin et al., 2002, Production and Purification of Serotype 1, 2, AND 5 Recombinant Adeno-Associated Viral Vectors" *Methods* 28:158-167.

13.2.12.2. CFH and CFHT ELISA Assays

CFH and CFHT ELISA assays were performed using cell culture supernatant diluted 1:10 in ELISA assay reagent diluent (1×PBS+0.5% BSA). Plates were coated with CFH R&D System ELISA (Cat. #DY4779) (1:190) and CFHT specific monoclonal aCTM119 (1:600) capture antibodies in Maxisorp coating buffer overnight at 4° C. After plates were washed three times in PBST, diluted samples (100 μl) were added to each well and incubated for 2 hours at room temperature. Plates were washed as above followed by CFH R&D Systems ELISA (1:190) or aCTM87b (1:800) detector antibodies; followed by Streptavidin-HRP and ECL to indirectly detect protein. CFH (R&D System) and CFHT (in-house purified) protein standard curves were generated to determine relative concentration for all samples. Protein concentration of cell lysate was measured using Pierce 660 nm Protein Assay Reagent (Pierce, Cat. #22660) following manufacturer's protocol.

13.2.12.3. Results and Discussion

To determine production of CFH and eCFHT protein using the BEST1-EP-454 and RPE65-EP-415 enhancer promoter elements we transduced RPE7, COS-7 and fetal RPE cells with AAV2 constructs. We compared the mini-enhancer promote elements to the smCBA promoter. When using the same number of infectious AAV2 particles the smaller BEST1 and RPE65 enhancer promoter elements can produce more CFH protein than the smCBA promoter (TABLE 22).

TABLE 22

AAV2 transduction of COS-7, RPE-7 and fetal RPE cells and expression of CFH protein using indicated enhancer promoter elements.

| pCTM # | Construct Name | COS-7 (ng/ml) | RPE-7 (ng/ml) | Fetal RPE (ng/ml) |
|---|---|---|---|---|
| 281 | BEST1-EP-454-CFH-TK | 698 | 353 | 79 |
| 282 | RPE65-EP-415-CFH-TK | 402 | 587 | 100 |
| 283 | BEST1-EP-454-eCFH/T-TK | 392 | 377 | 140 |
| 284 | RPE65-EP-415-eCFH/T-TK | 309 | 225 | 133 |
| 273 | smCBA-CFH-TK | 243 | 163 | 171 |
| 271 | smCBA-eCFH/T-TK | 65 | 64 | 124 |

13.3. Example 3. Construction of Protective Versions of CFH, CFHT and eCFH/T Transgenes We constructed protective versions of CFH (I62-Y402-E936; TABLE 33A), CFHT (I62-Y402; TABLE 33C) and eCFH/T (I62-Y402-E936)/(I62Y402) (TABLE 33E) transgenes. The amino acid sequence of the proteins encoded by these transgenes is provided in TABLE 33B (CFH), TABLE 33D (CFHT), and TABLE 33F (eCFH/T; two proteins, CFH and eCFHT are produced).

The eCFH/T transgene (TABLE 33E) includes exons 1-22 of the CFH gene and portions of intron 9 of the CFH gene that encodes for both CFHT and CFH. All of the transgenes were human codon-optimized. These protective CFH transgenes were subcloned into pTR-AAV2 plasmids to drive expression of reporter genes.

The following enhancer/promoter elements were tested with each of the transgenes: BEST1-EP-454 (TABLE 34A), RPE65-EP-415 (TABLE 34B), RPE65-EP-419 (TABLE 34C), VMD2 (high expressing RPE-specific promoter; TABLE 34D), smCBA (small CMV enhancer+chicken beta actin promoter; TABLE 34E), CBA (large CMV enhancer+chicken beta actin promoter, TABLE 34F), sctmCBA (TABLE 34G), BEST1-V3 (TABLE 341), RPE65-750 (TABLE 34J), and CFH (TABLE 34H). We also tested the HSV TK (TABLE 34L), SV40 (TABLE 34M) and bGH (TABLE 34K) poly adenylation sequences. These constructs included ITR sequences (TABLE 35A) and an AAV2 capsid sequence (pDG Vector; Grimm et al., 1998, Novel Tools for Production and Purification of Recombinant Adenoassociated Virus Vectors. *Hum Gene Ther.* 9(18):2745-60).

13.3.1. Rationale

CFH and CFHT proteins are generated via alternative mRNA transcripts from the CFH genetic locus. CFHT retains most of the essential domains for optimal alternative pathway regulation and is also subject to both I62V and Y402H AMD risk and protection polymorphisms. The risk alleles result in suboptimal alternative complement control on RPE-choroid cell surfaces and possibly Bruch's membrane and drusen. Since risk and protection alleles are present in CFH and CFHT encoded proteins we considered both CFHT and CFH augmentation as an AMD therapeutic angle.

13.3.2. Methods

Construction of Genetically eCFH/T Co-Expression Plasmids

Figure 12:
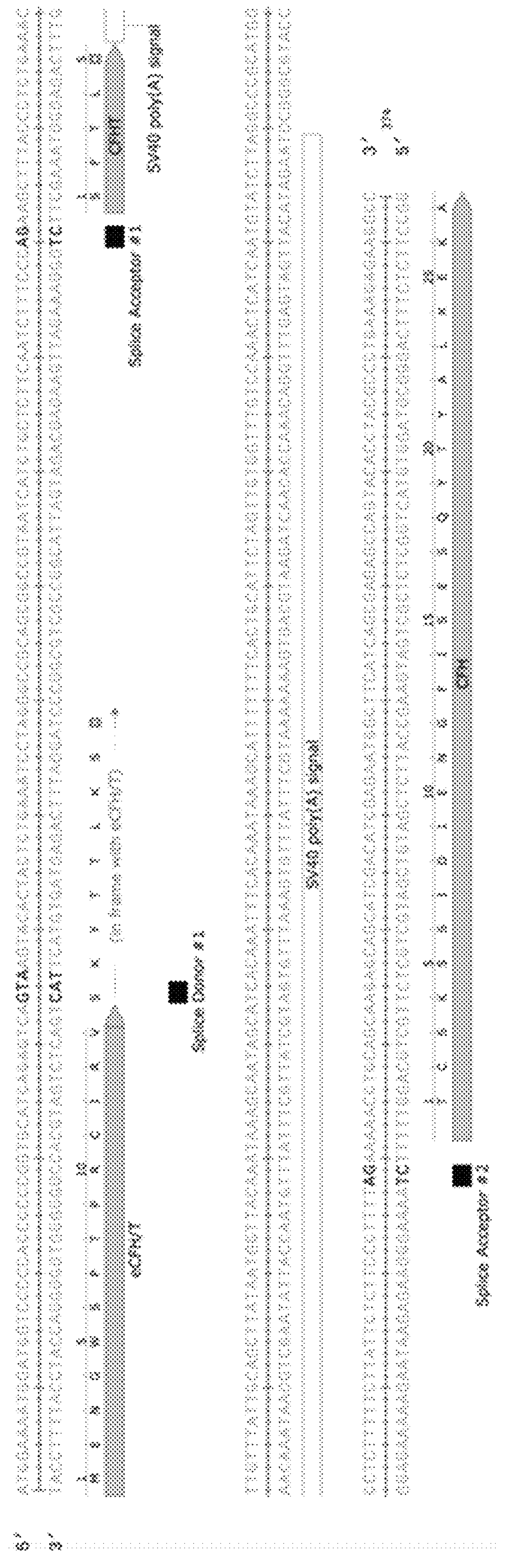
FIG. 12 shows key features of the v4.0 eCFH/T construct at the CFHT and CFH splicing junction. In v4.0 the SFTL C-terminal of CFHT is contained on a separate exon that requires a splicing event between the highlighted splice donor #1 (GTA) and highlighted splice acceptor #1 (AG). The splicing event creates a transcript that terminates with an SV40 poly(A) signal. The larger CFH transcript is generated using splice donor #1 (GTA), but a downstream splice acceptor #2 (AG), that removes the CFHT C-terminal tail and SV40 poly(A) signal) and terminates with an HSV TK poly(A) signal (not shown).
Figure 13:
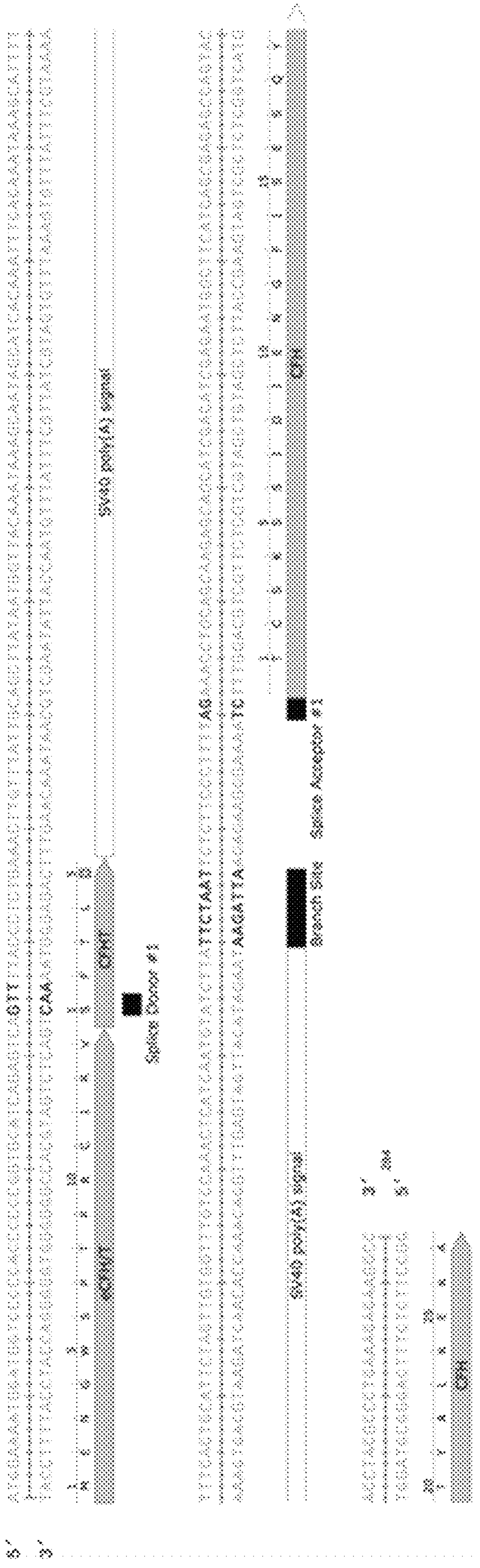
FIG. 13 shows key features of v4.1 eCFH/T construct at CFHT and CFH splicing junction. In v4.1 the SFTL C-terminus of CFHT is encoded without the need for a splicing event and the small transcript terminates with an SV40 poly(A) signal. The larger CFH transcript is generated using the highlighted splice donor #1 (GTT) and downstream highlighted splice acceptor #1 (AG) that removes the CFHT C-terminal tail and SV40 poly(A) signal) and terminates with an HSV TK poly(A) signal (not shown in this FIGURE). A consensus branch site has been included in this construct to increase efficiency of splicing.
Figure 14:
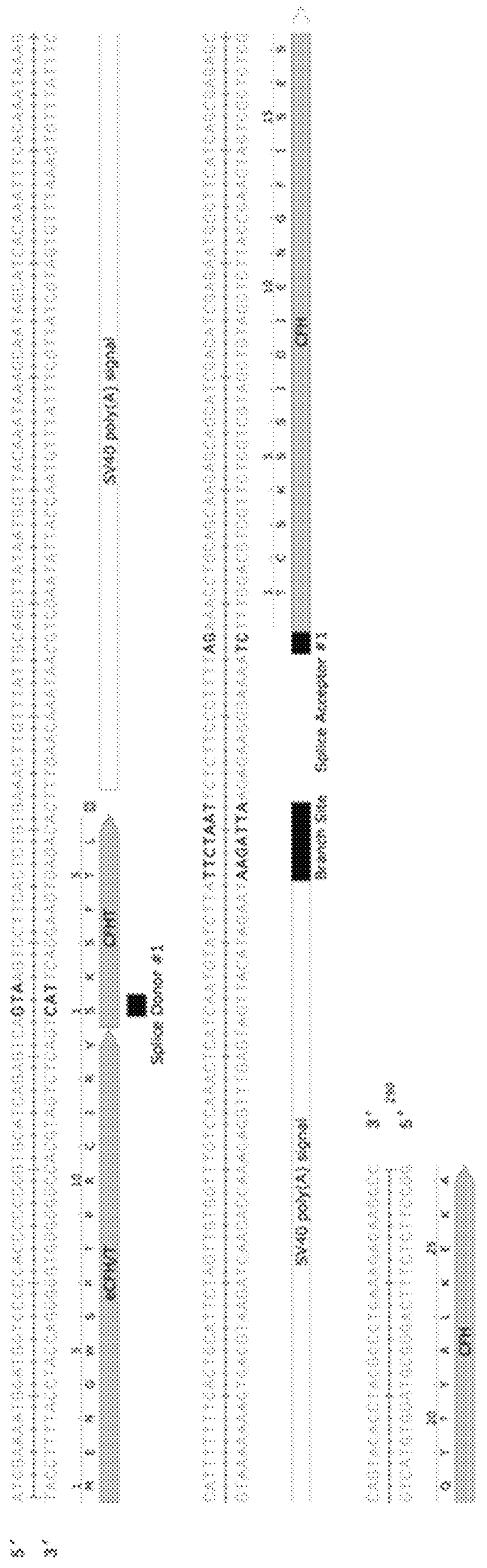
FIG. 14 shows key features of v4.2 eCFH/T construct at CFHT and CFH splicing junction. In v4.2 the SFTL C-terminus of CFHT is encoded without the need for a splicing event and the small transcript terminates with an SV40 poly(A) signal. A modified splice donor site (GTA) has been added that requires two additional amino acid residues (SK) prior to SFTL C-terminus of CFHT. The larger CFH transcript is generated using the highlighted splice donor #1 (GTA) and downstream highlighted splice acceptor #1 (AG)

We generated and tested four genetically engineered CFH/T (eCFH/T) constructs (v4.0, v4.1, v4.2 and v4.3) that co-express protective versions of CFH-I62-Y402-E936 and CFHT-I62-Y402. The four eCFH/T intron containing constructs were synthesized by GeneArt (ThermoFisher Scientific) and sub-cloned into the EcoRV/EcoRI sites of protective CFH plasmid using standard molecular biology techniques to generate v4.0 (FIG. 12), v4.1 (FIG. 13), v4.2 (FIG. 14) and v4.3 (FIG. 15) eCFH/T co-expression plasmids. For testing purposes, we generated all constructs in pcDNA3.1 mammalian expression plasmids to quickly monitor protein expression and RNA processing in RPE1 (ATCC # CRL-4000) electroporated cells. The four constructs share the same splice donor sequence (GT) but have different bases (e.g. T, A and G) following GT. We assayed production of eCFHT and CFH mRNA and protein by the four constructs.

Co-Expression of eCFH/T in RPE1 Cell Line

RPE1 (ATCC # CRL-4000) cells were electroporated with the following plasmids: pEGFP (control plasmid), pCTM133 transgene expression construct (CFH-I62-Y402-E936 expression only), pCTM134 transgene expression construct (CFHT-I62-Y402 expression only) and the four genetically engineered CFH/T (eCFH/T) constructs (v4.0, v4.1, v4.2 and v4.3). Forty-eight hours post-transfection, conditioned media was collected (supernatant) and cells were trypsinized and washed with 1×PBS. Half of the cells were used for protein extraction with M-PER buffer (ThermoFisher, Cat. #78501) and the other half was used for total RNA isolation using a RNeasy Mini Kit (Qiagen, Cat. #74106).

Western blotting was carried out using 20 μl cell culture supernatant per lane. Primary antibodies aCTM88 (Sigma, Cat. #HPA049176) and aCTM119 (New England Peptide generated rabbit polyclonal antibody targeting the SFTL tail) were diluted in StartingBlock T20 (TBS) blocking buffer (ThermoFisher, Cat. #375433) and in SuperBlock (PBS) Blocking Buffer (ThermoFisher, Cat. #37515), respectively. The membrane was then incubated for 1 hour at room temperature with HRP conjugated goat anti-rabbit antibody (Jackson Immunoresearch) 1:10,000 in blocking buffer. Western blot was imaged using SuperSignal West Dura Extended Duration Substrate (ThermoFisher, Cat. #34076) on a LAS4000 image analyzer.

CFH and CFHT protein ELISA assays were performed using cell culture supernatant diluted 1:50 with ELISA assay reagent diluent (1×PBS+0.5% BSA). Plates were coated with CFH R&D System ELISA (Cat. #DY4779) (1:190) and CFHT specific monoclonal aCTM119 (1:600) capture antibodies in Maxisorp coating buffer overnight at 4° C. After plates were washed three times in PBST, diluted samples (100 μl) were added to each well and incubated for 2 hours at room temperature. Plates were washed as above followed by CFH R&D Systems ELISA (1:190) or aCTM87b (1:800) detector antibodies; followed by Streptavidin-HRP and ECL to indirectly detect protein. CFH (R&D System) and CFHT (in-house purified) protein standard curves were generated to determine relative concentration for all samples. RNA was converted to cDNA using $RT^2$ HT First Strand kit (Qiagen, Cat. #330411) with random hexamers and oligo-dT. The cDNA was then used as template for PCR using primers spanning intronic region (forward primer [SEQ ID NO:78], reverse primer: CFH R-8 [SEQ ID NO:79]) in order to determine proper splicing of intron sequence. PCR analysis was performed using Platinum PCR SuperMix (ThermoFisher, Cat. #11306-016) following manufacturer's instructions.

13.3.3. Results and Discussion

We compared several synthetic eCFH/T co-expressing constructs to non-splicing, single mRNA transcript CFH and CFHT expressing transgene constructs and test for CFH and CFHT expression using Western blot, ELISA and RT-PCR. The ultimate goal is to express endogenous levels of CFH and CFHT proteins at protective tissue ratios (~10 to 100-fold more CFH than CFHT) in RPE tissue using an AAV delivery system.

The expression of recombinant CFH and CFHT proteins were first tested by Western blot using aCTM88 antibody that recognizes both CFH and CFHT protein. As seen in FIG. 16, the CFH and CFHT standard transgene expression plasmids abundantly and exclusively express CFHT (lane 2) or CFH (lane 7) protein in electroporated RPE1 cells. Interestingly, varying amounts of a correct size protein band (~50 kD) is detected in v4.0, v4.1, v4.2 and v4.3 when compared to both EGFP (negative control, lane 1) and CFH only control (lane 7) (FIG. 16). In addition, v4.0, v4.2 and v4.3 engineered constructs exhibit equal or more robust total CFH protein when compared to CFH transgene only electroporated cells (FIG. 16, compare lanes 3, 5, 6 to lane 7). We also use aCTM119 antibody that specifically recognizes the SFTL tail of CFHT protein to test for recombinant CFHT protein in RPE1 cells. The CFHT-specific antibody detects CFHT protein in RPE1 cells transfected with both CFHT transgene expression plasmid (faint band lane 2) and engineered construct v4.1 and v4.2 (lane 4 and 5). We do not detect an aCTM119 positive CFHT band in v4.0 as this construct generates an 8-amino acid tail (not containing SFTL) from non-spliced transcript that is detected by aCTM88 but not aCTM119. Both v4.1 and v4.2 express a truncated CFH protein that contains the SFTL tail as confirmed using aCTM119 antibody. Interestingly, v4.1 does not express CFH above endogenous levels (compare lanes 2 and 4) and suggests this construct does not faithfully splice to generate a CFH transcript for full-length protein production.

In order to more precisely quantitate the amount of CFH and CFHT protein produced with all eCFH/T co-expression constructs, we ran CFH-specific and CFHT-specific ELISAs using cell culture supernatant. In addition, we calculate the ratio of CFH and CFHT protein expression for all engineered co-expression constructs. As shown in TABLE 23 v4.0 exclusively produces CFH protein and v4.1, similar to CFHT transgene expression control plasmid, solely overexpresses CFHT protein at a very high level (~12 nM). As demonstrated above in Western blot studies, v4.3 produces mostly CFH protein with slightly elevated CFHT protein (~5-fold higher than control EGFP). The optimal construct is v4.2 and is capable of co-expressing high levels of both CFH and CFHT proteins at 23.3 nM and 4.5 nM, respectively. This equals a 32-fold and 75-fold higher level of CFH and CFHT than EGFP control cell culture supernatant, respectively. Equally important, the ratio of CFH to CFHT protein produced from the engineered eCFH/T v4.2 co-expression construct is ~15-fold higher CFH than CFHT protein. This is very close to endogenous RPE and choroid tissue proteins ratios that exhibit ~10 to 16-fold higher ratio of CFH over CFHT protein, depending on macular or extramacular location. Overall, ELISA results are consistent with findings from western blot studies and suggest all version 4 series of co-expression constructs are capable of producing CFH and/or CFHT proteins; with v4.2 being the best candidate for AAV-based studies.

TABLE 23

CFH- and CFHT-with indicated constructs.

| Construct | CFH (ng/ml) | CFHT (ng/ml) | CFH/CFHT Ratio |
|---|---|---|---|
| EGFP (−control) | 115.5* | 3.4* | 34* |
| CFHT (cDNA) | 24.9 | 220 | 0.11 |
| CFH (cDNA) | 1814 | 2.7 | 672 |
| eCFH/T v4.0 | 200 | 3.9 | 51 |
| eCFH/T v4.1 | 16.9 | 655 | 0.03 |
| eCFH/T v4.2 | 3615 | 246 | 14.7 |
| eCFH/T v4.3 | 1637 | 16.1 | 102 |

*endogenous level of secreted CFH and CFHT protein in RPE1 cell culture supernatant The four eCFH/T co-expression constructs contain one or two introns and if positioned in correct reading frames can potentially generate both CFH and CFHT protein. Since the various versions of intronic sequence used in these studies contain in-frame stop codons, the expression of CFH or CFHT protein is dependent on accurate removal of the intron(s) from pre-mRNA transcripts. Results from our western blot analysis indicate that constructs with a single intron (v4.1, v4.2 and v4.3) can undergo varying degree of accurate splicing. To confirm faithful and accurate splicing, we reverse transcribed RNA from RPE1 electroporated cells and performed PCR with a forward primer present in both CFH and CFHT mRNA and a reverse primer present only in CFH mRNA. As shown in FIG. 17, all three engineered constructs (v4.1, v4.2 and v4.3) generate PCR products from transgene that are ~161- to 248-bp less than PCR products from their corresponding DNA plasmid templates. This reduction in PCR product size is consistent with an intron splicing event in the transcript to generate full-length CFH mRNA. The CFH cDNA expression construct does not contain an intron and therefore products from engineered transgene and plasmid are equal in size. The lack of reverse primer binding site in the CFHT transcript explains why no PCR products are found in either transgene or cDNA plasmid templates. Accurate splicing of v4.1 does not occur since CFH protein is not detected; only v4.2 and v4.3 have the appropriate splice donor motif to generate CFH protein.

Results from these studies demonstrate that we have successfully engineered co-expression constructs with the ability to express both protective CFH (I62-Y402-E936) and eCFHT (I62-Y402) protein from a single DNA insert. The optimal splicing construct—v4.2 does encode two extra amino acids (SK) prior to SFTL C-terminal tail but allows for faithful and accurate splicing.

13.4. Example 4. Analytical Methods

13.4.1. Methods for DHT RNA Expression Study

Microarray data from DiaxonHit (DHT) derived from 260 eye donors (both extramacular and macular RPE/choroid and retina tissue) was uploaded as CEL files into Partek Genomics Suite software. Probes with a maximum intensity less than 4.5 were excluded. A gene level summary was generated to combine all probe sets to compare CFH and CFHT mRNA expression. ANOVA was conducted including age, scan date, sex and genotype, to accurately compare expression between risk and protection genotype groups. The median probe intensity for each gene in each tissue was included in the output as log 2 probe intensity.

13.4.2. Methods for Plasma Protein Study

13.4.2.1. Patient Selection and Demographics

We identified pure homozygous chromosome 1 risk patients that encode CFH-V62-H402-E936, CFH-V62-

H402 and protection patients the encode CFH-I62-Y402-E936 and CFHT-I62-Y402 from the combined Iowa and Utah patient cohort database (n=4291). To be included we selected Caucasian patients only between the ages of 57-94 that had no clinically observable AMD (grade 0) at time of enrollment and had plasma stored at −80° C. A total of 104 patients fulfilled the above genotype/phenotype criteria. Groups were then age and gender matched resulting in 63 total patients. A summary of patient demographics is shown in TABLE 24.

TABLE 24

Demographics of patients used in this study.

| Chromosome 1 Genotype Group | # Patients No AMD | Gender Male | Female | % Female | Age (years) Mean (±SD) | Median | Range |
|---|---|---|---|---|---|---|---|
| Pure CFH Risk | 32 | 13 | 19 | 59 | 76.3 ± 4.5 | 75.3 | 70-87 |
| Pure CFH Protection | 31 | 15 | 16 | 52 | 75.7 ± 9.6 | 74.0 | 57-94 |
| Total | 63 | 28 | 35 | 55.5 | 76 ± 7.5 | 75.0 | 57-94 |

13.4.2.2. Plasma CFH and CFHT ELISA

CFH and CFHT ELISAs were performed as described above. Each capture antibody was diluted in Maxisorp coating buffer (50 mM carbonate, pH 9.6) and a total of 100 μl of antibody/buffer solution added to each well of a black MaxiSorp 96-well microplate. Plates were covered and incubated overnight at 4° C. Wells were washed three times with PBST and then blocked for 90 min with reagent dilution buffer (1% BSA in 1×PBS). Plates were washed again after blocking. Plasma samples from patients were recovered from storage at −80° C. and thawed on ice. After thawing the samples were gently mixed and 15 μl placed in a 96-well polypropylene PCR plate, then diluted ten-fold with reagent dilution buffer (1% BSA in 1×PBS). These daughter plates, containing 10 μl of the diluted plasma sample, were prepared and stored at −20° C. and thawed on ice immediately prior to ELISA experiments. Additional dilutions using reagent dilution buffer was accomplished in 96 deep-well plates to the appropriate dilution range for each ELISA (see TABLE 25). Diluted plasma was added to antibody coated plates and allowed to incubate at room temperature for 90 min. Plates were washed as above then incubated for 1 hour with detection antibody followed by three washes. Finally, plates were washed again and incubated for 5 minutes with SuperSignal ELISA pico chemiluminescent substrate (ThermoFisher Scientific, Cat. #37069) before detection using the BioTek Synergy 4 plate reader. Each plate contained multiple positive and negative control wells to accurately compare intra-plate and inter-plate variability. Typical ELISA experiments exhibit <20% inter-plate variability and <20% intra-plate variability.

TABLE 25

Antibodies used and plasma dilutions for CFH and CFHT ELISA.

| ELISA Target | CFH | CFHT |
|---|---|---|
| Capture Ab | R&D DuoSet | aCTM119 |
| Capture Ab Cat. # | DY4779 | NEP |
| Capture Ab Dilution | R&D Protocol | 1:600 |
| Detection Ab | R&D DuoSet | aCTM87b |
| Detection Ab Cat. # | DY4779 | AbCam #112197 |

TABLE 25-continued

Antibodies used and plasma dilutions for CFH and CFHT ELISA.

| ELISA Target | CFH | CFHT |
|---|---|---|
| Detection Ab Dilution | R&D Protocol | 1:800 |
| Plasma Dilution | 1:25000 | 1:2500 |

13.5. Example 5. FH Expression in Cells Transduced with Protective CFH, CFHT and eCFH/T Constructs

13.5.1. AAV2 Transduction of RPE7 Cells with Protective CFH and eCFH/T Therapeutic Candidates Large Scale Production of AAV2 Particles and RPE7 Transduction Large scale plasmid DNA isolation and AAV2 viral production were carried out generally as described in Zolotukin et al., 2002, Production and Purification of Serotype 1, 2, AND 5 Recombinant Adeno-Associated Viral Vectors" *Methods* 28:158-167. Viral titer (vg/ml) was greater than 2.5E+12. Based on previous experiments using RPE7 (Sigma Cat. #09061602) cells we transduced cells at $1\times10^6$ viral particles/cell in a 24-well plate format in duplicate. Supernatant was collected 9 days post-transduction and conditioned for 96 hours to allow accumulation of CFH and CFHT proteins for ELISA detection.

CFH and CFHT ELISA Assays

CFH and CFHT ELISA assays were performed using cell culture supernatant diluted 1:10 in ELISA assay reagent diluent (1×PBS+0.5% BSA). Plates were coated with CFH R&D System ELISA (Cat. #DY4779) (1:190) and CFHT specific monoclonal aCTM119 (1:600) capture antibodies in Maxisorp coating buffer overnight at 4° C. After plates were washed three times in PBST, diluted samples (100 μl) were added to each well and incubated for 2 hours at room temperature. Plates were washed as above followed by CFH R&D Systems ELISA (1:190) or aCTM87b (1:800) detector antibodies; followed by Streptavidin-HRP and ECL to indirectly detect protein. CFH (R&D System) and CFHT (in-house purified) protein standard curves were generated to determine relative concentration for all samples. Protein concentration of cell lysate was measured using Pierce 660 nm Protein Assay Reagent (Pierce, Cat. #22660) following manufacturer's protocol.

13.5.2. Results and Discussion

In this study, we compare CFH and CFHT protein expression in RPE7 cells transduced with protective CFH and eCFH/T therapeutic candidates containing the smCBA promoter element and TK poly A UTR. We determine CFH and CFHT protein secreted into the supernatant 9 days post-transduction. CFH levels are higher than control cells with smCBA-CFH cells producing 7.6 ng/ml and smCBA-eCFH/T transduced cells producing 5.8 ng/ml (Table 22). The protein concentration from smCBA-CFHT-bGH transduced cells is >3000 ng/ml and smCBA-eCFH/T transduced cells show 40% higher protein concentration than AAV2 negative control transduced cells (CBA-EGFP) (TABLE 26).

TABLE 26

Expression of protective CFH, CFHT and eCFHT protein in RPE7 cells after AAV2 transduction (MOI = $10^6$). Protein signal in control AAV2 transduced cells (CBA-EGFP) represent endogenous levels of CFH and CFHT protein.

| pCTM # | Construct Name | CFH Protein (ng/ml) | CFHT Protein (ng/ml) |
|---|---|---|---|
| CBA-EGFP | CBA-GFP | 1.9 | 0.5 |
| 259 | smCBA-CFHT-bGH | 0 | 3391 |
| 273 | smCBA-CFH-TK | 7.6 | 0.5 |
| 271 | smCBA-eCFH/T-TK | 5.8 | 0.7 |

13.5.2.1. Transduction of African Green Monkey COS-7 Cell Line with AAV2 Protective Therapeutic Candidates Rationale We performed AAV2 transductions of protective CFH, CFHT and eCFH/T therapeutic candidates to accurately determine exogenous protein expression in supernatant of COS-7 cells (African Green Monkey kidney origin) by ELISA. We chose this cell line because of high transduction efficiency (~80-90%) and ELISA preference for detecting human CFH and CFHT proteins over endogenous AGM proteins. We tested several promoter and poly A constructs to more precisely compare AAV2-directed exogenous expression of protective CFH and CFHT therapeutic proteins. Both smCBA and CBA promoter constructs expressed very high levels of CFHT protein in AGM cells, whereas both smCBA-CFH-TK and smCBA-eCFH/T-TK AAV2 expressed modest amounts of CFH and eCFHT protein.

13.5.3. Methods

AAV2 Transduction of COS-7 Cell Line

COS-7 (ATCC #CRL-1651) kidney derived cells were maintained in Dulbecco's Modified Eagle's Medium (ATCC, Cat. #30-2002) with 10% FBS. Based on previous experimentation using COS-7 cells and AAV2 CBA-EGFP transduction we added $1\times10^6$ viral particles/cell in a 96-well plate format in duplicate. Viral titer (vg/ml) greater than 3.8E+12. Supernatant was conditioned for 96 hours to allow accumulation of CFH and CFHT protein and collected at 7 and 10 days post-transduction for CFH and CFHT ELISA. The stock AAV2

CFH and CFHT ELISA Assays

ELISA assays were performed using cell culture supernatant diluted with ELISA assay reagent diluent (1×PBS+0.5% BSA) at 1:30 for CFH detection and 1:300 for CFHT and eCFHT detection. Plates were coated with CFH R&D System ELISA (Cat. #DY4779) (1:190) and CFHT specific monoclonal aCTM119 (1:600) capture antibodies in Maxisorp coating buffer overnight at 4° C. After plates were washed three times in PBST, diluted samples (100 µl) were added to each well and incubated for 2 hours at room temperature. Plates were washed as above followed by CFH R&D Systems ELISA (1:190) or aCTM87b (1:800) detector antibodies; followed by Streptavidin-HRP and ECL to indirectly detect protein. CFH (R&D System) and CFHT (in-house purified) protein standard curves were generated to determine relative concentration for all samples. All results were analyzed using Excel and graphed with Prism 7.0 software.

13.5.4. Results and Discussion

In this study, we tested CFH and CFHT protein expression in COS-7 cells transduced with protective CFH, CFHT and eCFH/T AAV2 therapeutic candidates. We determined CFH, CFHT and eCFHT protein concentration was secreted into the supernatant at 7 and 10 days post-transduction. CFH protein concentration in COS-7 supernatant was significantly elevated at day 7 (165 ng/ml) and day 10 (130 ng/ml) post-transduction using smCBA-CFH-TK AAV2 virus. The smCBA-CFHT-bGH transduced cells generated 2070 ng/ml and 645 ng/ml (day 7 and 10, respectively) while CBA-CFHT-bGH produced 3784 ng/ml and 1950 ng/ml protective CFHT protein (day 7 and 10, respectively). The smCBA-eCFH/T AAV2 transduced cells were capable of generating CFH protein at 66 and 46 ng/ml over the study time course and eCFHT protein at 5.1 and 6.5 ng/ml. A summary of protective CFH, CFHT and eCFHT protein concentration after protective AAV2 transduction is shown in TABLE 27.

TABLE 27

Concentration of protective CFH, CFHT and eCFHT protein in COS-7 supernatant at indicated time points post-AAV2 transduction using 1 × $10^6$ particles/cell.

| | | CFH Protein (ng/ml) | | CFHT Protein (ng/ml) | |
|---|---|---|---|---|---|
| pCTM # | Construct Name | Day 7 | Day 10 | Day 7 | Day 10 |
| CBA-EGFP | CBA-GFP | 0 | 0 | 0.2 | 0 |
| 259 | smCBA-CFHT-bGH | 0 | 0 | 2072 | 647 |
| 261 | CBA-CFHT-bGH | 0 | 0 | 3785 | 1953 |
| 273 | smCBA-CFH-TK | 165 | 128 | 0.4 | 0.2 |
| 271 | smCBA-eCFH/T-TK | 66 | 46 | 5.1 | 6.5 |

13.6. Example 6. Evaluation of the Ocular Distribution and Tolerance of AAV Vector Candidates Expressing CFH, CFHT and eCFH/T Transgenes Following Subretinal Administration in African Green Monkeys Objective: To evaluate ocular tolerance and achieved transgene expression following subretinal administration of AAV vector candidates expressing human Complement Factor H (CFH) and truncated CFH (CFHT). Experiments were conducted by a CRO.

Test System

Species: St. Kitts African green monkeys (*Chlorocebus saboeus*)

Number of Animals: 10

Sex & Age: Adult males and females approximately equally distributed between treatment groups 13.6.1. Study Design Subject Recruitment: Selected monkeys will undergo baseline screening to assess general well-being and ocular health by slit lamp biomicroscopy, fundoscopy, color fundus photography and optical coherence tomography (OCT). Monkeys with normal findings will be enrolled in the study and randomized to treatment groups approximately by sex and body weight. For baseline screening and all subsequent procedures, anesthesia will be achieved with intramuscular ketamine (8 mg/kg) and xylazine (1.6 mg/kg) to effect, and pupil dilation with topical 10% phenylephrine and/or 1% cyclopentolate.

Dosing: Vector test articles will be prepared on the day of administration by thawing at ambient temperature. One vial of test article will be available per monkey. Each vial containing test article will be used for dosing within 2 hours of thawing. Monkeys will receive 2 subretinal injections in both eyes (OU) of vector test articles in accordance with the treatment assignment. Following each dosing one drop of the test article will be expelled out from the catheter tip and the remaining volume aspirated back into the syringe for the following injection for the same animal.

Subretinal Delivery: After eye speculum placement, a drop of proparacaine hydrochloride 0.5% will be administered and then 5% Betadine solution followed by a sterile saline rinse. A sterile eye drape will be placed and temporal exposure of the ocular surface expanded with a canthotomy performed by clamping the lateral canthus with a hemostat for ~20 seconds, then cutting with fine surgical scissors. A 25 or 23 gauge vitrectomy port (Alcon valved entry system 1-CT, or equivalent) will then be placed via included port introducer device at the level of the *Ora serrata* in the superotemporal quadrant (the 10 o'clock position OD and the 2 o'clock position OS). A second vitrectomy port will be placed at the level of the *Ora serrata* in the inferotemporal quadrant (the 8 o'clock position OD and the 4 o'clock position OS). Afterward a contact vitrectomy lens will be placed and centered on the cornea, employing carboxymethylcellulose 0.25% and hypromellose 0.3% (Genteal, or equivalent) as a coupling agent. With the surgeon positioned temporally a 25 gauge light pipe will be inserted through the vitrectomy port on the left (superotemporal OD) into the vitreous cavity for intraocular illumination, keeping the tip in the anterior vitreous. A subretinal cannula (MedOne 23/38g part number 3510, or similar device) will be introduced through the second vitrectomy port and moved through the vitreous maintaining visualization of the tip at all times. The 38-gauge flexible microtip will be advanced to gently touch the retinal surface, targeting a point superior to fovea just within the superior vascular arcade. Upon observing slight blanching of the retinal surface at the point of contact, a surgical assistant will gently advance the plunger on the attached syringe containing test article. When an initial bleb is raised, a target volume (100 microliters) of test article will then be administered, after which the cannula tip will be retained in place for several seconds then retracted, taking care not to tear the elevated retinal surface. The injection cannula will be repositioned to target a point inferior to fovea just within the inferior vascular arcade and second bleb placed, after which the injection cannula will be removed. The light pipe will additionally be removed from the eye, followed by removal of the vitrectomy ports and the lens and lens ring. Vitreous that exits the sclerotomy sites secondary to the introduced subretinal fluid volume will be trimmed and removed by Weck-Cel sponge or equivalent, and the sclerotomies will be self-sealing. The canthotomy will be closed with one 5-0 monofilament suture. A topical antibiotic ointment (neomycin/polymyxin B sulfates/bacitracin zinc, or equivalent) will be instilled in the eye after post-operative fundus imaging to document subretinal bleb location and dimension.

Studies including slit lamp biomicroscopy and fundoscopy, optical coherence tomography multifocal electroretinography, and ocular tissue collection will be carried out. After confirming the quality of final imaging prior to the defined terminus the monkeys will be euthanized with sodium pentobarbital, and exsanguination of the cephalic circulatory system by slow transcardial perfusion with chilled 0.9% saline if appropriate. Aqueous humor (~100 uL) will be sampled OU with a 0.3 mL insulin syringe with a 31 gauge needle, aliquoted into two samples (50 uL) for each eye, flash frozen and stored below −70° C. Eyes will be enucleated with connected optic nerve. A sample of orbital fat will be collected from each eye and flash frozen in pre-tared vials after weighing. Excess orbital tissue will be trimmed. The portion of the optic nerve extending beyond the sclera will be removed and flash frozen in pre-tared vials after weighing, and then globes OU will be dissected at room temperature, to isolate vitreous, retinal and choroidal sub-tissues.

After confirming the quality of final imaging prior to the defined terminus the monkeys will be euthanized with sodium pentobarbital, and exsanguination of the cephalic circulatory system by slow transcardial perfusion with chilled 0.9% saline if appropriate. Tissue collection will be conducted based on FIG. 18 and FIG. 19. Aqueous humor (~100 μL) will be sampled OU with a 0.3 ml insulin syringe with a 31-gauge needle, aliquoted into two samples (50 μL) for each eye, flash frozen and stored below −70° C. Eyes will be enucleated with connected optic nerve. A sample of orbital fat will be collected from each eye and flash frozen in pre-tared vials after weighing. Excess orbital tissue will be trimmed. The portion of the optic nerve extending beyond the sclera will be removed and flash frozen in pre-tared vials after weighing, and then globes OU will be dissected at room temperature, to isolate vitreous, retina-RPE-choroid (RRC) tissues.

For OS, the anterior segment will be removed, fixed in 4% (para)formaldehyde for 24 hours, transferred to a maintenance buffer and stored at 4° C. (fixative and maintenance buffer formulas will be provided by the SCTM). The vitreous will be collected from the posterior eyecup with a syringe, transferred to a cryotube and flash frozen. After collection of vitreous, longitudinal cuts will be made in the eyecup to allow flat mounting. 6 mm punches of regions 1 (centered on the AAV bleb) and 4 will be made. The punches will be transferred to pre-tared labeled cryotubes, weighed and stored (note: retina/RPE/choroid punches may be subdivided into retinal and RPE/choroid sub-tissues prior to freezing; this decision will be made prior to sacrifice). The remainder of the posterior pole will be fixed in 4% (para) formaldehyde for 24 hours, transferred to a maintenance buffer and stored at 4° C.

For OD, the anterior segment will be removed, transferred to a cryotube and flash frozen. The vitreous will be collected from the posterior eyecup with a syringe, transferred to a cryotube and flash frozen. After collection of vitreous, longitudinal cuts will be made in the eyecup to allow flat mounting, and 6 mm diameter punches of neural retina-RPE-choroid centered on the AAV blebs (regions 1 and 2) will be collected. The punches will be transferred to pre-tared labeled cryotubes, weighed and stored at −70° C. Six mm diameter punches will also be collected from the saline bleb (region 3) and the control non-bleb (region 4) regions. In some cases, retina/RPE/choroid punches may be subdivided into retinal and RPE/choroid sub-tissues prior to freezing. A 6 mm punch of the macula will be taken, transferred to pre-tared labeled cryotubes, weighed and stored. A 4 mm diameter punch of the optic nerve will be taken and transferred to pre-tared labeled cryotubes, weighed and stored. Finally, the remaining retina/RPE/choroid (region 7) will be transferred to pre-tared labeled cryotubes, weighed and stored.

Central Nervous System (CNS) Tissue Collection: Immediately after eye enucleation, the brain will be removed and dissected into 4 mm coronal sections with further sub-dissection of the superior colliculus and lateral geniculate nucleus bilaterally.

Peripheral Organs: After eye enucleation and brain removal. liver, heart, lung, spleen, muscle (diaphragm) and kidney samples will be collected. Five specimens of each tissue (~0.3 gm) will be collected and two post-fixed in 4% paraformaldehyde for possible histopathology processing and analysis and three remaining flash frozen stored.

13.6.2. Study Execution: rAAV2 Gene Therapy Candidates in African Green Monkey Model Experiments were conducted according to the protocol above to evaluate protective protein expression following subretinal administration of rAAV2 gene therapy candidates in African green monkey model. Total RNA, total protein and 4% PFA fixed sections from retina-RPE-choroid tissue punches, centered on subretinal blebs and control regions were used to determine CFH, CFHT and eCFHT mRNA, protein concentration and distribution by qRT-PCR, ELISA and immunohistochemistry, respectively.

The following recombinant polynucleotide constructs were administered using a rAAV2 vector:

1. vCTM261 (CBA-CFHT-bGH)
2. vCTM281 (BEST1-EP-454-CFH-TK)
3. vCTM282 (RPE65-EP-415-CFH-TK)
4. vCTM283 (BEST1-EP-454-eCFH/T-TK)
5. vCTM284 (RPE65-EP-415-eCFH/T-TK)

TABLE 28 shows rAAV2 treatment assignments. "Dose" refers to a target dose for each bleb.

TABLE 28

| Group | Monkey | Eye | Vector Treatment | Route* | Dose | Volume | Test Article Required |
|---|---|---|---|---|---|---|---|
| 1 | 1 | OD | AAV candidate 261 | Subretinal | 8E+10 vg/bleb | 2 × 100 µl | Candidate vCTM261 |
| | | OS | AAV candidate 261 | Subretinal | 8E+10 vg/bleb | 2 × 100 µl | 8E11 vg/ml |
| | 2 | OD | AAV candidate 261 | Subretinal | 8E+10 vg/bleb | 2 × 100 µl | (100 µl/eye + 100 µl dead |
| | | OS | AAV candidate 261 | Subretinal | 8E+10 vg/bleb | 2 × 100 µl | space) × 8 = 1500 µl |
| 2 | 3 | OD | AAV candidate 281 | Subretinal | 8E+10 vg/bleb | 2 × 100 µl | Candidate vCTM281 |
| | | OS | AAV candidate 281 | Subretinal | 8E+10 vg/bleb | 2 × 100 µl | 8E11 vg/ml |
| | 4 | OD | AAV candidate 281 | Subretinal | 8E+10 vg/bleb | 2 × 100 µl | (100 µl/eye + 100 µl dead |
| | | OS | AAV candidate 281 | Subretinal | 8E+10 vg/bleb | 2 × 100 µl | space) × 8 = 1600 µl |
| 3 | 5 | OD | AAV candidate 282 | Subretinal | 8E+10 vg/bleb | 2 × 100 µl | Candidate vCTM282 |
| | | OS | AAV candidate 282 | Subretinal | 8E+10 vg/bleb | 2 × 100 µl | 8E+11 vg/ml |
| | 6 | OD | AAV candidate 282 | Subretinal | 8E+10 vg/bleb | 2 × 100 µl | (100 µl/eye + 100 µl dead |
| | | OS | AAV candidate 282 | Subretinal | 8E+10 vg/bleb | 2 × 100 µl | space) × 8 = 1600 µl |
| 4 | 7 | OD | AAV candidate 283 | Subretinal | 9E+10 vg/bleb | 2 × 100 µl | Candidate vCTM283 |
| | | OS | AAV candidate 283 | Subretinal | 9E+10 vg/bleb | 2 × 100 µl | 9E+11 vg/ml |
| | 8 | OD | AAV candidate 283 | Subretinal | 9E+10 vg/bleb | 2 × 100 µl | (100 µl/eye + 100 µl dead |
| | | OS | AAV candidate 283 | Subretinal | 9E+10 vg/bleb | 2 × 100 µl | space) × 8 = 1600 µl |
| 5 | 9 | OD | AAV candidate 284 | Subretinal | 9E+10 vg/bleb | 2 × 100 µl | Candidate vCTIM284 |
| | | OS | AAV candidate 284 | Subretinal | 9E+10 vg/bleb | 2 × 100 µl | 9E+11 vg/ml |
| | 10 | OD | AAV candidate 284 | Subretinal | 9E+10 vg/bleb | 2 × 100 µl | (100 µl/eye + 100 µl dead |
| | | OS | AAV candidate 284 | Subretinal | 9E+10 vg/bleb | 2 × 100 µl | space) × 8 = 1500 µl |

*One subretinal bleb will be placed superior to the macula and one bleb will be placed inferior to the macula As noted above, injections and tissue collection were made as indicated in FIGS. 18 and 19. Tissue collection was carried out 57 days after subretinal injection.

14.6.2.1 Results

RNA Expression

TABLE 29 shows RNA quality and concentration from AGM retina-RPE-choroid tissue bleb #1 (and #3 as shown in FIG. 18). We isolated total RNA from retina-RPE-choroid (RRC) punches centered on the rAAV2 injected blebs (#1) and saline injected blebs (#3) from 5 monkeys. The total RNA quality (based on RIN score) and concentration (ng/μl) is sufficient for most RNA-based analysis. Therefore, we performed qRT-PCR using previously designed and tested human specific primer pairs to determine the relative concentration of protective CFH, CFHT and eCFHT mRNAs. When total RNA was used as template for qRT-PCR studies we detect inconsistent and variable results. We detect a robust signal for the expect rAAV2 transduced tissues and qRT-PCR primer pairs, but also detect a modest signal in the (−) RT controls reactions that is used for normalization. This suggests that viral ssDNA is not efficiently being removed during the DNAse step, making it difficult to discriminate between RNA and DNA signal in these studies.

TABLE 29

| | | RIN | | Punch RNA Concentration (ng/μl) | |
|---|---|---|---|---|---|
| Animal # | rAAV2 | Bleb #1 | Bleb #3 | Bleb #1 | Bleb #3 |
| A827 | vCTM261 | 7.6 | 6.9 | 360 | 266 |
| A521 | vCTM281 | 7.9 | 7.8 | 212 | 318 |
| A847 | vCTM282 | 7.6 | 7.8 | 412 | 286 |
| A543 | vCTM283 | 7.2 | 7.6 | 300 | 266 |
| A875 | vCTM284 | 7.7 | 8.1 | 350 | 256 |

We used RNA-sequencing of tissue RNAs to better ascertain RNA versus DNA signal in these tissue samples. RNA sequencing was able to identify both endogenous African green monkey CFH/CFHT and rAAV2 delivered CFH, CFHT and eCFHT mRNAs (FIG. 20). In the 5 AGM samples tested, the rAAV2 delivered RPKM mRNA signal (normalized) is ~100- to 1000-fold higher than endogenous AGM mRNA levels. We also see a minor signal from saline treated blebs which probably represent mis-mapped reads or minor rAAV2 spreading to these areas (FIG. 20). It is possible DNA is still contributing to the RPKM signal in these studies. In addition, it is not possible to determine absolute AGM CFHT or human protective eCFHT mRNA in these studies. For all comparisons, we assign 90% of the RPKM read count to CFH and 10% to CFHT or eCFHT, similar to endogenous human studies. We are in the process of identifying CFHT reads using the RNA-seq BAM files and Integrated Genome Viewer (IGV) software to more accurately assign expression values.

Protein Expression Determined by ELISA

Further evidence demonstrating gene therapy candidates transduced AGM ocular tissue generated protective protein was obtained using human-specific CFH and CFHT ELISAs to quantitate protein levels. Retina-RPE-choroid (RRC) tissue from rAAV2 transduced bleb #2 and control non-bleb #4 (see FIG. 18) were processed for total protein isolation and amounts are shown in TABLE 30. Total protein concentration from AGM retina-RPE-choroid tissue punch (6 mm) from indicated animals and blebs.

TABLE 30

| | | Punch Protein Concentration (mg/ml) | |
|---|---|---|---|
| Animal # | rAAV2 | Bleb #2 | Non-Bleb #4 |
| A827 | vCTM261 | 4.05 | 2.83 |
| A367 | | 2.31 | 1.65 |
| A521 | vCTM281 | 4.72 | 2.60 |
| A849 | | 3.10 | 1.36 |
| A847 | vCTM282 | 4.21 | 2.58 |
| A703 | | 2.70 | 1.40 |
| A543 | vCTM283 | 2.83 | 1.70 |
| A844 | | 3.17 | 2.27 |
| A875 | vCTM284 | 4.36 | 4.30 |
| A220 | | 2.37 | 2.23 |

Distribution of Protective CFHT Protein

To determine distribution of protective CFHT protein we performed immunohistochemistry (IHC) on monkey A827 transduced with vCTM261. Since this viral prep generates a robust protein signal in ELISA testing we expected to detect a signal by IHC. To this end, we are able to detect a modest signal in RPE cells with minimal signal in retina, Bruch's membrane and choroid. Minimal to no signal is detected in the non-bleb region (−rAAV2) and secondary antibody only treated slides. In addition to IHC, we performed histology on RRC epon-embedded sections using Richardson's stain. We did not detect any obvious morphological changes after subretinal injection of rAAV2 expressing high levels of human protective CFHT protein.

In addition to A827 tissue, we also tested tissue sections from animal A543 (vCTM283 transduced) using the aCTM88 antibody. No significant signal above background was detected in this tissue (data not shown). We are able to detect a modest signal in RPE cells with minimal signal in retina, Bruch's membrane and choroid. In addition to A827 tissue, we tested tissue sections from animal A543 (vCTM283 transduced) using the aCTM88 antibody. No significant signal above background was detected in this tissue (data not shown). Overall, the non-human primate AGM model provides validation that all rAAV2 constructs are capable of producing protective CFH, CFHT and eCFHT proteins at varying levels. To further demonstrate gene therapy candidates transduced AGM ocular tissue to generate protective protein we performed human-specific CFH and CFHT ELISAs to quantitate protein levels. Retina-RPE-choroid (RRC) tissue from rAAV2 transduced bleb #2 and control non-bleb #4 were processed for total protein isolation.

Results and Discussion

To gain more insight into protective protein expression after subretinal delivery of our 5 gene therapy candidates we present retina-RPE-choroid (RRC) protein concentration in the primary rAAV2 bleb (punch #2; FIG. 19), as well as nasal (punch #4) and macular (punch #5) control tissue regions. We also compare therapeutically delivered protective protein concentrations to human RRC tissue to determine endogenous target protein level. As expected, the strong CBA-directed CFHT expressing vCTM261 candidate does not show any CFH protein above background level (background AGM CFH ELISA signal averages ~6 ng/mg, dotted line). The vCTM281-284 candidates show a marginal increase in CFH protein (9-18 ng/mg); the one exception is animal A543 transduced with BEST1-EP-454-eCFH/T (vCTM283) rAAV2 candidate that generates an impressive 41 ng/mg CFH protein. For comparison, 4 human tissue donors exhibit 173-1055 ng/mg of CFH protein in RPE tissue within RRC tissue. Based on previous studies, separating retina, RPE and choroid tissues we predict the RPE region will contain between 35-211 ng/mg CFH protein (dotted region on bar graph, FIG. 21). This suggests that vCTM283 can produce therapeutic amounts of protective CFH-I62-Y402-E936 protein in RRC tissue transduced with 9E+10 rAAV2 particles. It is unclear at this point why monkey A844, transduced with an equivalent dose of vCTM283, does not show an elevated signal for CFH protein. This could be due to several technical factors including: complications during surgery, RRC tissue isolation and processing or ELISA testing.

CFH/CFHT Protein Migration

We determined protective CFHT and eCFHT protein concentration using the same RRC tissue protein lysates as above.

We detected a significant amount of CFHT protein (38 and 22 ng/mg) in both African green monkey treated blebs (animal A827 and A367, respectively) when using 8E+10 dose of vCTM261 (CBA-CFHT-bGH construct) (FIG. 22, top panel). Zero or near background signal (<0.2 ng/mg) is detected in vCTM281 and vCTM282 treated animals, while vCTM283 and vCTM284 both express detectable amounts (0.4-1.4 ng/mg) of protective eCFHT protein (FIG. 22, bottom panel).

For human target protein comparison we tested the same 4 human donors as above to determine the amount of CFHT protein expressed in total RRC tissue and predicted amount in RPE tissue (dotted region of bar graph in FIG. 22). CFHT protein concentration is 30- to 40-fold higher than predicted endogenous human CFHT protein (ranges from 0.1-0.7 ng/mg) in vCTM261 treated animals and near endogenous human level with animals A543, A844, A875 and A220 expressing engineered CFHT protein (vCTM283 and vCTM284). Based on these results we would expect human subretinal delivery of protective CFHT protein, for both vCTM261, vCTM283 and vCTM283, to successfully control, under the bleb region, alternative complement pathway activation via co-factor and decay accelerating activities (i.e. degradation or decay of C3b, C3b(H20)Bb, C3bBb and C3/C5 convertase) in the sub-RPE space to prevent MAC accumulation, loss of RPE adhesion leading to RPE cell death and subsequent late stage AMD.

CFHT Protein Migration

We detected CFHT protein in control blebs in two animals (A827 and A367). In AGM RRC tissue samples from vCTM261 treated animals was elevated CFHT protein (0.4-1.3 ng/mg) in control samples from both animals (punch #4). In these animals the distance from the injection site bleb to the control bleb was ~4-7 mm (nearest margins) and ~15 mm center-to-center. After additional testing using all available control punches (#4) (FIG. 23, bottom panel) and macula RRC tissue punches (see below) it became apparent that diffusion of protective CFHT protein was occurring from the primary rAAV2 bleb location to both nasal and macular regions of the eye in vCTM261 treated animal.

Both vCTM283 and vCTM284 treated animals did not show any detectable CFHT protein outside of the rAAV2 treated bleb. This is expected since eCFHT protein concentration is 30- to 40-fold lower than vCTM261 treated animals and eCFHT that diffuses out of the primary bleb area would be below ELISA detection limits.

Our observations are consistent with a mechanism in which CFHT protein crosses Bruch's membrane and enters the choriocapillaris to gain access to other regions of the eye.

As discussed above, we performed the same CFH and CFHT ELISA studies as above but used macula punches from AGM RRC tissue (punch #5, FIG. 18). As shown in FIG. 23 (top panel) we did not see CFH protein above our typical ELISA background signal (~6 ng/mg, dotted line) in any of the RRC tissue punches tested. We can detect ~3-fold more CFHT protein in the macular region of vCTM261 treated monkeys (0.52-0.61 ng/mg) and background level (dotted line) in all other tissue punches (FIG. 23, bottom panel). These results support the concept that CFHT protein produced under the control of the potent CBA promoter (vCTM261 candidate), diffuses from the original site (high protein concentration) to other areas of the eye including the macula and nasal tissue (lower protein concentration).

To determine if CFH protein migrates from the primary injection site toward control nasal punch we processed RRC punches (#4, FIG. 18) from the same eyes as above. Overall, a minor CFH protein signal is detected in several of the rAAV2 treated eyes, but levels do not correlate with expression levels in the primary bleb site (FIG. 23, bottom panel). Based on these results we do not detect a therapeutically useful amount of CFH protein in control RRC tissue punches at the 8E+10 or 9E+10 vg/dose.

FIG. 22 shows levels of protective CFHT in tissues of AGM treated with pCTM261 (CFHT) and pCTM283 (eCFH/CFHT), and reference values from four human donor eyes. Diffusion of protective protein from a superior bleb to the macula was measured for both constructs in quantities greater than (pCTM261) or close to (pCTM283) the average levels of CFHT in RPE from human donor eyes. TABLE 31 show calculated levels of CFH and CFHT protein in human donor tissue eye scrapes.

TABLE 31

Estimated amounts of CFH and CFHT protein in human RRC (Retina-RPE-Choroid) based on individual retina, RPE and Bruch's Membrane/choroid donor tissue scrapes.

| | Retina [ng/mg] | RPE [ng/mg] | BM/Choroid [ng/mg] |
|---|---|---|---|
| CFH | 45 | 163 | 1090 |
| CFHT | 0.4 | 1.8 | 1.1 |

Extent of CFHT Protein Migration

To confirm that human protective CFHT protein can diffuse from the subretinal bleb region and determine the extent of CFHT diffusion we perform a single subretinal injection of vCTM261 superior to the macula (region #1) (FIG. 24) in African green monkeys. Tissue punches were collected 56 days after the initial subretinal injection and processed as describe in the section above. All regions 1-13 (excluding optic nerve punch #6) were processed for total protein isolation and assayed for human protective CFHT protein level by ELISA. In the extramacular regions (#6-13) we pooled each respective quadrant (i.e. superior #6/7, nasal #8/9, inferior #10/11 and temporal #12/13) together which resulted in 4 total extramacular samples for ELISA testing.

Two AGM animals were tested for CFHT protein concentration, under the bleb and diffusion outside the bleb, and results are shown in FIG. 25. Similar to the studies presented above, human protective CFHT protein delivered by vCTM261 AAV2 is detected throughout the eye. In animal B180, the primary site of vCTM261 transduction (region #1) contains 51 ng/mg CFHT protein. The tissue region superior to the AAV2 bleb (combined punches #6/7) also contains a high level of CFHT protein. This may be diffusion of protein or the combined punches 6 and 7 include a portion of the AAV2 bleb resulting in elevated CFHT protein. All other regions tested (#2-13, excluding region #6) have CFHT protein levels ranging from 0.6-1.23 ng/mg total protein, which is above the background AGM signal of 0.3 ng/mg in this study. An independent animal B183 shows similar concentration of CFHT protein (51 ng/mg total protein) under the bleb (region #1) that is distributed throughout the eye (0.46-1.31 ng/mg total protein). For comparison, human calculated RPE tissue concentration is 1.8 ng/mg total protein.

To confirm CFH and eCFHT protein are produced from vCTM283 subretinal delivered AAV2 we also test both CFH and eCFHT protein by ELISA from two African green monkeys (B190 and B193). When using the RPE-specific BEST-1-EP-454 promoter we detect approximately 2-fold more protective CFH protein than background signal (45 ng/mg total protein) under the bleb (region #1) with varying amounts (16-41.5 ng/mg total protein) in other regions of the 2 AGM eyes (FIG. 26). A similar 2-fold increase in signal above background was detected when the same RRC tissue punches were tested for eCFHT protein levels by ELISA (FIG. 27). Collectively, subretinal delivery of vCTM283 AAV2 viral particles express both protective CFH and eCFHT proteins, but concentration under the bleb and diffusion to extramacular and macular regions are lower than vCTM261 treated animals.

14.6.2.2 Analytical Methods

CFH, CFHT and eCFHT qRT-PCR and RNA-Seq Assays

Total RNA was extracted from AGM RRC tissue using RNeasy kit (Qiagen, Cat. #74106). P234 P241 Complementary DNA was generated using 500 ng of total RNA and SuperScript IV VILO Master Mix kit (Invitrogen, Cat. #11756050). Quantitative RTPCR was performed using 12.5 ng of cDNA and TaqMan Gene Expression Master Mix (ThermoFisher Scientific, Cat. #4369016) following the manufacturer's protocol. CFH, CFHT and eCFHT specific qRT-PCR primers are the same as previously tested. AGM-GAPDH1 (Assay ID: APXGTE6) was used to normalize samples. PCR was performed in a Bio-Rad CFX96 Real-Time PCR System. The thermal cycling conditions were 10 minutes at 95° C. followed by 40 cycles at 95° C. for 15 seconds and 60° C. for 1 minute. The relative levels of exogenous CFH and CFHT mRNA was expressed as fold change above saline injected bleb punches in the same monkey. RNA sequencing libraries were prepared using the Illumina TruSeq Stranded Total RNA Sample Prep kit with Ribo-Zero Gold. The library was sequenced using Illumina NovaSeq platform with 100 million 50-bp reads per sample. Reads were mapped to *Chlorocebus sabaeus* and human codon optimized CFH, CFHT and eCFHT mRNA sequences.

Protein Expression

AGM retina-RPE-choroid tissue protein extraction For total protein extraction, frozen RRC tissue samples (6-mm punch) were washed once with 300 µl cold 1X PBS containing 1% Halt protease and phosphatase inhibitor cocktail+EDTA (Pierce Cat. #78440). After a single washing, tissue pieces were resuspended in 100 µl T-PER (Thermo Scientific Cat. #78510) containing 1% Halt protease and phosphatase inhibitor cocktail+EDTA. Samples were then homogenized on ice using a probe sonicator until the pellet was broken into small pieces, followed by shaking at 800 rpm every 20 seconds at 4° C. overnight. Finally, homogenized samples were centrifuged at 14000 rpm for 5 min and protein supernatant was used to determine total protein concentration using a 660 nm protein assay kit, (Thermo Scientific Cat. #1861426) following the supplied protocol.

CFH and CFHT protein concentrations in RRC tissue samples were normalized to total protein (µg/mg of total protein).

Human CFH and CFHT ELISAs

Each capture antibody was diluted in Maxisorp coating buffer (50 mM carbonate, pH 9.6) and a total of 100 µl of antibody/buffer solution added to each well of a black MaxiSorp 96-well microplate. Plates were covered and incubated overnight at 4° C. Wells were washed three times with PBST and then blocked for 90 min with reagent dilution buffer (1% BSA in 1×PBS). Plates were washed again after blocking. Diluted normal human serum (NHS), CFH-depleted human serum (dNHS), AGM serum, human choroid lysate or AGM RRC lysate was added to antibody coated plates and allowed to incubate at room temperature for 90 min. Plates were washed as above then incubated for 1 hour with detection antibody followed by three washes. Finally, plates were washed again and incubated for 5 minutes with SuperSignal ELISA pico chemiluminescent substrate (ThermoFisher Scientific, Cat. #37069) before detection using the BioTek Synergy 4 plate reader. CFH (R&D) CFH and CFHT (in-house produced) protein standard curves were generated to determine concentration for all samples.

Histology—Two 2-millimeter-diameter trephine-generated punches (region #2 and #3) of RRC were obtained from monkey A827. Tissue samples were fixed in ½K, dehydrated via an alcohol gradient and embedded in epon. One-micron sections were stained at 60° C. with Richardson's stain, photographed and montaged via Photoshop Adobe Creative Suite.

AGM immunohistochemistry—Two four-millimeter-diameter trephine-generated punches of retina-RPE-choroid (region #2 and temporal to #3 since retina was separated in region #3) were obtained from monkey A827. The tissue was embedded in 10% agarose at 45° C., and tissue sections of 100-µm thickness were made by using a Vibratome 1000. The retina and choroid stayed intact. After extensive washing with PBS, the tissue sections were blocked by incubation at room temperature for 6 hours with PBS containing 1 mg/mL BSA, and 0.1% (vol/vol) Triton X-100. Immunohistochemistry (IHC) was performed using the aCTM88 antibody that shows low background signal in AGM RRC tissue and primary antibody was diluted 1:200 in blocking buffer, applied to tissue sections (200 µl), followed by incubation for 16 hours at 4° C. After washing 3 times for 15 minutes at room temperature with PBT (PBS containing 1 mg/mL BSA and 0.1% Triton X-100) tissue sections were incubated with Rhodamine labeled secondary antibody (goat antirabbit) diluted 1:200 in PBT for 16 hours at 4° C. After washing 3 times for 15 minutes with PBT at room temperature, tissue sections were mounted on Superfrost microscope slides (Electron Microscopy Sciences) with Fluoro-Gel mounting medium (containing 4',6-diamidino-2-phenylindole [DAPI] as a nuclear counterstain; Electron Microscopy Services). No background autofluorescence was detected for AGM tissue and Rhodamine labeled secondary antibody only (goat antirabbit) did not show any appreciable background signal.

14.7 Example 7: Protective CFHT-I62 Protein can Augment CFH-Risk Protein Deficits in LPS-Driven Assay To explore the ability of protective CFHT-I62 protein to augment CFH-risk protein we compare several fixed concentrations of CFH-risk protein (0, 25, 50 and 100 nM) with increasing concentrations of protective CFHT-I62 protein. These studies suggest protective CFHT-I62 protein can augment CFH-risk protein deficits at multiple concentrations.

Methods

LPS-Driven Alternative Pathway (AP) Assay

The ability of CFH and CFHT proteins to modulate alternative pathway activation was evaluated using an ELISA-based assay using LPS as the complement AP activator. In brief, 50 μl LPS solution (50 μg/ml) from *Salmonella typhimurium* (Sigma-Aldrich, Cat. #L7261) was coated onto 96-well plates (Maxisorp; Nunc) in PBS overnight at 4° C., followed by washing three times with PBS+Tween 20. Plates were then blocked with 1% BSA/PBS for 1.5 hour at room temperature. Various dilutions of recombinant CFH-risk and protective CFHT-I62 protein (0.49-500 nM) in PBS (30 μl) were mixed with 30 μl 25% normal human serum containing 10 mM MgEGTA. In LPS competition assays, recombinant CFH-risk protein at several concentrations (0, 25, 50 and 100 nM) were mixed with varying amounts of CFHT-I62 proteins (concentration ranging from 0.98-1000 nM) in PBS. The protein mixture was then added to 30 μl 25% normal human serum containing 10 mM MgEGTA. The mixture of analytes in serum were added to LPS-coated wells and incubated for 1.5 hours at 37° C. prior to washing and subsequent exposure to HRP conjugated goat anti-human C3 (MP Biomedicals, Cat. #855237) at 1:10,000 dilution in 1% BSA/PBS for 1 hour at room temperature. After washing three times with PBST, C3b deposition on plates were indirectly detected using Super-Signal ELISA Pico Chemiluminescent Substrate and the BioTek Synergy 4 plate reader. PBS and EDTA (final concentration 5 mM) were used as positive and negative controls, respectively. All responses were normalized to the activity achieved when only PBS was added in the absence of a protein regulator. All raw data was manipulated in Excel then plotted using a nonlinear regression log(inhibitor) vs. response (three parameters) model in Prism 8.

Results and Discussion

We have optimized and thoroughly tested all variant protein activities individually (CFH, CFHT) in the LPS activation assay but not mixing risk and protective protein variants. The LPS-driven AP assay monitors the ability of CFH and CFHT protein variants to control alternative pathway activation in the presence of 12.5% normal human serum (source of C3) that is activated by LPS coated on 96-well plates. In the presence of buffer only (PBS), a maximal signal of C3b deposition occurs (100%), which can be inhibited to varying degrees with the negative AP regulator proteins CFH and CFHT to varying degrees, depending on variant protein tested (e.g. risk, neutral, deletion or protective I62).

To determine if protective CFHT-I62 protein can function in the presence of CFH-risk protein we spike in a fixed amount of CFH-risk protein (0, 25, 50 and 100 nM) and titrate into the assay protective CFHT-I62 protein. As shown in FIG. 31, the half-maximal inhibitory assay concentration ($IC_{50}$) for protective CFHT-I62 protein changes from 80, 122, 152 and 337 nM when 0, 25, 50 and 100 nM CFH-risk are included in the assay, respectively. At modest CFH-risk concentrations (25 and 50 nM) less than 2-fold more protective CFHT-I62 protein is required to reduce activity in half; while the highest CFH-risk protein concentration (100 nM) requires ~4-fold more protective CFHT-I62 protein. This indicates that introduction of exogenous protective CFHT into and around the RPE, sub-RPE space, Bruch's membrane, and choroid can reduce complement activation and complement-mediated tissue damage that occurs in patients with the risk forms of CFH and CFHT.

In addition to the individual protective CFHT-I62 protein $IC_{50}$ values required to inhibit half-maximal LPS-dependent C3b deposition, we also compare the ratio of CFH-risk protein/CFHT-I62 protein for AP inhibition TABLE 32. When comparing ratios, it is evident that regardless of the concentration of CFH-risk protein included into the assay, the amount of protective CFHT-I62 required to inhibit C3b deposition is a constant amount (ratio=0.35-0.38). These results suggest that CFH-risk and CFHT-I62 proteins are not in direct competition with each other for protein ligands (e.g. C3b, CFI, C3 and C5 convertase); but instead, increasing the amount of protective CFHT-I62 protein will augment CFH-risk protein by independently acting on C3b, CFI, C3 and C5 convertases to better control AP regulation. Therefore, in the sub-RPE space under conditions when CFH-risk protein levels are not sufficient to negatively control AP activity, protective CFHT-I62 protein will rescue the deficit. The therapeutic amount required for AP rescue is a function of many variables including: concentration of complement protein free-fraction, complement activation state, disease state, age-dependent changes, systemic levels of CRP, PTX3, CFD, CFHR-1 and CFHR-3 proteins and many additional factors that conspire to modulate AP in the sub-RPE space.

TABLE 32

LPS-dependent assay summary from two independent experiments.

| LPS Assay | CFH-risk Input [nM] | CFHT-I62 $IC_{50}$ [nM] | Ratio (CFH/CFHT) |
|---|---|---|---|
| Exp. #1 | 0 | 84 | — |
| Exp. #2 | 0 | 63 | — |
| Average | 0 | 74 | — |
| Exp. #1 | 25 | 122 | 0.21 |
| Exp. #2 | 25 | 52 | 0.48 |
| Average | 25 | 89 | 0.35 |
| Exp. #1 | 50 | 176 | 0.28 |
| Exp. #2 | 50 | 103 | 0.49 |
| Average | 50 | 140 | 0.38 |
| Exp. #1 | 100 | 336 | 0.30 |
| Exp. #2 | 100 | 162 | 0.40 |
| Average | 100 | 249 | 0.35 |

Table 33: Selected Sequences

TABLE 33A

| CFH DNA [SEQ ID NO: 1] |
|---|
| ATGAGACTGCTGGCCAAGATCATCTGCCTGATGCTGTGGGCCATCTGCG<br>TGGCCGAGGACTGCAACGAGCTGCCCCCCAGAAGAAACACCGAGATCCT<br>GACCGGCTCTTGGAGCGACCAGACCTACCCTGAGGGCACCCAGGCCATC<br>TACAAGTGCAGACCCGGCTACCGGTCCCTGGGCAACATCATCATGGTGT<br>GCAGAAAGGGCGAGTGGGTGGCCCTGAACCCCCTGAGAAAGTGCCAGAA<br>GAGGCCCTGCGGACACCCCGGCGATACCCCTTTTGGCACCTTCACACTG<br>ACCGGCGGCAACGTGTTCGAGTACGGCGTGAAGGCCGTGTACACCTGTA<br>ACGAGGGCTACCAGCTGCTGGGCGAGATCAACTACAGAGAGTGCGACAC<br>CGACGGCTGGACCAACGATATCCCCATCTGCGAGGTCGTGAAGTGCCTG<br>CCTGTGACCGCCCCAGAGAACGGCAAGATCGTGTCCAGCGCCATGGAAC<br>CCGACAGAGAGTACCACTTCGGCCAGGCCGTCAGATTCGTGTGCAACAG<br>CGGCTACAAGATCGAGGGCGACGAGGAAATGCACTGCAGCGACGACGGC<br>TTCTGGTCCAAAGAAAAGCCTAAGTGCGTGGAAATCAGCTGCAAGAGCC<br>CCGACGTGATCAACGGCAGCCCCATCAGCCAGAAGATCATCTACAAAGA<br>GAACGAGCGGTTCCAGTACAAGTGTAACATGGGCTACGAGTACAGCGAG<br>CGGGGCGACGCCGTGTGTACAGAATCTGGATGGCGGCCTCTGCCCAGCT<br>GCGAGGAAAAGAGCTGCGACAACCCCTACATCCCCAACGGCGACTACAG<br>CCCCCTGCGGATCAAGCACAGAACCGGCGACGAGATCACCTACCAGTGC |

TABLE 33A-continued

| CFH DNA [SEQ ID NO: 1] |
|---|
| CGGAACGGCTTCTACCCCGCCACCAGAGGCAATACCGCCAAGTGTACCA |
| GCACCGGCTGGATCCCTGCCCCCAGATGTACCCTGAAGCCCTGCGACTA |
| CCCTGACATCAAGCACGGCGGCCTGTACCACGAGAACATGCGGAGGCCC |
| TACTTCCCTGTGGCCGTGGGCAAGTACTACAGCTACTACTGCGACGAGC |
| ACTTCGAGACACCCAGCGGCAGCTACTGGGACCACATCCACTGTACCCA |
| GGACGGCTGGTCCCCTGCCGTGCCCTGCCTGAGGAAGTGCTACTTCCCC |
| TACCTGGAAAACGGCTACAACCAGAACTACGGCCGGAAGTTCGTGCAGG |
| GCAAGAGCATCGATGTGGCCTGCCACCCTGGATACGCCCTGCCTAAGGC |
| CCAGACCACCGTGACCTGCATGGAAAATGGATGGTCCCCCACCCCCCGG |
| TGCATCAGAGTGAAAACCTGCAGCAAGAGCAGCATCGACATCGAGAATG |
| GCTTCATCAGCGAGAGCCAGTACACCTACGCCCTGAAAGAGAAGGCCAA |
| GTACCAGTGCAAGCTGGGCTACGTGACCGCCGACGGCGAGACAAGCGGC |
| AGCATCACCTGTGGCAAGGATGGGTGGAGCGCCCAGCCCACCTGTATCA |
| AGTCCTGCGACATCCCTGTGTTCATGAATGCCCGGACCAAGAACGACTT |
| CACCTGGTTCAAGCTGAACGACACACTGGACTACGAGTGCCACGACGGC |
| TACGAGAGCAACACCGGCAGCACCACAGGCAGCATCGTGTGTGGCTACA |
| ACGGGTGGAGTGACCTGCCCATCTGTTACGAGCGCGAGTGCGAGCTGCC |
| TAAGATCGACGTGCACCTGGTGCCCGACCGGAAGAAAGACCAGTACAAA |
| GTGGGCGAGGTGCTGAAGTTCTCCTGCAAGCCCGGCTTCACCATCGTGG |
| GCCCCAATAGCGTGCAGTGCTACCACTTTGGCCTGTCCCCCGATCTGCC |
| TATCTGCAAAGAACAGGTGCAGAGCTGCGGCCCTCCACCCGAGCTGCTG |
| AACGGCAATGTGAAAGAAAAGACCAAAGAGGAATACGGCCACTCCGAGG |
| TGGTGGAATATTACTGCAACCCCCGGTTCCTGATGAAGGGCCCCAACAA |
| GATTCAGTGTGTGGACGGCGAGTGGACCACCCTGCCCGTGTGTATCGTG |
| GAAGAGTCTACCTGCGGAGACATCCCCGAGCTGGAACACGGATGGGCCC |
| AGCTGAGCAGCCCCCCTTACTACTACGGCGACAGCGTGGAATTCAACTG |
| CTCCGAGAGCTTTACCATGATCGGCCACCGGTCCATCACATGCATCCAC |
| GGCGTGTGGACACAGCTGCCACAGTGCGTGGCCATCGACAAGCTGAAGA |
| AGTGCAAGTCCAGCAACCTGATCATCCTGGAAGAACACCTGAAGAACAA |
| GAAAGAGTTCGACCACAACAGCAACATCCGGTACAGATGCCGGGGCAAA |
| GAGGGATGGATCCACACCGTGTGCATCAATGGCAGATGGGACCCCGAAG |
| TGAACTGCAGCATGGCCCAGATCCAGCTGTGCCCCCCACCTCCCCAGAT |
| CCCCAACAGCCACAACATGACCACCACCCTGAACTACCGGGATGGCGAG |
| AAGGTGTCCGTGCTGTGCCAGGAAAACTACCTGATCCAGGAAGGCGAAG |
| AGATTACCTGCAAGGACGGCCGGTGGCAGAGCATCCCCCTGTGTGTGGA |
| AAAGATCCCCTGCAGCCAGCCCCCCCAGATCGAGCACGGCACCATCAAC |
| AGCAGCAGAAGCAGCCAGGAATCCTACGCCCACGGCACAAAGCTGAGCT |
| ACACATGCGAGGGCGGCTTCCGGATCTCCGAGGAAAACGAGACAACCTG |
| CTACATGGGCAAGTGGTCCTCCCCACCTCAGTGCGAGGGACTGCCTTGC |
| AAGTCCCCACCCGAGATCTCTCATGGCGTGGTGGCCCACATGAGCGACA |
| GCTACCAGTACGGCGAGGAAGTGACCTACAAGTGTTTCGAGGGCTTCGG |
| CATCGACGGCCCTGCCATTGCCAAGTGCCTGGGAGAGAAGTGGTCCCAC |
| CCTCCCAGCTGCATCAAGACCGACTGCCTGAGCCTGCCTAGCTTCGAGA |
| ACGCCATCCCCATGGGCGAGAAAAAGGACGTGTACAAGGCCGGCGAACA |
| AGTGACATACACCTGTGCCACCTACTACAAGATGGACGGCGCCAGCAAC |
| GTGACCTGTATTAACAGCCGGTGGACCGGCAGGCCTACCTGCAGAGATA |
| CCTCCTGCGTGAACCCCCCCACCGTGCAGAACGCCTACATCGTGTCTCG |
| GCAGATGAGCAAGTACCCCAGCGGCGAACGCGTGCGCTACCAGTGTAGA |
| AGCCCCTACGAGATGTTCGGCGACGAAGAAGTGATGTGCCTGAATGGCA |
| ACTGGACCGAGCCCCCTCAGTGCAAGGATAGCACCGGCAAGTGTGGCCC |
| CCCTCCCCCCATCGATAACGGCGACATCACCAGCTTCCCCCTGTCCGTG |
| TATGCCCCTGCCAGCTCCGTGGAATATCAGTGCCAGAACCTGTACCAGC |
| TGGAAGGCAACAAGCGGATCACCTGTCGGAACGGCCAGTGGAGCGAGCC |
| TCCCAAGTGTCTGCACCCCTGCGTGATCTCCAGAGAAATCATGGAAAAC |
| TATAATATCGCCCTGCGCTGGACCGCCAAGCAGAAGCTGTACTCTAGGA |
| CCGGCGAGTCTGTGGAATTTGTGTGCAAGCGGGGATACAGACTGAGCAG |
| CAGATCCCACACCCTGAGAACCACCTGTTGGGACGGCAAGCTGGAATAC |
| CCTACCTGCGCCAAGAGATGA3' |

TABLE 33B

| CFH Protein [SEQ ID NO: 2] |
|---|
| MRLLAKIICLMLWAICVAEDCNELPPRRNTEILTGSWSDQTYPEGTQAIY |
| KCRPGYRSLGNIIMVCRKGEWVALNPLRKCQKRPCGHPGDTPEGTFTLTG |
| GNVFEYGVKAVYTCNEGYQLLGEINYRECDTDGWTNDIPICEVVKCLPVT |
| APENGKIVSSAMEPDREYHFGQAVRFVCNSGYKIEGDEEMHCSDDGFWSK |
| EKPKCVEISCKSPDVINGSPISQKIIYKENERFQYKCNMGYEYSERGDAV |
| CTESGWRPLPSCEEKSCDNPYIPNGDYSPLRIKHRIGDEITYQCRNGFYP |

TABLE 33B-continued

| CFH Protein [SEQ ID NO: 2] |
|---|
| ATRGNTAKCTSTGWIPAPRCTLKPCDYPDIKHGGLYHENMRRPYFPVAVG |
| KYYSYYCDEHFETPSGSYWDHIHCTQDGWSPAVPCLRKCYFPYLENGYNQ |
| NYGRKFVQGKSIDVACHPGYALPKAQTTVTCMENGWSPTPRCIRVKTCSK |
| SSIDIENGFISESQYTYALKEKAKYQCKLGYVTADGETSGSITCGKDGWS |
| AQPTCIKSCDIPVFMNARTKNDFTWFKLNDTLDYECHDGYESNTGSTTGS |
| IVCGYNGWSDLPICYERECELPKIDVHLVPDRKKDQYKVGEVLKFSCKPG |
| FTIVGPNSVQCYHFGLSPDLPICKEQVQSCGPPPELLNGNVKEKTKEEYG |
| HSEVVEYYCNPRFLMKGPNKIQCVDGEWTTLPVCIVEESTCGDIPELEHG |
| WAQLSSPPYYYGDSVEFNCSESFTMIGHRSITCIHGVWTQLPQCVAIDKL |
| KKCKSSNLIILEEHLKNKKEFDHNSNIRYRCRGKEGWIHTVCINGRWDPE |
| VNCSMAQIQLCPPPPQIPNSHNMTTTLNYRDGEKVSVLCQENYLIQEGEE |
| ITCKDGRWQSIPLCVEKIPCSQPPQIEHGTINSSRSSQESYAHGTKLSYT |
| CEGGFRISEENETTCYMGKWSSPPQCEGLPCKSPPEISHGVVAHMSDSYQ |
| YGEEVTYKCFEGFGIDGPAIAKCLGEKWSHPPSCIKTDCLSLPSFENAIP |
| MGEKKDVYKAGEQVTYTCATYYKMDGASNVTCINSRWTGRPTCRDTSCVN |
| PPTVQNAYIVSRQMSKYPSGERVRYQCRSPYEMFGDEEVMCLNGNWTEPP |
| QCKDSTGKCGPPPPIDNGDITSFPLSVYAPASSVEYQCQNLYQLEGNKRI |
| TCRNGQWSEPPKCLHPCVISREIMENYNIALRWTAKQKLYSRTGESVEFV |
| CKRGYRLSSRSHTLRTTCWDGKLEYPTCAKR |

TABLE 33C

| CFHT DNA [SEQ ID NO: 3] |
|---|
| ATGAGACTGCTGGCCAAGATCATCTGCCTGATGCTGTGGGCCATCTGCGT |
| GGCCGAGGACTGCAACGAGCTGCCCCCCAGAAGAAACACCGAGATCCTGA |
| CCGGCTCTTGGAGCGACCAGACCTACCCTGAGGGCACCCAGGCCATCTAC |
| AAGTGCAGACCCGGCTACCGGTCCCTGGGCAACATCATCATGGTGTGCAG |
| AAAGGGCGAGTGGGTGGCCCTGAACCCCCTGAGAAAGTGCCAGAAGAGGC |
| CCTGCGGACACCCCGGCGATACCCCTTTTGGCACCTTCACACTGACCGGC |
| GGCAACGTGTTCGAGTACGGCGTGAAGGCCGTGTACACCTGTAACGAGGG |
| CTACCAGCTGCTGGGCGAGATCAACTACAGAGAGTGCGACACCGACGGCT |
| GGACCAACGATATCCCCATCTGCGAGGTCGTGAAGTGCCTGCCTGTGACC |
| GCCCCAGAGAACGGCAAGATCGTGTCCAGCGCCATGGAACCCGACAGAGA |
| GTACCACTTCGGCCAGGCCGTCAGATTCGTGTGCAACAGCGGCTACAAGA |
| TCGAGGGCGACGAGGAAATGCACTGCAGCGACGACGGCTTCTGGTCCAAA |
| GAAAAGCCTAAGTGCGTGGAAATCAGCTGCAAGAGCCCCGACGTGATCAA |
| CGGCAGCCCCATCAGCCAGAAGATCATCTACAAAGAGAACGAGCGGTTCC |
| AGTACAAGTGTAACATGGGCTACGAGTACAGCGAGCGGGGCGACGCCGTG |
| TGTACAGAATCTGGATGGCGGCCTCTGCCCAGCTGCGAGGAAAAGAGCTG |
| CGACAACCCCTACATCCCCAACGGCGACTACAGCCCCCTGCGGATCAAGC |

TABLE 33C-continued

| CFHT DNA [SEQ ID NO: 3] |
|---|
| ACAGAACCGGCGACGAGATCACCTACCAGTGCCGGAACGGCTTCTACCCC |
| GCCACCAGAGGCAATACCGCCAAGTGTACCAGCACCGGCTGGATCCCTGC |
| CCCCAGATGTACCCTGAAGCCCTGCGACTACCCTGACATCAAGCACGGCG |
| GCCTGTACCACGAGAACATGCGGAGGCCCTACTTCCCTGTGGCCGTGGGC |
| AAGTACTACAGCTACTACTGCGACGAGCACTTCGAGACACCCAGCGGCAG |
| CTACTGGGACCACATCCACTGTACCCAGGACGGCTGGTCCCCTGCCGTGC |
| CCTGCCTGAGGAAGTGCTACTTCCCCTACCTGGAAAACGGCTACAACCAG |
| AACTACGGCCGGAAGTTCGTGCAGGGCAAGAGCATCGATGTGGCCTGCCA |
| CCCTGGATACGCCCTGCCTAAGGCCCAGACCACCGTGACCTGCATGGAAA |
| ATGGATGGTCCCCCACCCCCCGGTGCATCAGAGTGTCCTTCACCCTGTGA |

TABLE 33D

| CFHT Protein [SEQ ID NO: 4] |
|---|
| MRLLAKIICLMLWAICVAEDCNELPPRRNTEILTGSWSDQTYPEGTQAIY |
| KCRPGYRSLGNIIMVCRKGEWVALNPLRKCQKRPCGHPGDTPFGTFTLTG |
| GNVFEYGVKAVYTCNEGYQLLGEINYRECDTDGWTNDIPICEVVKCLPVT |
| APENGKIVSSAMEPDREYHFGQAVRFVCNSGYKIEGDEEMHCSDDGFWSK |
| EKPKCVEISCKSPDVINGSPISQKIIYKENERFQYKCNMGYEYSERGDAV |
| CTESGWRPLPSCEEKSCDNPYIPNGDYSPLRIKHRTGDEITYQCRNGFYP |
| ATRGNTAKCTSTGWIPAPRCTLKPCDYPDIKHGGLYHENMRRPYFPVAVG |
| KYYSYYCDEHFETPSGSYWDHIHCTQDGWSPAVPCLRKCYFPYLENGYNQ |
| NYGRKFVQGKSIDVACHPGYALPKAQTTVTCMENGWSPTPRCIRVSFTL |

TABLE 33E

| eCFHT Protein [SEQ ID NO: 6] |
|---|
| MRLLAKIICLMLWAICVAEDCNELPPRRNTEILTGSWSDQTYPEGTQATY |
| KCRPGYRSLGNIIMVCRKGEWVALNPLRKCQKRPCGHPGDTPFGTFTLTG |
| GNVFEYGVKAVYTCNEGYQLLGEINYRECDTDGWTNDIPICEVVKCLPVT |
| APENGKIVSSAMEPDREYHFGQAVRFVCNSGYKIEGDEEMHCSDDGFWSK |
| EKPKCVEISCKSPDVINGSPISQKIIYKENERFQYKCNMGYEYSERGDAV |
| CTESGWRPLPSCEEKSCDNPYIPNGDYSPLRIKHRTGDEITYQCRNGFYP |
| ATRGNTAKCTSTGWIPAPRCTLKPCDYPDIKHGGLYHENMRRPYFPVAVG |
| KYYSYYCDEHFETPSGSYWDHIHCTQDGWSPAVPCLRKCYFPYLENGYNQ |
| NYGRKFVQGKSIDVACHPGYALPKAQTTVTCMENGWSPTPRCIRVSKSFT |
| L |

TABLE 33F

| eCFH/T DNA [SEQ ID NO: 5] |
|---|
| ATGAGACTGCTGGCCAAGATCATCTGCCTGATGCTGTGGGCCATCTGCGT |
| GGCCGAGGACTGCAACGAGCTGCCCCCCAGAAGAAACACCGAGATCCTGA |
| CCGGCTCTTGGAGCGACCAGACCTACCCTGAGGGCACCCAGGCCATCTAC |
| AAGTGCAGACCCGGCTACCGGTCCCTGGGCAACATCATCATGGTGTGCAG |
| AAAGGGCGAGTGGGTGGCCCTGAACCCCCTGAGAAAGTGCCAGAAGAGGC |
| CCTGCGGACACCCCGGCGATACCCCTTTTGGCACCTTCACACTGACCGGC |
| GGCAACGTGTTCGAGTACGGCGTGAAGGCCGTGTACACCTGTAACGAGGG |
| CTACCAGCTGCTGGGCGAGATCAACTACAGAGAGTGCGACACCGACGGCT |
| GGACCAACGATATCCCCATCTGCGAGGTCGTGAAGTGCCTGCCTGTGACC |
| GCCCCAGAGAACGGCAAGATCGTGTCCAGCGCCATGGAACCCGACAGAGA |
| GTACCACTTCGGCCAGGCCGTCAGATTCGTGTGCAACAGCGGCTACAAGA |
| TCGAGGGCGACGAGGAAATGCACTGCAGCGACGACGGCTTCTGGTCCAAA |
| GAAAAGCCTAAGTGCGTGGAAATCAGCTGCAAGAGCCCCGACGTGATCAA |
| CGGCAGCCCCATCAGCCAGAAGATCATCTACAAAGAGAACGAGCGGTTCC |
| AGTACAAGTGTAACATGGGCTACGAGTACAGCGAGCGGGGCGACGCCGTG |
| TGTACAGAATCTGGATGGCGGCCTCTGCCCAGCTGCGAGGAAAAGAGCTG |
| CGACAACCCCTACATCCCCAACGGCGACTACAGCCCCCTGCGGATCAAGC |
| ACAGAACCGGCGACGAGATCACCTACCAGTGCCGGAACGGCTTCTACCCC |
| GCCACCAGAGGCAATACCGCCAAGTGTACCAGCACCGGCTGGATCCCTGC |
| CCCCAGATGTACCCTGAAGCCCTGCGACTACCCTGACATCAAGCACGGCG |
| GCCTGTACCACGAGAACATGCGGAGGCCCTACTTCCCTGTGGCCGTGGGC |
| AAGTACTACAGCTACTACTGCGACGAGCACTTCGAGACACCCAGCGGCAG |
| CTACTGGGACCACATCCACTGTACCCAGGACGGCTGGTCCCCTGCCGTGC |
| CCTGCCTGAGGAAGTGCTACTTCCCCTACCTGGAAAACGGCTACAACCAG |
| AACTACGGCCGGAAGTTCGTGCAGGGCAAGAGCATCGATGTGGCCTGCCA |
| CCCTGGATACGCCCTGCCTAAGGCCCAGACCACCGTGACCTGCATGGAAA |
| ATGGATGGTCCCCCACCCCCCGGTGCATCAGAGTCAGTAAGTCCTTCACT |
| CTGTGAAACTTGTTTATTGCAGCTTATAATGGTTACAAATAAAGCAATAG |
| CATCACAAATTTCACAAATAAAGCATTTTTTTCACTGCATTCTAGTTGTG |
| GTTTGTCCAAACTCATCAATGTATCTTATTCTAATTCTCTTCCCTTTTAG |
| AAACCTGCAGCAAGAGCAGCATCGACATCGAGAATGGCTTCATCAGCGAG |
| AGCCAGTACACCTACGCCCTGAAAGAGAAGGCCAAGTACCAGTGCAAGCT |
| GGGCTACGTGACCGCCGACGGCGAGACAAGCGGCAGCATCACCTGTGGCA |
| AGGATGGGTGGAGCGCCCAGCCCACCTGTATCAAGTCCTGCGACATCCCT |
| GTGTTCATGAATGCCCGGACCAAGAACGACTTCACCTGGTTCAAGCTGAA |
| CGACACACTGGACTACGAGTGCCACGACGGCTACGAGAGCAACACCGGCA |
| GCACCACAGGCAGCATCGTGTGTGGCTACAACGGGTGGAGTGACCTGCCC |
| ATCTGTTACGAGCGCGAGTGCGAGCTGCCTAAGATCGACGTGCACCTGGT |
| GCCCGACCGGAAGAAAGACCAGTACAAAGTGGGCGAGGTGCTGAAGTTCT |

TABLE 33F-continued

| eCFH/T DNA [SEQ ID NO: 5] |
| --- |
| CCTGCAAGCCCGGCTTCACCATCGTGGGCCCCAATAGCGTGCAGTGCTAC |
| CACTTTGGCCTGTCCCCCGATCTGCCTATCTGCAAAGAACAGGTGCAGAG |
| CTGCGGCCCTCCACCCGAGCTGCTGAACGGCAATGTGAAAGAAAAGACCA |
| AAGAGGAATACGGCCACTCCGAGGTGGTGGAATATTACTGCAACCCCCGG |
| TTCCTGATGAAGGGCCCCAACAAGATTCAGTGTGTGGACGGCGAGTGGAC |
| CACCCTGCCCGTGTGTATCGTGGAAGAGTCTACCTGCGGAGACATCCCCG |
| AGCTGGAACACGGATGGGCCCAGCTGAGCAGCCCCCCTTACTACTACGGC |
| GACAGCGTGGAATTCAACTGCTCCGAGAGCTTTACCATGATCGGCCACCG |
| GTCCATCACATGCATCCACGGCGTGTGGACACAGCTGCCACAGTGCGTGG |
| CCATCGACAAGCTGAAGAAGTGCAAGTCCAGCAACCTGATCATCCTGGAA |
| GAACACCTGAAGAACAAGAAAGAGTTCGACCACAACAGCAACATCCGGTA |
| CAGATGCCGGGGCAAAGAGGGATGGATCCACACCGTGTGCATCAATGGCA |
| GATGGGACCCCGAAGTGAACTGCAGCATGGCCCAGATCCAGCTGTGCCCC |
| CCACCTCCCCAGATCCCCAACAGCCACAACATGACCACCACCCTGAACTA |
| CCGGGATGGCGAGAAGGTGTCCGTGCTGTGCCAGGAAAACTACCTGATCC |
| AGGAAGGCGAAGAGATTACCTGCAAGGACGGCCGGTGGCAGAGCATCCCC |
| CTGTGTGTGGAAAAGATCCCCTGCAGCCAGCCCCCCCAGATCGAGCACGG |
| CACCATCAACAGCAGCAGAAGCAGCCAGGAATCCTACGCCCACGGCACAA |
| AGCTGAGCTACACATGCGAGGGCGGCTTCCGGATCTCCGAGGAAAACGAG |
| ACAACCTGCTACATGGGCAAGTGGTCCTCCCCACCTCAGTGCGAGGGACT |
| GCCTTGCAAGTCCCCACCCGAGATCTCTCATGGCGTGGTGGCCCACATGA |
| GCGACAGCTACCAGTACGGCGAGGAAGTGACCTACAAGTGTTTCGAGGGC |
| TTCGGCATCGACGGCCCTGCCATTGCCAAGTGCCTGGGAGAGAAGTGGTC |
| CCACCCTCCCAGCTGCATCAAGACCGACTGCCTGAGCCTGCCTAGCTTCG |
| AGAACGCCATCCCCATGGGCGAGAAAAAGGACGTGTACAAGGCCGGCGAA |
| CAAGTGACATACACCTGTGCCACCTACTACAAGATGGACGGCGCCAGCAA |
| CGTGACCTGTATTAACAGCCGGTGGACCGGCAGGCCTACCTGCAGAGATA |
| CCTCCTGCGTGAACCCCCCCACCGTGCAGAACGCCTACATCGTGTCTCGG |
| CAGATGAGCAAGTACCCCAGCGGCGAACGCGTGCGCTACCAGTGTAGAAG |
| CCCCTACGAGATGTTCGGCGACGAAGAAGTGATGTGCCTGAATGGCAACT |
| GGACCGAGCCCCCTCAGTGCAAGGATAGCACCGGCAAGTGTGGCCCCCCT |
| CCCCCCATCGATAACGGCGACATCACCAGCTTCCCCCTGTCCGTGTATGC |
| CCCTGCCAGCTCCGTGGAATATCAGTGCCAGAACCTGTACCAGCTGGAAG |
| GCAACAAGCGGATCACCTGTCGGAACGGCCAGTGGAGCGAGCCTCCCAAG |
| TGTCTGCACCCCTGCGTGATCTCCAGAGAAATCATGGAAAACTATAATAT |
| CGCCCTGCGCTGGACCGCCAAGCAGAAGCTGTACTCTAGGACCGGCGAGT |
| CTGTGGAATTTGTGTGCAAGCGGGGATACAGACTGAGCAGCAGATCCCAC |
| ACCCTGAGAACCACCTGTTGGGACGGCAAGCTGGAATACCCTACCTGCGC |
| CAAGAGATGA |

TABLE 34: SELECTED SEQUENCES

TABLE 34A

| BEST1-EP-454 Enhancer Promoter [SEQ ID NO: 8] |
| --- |
| CGTTACATAACTTACGGTAAATGGCCCGCCTGGCTGACCGCCCAACGACC |
| CCCGCCCATTGACGTCAATAATGACGTATGTTCCCATAGTAACGCCAATA |
| GGGACTTTCCATTGACGTCAATGGGTGGAGTATTTACGGTAAACTGCCCA |
| CTTGGCAGTACATCAAGTGTATCATATGCCAAGTACGCCCCCTATTGACG |
| TCAATGACGGTAAATGGCCCGCCTGGCATTATGCCCAGTACATGACCTTA |
| TGGGACTTTCCTACTTGGCAGTACATCTACGTATTAGTCATCGCTATTAC |
| CATGCTCGAGCTAGGGTGATGAAATTCCCAAGCAACACCATCCTTTTCAA |
| GTGACGGCGGCTCAGCACTCACGTGGGCAGTGCCAGCCTCTAAGAGTGGG |
| CAGGGGCACTGGCCACAGAGTCCCAGGGAGTCCCACCAGCCTAGTCGCCA |
| GACC |

TABLE 34B

| RPE65-EP-415 Enhancer Promoter [SEQ ID NO: 9] |
| --- |
| CGTTACATAACTTACGGTAAATGGCCCGCCTGGCTGACCGCCCAACGACC |
| CCCGCCCATTGACGTCAATAATGACGTATGTTCCCATAGTAACGCCAATA |
| GGGACTTTCCATTGACGTCAATGGGTGGAGTATTTACGGTAAACTGCCCA |
| CTTGGCAGTACATCAAGTGTATCATATGCCAAGTACGCCCCCTATTGACG |
| TCAATGACGGTAAATGGCCCGCCTGGCATTATGCCCAGTACATGACCTTA |
| TGGGACTTTCCTACTTGGCAGTACATCTACGTATTAGTCATCGCTATTAC |
| CATGCTCGAGCAAATAAAGCCAAGCATCAGGGGGATCTGAGAGCTGAAAG |
| CAACTTCTGTTCCCCCTCCCTCAGCTGAAGGGGTGGGGAAGGGCTCCCAA |
| AGCCATAACTCCTTT |

TABLE 34C

| RPE65-EP-419 Enhancer Promoter [SEQ ID NO: 10] |
| --- |
| CGTTACATAACTTACGGTAAATGGCCCGCCTGGCTGACCGCCCAACGACC |
| CCCGCCCATTGACGTCAATAATGACGTATGTTCCCATAGTAACGCCAATA |
| GGGACTTTCCATTGACGTCAATGGGTGGACTATTTACGGTAAACTGCCCA |
| CTTGGCAGTACATCAAGTGTATCATATGCCAAGTACGCCCCCTATTGACG |
| TCAATGACGGTAAATGGCCCGCCTGGCATTATGCCCAGTACATGACCTTA |
| TGGGACTTTCCTACTTGGCAGTACATCTACGTATTAGTCATCGCTATTAC |
| CATGCTCGAGGAAGGATTGAGGTCTCTGGAAAACAGCCAAACAACTGTTA |
| TGGGAACAGCAAGCCCAAATAAAGCCAAGCATCAGGGGGATCTGAGAGCT |
| GAAAGCAACTTCTGTTCCC |

TABLE 34D

| BEST1-723 Promoter/ [SEQ ID NO: 11] |
|---|
| CTCTGAAGCAACTTACTGATGGGCCCTGCCAGCCAATCACAGCCAGAATA |
| ACGTATGATGTCACCAGCAGCCAATCAGAGCTCCTCGTCAGCATATGCAG |
| AATTCTGTCATTTTACTAGGGTGATGAAATTCCCAAGCAACACCATCCTT |
| TTCAGATAAGGGCACTGAGGCTGAGAGAGGAGCTGAAACCTACCCGGGGT |
| CACCACACACAGGTGGCAAGGCTGGGACCAGAAACCAGGACTGTTGACTG |
| CAGCCCGGTATTCATTCTTTCCATAGCCCACAGGGCTGTCAAAGACCCCA |
| GGGCCTAGTCAGAGGCTCCTCCTTCCTGGAGAGTTCCTGGCACAGAAGTT |
| GAAGCTCAGCACAGCCCCCTAACCCCCAACTCTCTCTGCAAGGCCTCAGG |
| GGTCAGAACACTGGTGGAGCAGATCCTTTAGCCTCTGGATTTTAGGGCCA |
| TGGTAGAGGGGGTGTTGCCCTAAATTCCAGCCCTGGTCTCAGCCCAACAC |
| CCTCCAAGAAGAAATTAGAGGGGCCATGGCCAGGCTGTGCTAGCCGTTGC |
| TTCTGAGCAGATTACAAGAAGGGACTAAGACAAGGACTCCTTTGTGGAGG |
| TCCTGGCTTAGGGAGTCAAGTGACGGCGGCTCAGCACTCACGTGGGCAGT |
| GCCAGCCTCTAAGAGTGGGCAGGGGCACTGGCCACAGAGTCCCAGGGAGT |
| CCCACCAGCCTAGTCGCCAGACC |

TABLE 34E

| smCBA Enhancer Promoter [SEQ ID NO: 12] |
|---|
| CTAGTTATTAATAGTAATCAATTACGGGGTCATTAGTTCATAGCCCATAT |
| ATGGAGTTCCGCGTTACATAACTTACGGTAAATGGCCCGCCTGGCTGACC |
| GCCCAACGACCCCCGCCCATTGACGTCAATAATGACGTATGTTCCCATAG |
| TAACGCCAATAGGGACTTTCCATTGACGTCAATGGGTGGACTATTTACGG |
| TAAACTGCCCACTTGGCAGTACATCAAGTGTATCATATGCCAAGTACGCC |
| CCCTATTGACGTCAATGACGGTAAATGGCCCGCCTGGCATTATGCCCAGT |
| ACATGACCTTATGGGACTTTCCTACTTGGCAGTACATCTACGTATTAGTC |
| ATCGCTATTACCATGGTCGAGGTGAGCCCCACGTTCTGCTTCACTCTCCC |
| CATCTCCCCCCCCTCCCCACCCCCAATTTTGTATTTATTTATTTTTTAAT |
| TATTTTGTGCAGCGATGGGGGCGGGGGGGGGGGGGGGGCGCGCGCCAGGC |
| GGGGCGGGGCGGGGCGAGGGGCGGGGCGGGGCGAGGCGGAGAGGTGCGGC |
| GGCAGCCAATCAGAGCGGCGCGCTCCGAAAGTTTCCTTTTATGGCGAGGC |
| GGCGGCGGCGGCGGCCCTATAAAAAGCGAAGCGCGCGGCGGGCGGGAGTC |
| GCTGCGACGCTGCCTTCGCCCCGTGCCCCGCTCCGCCGCCGCCTCGCGCC |
| GCCCGCCCCGGCTCTGACTGACCGCGTTACTCCCACAGGTGAGCGGGCGG |
| GACGGCCCTTCTCCTCCGGGCTGTAATTAGCGCTTGGTTTAATGACGGCT |
| TGTTTCTTTTCTGTGGCTGCGTGAAAGCCTTGAGGGGCTCCGGGAGCTAG |
| AGCCTCTGCTAACCATGTTCATGCCTTCTTCTTTTTCCTACAGCTCCTGG |
| GCAACGTGCTGGTTATTGTGCTGTCTCATCATTTTGGCA |

TABLE 34F

| CBA Enhancer Promoter [SEQ ID NO: 13] |
|---|
| CCGCGTTACATAACTTACGGTAAATGGCCCGCCTGGCTGACCGCCCAACG |
| ACCCCCGCCCATTGACGTCAATAATGACGTATGTTCCCATAGTAACGCCA |
| ATAGGGACTTTCCATTGACGTCAATGGGTGGAGTATTTACGGTAAACTGC |
| CCACTTGGCAGTACATCAAGTGTATCATATGCCAAGTACGCCCCCTATTG |
| ACGTCAATGACGGTAAATGGCCCGCCTGGCATTATGCCCAGTACATGACC |
| TTATGGGACTTTCCTACTTGGCAGTACATCTACGTATTAGTCATCGCTAT |
| TACCATGGTCGAGGTGAGCCCCACGTTCTGCTTCACTCTCCCCATCTCCC |
| CCCCCTCCCCACCCCCAATTTTGTATTTATTTATTTTTTAATTATTTTGT |
| GCAGCGATGGGGGCGGGGGGGGGGGGGGGGCGCGCGCCAGGCGGGGCGGG |
| GCGGGGCGAGGGGCGGGGCGGGGCGAGGCGGAGAGGTGCGGCGGCAGCCA |
| ATCAGAGCGGCGCGCTCCGAAAGTTTCCTTTTATGGCGAGGCGGCGGCGG |
| CGGCGGCCCTATAAAAAGCGAAGCGCGCGGCGGGCGGGAGTCGCTGCGCG |
| CTGCCTTCGCCCCGTGCCCCGCTCCGCCGCCGCCTCGCGCCGCCCGCCCC |
| GGCTCTGACTGACCGCGTTACTCCCACAGGTGAGCGGGCGGGACGGCCCT |
| TCTCCTCCGGGCTGTAATTAGCGCTTGGTTTAATGACGGCTTGTTTCTTT |
| TCTGTGGCTGCGTGAAAGCCTTGAGGGGCTCCGGGAGGGCCCTTTGTGCG |
| GGGGGAGCGGCTCGGGGGGTGCGTGCGTGTGTGTGTGCGTGGGGAGCGCC |
| GCGTGCGGCTCCGCGCTGCCCGGCGGCTGTGAGCGCTGCGGGCGCGGCGC |
| GGGGCTTTGTGCGCTCCGCAGTGTGCGCGAGGGGAGCGCGGCCGGGGGCG |
| GTGCCCCGCGGTGCGGGGGGGGCTGCGAGGGGAACAAAGGCTGCGTGCGG |
| GGTGTGTGCGTGGGGGGGTGAGCAGGGGGTGTGGGCGCGTCGGTCGGGCT |
| GCAACCCCCCCTGCACCCCCCTCCCCGAGTTGCTGAGCACGGCCCGGCTT |
| CGGGTGCGGGGCTCCGTACGGGGCGTGGCGCGGGGCTCGCCGTGCCGGGC |
| GGGGGGTGGCGGCAGGTGGGGGTGCCGGGCGGGGCGGGGCCGCCTCGGGC |
| CGGGGAGGGCTCGGGGGAGGGGCGCGGCGGCCCCCGGAGCGCCGGCGGCT |
| GTCGAGGCGCGGCGAGCCGCAGCCATTGCCTTTTATGGTAATCGTGCGAG |
| AGGGCGCAGGGACTTCCTTTGTCCCAAATCTGTGCGGAGCCGAAATCTGG |
| GAGGCGCCGCCGCACCCCCTCTAGCGGGCGCGGGGCGAAGCGGTGCGGCG |
| CCGGCAGGAAGGAAATGGGCGGGGAGGGCCTTCGTGCGTCGCCGCGCCGC |
| CGTCCCCTTCTCCCTCTCCAGCCTCGGGGCTGTCCGCGGGGGGACGGCTG |
| CCTTCGGGGGGGACGGGGCAGGGCGGGGTTCGGCTTCTGGCGTGTGACCG |
| GCGGCTCTAGAGCCTCTGCTAACCATGTTCATGCCTTCTTCTTTTTCCTA |
| CAGCTCCTGGGCAACGTGCTGGTTATTGTGCTGTCTCATCATTTTGGCAA |
| AGAATTC |

TABLE 34G-i

| sctmCBA Enhancer Promoter [SEQ ID NO: 14] |
|---|
| 5'CGTTACATAACTTACGGTAAATGGCCCGCCTGGCTGACCGCCCAACGA |
| CCCCCGCCCATTGACGTCAATAATGACGTATGTTCCCATAGTAACGCCAA |

TABLE 34G-i-continued

| sctmCBA Enhancer Promoter [SEQ ID NO: 14] |
|---|
| TAGGGACTTTCCATTGACGTCAATGGGTGGAGTATTTACGGTAAACTGCC |
| CACTTGGCAGTACATCAAGTGTATCATATGCCAAGTACGCCCCCTATTGA |
| CGTCAATGACGGTAAATGGCCCGCCTGGCATTATGCCCAGTACATGACCT |
| TATGGGACTTTCCTACTTGGCAGTACATCTACGTATTAGTCATCGCTATT |
| ACCATGGTCGAGGTGAGCCCCACGTTCTGCTTCACTCTCCCCATCTCCCC |
| CCCCTCCCCACCCCCAATTTTGTATTTATTTATTTTTTAATTATTTTGTG |
| CAGCGATGGGGGCGGGGGGGGGGGGGGGGCGCGCGCCAGGCGGGGCGGGG |
| CGGGGCGAGGGGCGGGGCGGGGCGAGGCGGAGAGGTGCGGCGGCAGCCAA |
| TCAGAGCGGCGCGCTCCGAAAGTTTCCTTTTATGGCGAGGCGGCGGCGGC |
| GGCGGCCCTATAAAAAGCGAAGCGCGCGGCGGGCGGGAGTCGCTGCGCGC |
| TGCCTTCGCCCCGTGCCCCGCTCCGCCGCCGCCTCGCGCCGCCCGCCCCG |
| GCTCTGACTGACCGCGTTACTCCCACAGGTGAGCGGGCGGGACGGCCCTT |
| CTCCTCCGGGCTGTAATTAGC |

TABLE 34G-ii

| CMV-Immediate/Early (I/E) Enhancer Sequence [SEQ ID NO: 7] |
|---|
| CGTTACATAACTTACGGTAAATGGCCCGCCTGGCTGACCGCCCAACGACC |
| CCCGCCCATTGACGTCAATAATGACGTATGTTCCCATAGTAACGCCAATA |
| GGGACTTTCCATTGACGTCAATGGGTGGAGTATTTACGGTAAACTGCCCA |
| CTTGGCAGTACATCAAGTGTATCATATGCCAAGTACGCCCCCTATTGACG |
| TCAATGACGGTAAATGGCCCGCCTGGCATTATGCCCAGTACATGACCTTA |
| TGGGACTTTCCTACTTGGCAGTACATCTACGTATTAGTCATCGCTATTAC |
| CATG |

TABLE 34H

| CFH Promoter [SEQ ID NO: 15] |
|---|
| CATTTCTGGGCTTGTGGCTTGTGGTTGATTTTTTATTTACTTTGCAAAAG |
| TTTCTGATAGGCGGAGCATCTAGTTTCAACTTCCTTTTGCAGCAAGTTCT |
| TTCCTGCACTAATCACAATTCTTGGAAGAGGAGAACTGGACGTTGTGAAC |
| AGAGTTAGCTGGTAATTGTCCTCTTAAAAGATCCAAAAA |

TABLE 34I

| BEST1-V3 Promoter [SEQ ID NO: 16] |
|---|
| CTAGGGTGATGAAATTCCCAAGCAACACCATCCTTTTCAAGTGACGGCGG |
| CTCAGCACTCACGTGGGCAGTGCCAGCCTCTAAGAGTGGGCAGGGGCACT |
| GGCCACAGAGTCCCAGGGAGTCCCACCAGCCTAGTCGCCAGACC |

TABLE 34J

| RPE65-750 Promoter [SEQ ID NO: 17] |
|---|
| ATACTCTCAGAGTGCCAAACATATACCAATGGACAAGAAGGTGAGGCAG |
| AGAGCAGACAGGCATTAGTGACAAGCAAAGATATGCAGAATTTCATTCT |
| CAGCAAATCAAAAGTCCTCAACCTGGTTGGAAGAATATTGGCACTGAAT |
| GGTATCAATAAGGTTGCTAGAGAGGGTTAGAGGTGCACAATGTGCTTCC |
| ATAACATTTTATACTTCTCCAATCTTAGCACTAATCAAACATGGTTGAA |
| TACTTTGTTTACTATAACTCTTACAGAGTTATAAGATCTGTGAAGACAG |
| GGACAGGGACAATACCCATCTCTGTCTGGTTCATAGGTGGTATGTAATA |
| GATATTTTTAAAAATAAGTGAGTTAATGAATGAGGGTGAGAATGAAGGC |
| ACAGAGGTATTAGGGGGAGGTGGGCCCCAGAGAATGGTGCCAAGGTCCA |
| GTGGGGTGACTGGGATCAGCTCAGGCCTGACGCTGGCCACTCCCACCTA |
| GCTCCTTTCTTTCTAATCTGTTCTCATTCTCCTTGGGAAGGATTGAGGT |
| CTCTGGAAAACAGCCAAACAACTGTTATGGGAACAGCAAGCCCAAATAA |
| AGCCAAGCATCAGGGGGATCTGAGAGCTGAAAGCAACTTCTGTTCCCCC |
| TCCCTCAGCTGAAGGGGTGGGGAAGGGCTCCCAAAGCCATAACTCCTTT |
| TAAGGGATTTAGAAGGCATAAAAAGGCCCCTGGCTGAGAACTTCCTTCT |
| TCATTCTGCAGTTGG |

TABLE 34K

| bGH Poly A sequence [SEG ID NO: 29] |
|---|
| CTGTGCCTTCTAGTTGCCAGCCATCTGTTGTTTGCCCCTCCCCCGTGCC<br>TTCCTTGACCCTGGAAGGTGCCACTCCCACTGTCCTTTCCTAATAAAAT<br>GAGGAAATTGCATCGCATTGTCTGAGTAGGTGTCATTCTATTCTGGGGG<br>GTGGGGTGGGGCAGGACAGCAAGGGGGAGGATTGGGAAGACAATAGCAG<br>GCATGCTGGGGA |

TABLE 34L

| HSV TK Poly A Sequence [SEQ ID NO: 28] |
|---|
| CGGCAATAAAAAGACAGAATAAAACGCACGGGTGTTGGGTCGTTTGTTC |

TABLE 34M

| SV40 Poly A Sequence [SEQ ID NO: 26] |
|---|
| AACTTGTTTATTGCAGCTTATAATGGTTACAAATAAAGCAATAGCATCA<br>CAAATTTCACAAATAAAGCATTTTTTTCACTGCATTCTAGTTGTGGTTT<br>GTCCAAACTCATCAATGTATCTTA |

TABLE 34N

| VMD2 Promoter |
|---|
| CAATTCTGTCATTTTACTAGGGTGATGAAATTCCCAAGCAACACCATCC<br>TTTTCAGATAAGGGCACTGAGGCTGAGAGAGGAGCTGAAACCTACCCGG<br>CGTCACCACACACAGGTGGCAAGGCTGGGACCAGAAACCAGGACTGTTG<br>ACTGCAGCCCGGTATTCATTCTTTCCATAGCCCACAGGGCTGTCAAAGA<br>CCCCAGGGCCTAGTCAGAGGCTCCTCCTTCCTGGAGAGTTCCTGGCACA<br>GAAGTTGAAGCTCAGCACAGCCCCCTAACCCCCAACTCTCTCTGCAAGG<br>CCTCAGGGGTCAGAACACTGGTGGAGCAGATCCTTTAGCCTCTGGATTT<br>TAGGGCCATGGTAGAGGGGGTGTTGCCCTAAATTCCAGCCCTGGTCTCA<br>GCCCAACACCCTCCAAGAAGAAATTAGAGGGGCCATGGCCAGGCTGTGC<br>TAGCCGTTGCTTCTGAGCAGATTACAAGAAGGGACCAAGACAAGGACTC<br>CTTTGTGGAGGTCCTGGCTTAGGGAGTCAAGTGACGGCGGCTCAGCACT<br>CACGTGGGCAGTGCCAGCCTCTAAGAGTGGGCAGGGGCACTGGCCACAG<br>AGTCCCAGGGAGTCCCACCAGCCTAGTCGCCAGACCGGGGATCCTCTAG<br>AGGATCCGGTACTCGAGGAACTGAAAAACCAGAAAGTTAACTGGTAAGT<br>TTAGTCTTTTTGTCTTTTATTTCAGGTCCCGGATCCGGTGGTGGTGCAA<br>ATCAAAGAACTGCTCCTCAGTGGATGTTGCCTTTACTTCTAG |

TABLE 35: SELECTED SEQUENCES

TABLE 35A

| AAV2 5' ITR DNA [SEQ ID NO: 18] |
|---|
| GGCCACTCCCTCTCTGCGCGCTCGCTCGCTCACTGAGGCCGGGCGACCAA |
| AGGTCGCCCGACGCCCGGGCTTTGCCCGGGCGGCCTCAGTGAGCGAGCGA |
| GCGCGCAGAGAGGGAGTGGCCAACTCCATCACTAGGGGTTCC |

TABLE 35B

| AAV2 3' ITR_R-short DNA [SEQ ID NO: 125] |
|---|
| GCGCGCTCGCTCGCTCACTGAGGCCGCCCGGGCAAAGCCCGGGCGTCGGG |
| CGACCTTTGGTCGCCCGGCCTCAGTGAGCGAGCGAGCGCGCAGAGAGGGA |
| GTGGCCAACTCCATCACTAGGGGTTCCT |

TABLE 35C

| eCFH/T V4.0 [SEQ ID NO: 30] |
|---|
| ATGGAAAATGGATGGTCCCCCACCCCCCGGTGCATCAGAGTCAGTAAGTA |
| CACTACTCTGAAATCCTAGGGCCGCAGCGGCCGTAATCATCTGCTCTTCA |
| ATCTTTCCCAGAAGCTTTACCCTCTGAAACTTGTTTATTGCAGCTTATAA |
| TGGTTACAAATAAAGCAATAGCATCACAAATTTCACAAATAAAGCATTTT |
| TTTCACTGCATTCTAGTTGTGGTTTGTCCAAACTCATCAATGTATCTTAG |
| GCCCGCATGGCCTCTTTTTCTTATTCTCTTCCCTTTTAGAAAAACCTGCA |
| GCAAGAGCAGCATCGACATCGAGAATGGCTTCATCAGCGAGAGCCAGTAC |
| ACCTACGCCCTGAAAGAGAAGGCC3 |

TABLE 35D

| eCFH/T V4.1 [SEQ ID NO: 31] |
|---|
| ATGGAAAATGGATGGTCCCCCACCCCCCGGTGCATCAGAGTCAGTTTTAC |
| CCTCTGAAACTTGTTTATTGCAGCTTATAATGGTTACAAATAAAGCAATA |
| GCATCACAAATTTCACAAATAAAGCATTTTTTTCACTGCATTCTAGTTGT |
| GGTTTGTCCAAACTCATCAATGTATCTTATTCTAATTCTCTTCCCTTTTA |
| GAAACCTGCAGCAAGAGCAGCATCGACATCGAGAATGGCTTCATCAGCGA |
| GAGCCAGTACACCTACGCCCTGAAAGAGAAGGCC3' |

TABLE 35E

| eCFH/T V4.2 [SEQ ID NO: 32] |
|---|
| ATGGAAAATGGATGGTCCCCCACCCCCCGGTGCATCAGAGTCAGTAAGTC |
| CTTCACTCTGTGAAACTTGTTTATTGCAGCTTATAATGGTTACAAATAAA |
| GCAATAGCATCACAAATTTCACAAATAAAGCATTTTTTTCACTGCATTCT |
| AGTTGTGGTTTGTCCAAACTCATCAATGTATCTTATTCTAATTCTCTTCC |
| CTTTTAGAAACCTGCAGCAAGAGCAGCATCGACATCGAGAATGGCTTCAT |
| CAGCGAGAGCCAGTACACCTACGCCCTGAAAGAGAAGGCC3' |

TABLE 35F

| eCFH/T v4.3 [SEQ ID NO: 3] |
|---|
| 5'ATGGAAAATGGATGGTCCCCCACCCCCCGGTGCATCAGAGTCAGTGAG |
| TCCTTCACTCTGTGAAACTTGTTTATTGCAGCTTATAATGGTTACAAATA |
| AAGCAATAGCATCACAAATTTCACAAATAAAGCATTTTTTTCACTGCATT |
| CTAGTTGTGGTTTGTCCAAACTCATCAATGTATCTTATTCTAATTCTCTT |
| CCCTTTTAGAAACCTGCAGCAAGAGCAGCATCGACATCGAGAATGGCTTC |
| ATCAGCGAGAGCCAGTACACCTACGCCCTGAAAGAGAAGGCC3' |

TABLE 35G

| eCFH/T DNA co-expressing construct V4.0 [SEQ ID NO: 34] |
|---|
| 5'ATGAGACTGCTGGCCAAGATCATCTGCCTGATGCTGTGGGCCATCTG |
| CGTGGCCGAGGACTGCAACGAGCTGCCCCCCAGAAGAAACACCGAGATC |
| CTGACCGGCTCTTGGAGCGACCAGACCTACCCTGAGGGCACCCAGGCCA |
| TCTACAAGTGCAGACCCGGCTACCGGTCCCTGGGCAACATCATCATGGT |
| GTGCAGAAAGGGCGAGTGGGTGGCCCTGAACCCCCTGAGAAAGTGCCAG |
| AAGAGGCCCTGCGGACACCCCGGCGATACCCCTTTTGGCACCTTCACAC |
| TGACCGGCGGCAACGTGTTCGAGTACGGCGTGAAGGCCGTGTACACCTG |
| TAACGAGGGCTACCAGCTGCTGGGCGAGATCAACTACAGAGAGTGCGAC |
| ACCGACGGCTGGACCAACGATATCCCCATCTGCGAGGTCGTGAAGTGCC |
| TGCCTGTGACCGCCCCAGAGAACGGCAAGATCGTGTCCAGCGCCATGGA |
| ACCCGACAGAGAGTACCACTTCGGCCAGGCCGTCAGATTCGTGTGCAAC |
| AGCGGCTACAAGATCGAGGGCGACGAGGAAATGCACTGCAGCGACGACG |
| GCTTCTGGTCCAAAGAAAAGCCTAAGTGCGTGGAAATCAGCTGCAAGAG |
| CCCCGACGTGATCAACGGCAGCCCCATCAGCCAGAAGATCATCTACAAA |
| GAGAACGAGCGGTTCCAGTACAAGTGTAACATGGGCTACGAGTACAGCG |
| AGCGGGGCGACGCCGTGTGTACAGAATCTGGATGGCGGCCTCTGCCCAG |
| CTGCGAGGAAAAGAGCTGCGACAACCCCTACATCCCCAACGGCGACTAC |
| AGCCCCCTGCGGATCAAGCACAGAACCGGCGACGAGATCACCTACCAGT |
| GCCGGAACGGCTTCTACCCCGCCACCAGAGGCAATACCGCCAAGTGTAC |
| CAGCACCGGCTGGATCCCTGCCCCCAGATGTACCCTGAAGCCCTGCGAC |
| TACCCTGACATCAAGCACGGCGGCCTGTACCACGAGAACATGCGGAGGC |
| CCTACTTCCCTGTGGCCGTGGGCAAGTACTACAGCTACTACTGCGACGA |
| GCACTTCGAGACACCCAGCGGCAGCTACTGGGACCACATCCACTGTACC |
| CAGGACGGCTGGTCCCCTGCCGTGCCCTGCCTGAGGAAGTGCTACTTCC |
| CCTACCTGGAAAACGGCTACAACCAGAACTACGGCCGGAAGTTCGTGCA |
| GGGCAAGAGCATCGATGTGGCCTGCCACCCTGGATACGCCCTGCCTAAG |
| GCCCAGACCACCGTGACCTGCATGGAAAATGGATGGTCCCCCACCCCCC |
| GGTGCATCAGAGTCAGTAAGTACACTACTCTGAAATCCTAGGGCCGCAG |
| CGGCCGTAATCATCTGCTCTTCAATCTTTCCCAGAAGCTTTACCCTCTG |
| AAACTTGTTTATTGCAGCTTATAATGGTTACAAATAAAGCAATAGCATC |
| ACAAATTTCACAAATAAAGCATTTTTTTCACTGCATTCTAGTTGTGGTT |
| TGTCCAAACTCATCAATGTATCTTAGGCCCGCATGGCCTCTTTTTCGAG |
| AGCCAGTACACCTACGCCCTGAAAGAGAAGGCCAAGTACCAGTGCAAGC |
| TGGGCTACGTGACCGCCGACGGCGAGACAAGCGGCAGCATCACCTGTGG |
| CAAGGATGGGTGGAGCGCCGAGCCCACCTGTATCAAGTCCTGCGACATC |
| CCTGTGTTCATGAATGCCCGGACCAAGAACGACTTCACCTGGTTCAAGC |
| TGAACGACACACTGGACTACGAGTGCCACGACGGCTACGAGAGCAACAC |
| CGGCAGCACCACAGGCAGCATCGTGTGTGGCTACAACGGGTGGAGTGAC |
| CTGCCCATCTGTTACGAGCGCGAGTGCGAGCTGCCTAAGATCGACGTGC |
| ACCTGGTGCCCGACCGGAAGAAAGACCAGTACAAAGTGGGCGAGGTGCT |
| GAAGTTCTCCTGCAAGCCCGGCTTCACCATCGTGGGCCCCAATAGCGTG |
| CAGTGCTACCACTTTGGCCTGTCCCCCGATCTGCCTATCTGCAAAGAAC |
| AGGTGCAGAGCTGCGGCCCTCCACCCGAGCTGCTGAACGGCAATGTGAA |
| AGAAAAGACCAAAGAGGAATACGGCCACTCCGAGGTGGTGGAATATTAC |
| TGCAACCCCCGGTTCCTGATGAAGGGCCCCAACAAGATTCAGTGTGTGG |
| ACGGCGAGTGGACCACCCTGCCCGTGTGTATCGTGGAAGAGTCTACCTG |
| CGGAGACATCCCCGAGCTGGAACACGGATGGGCCCAGCTGAGCAGCCCC |
| CCTTACTACTACGGCGACAGCGTGGAATTCAACTGCTCCGAGAGCTTTA |
| CCATGATCGGCCACCGGTCCATCACATGCATCCACGGCGTGTGGACACA |
| GCTGCCACAGTGCGTGGCCATCGACAAGCTGAAGAAGTGCAAGTCCAGC |
| AACCTGATCATCCTGGAAGAACACCTGAAGAACAAGAAAGAGTTCGACC |
| ACAACAGCAACATCCGGTACAGATGCCGGGGCAAAGAGGGATGGATCCA |
| CACCGTGTGCATCAATGGCAGATGGGACCCCGAAGTGAACTGCAGCATG |
| GCCCAGATCCAGCTGTGCCCCCCACCTCCCCAGATCCCCAACAGCCACA |
| ACATGACCACCACCCTGAACTACCGGGATGGCGAGAAGGTGTCCGTGCT |
| GTGCCAGGAAAACTACCTGATCCAGGAAGGCGAAGAGATTACCTGCAAG |
| GACGGCCGGTGGCAGAGCATCCCCCTGTGTGTGGAAAAGATCCCCTGCA |
| GCCAGCCCCCCCAGATCGAGCACGGCACCATCAACAGCAGCAGAAGCAG |
| CCAGGAATCCTACGCCCACGGCACAAAGCTGAGCTACACATGCGAGGGC |
| GGCTTCCGGATCTCCGAGGAAAACGAGACAACCTGCTACATGGGCAAGT |
| GGTCCTCCCCACCTCAGTGCGAGGGACTGCCTTGCAAGTCCCCACCCGA |
| GATCTCTCATGGCGTGGTGGCCCACATGAGCGACAGCTACCAGTACGGC |
| GAGGAAGTGACCTACAAGTGTTTCGAGGGCTTCGGCATCGACGGCCCTG |
| CCATTGCCAAGTGCCTGGGAGAGAAGTGGTCCCACCCTCCCAGCTGCAT |
| CAAGACCGACTGCCTGAGCCTGCCTAGCTTCGAGAACGCCATCCCCATG |
| GGCGAGAAAAAGGACGTGTACAAGGCCGGCGAACAAGTGACATACACCT |
| GTGCCACCTACTACAAGATGGACGGCGCCAGCAACGTGACCTGTATTAA |
| CAGCCGGTGGACCGGCAGGCCTACCTGCAGAGATACCTCCTGCGTGAAC |
| CCCCCCACCGTGCAGAACGCCTACATCGTGTCTCGGCAGATGAGCAAGT |
| ACCCCAGCGGCGAACGCGTGCGCTACCAGTGTAGAAGCCCCTACGAGAT |
| GTTCGGCGACGAAGAAGTGATGTGCCTGAATGGCAACTGGACCGAGCCC |
| CCTCAGTGCAAGGATAGCACCGGCAAGTGTGGCCCCCCTCCCCCCATCG |
| ATAACGGCGACATCACCAGCTTCCCCCTGTCCGTGTATGCCCCTGCCAG |
| CTCCGTGGAATATCAGTGCCAGAACCTGTACCAGCTGGAAGGCAACAAG |
| CGGATCACCTGTCGGAACGGCCAGTGGAGCGAGCCTCCCAAGTGTCTGC |
| ACCCCTGCGTGATCTCCAGAGAAATCATGGAAAACTATAATATCGCCCT |
| GCGCTGGACCGCCAAGCAGAAGCTGTACTCTAGGACCGGCGAGTCTGTG |

TABLE 35G-continued

| eCFH/T DNA co-expressing construct V4.0 [SEQ ID NO: 34] |
|---|
| GAATTTGTGTGCAAGCGGGGATACAGACTGAGCAGCAGATCCCACACCC<br>TGAGAACCACCTGTTGGGACGGCAAGCTGGAATACCCTACCTGCGCCAA<br>GAGATGA |

TABLE 35H

| eCFH/T DNA co-expressing construct V4.1 [SEQ ID NO: 35] |
|---|
| 5'ATGAGACTGCTGGCCAAGATCATCTGCCTGATGCTGTGGGCCATCTG<br>CGTGGCCGAGGACTGCAACGAGCTGCCCCCCAGAAGAAACACCGAGATC<br>CTGACCGGCTCTTGGAGCGACCAGACCTACCCTGAGGGCACCCAGGCCA<br>TCTACAAGTGCAGACCCGGCTACCGGTCCCTGGGCAACATCATCATGGT<br>GTGCAGAAAGGGCGAGTGGGTGGCCCTGAACCCCCTGAGAAAGTGCCAG<br>AAGAGGCCCTGCGGACACCCCGGCGATACCCCTTTTGGCACCTTCACAC<br>TGACCGGCGGCAACGTGTTCGAGTACGGCGTGAAGGCCGTGTACACCTG<br>TAACGAGGGCTACCAGCTGCTGGGCGAGATCAACTACAGAGAGTGCGAC<br>ACCGACGGCTGGACCAACGATATCCCCATCTGCGAGGTCGTGAAGTGCC<br>TGCCTGTGACCGCCCCAGAGAACGGCAAGATCGTGTCCAGCGCCATGGA<br>ACCCGACAGAGAGTACCACTTCGGCCAGGCCGTCAGATTCGTGTGCAAC<br>AGCGGCTACAAGATCGAGGGCGACGAGGAAATGCACTGCAGCGACGAGG<br>GCTTCTGGTCCAAAGAAAAGCCTAAGTGCGTGGAAATCAGCTGCAAGAG<br>CCCCGACGTGATCAACGGCAGCCCCATCAGCCAGAAGATCATCTACAAA<br>GAGAACGAGCGGTTCCAGTACAAGTGTAACATGGGCTACGAGTACAGCG<br>AGCGGGGCGACGCCGTGTGTACAGAATCTGGATGGCGGCCTCTGCCCAG<br>CTGCGAGGAAAAGAGCTGCGACAACCCCTACATCCCCAACGGCGACTAC<br>AGCCCCCTGCGGATCAAGCACAGAACCGGCGACGAGATCACCTACCAGT<br>GCCGGAACGGCTTCTACCCCGCCACCAGAGGCAATACCGCCAAGTGTAC<br>CAGCACCGGCTGGATCCCTGCCCCCAGATGTACCCTGAAGCCCTGCGAC<br>TACCCTGACATCAAGCACGGCGGCCTGTACCACGAGAACATGCGGAGGC<br>CCTACTTCCCTGTGGCCGTGGGCAAGTACTACAGCTACTACTGCGACGA<br>GCACTTCGAGACACCCAGCGGCAGCTACTGGGACCACATCCACTGTACC<br>CAGGACGGCTGGTCCCCTGCCGTGCCCTGCCTGAGGAAGTGCTACTTCC<br>CCTACCTGGAAAACGGCTACAACCAGAACTACGGCCGGAAGTTCGTGCA<br>GGGCAAGAGCATCGATGTGGCCTGCCACCCTGGATACGCCCTGCCTAAG<br>GCCCAGACCACCGTGACCTGCATGGAAAATGGATGGTCCCCCACCCCCC<br>GGTGCATCAGAGTCAGTTTTACCCTCTGAAACTTGTTTATTGCAGCTTA<br>TAATGGTTACAAATAAAGCAATAGCATCACAAATTTCACAAATAAAGCA<br>TTTTTTTCACTGCATTCTAGTTGTGGTTTGTCCAAACTCATCAATGTAT<br>CTTATTCTAATTCTCTTCCCTTTTAGAAACCTGCAGCAAGAGCAGCATC<br>GACATCGAGAATGGCTTCATCAGCGAGAGCCAGTACACCTACGCCCTGA<br>AAGAGAAGGCCAAGTACCAGTGCAAGCTGGGCTACGTGACCGCCGACGG<br>CGAGACAAGCGGCAGCATCACCTGTGGCAAGGATGGGTGGAGCGCCCAG<br>CCCACCTGTATCAAGTCCTGCGACATCCCTGTGTTCATGAATGCCCGGA<br>CCAAGAACGACTTCACCTGGTTCAAGCTGAACGACACACTGGACTACGA<br>GTGCCACGACGGCTACGAGAGCAACACCGGCAGCACCACAGGCAGCATC<br>GTGTGTGGCTACAACGGGTGGAGTGACCTGCCCATCTGTTACGAGCGCG<br>AGTGCGAGCTGCCTAAGATCGACGTGCACCTGGTGCCCGACCGGAAGAA<br>AGACCAGTACAAAGTGGGCGAGGTGCTGAAGTTCTCCTGCAAGCCCGGC<br>TTCACCATCGTGGGCCCCAATAGCGTGCAGTGCTACCACTTTGGCCTGT<br>CCCCCGATCTGCCTATCTGCAAAGAACAGGTGCAGAGCTGCGGCCCTCC<br>ACCCGAGCTGCTGAACGGCAATGTGAAAGAAAAGACCAAAGAGGAATAC<br>GGCCACTCCGAGGTGGTGGAATATTACTGCAACCCCCGGTTCCTGATGA<br>AGGGCCCCAACAAGATTCAGTGTGTGGACGGCGAGTGGACCACCCTGCC<br>CGTGTGTATCGTGGAAGAGTCTACCTGCGGAGACATCCCCGAGCTGGAA<br>CACGGATGGGCCCAGCTGAGCAGCCCCCCTTACTACTACGGCGACAGCG<br>TGGAATTCAACTGCTCCGAGAGCTTTACCATGATCGGCCACCGGTCCAT<br>CACATGCATCCACGGCGTGTGGACACAGCTGCCACAGTGCGTGGCCATC<br>GACAAGCTGAAGAAGTGCAAGTCCAGCAACCTGATCATCCTGGAAGAAC<br>ACCTGAAGAACAAGAAAGAGTTCGACCACAACAGCAACATCCGGTACAG<br>ATGCCGGGGCAAAGAGGGATGGATCCACACCGTGTGCATCAATGGCAGA<br>TGGGACCCCGAAGTGAACTGCAGCATGGCCCAGATCCAGCTGTGCCCCC<br>CACCTCCCCAGATCCCCAACAGCCACAACATGACCACCACCCTGAACTA<br>CCGGGATGGCGAGAAGGTGTCCGTGCTGTGCCAGGAAAACTACCTGATC<br>CAGGAAGGCGAAGAGATTACCTGCAAGGACGGCCGGTGGCAGAGCATCC<br>CCCTGTGTGTGGAAAAGATCCCCTGCAGCCAGCCCCCCCAGATCGAGCA<br>CGGCACCATCAACAGCAGCAGAAGCAGCCAGGAATCCTACGCCCACGGC<br>ACAAAGCTGAGCTACACATGCGAGGGCGGCTTCCGGATCTCCGAGGAAA<br>ACGAGACAACCTGCTACATGGGCAAGTGGTCCTCCCCACCTCAGTGCGA<br>GGGACTGCCTTGCAAGTCCCCACCCGAGATCTCTCATGGCGTGGTGGCC<br>CACATGAGCGACAGCTACCAGTACGGCGAGGAAGTGACCTACAAGTGTT<br>TCGAGGGCTTCGGCATCGACGGCCCTGCCATTGCCAAGTGCCTGGGAGA<br>GAAGTGGTCCCACCCTCCCAGCTGCATCAAGACCGACTGCCTGAGCCTG<br>CCTAGCTTCGAGAACGCCATCCCCATGGGCGAGAAAAAGGACGTGTACA |

TABLE 35H-continued

| eCFH/T DNA co-expressing construct V4.1 [SEQ ID NO: 35] |
|---|
| AGGCCGGCGAACAAGTGACATACACCTGTGCCACCTACTACAAGATGGA<br>CGGCGCCAGCAACGTGACCTGTATTAACAGCCGGTGGACCGGCAGGCCT<br>ACCTGCAGAGATACCTCCTGCGTGAACCCCCCCACCGTGCAGAACGCCT<br>ACATCGTGTCTCGGCAGATGAGCAAGTACCCCAGCGGCGAACGCGTGCG<br>CTACCAGTGTAGAAGCCCCTACGAGATGTTCGGCGACGAAGAAGTGATG<br>TGCCTGAATGGCAACTGGACCGAGCCCCCTCAGTGCAAGGATAGCACCG<br>GCAAGTGTGGCCCCCCTCCCCCCATCGATAACGGCGACATCACCAGCTT<br>CCCCCTGTCCGTGTATGCCCCTGCCAGCTCCGTGGAATATCAGTGCCAG<br>AACCTGTACCAGCTGGAAGGCAACAAGCGGATCACCTGTCGGAACGGCC<br>AGTGGAGCGAGCCTCCCAAGTGTCTGCACCCCTGCGTGATCTCCAGAGA<br>AATCATGGAAAACTATAATATCGCCCTGCGCTGGACCGCCAAGCAGAAG<br>CTGTACTCTAGGACCGGCGAGTCTGTGGAATTTGTGTGCAAGCGGGGAT<br>ACAGACTGAGCAGCAGATCCCACACCCTGAGAACCACCTGTTGGGACGG<br>CAAGCTGGAATACCCTACCTGCGCCAAGAGATGA3' |

TABLE 35I

| eCFH/T DNA co-expressing construct V4.2 [SEQ ID NO: 36] |
|---|
| ATGAGACTGCTGGCCAAGATCATCTGCCTGATGCTGTGGGCCATCTGCG<br>TGGCCGAGGACTGCAACGAGCTGCCCCCCAGAAGAAACACCGAGATCCT<br>GACCGGCTCTTGGAGCGACCAGACCTACCCTGAGGGCACCCAGGCCATC<br>TACAAGTGCAGACCCGGCTACCGGTCCCTGGGCAACATCATCATGGTGT<br>GCAGAAAGGGCGAGTGGGTGGCCCTGAACCCCCTGAGAAAGTGCCAGAA<br>GAGGCCCTGCGGACACCCCGGCGATACCCCTTTTGGCACCTTCACACTG<br>ACCGGCGGCAACGTGTTCGAGTACGGCGTGAAGGCCGTGTACACCTGTA<br>ACGAGGGCTACCAGCTGCTGGGCGAGATCAACTACAGAGAGTGCGACAC<br>CGACGGCTGGACCAACGATATCCCCATCTGCGAGGTCGTGAAGTGCCTG<br>CCTGTGACCGCCCCAGAGAACGGCAAGATCGTGTCCAGCGCCATGGAAC<br>CCGACAGAGAGTACCACTTCGGCCAGGCCGTCAGATTCGTGTGCAACAG<br>CGGCTACAAGATCGAGGGCGACGAGGAAATGCACTGCAGCGACGACGGC<br>TTCTGGTCCAAAGAAAAGCCTAAGTGCGTGGAAATCAGCTGCAAGAGCC<br>CCGACGTGATCAACGGCAGCCCCATCAGCCAGAAGATCATCTACAAAGA<br>GAACGAGCGGTTCCAGTACAAGTGTAACATGGGCTACGAGTACAGCGAG<br>CGGGGCGACGCCGTGTGTACAGAATCTGGATGGCGGCCTCTGCCCAGCT<br>GCGAGGAAAAGAGCTGCGACAACCCCTACATCCCCAACGGCGACTACAG<br>CCCCCTGCGGATCAAGCACAGAACCGGCGACGAGATCACCTACCAGTGC<br>CGGAACGGCTTCTACCCCGCCACCAGAGGCAATACCGCCAAGTGTACCA<br>GCACCGGCTGGATCCCTGCCCCCAGATGTACCCTGAAGCCCTGCGACTA<br>CCCTGACATCAAGCACGGCGGCCTGTACCACGAGAACATGCGGAGGCCC<br>TACTTCCCTGTGGCCGTGGGCAAGTACTACAGCTACTACTGCGACGAGC<br>ACTTCGAGACACCCAGCGGCAGCTACTGGGACCACATCCACTGTACCCA<br>GGACGGCTGGTCCCCTGCCGTGCCCTGCCTGAGGAAGTGCTACTTCCCC<br>TACCTGGAAAACGGCTACAACCAGAACTACGGCCGGAAGTTCGTGCAGG<br>GCAAGAGCATCGATGTGGCCTGCCACCCTGGATACGCCCTGCCTAAGGC<br>CCAGACCACCGTGACCTGCATGGAAAATGGATGGTCCCCCACCCCCCGG<br>TGCATCAGAGTCAGTAAGTCCTTCACTCTGTGAAACTTGTTTATTGCAG<br>CTTATAATGGTTACAAATAAAGCAATAGCATCACAAATTTCACAAATAA<br>AGCATTTTTTTCACTGCATTCTAGTTGTGGTTTGTCCAAACTCATCAAT<br>GTATCTTATTCTAATTCTCTTCCCTTTTAGAAACCTGCAGCAAGAGCAG<br>CATCGACATCGAGAATGGCTTCATCAGCGAGAGCCAGTACACCTACGCC<br>CTGAAAGAGAAGGCCAAGTACCAGTGCAAGCTGGGCTACGTGACCGCCG<br>ACGGCGAGACAAGCGGCAGCATCACCTGTGGCAAGGATGGGTGGAGCGC<br>CCAGCCCACCTGTATCAAGTCCTGCGACATCCCTGTGTTCATGAATGCC<br>CGGACCAAGAACGACTTCACCTGGTTCAAGCTGAACGACACACTGGACT<br>ACGAGTGCCACGACGGCTACGAGAGCAACACCGGCAGCACCACAGGCAG<br>CATCGTGTGTGGCTACAACGGGTGGAGTGACCTGCCCATCTGTTACGAG<br>CGCGAGTGCGAGCTGCCTAAGATCGACGTGCACCTGGTGCCCGACCGGA<br>AGAAAGACCAGTACAAAGTGGGCGAGGTGCTGAAGTTCTCCTGCAAGCC<br>CGGCTTCACCATCGTGGGCCCCAATAGCGTGCAGTGCTACCACTTTGGC<br>CTGTCCCCCGATCTGCCTATCTGCAAAGAACAGGTGCAGAGCTGCGGCC<br>CTCCACCCGAGCTGCTGAACGGCAATGTGAAAGAAAAGACCAAAGAGGA<br>ATACGGCCACTCCGAGGTGGTGGAATATTACTGCAACCCCCGGTTCCTG<br>ATGAAGGGCCCCAACAAGATTCAGTGTGTGGACGGCGAGTGGACCACCC<br>TGCCCGTGTGTATCGTGGAAGAGTCTACCTGCGGAGACATCCCCGAGCT<br>GGAACACGGATGGGCCCAGCTGAGCAGCCCCCCTTACTACTACGGCGAC<br>AGCGTGGAATTCAACTGCTCCGAGAGCTTTACCATGATCGGCCACCGGT<br>CCATCACATGCATCCACGGCGTGTGGACACAGCTGCCACAGTGCGTGGC<br>CATCGACAAGCTGAAGAAGTGCAAGTCCAGCAACCTGATCATCCTGGAA<br>GAACACCTGAAGAACAAGAAAGAGTTCGACCACAACAGCAACATCCGGT<br>ACAGATGCCGGGGCAAAGAGGGATGGATCCACACCGTGTGCATCAATGG<br>CAGATGGGACCCCGAAGTGAACTGCAGCATGGCCCAGATCCAGCTGTGC<br>CCCCCACCTCCCCAGATCCCCAACAGCCACAACATGACCACCACCCTGA |

TABLE 35I-continued

| eCFH/T DNA co-expressing construct V4.2 [SEQ ID NO: 36] |
|---|
| ACTACCGGGATGGCGAGAAGGTGTCCGTGCTGTGCCAGGAAAACTACCT |
| GATCCAGGAAGGCGAAGAGATTACCTGCAAGGACGGCCGGTGGCAGAGC |
| ATCCCCCTGTGTGTGGAAAAGATCCCCTGCAGCCAGCCCCCCCAGATCG |
| AGCACGGCACCATCAACAGCAGCAGAAGCAGCCAGGAATCCTACGCCCA |
| CGGCACAAAGCTGAGCTACACATGCGAGGGCGGCTTCCGGATCTCCGAG |
| GAAAACGAGACAACCTGCTACATGGGCAAGTGGTCCTCCCCACCTCAGT |
| GCGAGGGACTGCCTTGCAAGTCCCCACCCGAGATCTCTCATGGCGTGGT |
| GGCCCACATGAGCGACAGCTACCAGTACGGCGAGGAAGTGACCTACAAG |
| TGTTTCGAGGGCTTCGGCATCGACGGCCCTGCCATTGCCAAGTGCCTGG |
| GAGAGAAGTGGTCCCACCCTCCCAGCTGCATCAAGACCGACTGCCTGAG |
| CCTGCCTAGCTTCGAGAACGCCATCCCCATGGGCGAGAAAAAGGACGTG |
| TACAAGGCCGGCGAACAAGTGACATACACCTGTGCCACCTACTACAAGA |
| TGGACGGCGCCAGCAACGTGACCTGTATTAACAGCCGGTGGACCGGCAG |
| GCCTACCTGCAGAGATACCTCCTGCGTGAACCCCCCCACCGTGCAGAAC |
| GCCTACATCGTGTCTCGGCAGATGAGCAAGTACCCCAGCGGCGAACGCG |
| TGCGCTACCAGTGTAGAAGCCCCTACGAGATGTTCGGCGACGAAGAAGT |
| GATGTGCCTGAATGGCAACTGGACCGAGCCCCCTCAGTGCAAGGATAGC |
| ACCGGCAAGTGTGGCCCCCCTCCCCCCATCGATAACGGCGACATCACCA |
| GCTTCCCCCTGTCCGTGTATGCCCCTGCCAGCTCCGTGGAATATCAGTG |
| CCAGAACCTGTACCAGCTGGAAGGCAACAAGCGGATCACCTGTCGGAAC |
| GGCCAGTGGAGCGAGCCTCCCAAGTGTCTGCACCCCTGCGTGATCTCCA |
| GAGAAATCATGGAAAACTATAATATCGCCCTGCGCTGGACCGCCAAGCA |
| GAAGCTGTACTCTAGGACCGGCGAGTCTGTGGAATTTGTGTGCAAGCGG |
| GGATACAGACTGAGCAGCAGATCCCACACCCTGAGAACCACCTGTTGGG |
| ACGGCAAGCTGGAATACCCTACCTGCGCCAAGAGATGA |

TABLE 35J

| eCFH/T DNA co-expressing construct V4.3 [SEQ ID NO: 37] |
|---|
| 5'ATGAGACTGCTGGCCAAGATCATCTGCCTGATGCTGTGGGCCATCTG |
| CGTGGCCGAGGACTGCAACGAGCTGCCCCCCAGAAGAAACACCGAGATC |
| CTGACCGGCTCTTGGAGCGACCAGACCTACCCTGAGGGCACCCAGGCCA |
| TCTACAAGTGCAGACCCGGCTACCGGTCCCTGGGCAACATCATCATGGT |
| GTGCAGAAAGGGCGAGTGGGTGGCCCTGAACCCCCTGAGAAAGTGCCAG |
| AAGAGGCCCTGCGGACACCCCGGCGATACCCCTTTTGGCACCTTCACAC |
| TGACCGGCGGCAACGTGTTCGAGTACGGCGTGAAGGCCGTGTACACCTG |
| TAACGAGGGCTACCAGCTGCTGGGCGAGATCAACTACAGAGAGTGCGAC |
| ACCGACGGCTGGACCAACGATATCCCCATCTGCGAGGTCGTGAAGTGCC |
| TGCCTGTGACCGCCCCAGAGAACGGCAAGATCGTGTCCAGCGCCATGGA |
| ACCCGACAGAGAGTACCACTTCGGCCAGGCCGTCAGATTCGTGTGCAAC |
| AGCGGCTACAAGATCGAGGGCGACGAGGAAATGCACTGCAGCGACGACG |
| GCTTCTGGTCCAAAGAAAAGCCTAAGTGCGTGGAAATCAGCTGCAAGAG |
| CCCCGACGTGATCAACGGCAGCCCCATCAGCCAGAAGATCATCTACAAA |
| GAGAACGAGCGGTTCCAGTACAAGTGTAACATGGGCTACGAGTACAGCG |
| AGCGGGGCGACGCCGTGTGTACAGAATCTGGATGGCGGCCTCTGCCCAG |
| CTGCGAGGAAAAGAGCTGCGACAACCCCTACATCCCCAACGGCGACTAC |
| AGCCCCCTGCGGATCAAGCACAGAACCGGCGACGAGATCACCTACCAGT |
| GCCGGAACGGCTTCTACCCCGCCACCAGAGGCAATACCGCCAAGTGTAC |
| CAGCACCGGCTGGATCCCTGCCCCCAGATGTACCCTGAAGCCCTGCGAC |
| TACCCTGACATCAAGCACGGCGGCCTGTACCACGAGAACATGCGGAGGC |
| CCTACTTCCCTGTGGCCGTGGGCAAGTACTACAGCTACTACTGCGACGA |
| GCACTTCGAGACACCCAGCGGCAGCTACTGGGACCACATCCACTGTACC |
| CAGGACGGCTGGTCCCCTGCCGTGCCCTGCCTGAGGAAGTGCTACTTCC |
| CCTACCTGGAAAACGGCTACAACCAGAACTACGGCCGGAAGTTCGTGCA |
| GGGCAAGAGCATCGATGTGGCCTGCCACCCTGGATACGCCCTGCCTAAG |
| GCCCAGACCACCGTGACCTGCATGGAAAATGGATGGTCCCCCACCCCCC |
| GGTGCATCAGAGTCAGTGAGTCCTTCACTCTGTGAAACTTGTTTATTGC |
| AGCTTATAATGGTTACAAATAAAGCAATAGCATCACAAATTTCACAAAT |
| AAAGCATTTTTTTCACTGCATTCTAGTTGTGGTTTGTCCAAACTCATCA |
| ATGTATCTTATTCTAATTCTCTTCCCTTTTAGAAACCTGCAGCAAGAGC |
| AGCATCGACATCGAGAATGGCTTCATCAGCGAGAGCCAGTACACCTACG |
| CCCTGAAAGAGAAGGCCAAGTACCAGTGCAAGCTGGGCTACGTGACCGC |
| CGACGGCGAGACAAGCGGCAGCATCACCTGTGGCAAGGATGGGTGGAGC |
| GCCCAGCCCACCTGTATCAAGTCCTGCGACATCCCTGTGTTCATGAATG |
| CCCGGACCAAGAACGACTTCACCTGGTTCAAGCTGAACGACACACTGGA |
| CTACGAGTGCCACGACGGCTACGAGAGCAACACCGGCAGCACCACAGGC |
| AGCATCGTGTGTGGCTACAACGGGTGGAGTGACCTGCCCATCTGTTACG |
| AGCGCGAGTGCGAGCTGCCTAAGATCGACGTGCACCTGGTGCCCGACCG |
| GAAGAAAGACCAGTACAAAGTGGGCGAGGTGCTGAAGTTCTCCTGCAAG |
| CCCGGCTTCACCATCGTGGGCCCCAATAGCGTGCAGTGCTACCACTTTG |
| GCCTGTCCCCCGATCTGCCTATCTGCAAAGAACAGGTGCAGAGCTGCGG |
| CCCTCCACCCGAGCTGCTGAACGGCAATGTGAAAGAAAAGACCAAAGAG |

TABLE 35J-continued

| eCFH/T DNA co-expressing construct V4.3 [SEQ ID NO: 37] |
|---|
| GAATACGGCCACTCCGAGGTGGTGGAATATTACTGCAACCCCCGGTTCC |
| TGATGAAGGGCCCCAACAAGATTCAGTGTGTGGACGGCGAGTGGACCAC |
| CCTGCCCGTGTGTATCGTGGAAGAGTCTACCTGCGGAGACATCCCCGAG |
| CTGGAACACGGATGGGCCCAGCTGAGCAGCCCCCCTTACTACTACGGCG |
| ACAGCGTGGAATTCAACTGCTCCGAGAGCTTTACCATGATCGGCCACCG |
| GTCCATCACATGCATCCACGGCGTGTGGACACAGCTGCCACAGTGCGTG |
| GCCATCGACAAGCTGAAGAAGTGCAAGTCCAGCAACCTGATCATCCTGG |
| AAGAACACCTGAAGAACAAGAAAGAGTTCGACCACAACAGCAACATCCG |
| GTACAGATGCCGGGGCAAAGAGGGATGGATCCACACCGTGTGCATCAAT |
| GGCAGATGGGACCCCGAAGTGAACTGCAGCATGGCCCAGATCCAGCTGT |
| GCCCCCCACCTCCCCAGATCCCCAACAGCCACAACATGACCACCACCCT |
| GAACTACCGGGATGGCGAGAAGGTGTCCGTGCTGTGCCAGGAAAACTAC |
| CTGATCCAGGAAGGCGAAGAGATTACCTGCAAGGACGGCCGGTGGCAGA |
| GCATCCCCCTGTGTGTGGAAAAGATCCCCTGCAGCCAGCCCCCCCAGAT |
| CGAGCACGGCACCATCAACAGCAGCAGAAGCAGCCAGGAATCCTACGCC |
| CACGGCACAAAGCTGAGCTACACATGCGAGGGCGGCTTCCGGATCTCCG |
| AGGAAAACGAGACAACCTGCTACATGGGCAAGTGGTCCTCCCCACCTCA |
| GTGCGAGGGACTGCCTTGCAAGTCCCCACCCGAGATCTCTCATGGCGTG |
| GTGGCCCACATGAGCGACAGCTACCAGTACGGCGAGGAAGTGACCTACA |
| AGTGTTTCGAGGGCTTCGGCATCGACGGCCCTGCCATTGCCAAGTGCCT |
| GGGAGAGAAGTGGTCCCACCCTCCCAGCTGCATCAAGACCGACTGCCTG |
| AGCCTGCCTAGCTTCGAGAACGCCATCCCCATGGGCGAGAAAAAGGACG |
| TGTACAAGGCCGGCGAACAAGTGACATACACCTGTGCCACCTACTACAA |
| GATGGACGGCGCCAGCAACGTGACCTGTATTAACAGCCGGTGGACCGGC |
| AGGCCTACCTGCAGAGATACCTCCTGCGTGAACCCCCCCACCGTGCAGA |
| ACGCCTACATCGTGTCTCGGCAGATGAGCAAGTACCCCAGCGGCGAACG |
| CGTGCGCTACCAGTGTAGAAGCCCCTACGAGATGTTCGGCGACGAAGAA |
| GTGATGTGCCTGAATGGCAACTGGACCGAGCCCCCTCAGTGCAAGGATA |
| GCACCGGCAAGTGTGGCCCCCCTCCCCCCATCGATAACGGCGACATCAC |
| CAGCTTCCCCCTGTCCGTGTATGCCCCTGCCAGCTCCGTGGAATATCAG |
| TGCCAGAACCTGTACCAGCTGGAAGGCAACAAGCGGATCACCTGTCGGA |
| ACGGCCAGTGGAGCGAGCCTCCCAAGTGTCTGCACCCCTGCGTGATCTC |
| CAGAGAAATCATGGAAAACTATAATATCGCCCTGCGCTGGACCGCCAAG |
| CAGAAGCTGTACTCTAGGACCGGCGAGTCTGTGGAATTTGTGTGCAAGC |
| GGGGATACAGACTGAGCAGCAGATCCCACACCCTGAGAACCACCTGTTG |
| GGACGGCAAGCTGGAATACCCTACCTGCGCCAAGAGATGA3' |

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates that may need to be independently confirmed.

What is claimed is:

1. A viral vector comprising:

(i) a recombinant polynucleotide transgene comprising a polynucleotide sequence that has at least 98% identity to SEQ ID NO:3, wherein the polynucleotide sequence encodes a truncated complement factor H (CFHT) polypeptide, wherein the CFHT polypeptide comprises isoleucine (I) at position 62 and tyrosine (Y) at position 402 a;

(ii) a CBA promoter operably linked to the polynucleotide transgene, wherein the CBA promoter comprises a polynucleotide sequence having at least 98% identity to any of SEQ ID NO: 12-14;

(iii) a Bovine Growth Factor (bGH) polyadenylation sequence; and (iv) left and right inverted terminal repeat (ITR) sequences, wherein the viral vector is an adeno-associated virus 2 (AAV2) vector, and wherein introduction of the polynucleotide transgene into a mammalian cell results in expression of the CFHT polypeptide.

2. The viral vector of claim 1 wherein the CFHT polypeptide comprises (a) residues 1-431 of SEQ ID NO:21; or (b) a variant CFHT with at least 98% identity to residues 1-431 of SEQ ID NO:21.

3. The viral vector of claim 1 wherein the promoter is a CBA promoter comprising SEQ ID NO:13.

4. The viral vector of claim 1 wherein the polyadenylation sequence is a Bovine Growth Factor (bGH) polyadenylation sequence comprising SEQ ID NO: 29.

5. The viral vector of claim 1 wherein the CFHT polypeptide is encoded by a polynucleotide sequence having at least 99% identity to SEQ ID NO:3.

6. The viral vector of claim 1, wherein the CBA promoter comprises the polynucleotide sequence set forth as any one of SEQ ID NO:12-14.

7. The viral vector of claim 1 wherein the CFHT polypeptide comprises (a) residues 1-449 of SEQ ID NO:4; or (b) a variant CFHT with at least 98% identity to residues 1-449 of SEQ ID NO: 4.

8. The viral vector of claim 1 wherein one of the left and right ITRs comprises SEQ ID NO: 18 and the other ITR comprises the reverse complement of SEQ ID NO: 18.

9. The viral vector of claim 8 wherein the CFHT polypeptide is encoded by a polynucleotide sequence comprising SEQ ID NO:3.

10. The viral vector of claim 1 wherein the CFHT polypeptide comprises SEQ ID NO:21, the promoter comprises SEQ ID NO:13; and the bGH polyadenylation sequence comprises SEQ ID NO:29.

11. The viral vector of claim 10 wherein the polynucleotide sequence encoding the CFHT polypeptide comprises SEQ ID NO:3.

12. A pharmaceutical composition comprising a therapeutic amount of the viral vector of claim 1, and a pharmaceutically acceptable carrier or excipient.

13. A method comprising administering a therapeutically effective amount of the pharmaceutical composition of claim 12 to a subject in need of treatment for AMD, wherein the pharmaceutical composition is administered subretinally, intravitreally, intravascularly, extraocularly, or to the choroid.

14. The method of claim 13 wherein the truncated CFHT polypeptide is expressed by retinal pigment epithelial (RPE) cells.

15. A method comprising administering a therapeutically effective amount of the pharmaceutical composition of claim 12 to reduce a subject's risk of developing AMD, wherein the subject is selected to be homozygous or heterozygous for a Chromosome 1 CFH risk allele, wherein the subject comprises the following CFH proteins encoded by the CFH risk alleles present in the subject: VV62/HH402/EE936, VV62/YH402/ED936, IV62/YH402/EE936, VV62/YH402/EE936, VV62/YY402/DD936/IV62/YY402/ED936, VV62/YY402/ED936, 1162/YY402/EE936, IV62/YY402/EE936, or VV62/YY402/EE936.

16. The method of claim 15 wherein the CFH proteins encoded by the CFH risk alleles present in the subject comprise VV62/HH402/EE936, VV62/YH402/ED936, VV62/YH402/EE936, or IV62/YH402/EE936, and the subject is heterozygous or homozygous for a CFHR3/1 no deletion risk allele.

* * * * *